US010428131B2

(12) United States Patent
Stewart et al.

(10) Patent No.: US 10,428,131 B2
(45) Date of Patent: Oct. 1, 2019

(54) GITRL FUSION PROTEINS COMPRISING A HUMAN CORONIN 1A DERIVED TRIMERIZATION DOMAIN

(71) Applicant: MEDIMMUNE LIMITED, Cambridge (GB)

(72) Inventors: Ross Anthony Stewart, Cambridge (GB); Natalie Jo Tigue, Cambridge (GB); Lesley Lynn Young, Cambridge (GB); Daniel Ramsay Higazi, Cambridge (GB); Lisa Bamber, Cambridge (GB); Sudharsan Sridharan, Cambridge (GB); Rebecca Leyland, Cambridge (GB); Nicholas Mason Durham, Gaithersburg, MD (US)

(73) Assignee: MEDIMMUNE LIMITED, Cambridge (GB)

( * ) Notice: Subject to any disclaimer, the term of this patent is extended or adjusted under 35 U.S.C. 154(b) by 0 days.

(21) Appl. No.: 15/234,551

(22) Filed: Aug. 11, 2016

(65) Prior Publication Data

US 2017/0073386 A1 Mar. 16, 2017

Related U.S. Application Data

(60) Provisional application No. 62/350,447, filed on Jun. 15, 2016, provisional application No. 62/204,212, filed on Aug. 12, 2015.

(51) Int. Cl.

| *C07K 14/525* | (2006.01) |
| *C07K 14/705* | (2006.01) |
| *A61K 38/19* | (2006.01) |
| *A61K 45/06* | (2006.01) |
| *C07K 16/00* | (2006.01) |
| *C07K 16/28* | (2006.01) |
| *A61K 38/00* | (2006.01) |
| *A61K 39/00* | (2006.01) |

(52) U.S. Cl.
CPC .......... *C07K 14/525* (2013.01); *A61K 38/191* (2013.01); *A61K 45/06* (2013.01); *C07K 14/70575* (2013.01); *C07K 16/00* (2013.01); *C07K 16/2878* (2013.01); *A61K 38/00* (2013.01); *A61K 2039/505* (2013.01); *C07K 2317/622* (2013.01); *C07K 2317/75* (2013.01); *C07K 2319/30* (2013.01); *C07K 2319/35* (2013.01); *C07K 2319/73* (2013.01); *C07K 2319/735* (2013.01)

(58) Field of Classification Search
None
See application file for complete search history.

(56) References Cited

U.S. PATENT DOCUMENTS

| 6,413,746 | B1 | 7/2002 | Field | |
| 6,660,501 | B2 | 12/2003 | Field | |
| 7,959,925 | B2 * | 6/2011 | Weinberg | ............. A61K 38/191 424/178.1 |
| 2008/0187954 | A1 | 8/2008 | Kallmeier et al. | |
| 2013/0164286 | A1 * | 6/2013 | Chou | ..................... C07K 16/40 424/134.1 |
| 2016/0024176 | A1 | 1/2016 | Damschroder et al. | |

FOREIGN PATENT DOCUMENTS

| WO | WO 2004/009823 | 1/2004 |
| WO | 2009009116 A2 | 1/2009 |
| WO | 2015116178 A1 | 8/2015 |

OTHER PUBLICATIONS

Aalberse et al., IgG4 breaking the rules. Immunol. 105, 9-19, 2002.*
Chen et al., Fusion protein linkers: Property, design and functionality. Adv. Drug. Del. Rev. 65, 1357-1369, 2013.*
Gatfield et al., Association of the leukocyte plasma membrane with the actin cytoskeleton through coiled coil-mediated trimeric coronin 1 molecules. Mol. Biol. Cell, 16, 2786-2798, 2005.*
RID=PG5CDR, NCBI search result. Jul. 14, 2017.*
A. Wyzgol et al: "Trimer Stabilization, Oligomerization, and Antibody-Mediated Cell Surface Immobilization Improve the Activity of Soluble Trimers of CD27L, CD40L, 41BBL, and Glucocorticoid-Induced TNF Receptor Ligand", The Journal of Immunology, vol. 183, No. 3, Aug. 1, 2009 (Aug. 1, 2009), pp. 1851-1861.
Giuseppe Nocentini et al: "Pharmacological modulation of GITRL/GITR system: therapeutic perspectives", British Journal of Pharmacology, vol. 165, No. 7, Mar. 9, 2012 (Mar. 9, 2012), pp. 2089-2099.
Harbury et al., "A switch between two-, three-, and four-stranded coiled coils in GCN4 leucine zipper mutants." Science 262(5138):1401-07 (Nov. 1993).

* cited by examiner

*Primary Examiner* — Elly-Gerald Stoica
(74) *Attorney, Agent, or Firm* — McDonnell Boehnen Hulbert & Berghoff LLP

(57) ABSTRACT

The disclosure provides GITRL fusion polypeptide subunits comprising an IgG Fc domain, a trimerization domain, and the receptor binding domain of GITR ligand, where the fusion polypeptide subunits can self-assemble into hexameric proteins. Also provided are methods of making fusion polypeptide subunits and hexameric proteins, and methods of use, e.g., treatment of cancer.

20 Claims, 59 Drawing Sheets
Specification includes a Sequence Listing.

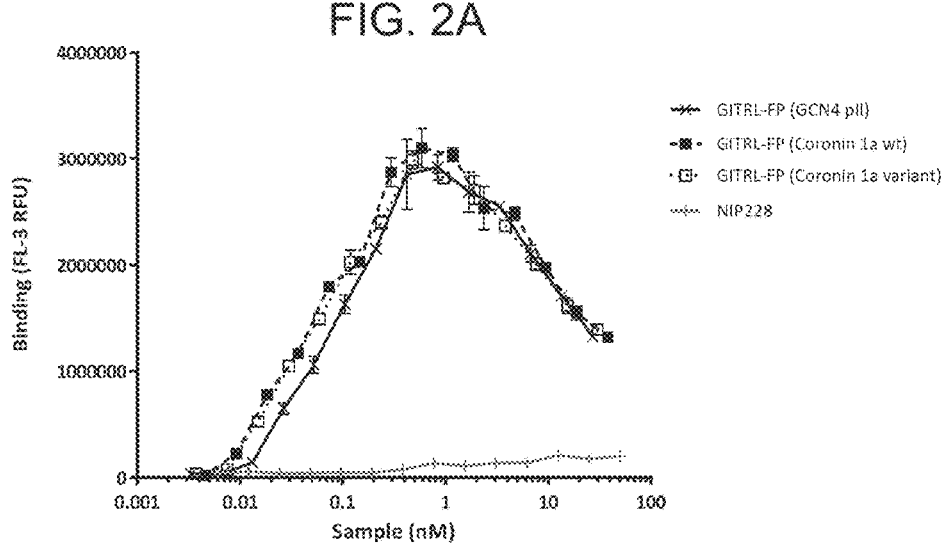
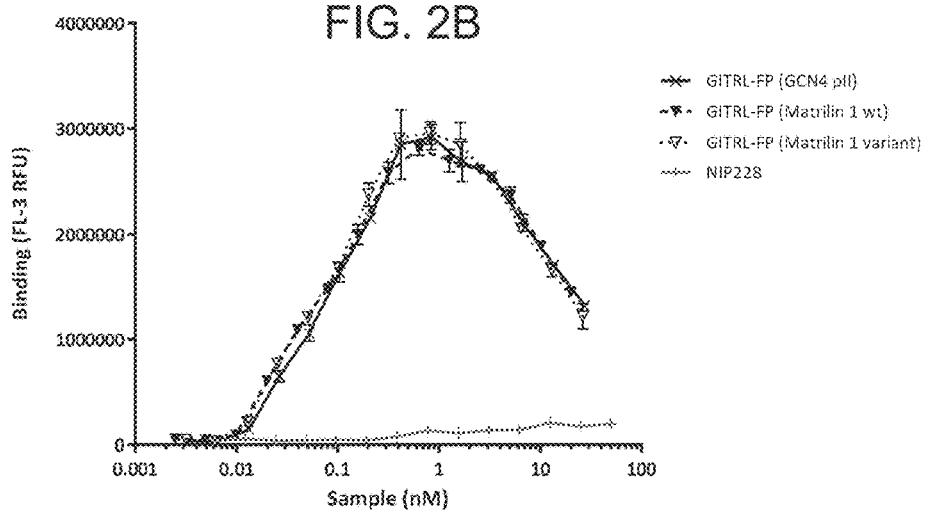

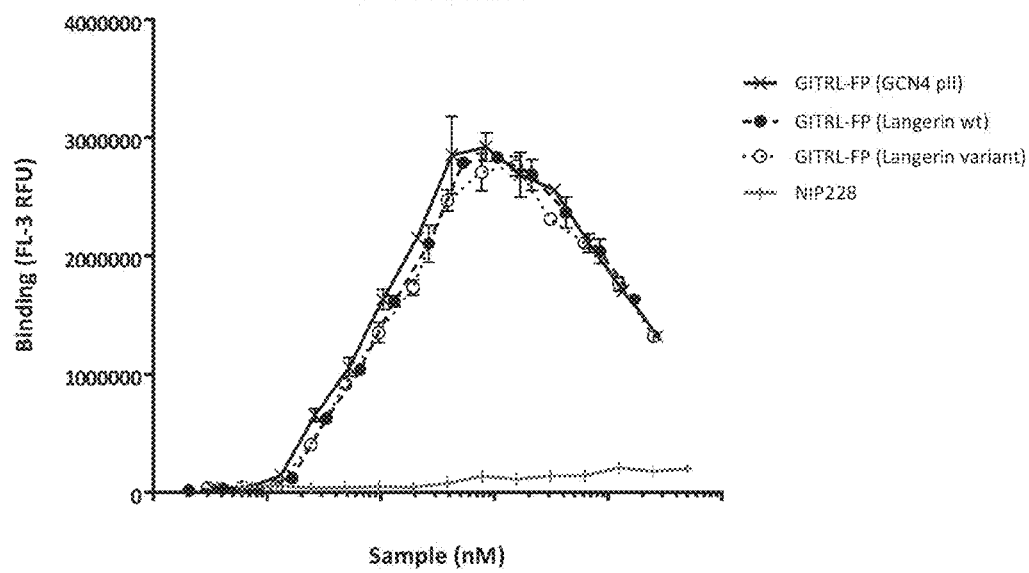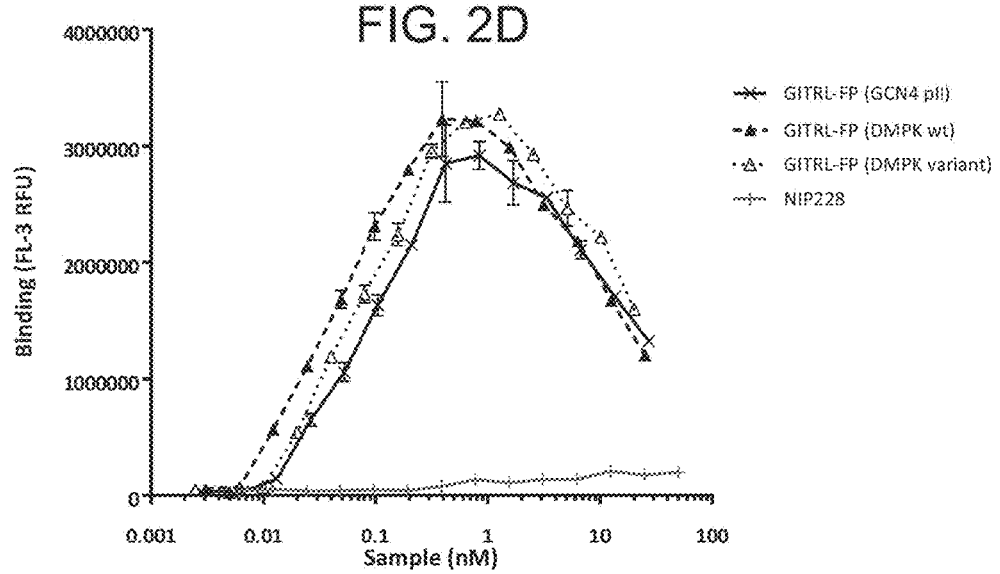

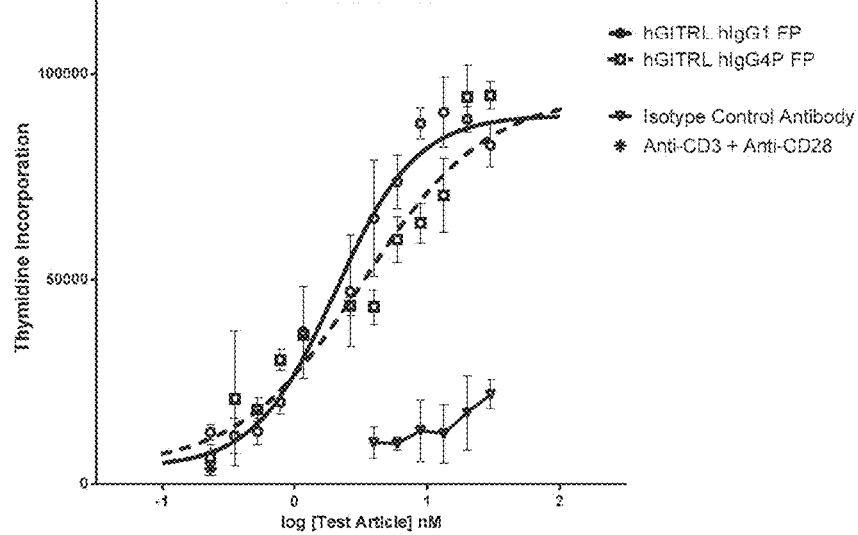
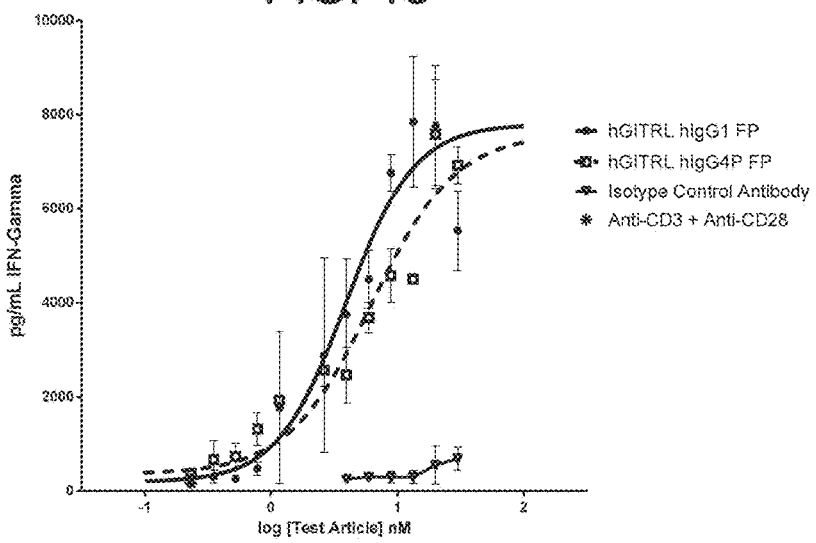

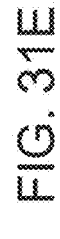

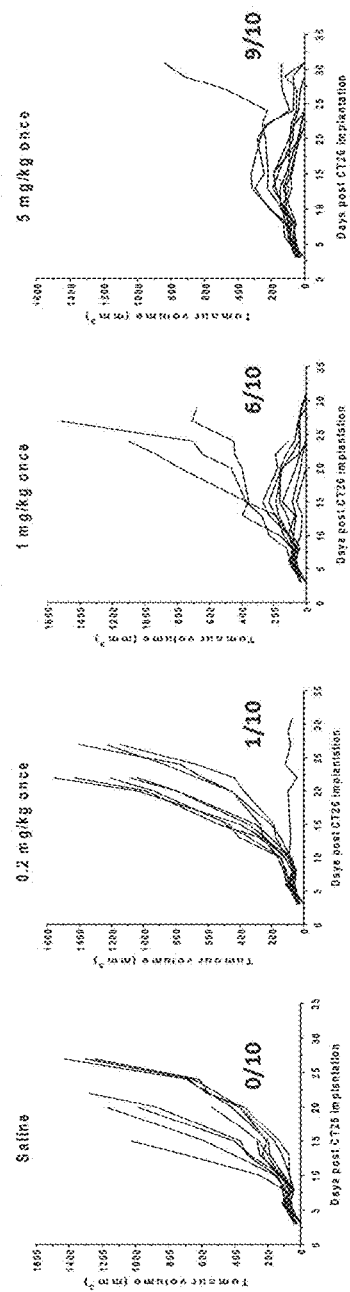

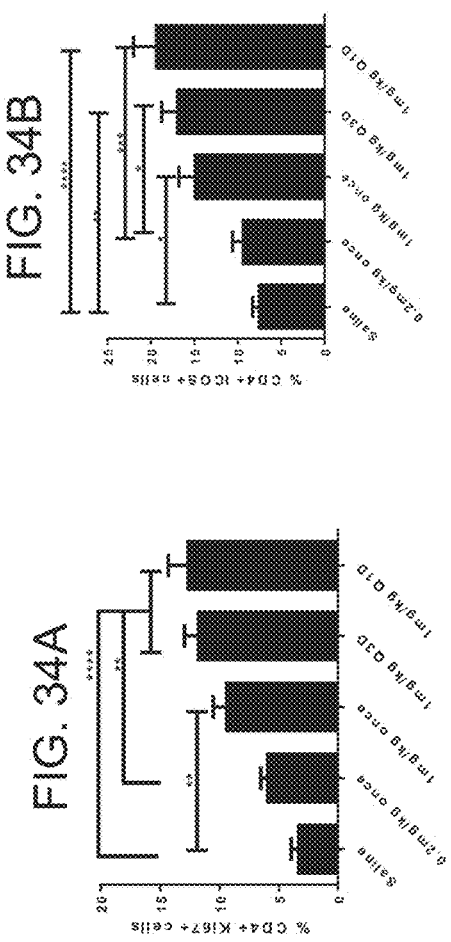
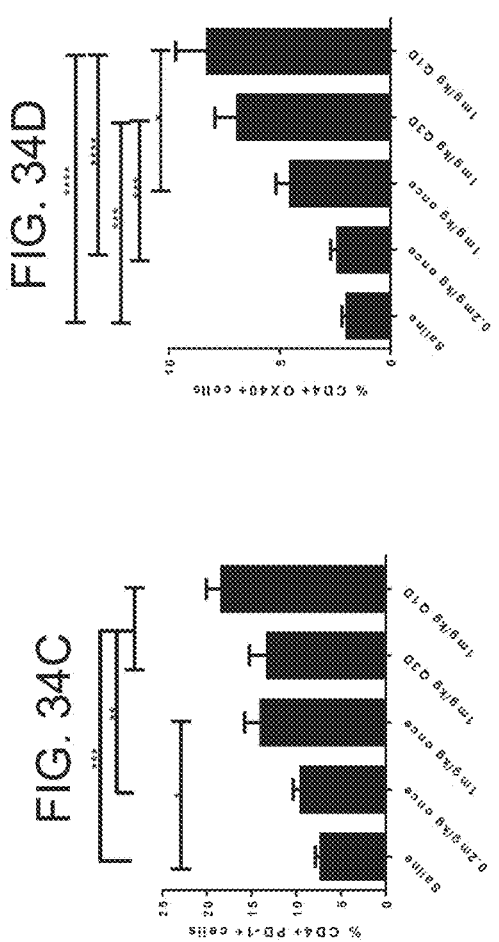
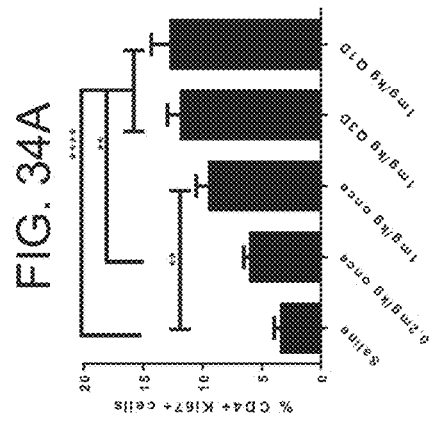
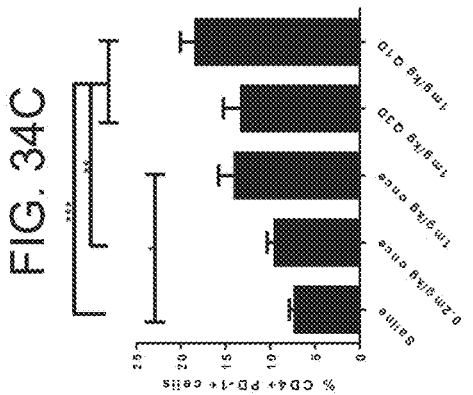

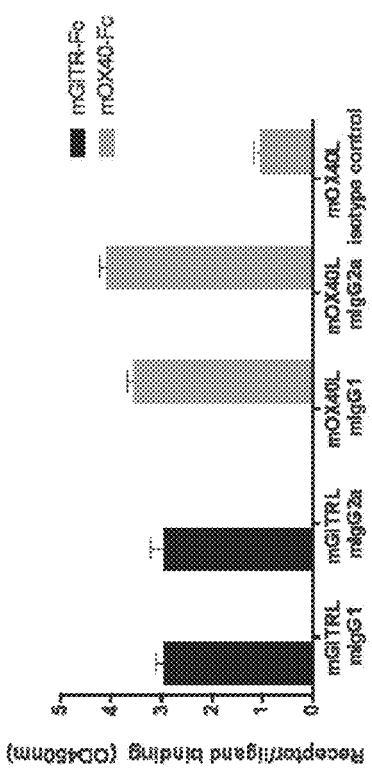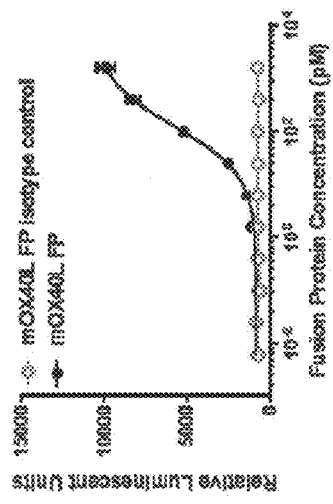
FIG. 35A
FIG. 35B

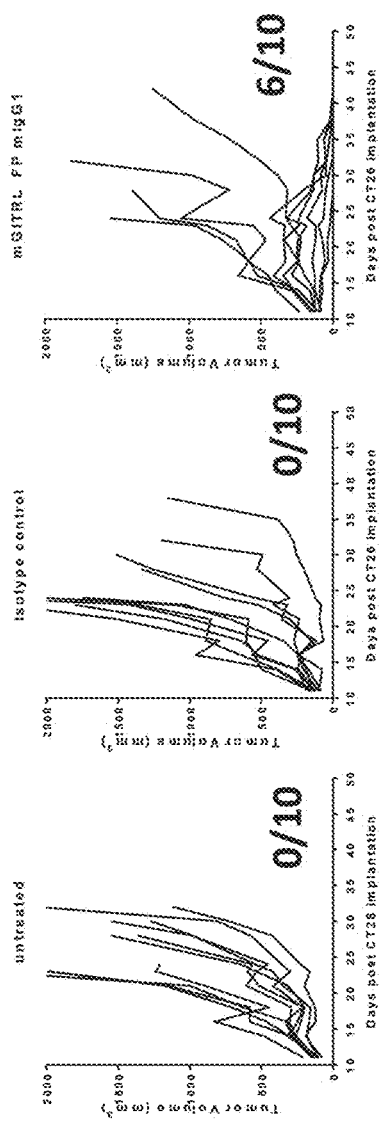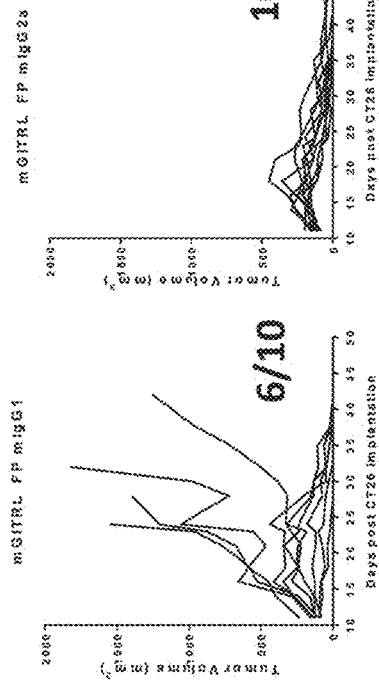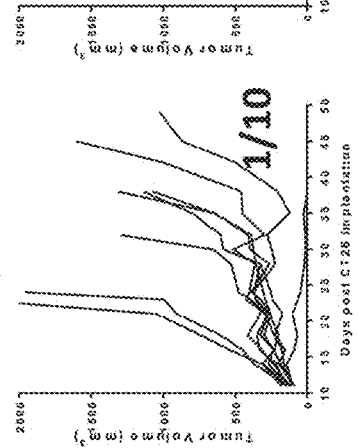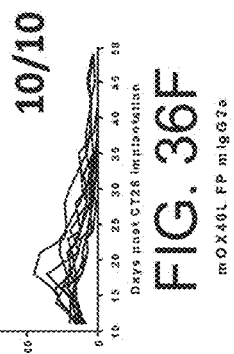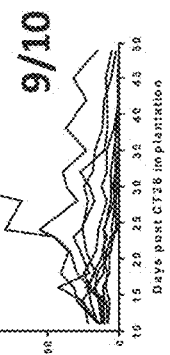

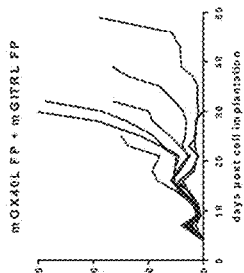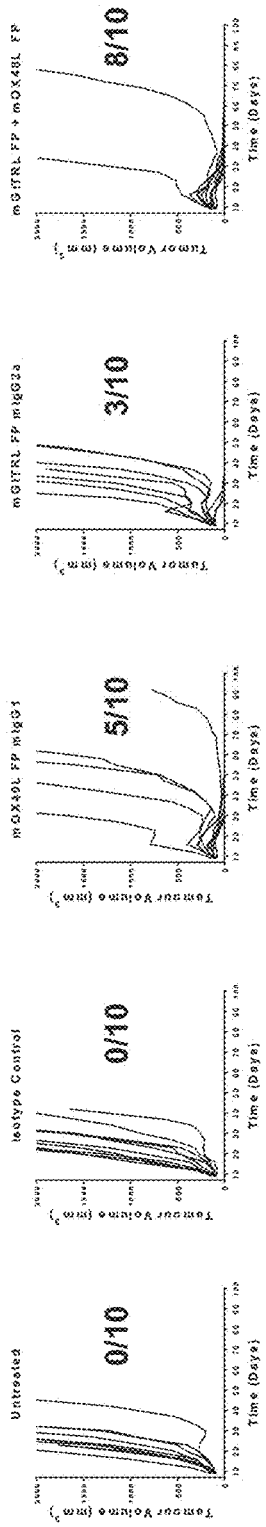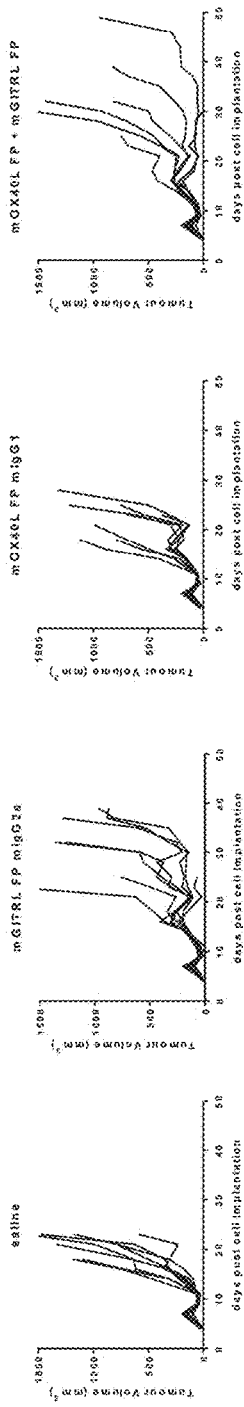

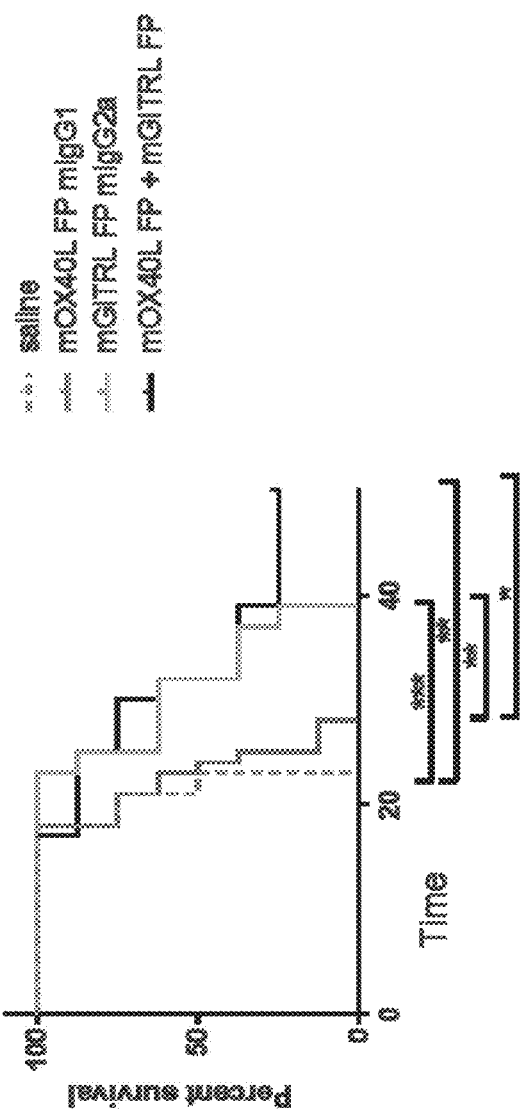

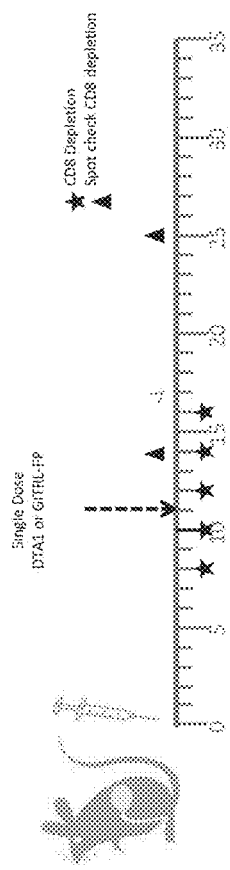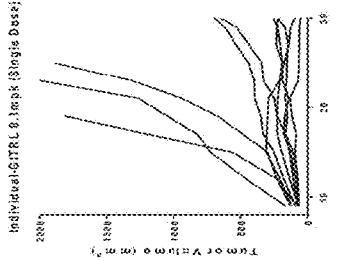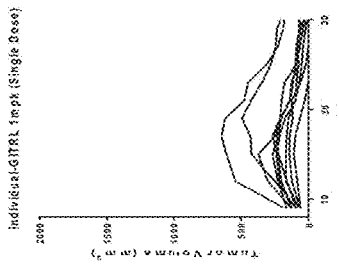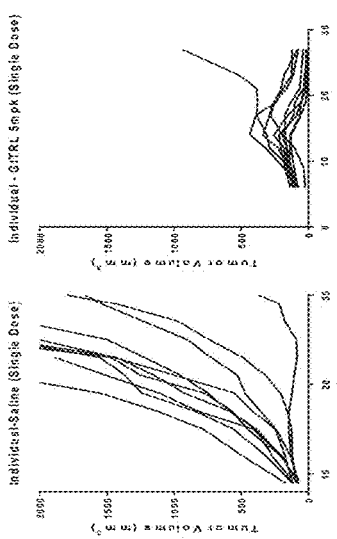

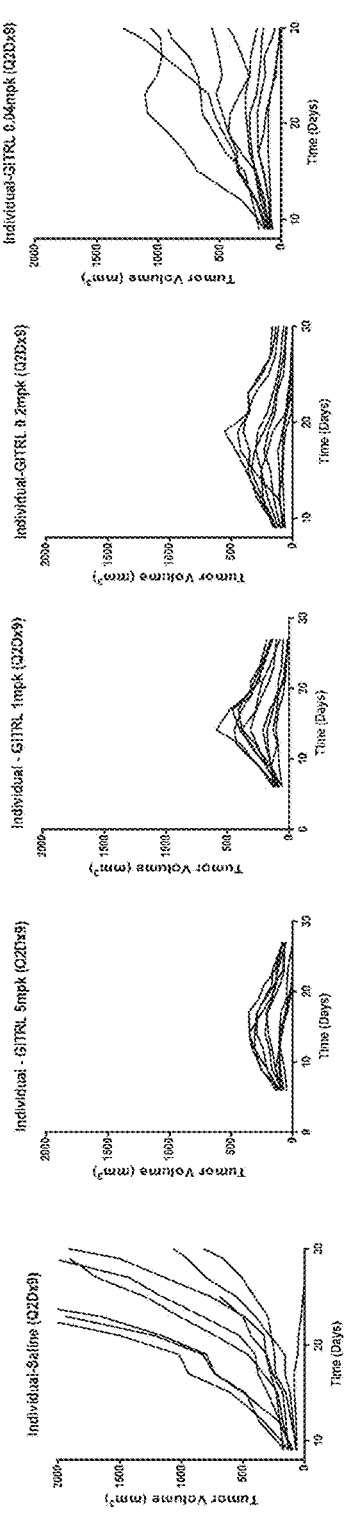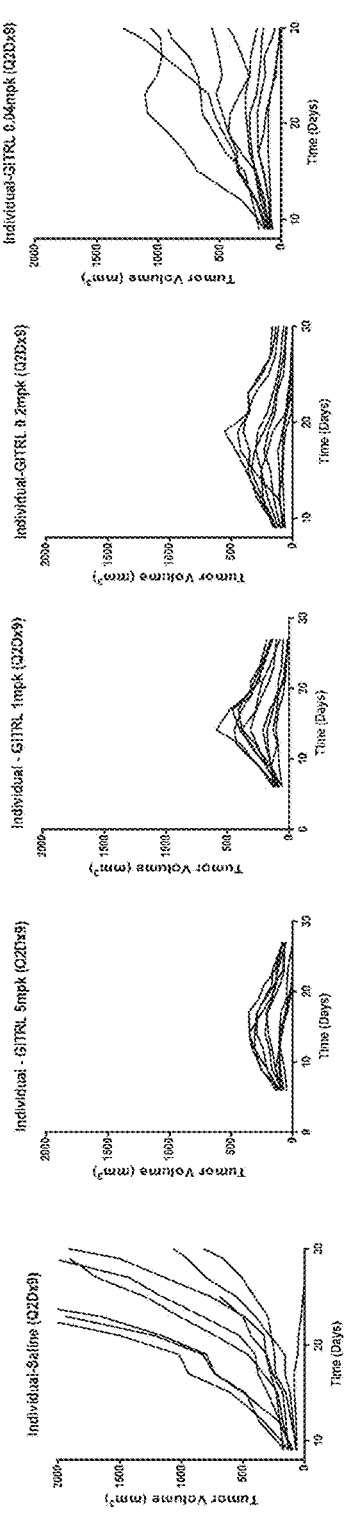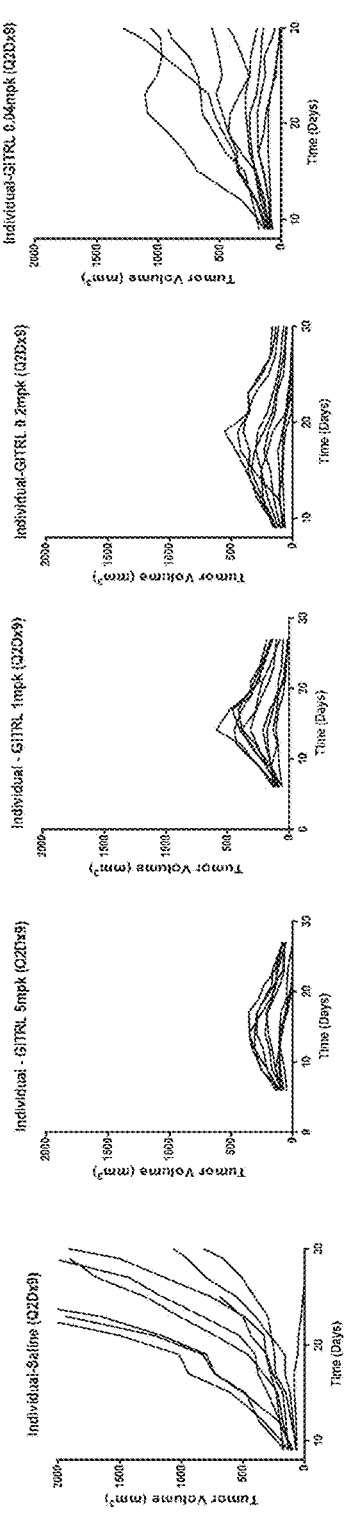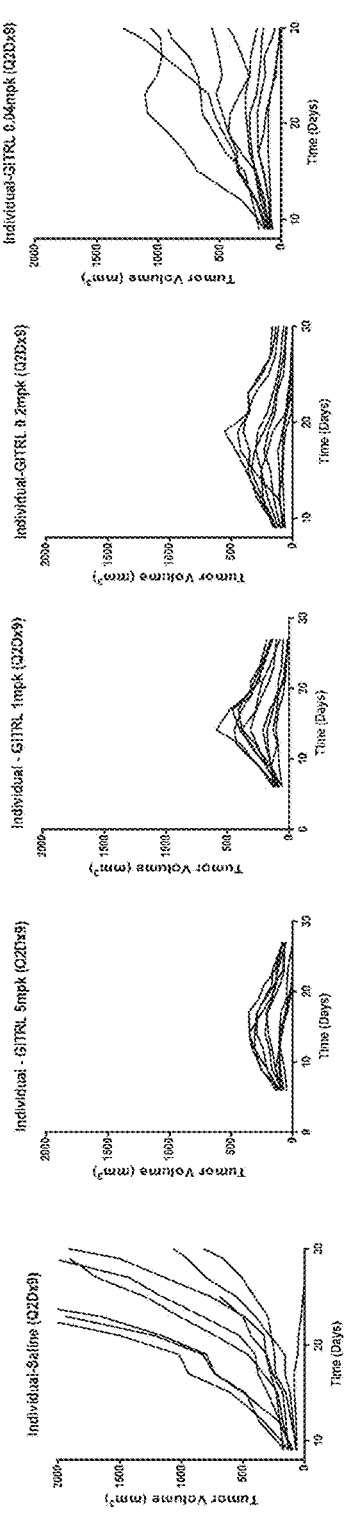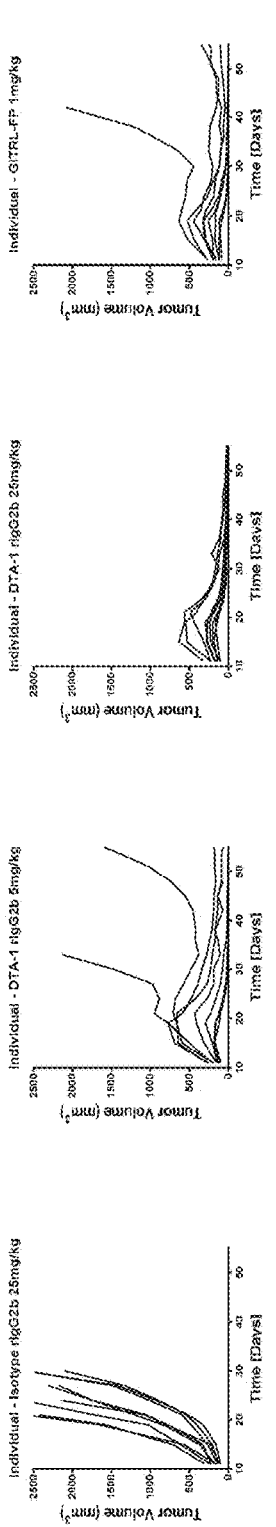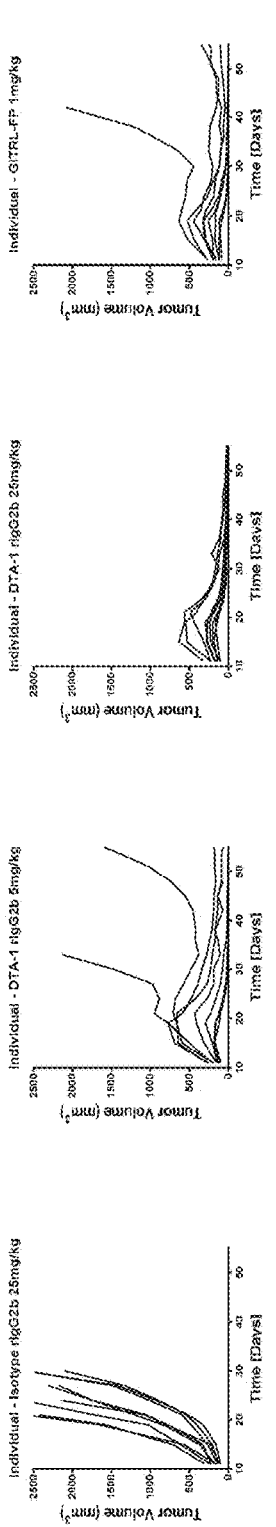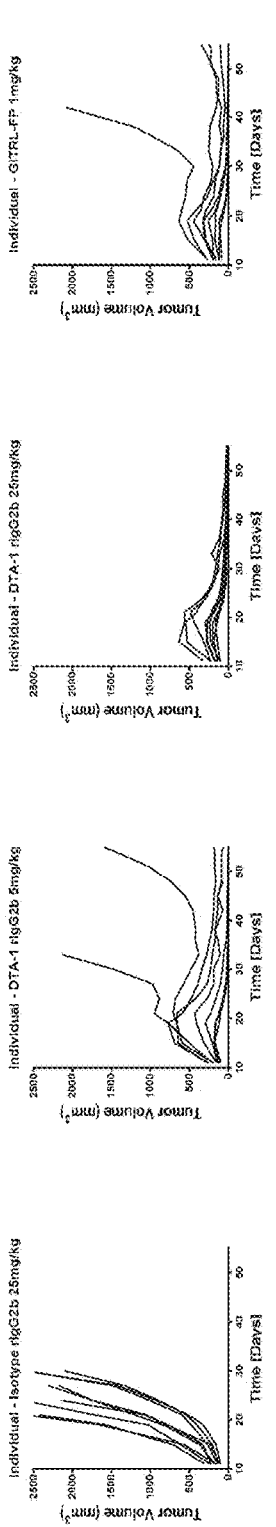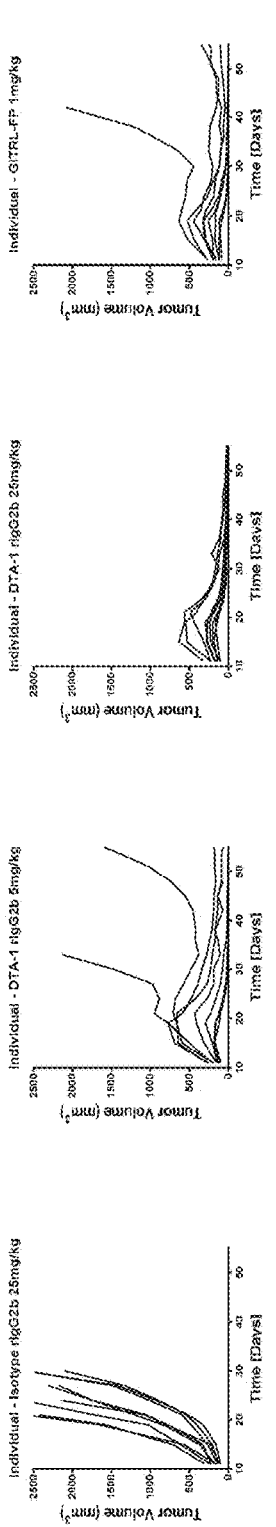

| CD8 Depletion Group | Dose (mg/kg) | Median Survival (days) |
|---|---|---|
| Isotype | 25 | 24 |
| DTA-1 | 5 | 42 |
| DTA-1 | 25 | 48 |
| GITRL-FP | 1 | 27 |

Spleen AH1 Restim

Tumor AH1 Restim

Spleen Tregs

Tumor Tregs

Spleen CD8

Tumor CD8

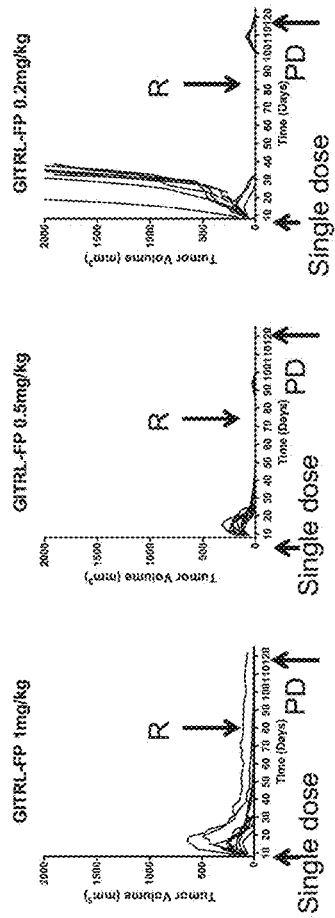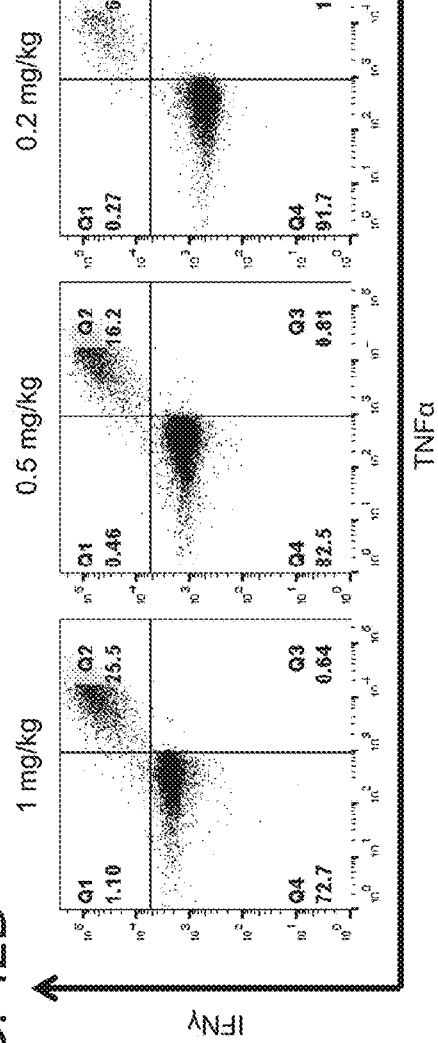

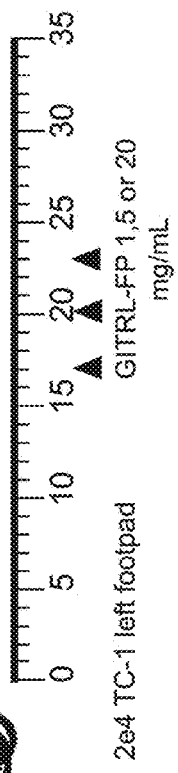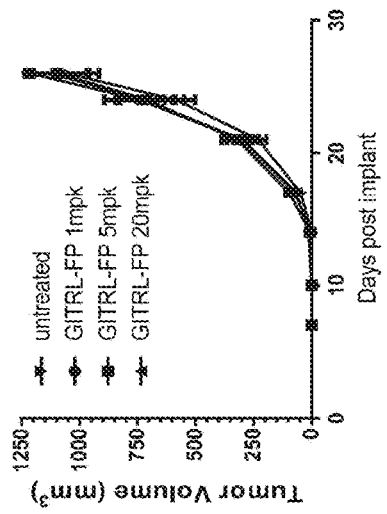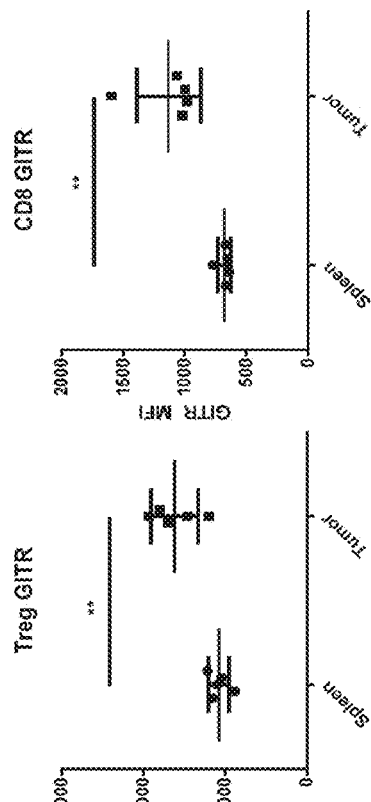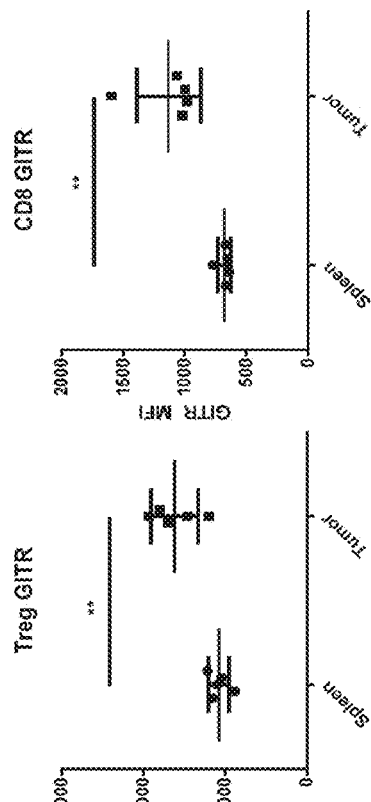
FIG. 43A
FIG. 43B
FIG. 43C
FIG. 43D

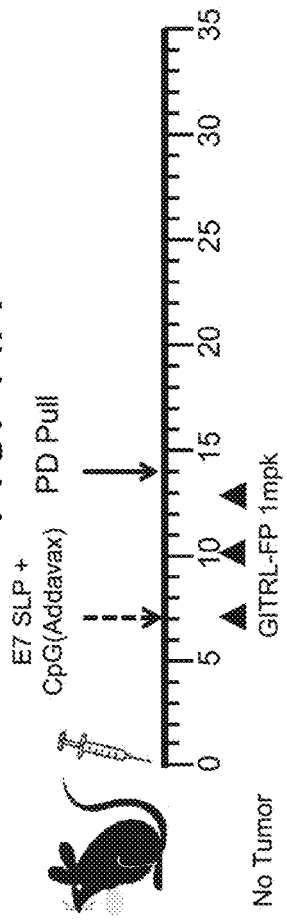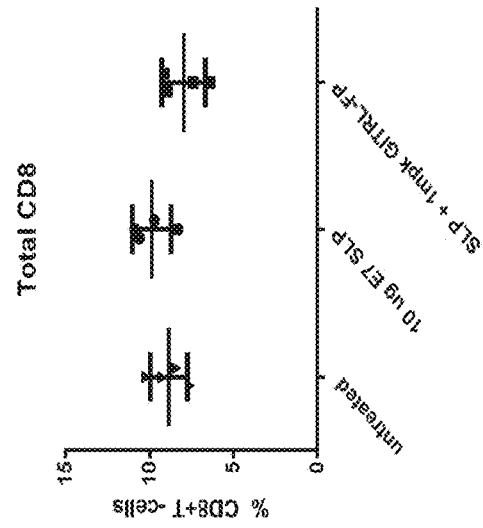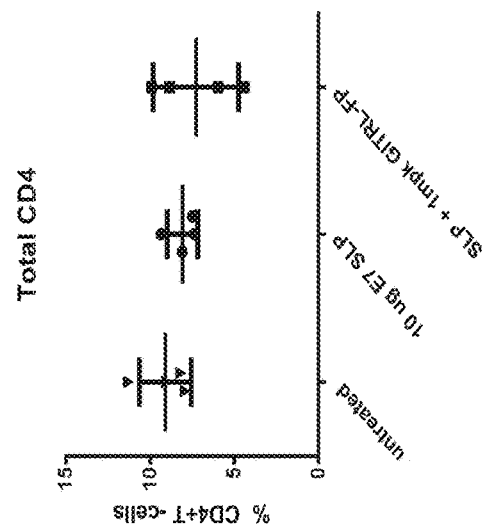

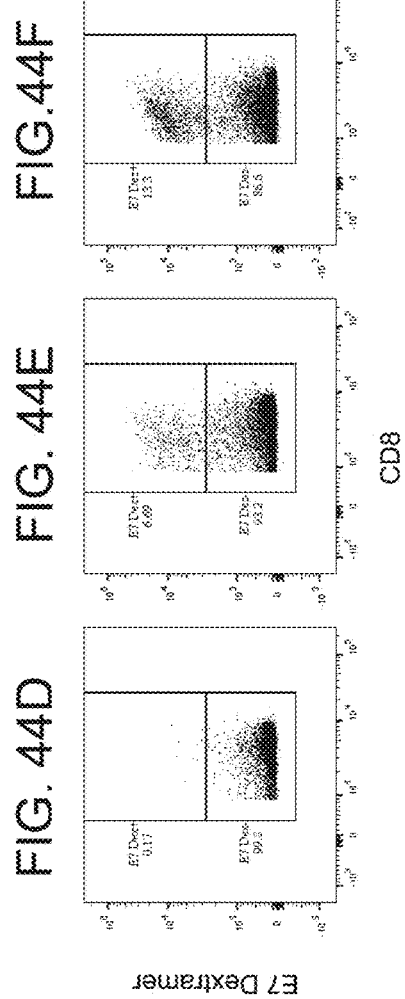
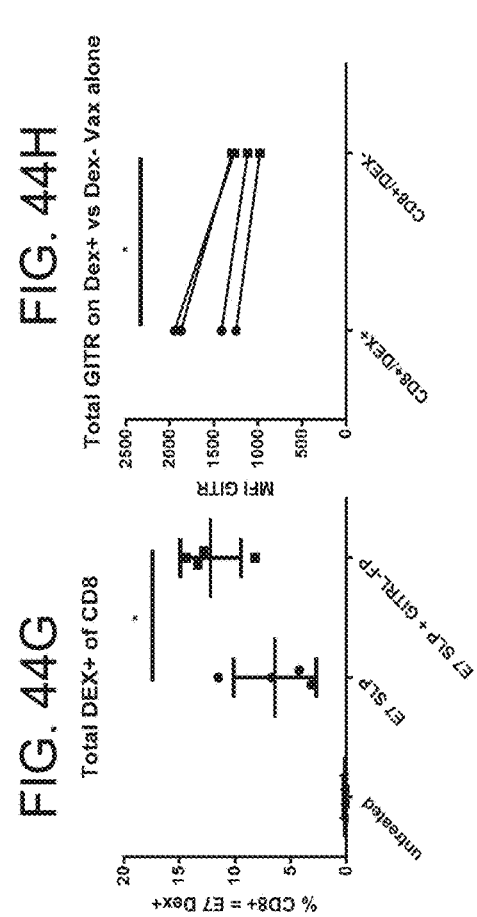

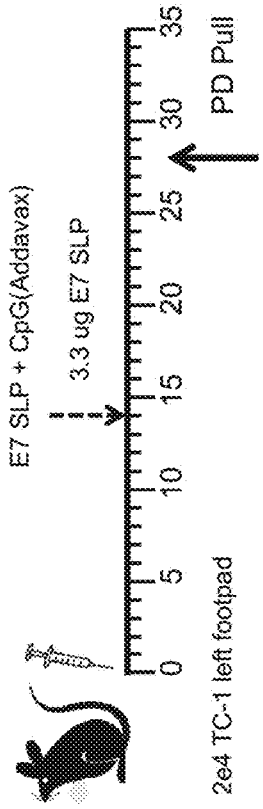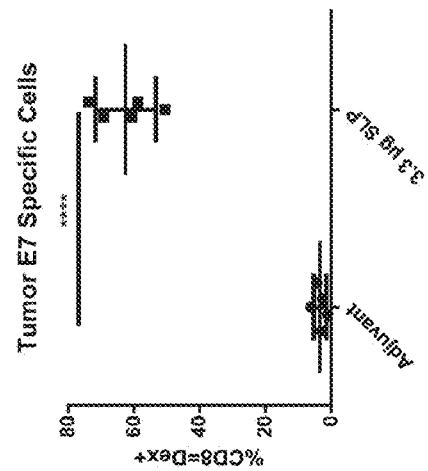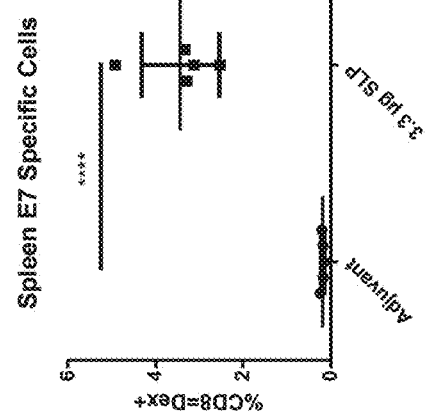

FIG. 45F
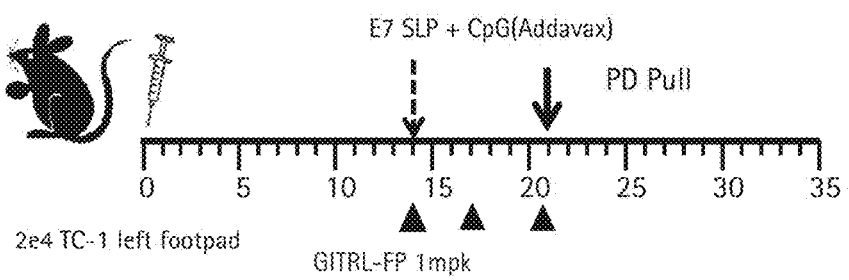
| Group | Median Survival |
|---|---|
| Untreated | 27 |
| E7 SLP Alone | 46.5 |
| E7 SLP + GITRL-FP(1) | 80.5 |
| E7 SLP + GITRL-FP(10) | 75.5 |
FIG. 45G
FIG. 45H
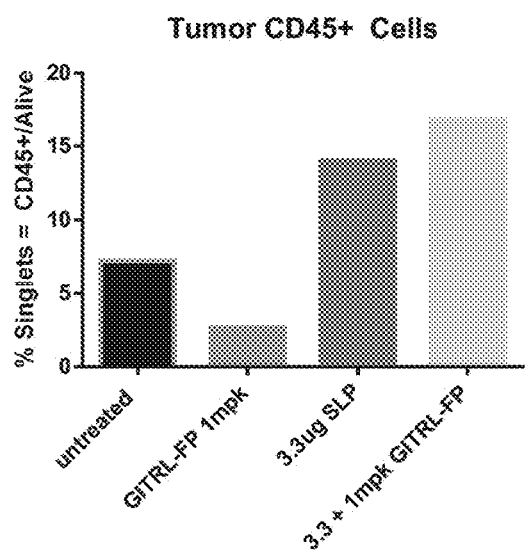

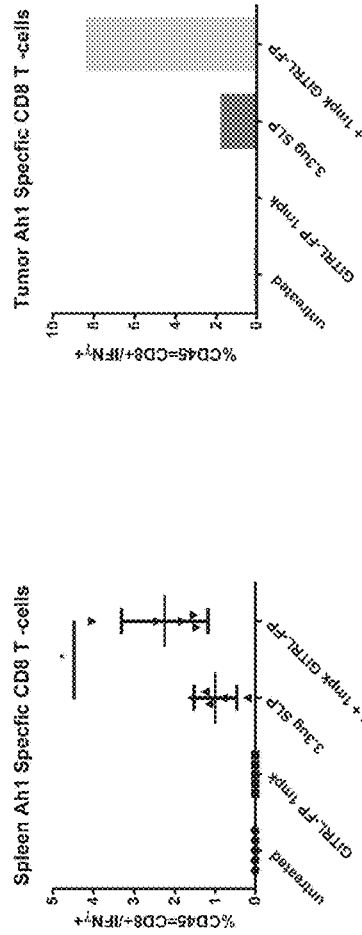
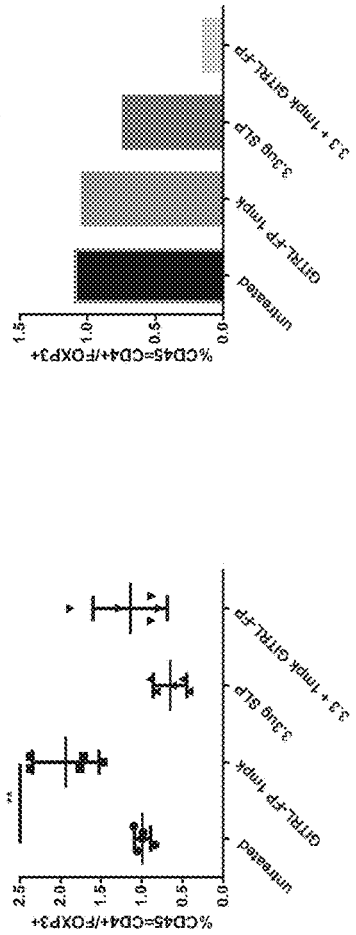
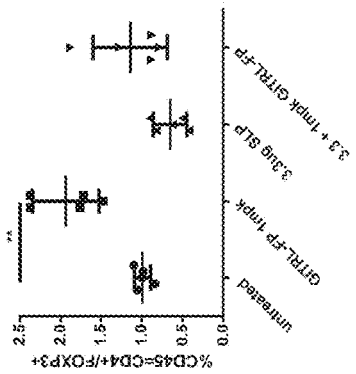
FIG. 45I
FIG. 45J
FIG. 45K
FIG. 45L

SEQUENCE LISTING

```
<160> NUMBER OF SEQ ID NOS: 47

<210> SEQ ID NO 1
<211> LENGTH: 177
<212> TYPE: PRT
<213> ORGANISM: Homo sapiens

<400> SEQUENCE: 1

Met Cys Leu Ser His Leu Glu Asn Met Pro Leu Ser His Ser Arg Thr
1               5                   10                  15

Gln Gly Ala Gln Arg Ser Ser Trp Lys Leu Trp Leu Phe Cys Ser Ile
            20                  25                  30

Val Met Leu Leu Phe Leu Cys Ser Phe Ser Trp Leu Ile Phe Ile Phe
        35                  40                  45

Leu Gln Leu Glu Thr Ala Lys Glu Pro Cys Met Ala Lys Phe Gly Pro
    50                  55                  60

Leu Pro Ser Lys Trp Gln Met Ala Ser Ser Glu Pro Pro Cys Val Asn
65                  70                  75                  80

Lys Val Ser Asp Trp Lys Leu Glu Ile Leu Gln Asn Gly Leu Tyr Leu
                85                  90                  95

Ile Tyr Gly Gln Val Ala Pro Asn Ala Asn Tyr Asn Asp Val Ala Pro
```

```
                    100                 105                 110
Phe Glu Val Arg Leu Tyr Lys Asn Lys Asp Met Ile Gln Thr Leu Thr
        115                 120                 125

Asn Lys Ser Lys Ile Gln Asn Val Gly Gly Thr Tyr Glu Leu His Val
    130                 135                 140

Gly Asp Thr Ile Asp Leu Ile Phe Asn Ser Glu His Gln Val Leu Lys
145                 150                 155                 160

Asn Asn Thr Tyr Trp Gly Ile Ile Leu Leu Ala Asn Pro Gln Phe Ile
                165                 170                 175

Ser
```

```
<210> SEQ ID NO 2
<211> LENGTH: 177
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (33)..(33)
<223> OTHER INFORMATION: Xaa is Gly or Val
<220> FEATURE:
<221> NAME/KEY: MISC_FEATURE
<222> LOCATION: (34)..(34)
<223> OTHER INFORMATION: Xaa is Thr, Met, or Val
<220> FEATURE:
<221> NAME/KEY: MISC_FEATURE
<222> LOCATION: (52)..(52)
<223> OTHER INFORMATION: Xaa is Glu or Ala
<220> FEATURE:
<221> NAME/KEY: MISC_FEATURE
<222> LOCATION: (62)..(62)
<223> OTHER INFORMATION: Xaa is Ser or Phe
<220> FEATURE:
<221> NAME/KEY: MISC_FEATURE
<222> LOCATION: (66)..(66)
<223> OTHER INFORMATION: Xaa is Thr or Pro
<220> FEATURE:
<221> NAME/KEY: MISC_FEATURE
<222> LOCATION: (67)..(67)
<223> OTHER INFORMATION: Xaa is Leu or Ser
<220> FEATURE:
<221> NAME/KEY: MISC_FEATURE
<222> LOCATION: (71)..(71)
<223> OTHER INFORMATION: Xaa is Thr or Met
<220> FEATURE:
<221> NAME/KEY: MISC_FEATURE
<222> LOCATION: (77)..(77)
<223> OTHER INFORMATION: Xaa is Leu or Pro
<220> FEATURE:
<221> NAME/KEY: MISC_FEATURE
<222> LOCATION: (79)..(79)
<223> OTHER INFORMATION: Xaa is Met or Val
<220> FEATURE:
<221> NAME/KEY: MISC_FEATURE
<222> LOCATION: (83)..(83)
<223> OTHER INFORMATION: Xaa is Thr, Phe, or Ser
<220> FEATURE:
<221> NAME/KEY: MISC_FEATURE
<222> LOCATION: (99)..(99)
<223> OTHER INFORMATION: Xaa is Ser or Gly
<220> FEATURE:
<221> NAME/KEY: MISC_FEATURE
<222> LOCATION: (112)..(112)
<223> OTHER INFORMATION: Xaa is Arg or Pro
<220> FEATURE:
<221> NAME/KEY: MISC_FEATURE
<222> LOCATION: (116)..(116)
<223> OTHER INFORMATION: Xaa is Trp or Arg
<220> FEATURE:
<221> NAME/KEY: MISC_FEATURE
<222> LOCATION: (123)..(123)
<223> OTHER INFORMATION: Xaa is Leu or Met
```

-continued

```
<220> FEATURE:
<221> NAME/KEY: MISC_FEATURE
<222> LOCATION: (153)..(153)
<223> OTHER INFORMATION: Xaa is Ser or Asn
<220> FEATURE:
<221> NAME/KEY: MISC_FEATURE
<222> LOCATION: (158)..(158)
<223> OTHER INFORMATION: Xaa is Phe or Val
<220> FEATURE:
<221> NAME/KEY: MISC_FEATURE
<222> LOCATION: (161)..(161)
<223> OTHER INFORMATION: Xaa is any amino acid other than Asn
<220> FEATURE:
<221> NAME/KEY: MISC_FEATURE
<222> LOCATION: (167)..(167)
<223> OTHER INFORMATION: Xaa is Val or Ile
<220> FEATURE:
<221> NAME/KEY: MISC_FEATURE
<222> LOCATION: (168)..(168)
<223> OTHER INFORMATION: Xaa is Leu or Ile

<400> SEQUENCE: 2

Met Cys Leu Ser His Leu Glu Asn Met Pro Leu Ser His Ser Arg Thr
1               5                   10                  15

Gln Gly Ala Gln Arg Ser Ser Trp Lys Leu Trp Leu Phe Cys Ser Ile
            20                  25                  30

Xaa Xaa Leu Leu Phe Leu Cys Ser Phe Ser Trp Leu Ile Phe Ile Phe
        35                  40                  45

Leu Gln Leu Xaa Thr Ala Lys Glu Pro Cys Met Ala Lys Xaa Gly Pro
50                  55                  60

Leu Xaa Xaa Lys Trp Gln Xaa Ala Ser Ser Glu Pro Xaa Cys Xaa Asn
65                  70                  75                  80

Lys Val Xaa Asp Trp Lys Leu Glu Ile Leu Gln Asn Gly Leu Tyr Leu
                85                  90                  95

Ile Tyr Xaa Gln Val Ala Pro Asn Ala Asn Tyr Asn Asp Val Ala Xaa
            100                 105                 110

Phe Glu Val Xaa Leu Tyr Lys Asn Lys Asp Xaa Ile Gln Thr Leu Thr
            115                 120                 125

Asn Lys Ser Lys Ile Gln Asn Val Gly Gly Thr Tyr Glu Leu His Val
130                 135                 140

Gly Asp Thr Ile Asp Leu Ile Phe Xaa Ser Glu His Gln Xaa Leu Lys
145                 150                 155                 160

Xaa Asn Thr Tyr Trp Gly Xaa Xaa Leu Leu Ala Asn Pro Gln Phe Ile
                165                 170                 175

Ser

<210> SEQ ID NO 3
<211> LENGTH: 177
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (161)..(161)
<223> OTHER INFORMATION: Xaa is any amino acid other than Asn

<400> SEQUENCE: 3

Met Cys Leu Ser His Leu Glu Asn Met Pro Leu Ser His Ser Arg Thr
1               5                   10                  15

Gln Gly Ala Gln Arg Ser Ser Trp Lys Leu Trp Leu Phe Cys Ser Ile
            20                  25                  30

Val Met Leu Leu Phe Leu Cys Ser Phe Ser Trp Leu Ile Phe Ile Phe
```

```
                35                  40                  45

Leu Gln Leu Glu Thr Ala Lys Glu Pro Cys Met Ala Lys Phe Gly Pro
 50                  55                  60

Leu Pro Ser Lys Trp Gln Met Ala Ser Ser Glu Pro Pro Cys Val Asn
 65                  70                  75                  80

Lys Val Ser Asp Trp Lys Leu Glu Ile Leu Gln Asn Gly Leu Tyr Leu
                 85                  90                  95

Ile Tyr Gly Gln Val Ala Pro Asn Ala Asn Tyr Asn Asp Val Ala Pro
                100                 105                 110

Phe Glu Val Arg Leu Tyr Lys Asn Lys Asp Met Ile Gln Thr Leu Thr
                115                 120                 125

Asn Lys Ser Lys Ile Gln Asn Val Gly Gly Thr Tyr Glu Leu His Val
            130                 135                 140

Gly Asp Thr Ile Asp Leu Ile Phe Asn Ser Glu His Gln Val Leu Lys
145                 150                 155                 160

Xaa Asn Thr Tyr Trp Gly Ile Ile Leu Leu Ala Asn Pro Gln Phe Ile
                165                 170                 175

Ser

<210> SEQ ID NO 4
<211> LENGTH: 177
<212> TYPE: PRT
<213> ORGANISM: Artificial
<220> FEATURE:
<223> OTHER INFORMATION: synthetic

<400> SEQUENCE: 4

Met Cys Leu Ser His Leu Glu Asn Met Pro Leu Ser His Ser Arg Thr
 1               5                  10                  15

Gln Gly Ala Gln Arg Ser Ser Trp Lys Leu Trp Leu Phe Cys Ser Ile
                20                  25                  30

Val Met Leu Leu Phe Leu Cys Ser Phe Ser Trp Leu Ile Phe Ile Phe
                35                  40                  45

Leu Gln Leu Glu Thr Ala Lys Glu Pro Cys Met Ala Lys Phe Gly Pro
 50                  55                  60

Leu Pro Ser Lys Trp Gln Met Ala Ser Ser Glu Pro Pro Cys Val Asn
 65                  70                  75                  80

Lys Val Ser Asp Trp Lys Leu Glu Ile Leu Gln Asn Gly Leu Tyr Leu
                 85                  90                  95

Ile Tyr Gly Gln Val Ala Pro Asn Ala Asn Tyr Asn Asp Val Ala Pro
                100                 105                 110

Phe Glu Val Arg Leu Tyr Lys Asn Lys Asp Met Ile Gln Thr Leu Thr
                115                 120                 125

Asn Lys Ser Lys Ile Gln Asn Val Gly Gly Thr Tyr Glu Leu His Val
            130                 135                 140

Gly Asp Thr Ile Asp Leu Ile Phe Asn Ser Glu His Gln Val Leu Lys
145                 150                 155                 160

Asp Asn Thr Tyr Trp Gly Ile Ile Leu Leu Ala Asn Pro Gln Phe Ile
                165                 170                 175

Ser

<210> SEQ ID NO 5
<211> LENGTH: 1251
<212> TYPE: DNA
<213> ORGANISM: Artificial
<220> FEATURE:
```

<223> OTHER INFORMATION: synthetic

<400> SEQUENCE: 5

```
ctggacaaga cccatacctg tcctccatgc cctgccccg aactgctggg aggcccttct      60
gtgttcctgt tcccccaaa gcccaaggac accctgatga tctcccggac ccccgaagtg     120
acctgcgtgg tggtggatgt gtcccacgag gaccctgaag tgaagttcaa ttggtacgtg    180
gacggcgtgg aagtgcacaa cgccaagacc aagcccagag aggaacagta caactccacc    240
taccgggtgg tgtccgtgct gaccgtgctg caccaggatt ggctgaacgg caaagagtac    300
aagtgcaagg tgtccaacaa ggccctgcct gcccccatcg aaaagaccat ctccaaggcc    360
aagggccagc cccgggaacc ccaggtgtac acactgcccc ctagccggga agagatgacc    420
aagaaccagg tgtccctgac ctgtctcgtg aagggcttct accctccga tatcgccgtg    480
gaatgggagt ccaacggcca gcctgagaac aactacaaga ccacccccc tgtgctggac    540
tccgacggct cattcttcct gtactccaag ctgacagtgg acaagtcccg gtggcagcag    600
ggcaacgtgt tctcctgctc cgtgatgcac gaggccctgc acaaccacta cacccagaag    660
tccctgtccc tgagccctgg aaaaggcggc ggaggatctg gcggaggcgg ttctggtggt    720
ggcggatctg ggggcggagg tagcggaggt ggtggctctg tgtctcggct ggaagaggaa    780
atgcggaagc tgcaggccac cgtgcaggaa ctgcagaagc ggctggacag actggaagag    840
acagtgcagg ctaagggcgg tggcggacag ctcgagacag ccaaagaacc ctgcatggcc    900
aagttcggcc ccctgccttc caagtggcag atggcctctt ccgagccccc ctgcgtgaac    960
aaagtgtccg actggaagct ggaaatcctg cagaacggcc tgtacctgat ctacggccag   1020
gtggcccca cgccaactac aacgatgtg gccccttcg aagtgcggct gtacaagaac     1080
aaggacatga tccagaccct gaccaacaag agcaagatcc agaacgtggg cggcacctac   1140
gagctgcacg tgggcgatac catcgacctg atcttcaact ccgagcacca ggtgctgaag   1200
gacaacacct actggggcat catcctgctg gccaaccccc agttcatctc c           1251
```

<210> SEQ ID NO 6
<211> LENGTH: 417
<212> TYPE: PRT
<213> ORGANISM: Artificial
<220> FEATURE:
<223> OTHER INFORMATION: synthetic

<400> SEQUENCE: 6

```
Leu Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125
```

Val Tyr Thr Leu Pro Pro Ser Arg Glu Glu Met Thr Lys Asn Gln Val
            130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
                180                 185                 190

Val Asp Lys Ser Arg Trp Gln Gln Gly Asn Val Phe Ser Cys Ser Val
            195                 200                 205

Met His Glu Ala Leu His Asn His Tyr Thr Gln Lys Ser Leu Ser Leu
210                 215                 220

Ser Pro Gly Lys Gly Gly Gly Ser Gly Gly Gly Ser Gly Gly
225                 230                 235                 240

Gly Gly Ser Gly Gly Gly Ser Gly Gly Gly Ser Val Ser Arg
                245                 250                 255

Leu Glu Glu Glu Met Arg Lys Leu Gln Ala Thr Val Gln Glu Leu Gln
                260                 265                 270

Lys Arg Leu Asp Arg Leu Glu Glu Thr Val Gln Ala Lys Gly Gly Gly
            275                 280                 285

Gly Gln Leu Glu Thr Ala Lys Glu Pro Cys Met Ala Lys Phe Gly Pro
290                 295                 300

Leu Pro Ser Lys Trp Gln Met Ala Ser Ser Glu Pro Pro Cys Val Asn
305                 310                 315                 320

Lys Val Ser Asp Trp Lys Leu Glu Ile Leu Gln Asn Gly Leu Tyr Leu
                325                 330                 335

Ile Tyr Gly Gln Val Ala Pro Asn Ala Asn Tyr Asn Asp Val Ala Pro
            340                 345                 350

Phe Glu Val Arg Leu Tyr Lys Asn Lys Asp Met Ile Gln Thr Leu Thr
                355                 360                 365

Asn Lys Ser Lys Ile Gln Asn Val Gly Gly Thr Tyr Glu Leu His Val
370                 375                 380

Gly Asp Thr Ile Asp Leu Ile Phe Asn Ser Glu His Gln Val Leu Lys
385                 390                 395                 400

Asp Asn Thr Tyr Trp Gly Ile Ile Leu Leu Ala Asn Pro Gln Phe Ile
                405                 410                 415

Ser

<210> SEQ ID NO 7
<211> LENGTH: 1295
<212> TYPE: DNA
<213> ORGANISM: Artificial
<220> FEATURE:
<223> OTHER INFORMATION: synthetic

<400> SEQUENCE: 7
tggccatcat ctacctgatc ctgctgttca ccgccgtgcg gggcctggac aagacccata    60
cctgtcctcc atgccctgcc cccgaactgc tgggaggccc ttctgtgttc ctgttccccc   120
caaagcccaa ggacaccctg atgatctccc ggaccccga agtgacctgc gtggtggtgg   180
atgtgtccca cgaggaccct gaagtgaagt tcaattggta cgtggacggc gtggaagtgc   240
acaacgccaa gaccaagccc agagaggaac agtacaactc cacctaccgg gtggtgtccg   300
tgctgaccgt gctgcaccag gattggctga acggcaaaga gtacaagtgc aaggtgtcca   360

| | |
|---|---:|
| acaaggccct gcctgccccc atcgaaaaga ccatctccaa ggccaagggc cagccccggg | 420 |
| aaccccaggt gtacacactg cccccctagcc gggaagagat gaccaagaac caggtgtccc | 480 |
| tgacctgtct cgtgaagggc ttctacccct ccgatatcgc cgtggaatgg gagtccaacg | 540 |
| gccagcctga gaacaactac aagaccaccc ccctgtgct ggactccgac ggctcattct | 600 |
| tcctgtactc caagctgaca gtggacaagt cccggtggca gcagggcaac gtgttctcct | 660 |
| gctccgtgat gcacgaggcc ctgcacaacc actacaccca gaagtccctg tccctgagcc | 720 |
| ctggaaaagg cggcggagga tctggcggag gcggttctgg tggtggcgga tctggggggcg | 780 |
| gaggtagcgg aggtggtggc tctgtgtctc ggctggaaga ggaaatgcgg aagctgcagg | 840 |
| ccaccgtgca ggaactgcag aagcggctgg acagactgga agagacagtg caggctaagg | 900 |
| gcggtggcgg acagctcgag acagccaaag aaccctgcat ggccaagttc ggccccctgc | 960 |
| cttccaagtg gcagatggcc tcttccgagc cccctgcgt gaacaaagtg tccgactgga | 1020 |
| agctggaaat cctgcagaac ggcctgtacc tgatctacgg ccaggtggcc cccaacgcca | 1080 |
| actacaacga tgtggccccc ttcgaagtgc ggctgtacaa gaacaaggac atgatccaga | 1140 |
| ccctgaccaa caagagcaag atccagaacg tgggcggcac ctacgagctg cacgtgggcg | 1200 |
| ataccatcga cctgatcttc aactccgagc caccaggtgct gaaggacaac acctactggg | 1260 |
| gcatcatcct gctggccaac ccccagttca tctcc | 1295 |

<210> SEQ ID NO 8
<211> LENGTH: 432
<212> TYPE: PRT
<213> ORGANISM: Artificial
<220> FEATURE:
<223> OTHER INFORMATION: synthetic

<400> SEQUENCE: 8

Met Ala Ile Ile Tyr Leu Ile Leu Leu Phe Thr Ala Val Arg Gly Leu
1               5                   10                  15

Asp Lys Thr His Thr Cys Pro Pro Cys Pro Ala Pro Glu Leu Leu Gly
            20                  25                  30

Gly Pro Ser Val Phe Leu Phe Pro Pro Lys Pro Lys Asp Thr Leu Met
        35                  40                  45

Ile Ser Arg Thr Pro Glu Val Thr Cys Val Val Val Asp Val Ser His
    50                  55                  60

Glu Asp Pro Glu Val Lys Phe Asn Trp Tyr Val Asp Gly Val Glu Val
65                  70                  75                  80

His Asn Ala Lys Thr Lys Pro Arg Glu Glu Gln Tyr Asn Ser Thr Tyr
                85                  90                  95

Arg Val Val Ser Val Leu Thr Val Leu His Gln Asp Trp Leu Asn Gly
            100                 105                 110

Lys Glu Tyr Lys Cys Lys Val Ser Asn Lys Ala Leu Pro Ala Pro Ile
        115                 120                 125

Glu Lys Thr Ile Ser Lys Ala Lys Gly Gln Pro Arg Glu Pro Gln Val
    130                 135                 140

Tyr Thr Leu Pro Pro Ser Arg Glu Glu Met Thr Lys Asn Gln Val Ser
145                 150                 155                 160

Leu Thr Cys Leu Val Lys Gly Phe Tyr Pro Ser Asp Ile Ala Val Glu
                165                 170                 175

Trp Glu Ser Asn Gly Gln Pro Glu Asn Asn Tyr Lys Thr Thr Pro Pro
            180                 185                 190

Val Leu Asp Ser Asp Gly Ser Phe Phe Leu Tyr Ser Lys Leu Thr Val

```
            195                 200                 205
Asp Lys Ser Arg Trp Gln Gln Gly Asn Val Phe Ser Cys Ser Val Met
210                 215                 220

His Glu Ala Leu His Asn His Tyr Thr Gln Lys Ser Leu Ser Leu Ser
225                 230                 235                 240

Pro Gly Lys Gly Gly Gly Gly Ser Gly Gly Gly Ser Gly Gly Gly
                245                 250                 255

Gly Ser Gly Gly Gly Gly Ser Gly Gly Gly Ser Val Ser Arg Leu
                260                 265                 270

Glu Glu Glu Met Arg Lys Leu Gln Ala Thr Val Gln Glu Leu Gln Lys
                275                 280                 285

Arg Leu Asp Arg Leu Glu Glu Thr Val Gln Ala Lys Gly Gly Gly Gly
                290                 295                 300

Gln Leu Glu Thr Ala Lys Glu Pro Cys Met Ala Lys Phe Gly Pro Leu
305                 310                 315                 320

Pro Ser Lys Trp Gln Met Ala Ser Ser Glu Pro Pro Cys Val Asn Lys
                325                 330                 335

Val Ser Asp Trp Lys Leu Glu Ile Leu Gln Asn Gly Leu Tyr Leu Ile
                340                 345                 350

Tyr Gly Gln Val Ala Pro Asn Ala Asn Tyr Asn Asp Val Ala Pro Phe
                355                 360                 365

Glu Val Arg Leu Tyr Lys Asn Lys Asp Met Ile Gln Thr Leu Thr Asn
370                 375                 380

Lys Ser Lys Ile Gln Asn Val Gly Gly Thr Tyr Glu Leu His Val Gly
385                 390                 395                 400

Asp Thr Ile Asp Leu Ile Phe Asn Ser Glu His Gln Val Leu Lys Asp
                405                 410                 415

Asn Thr Tyr Trp Gly Ile Ile Leu Leu Ala Asn Pro Gln Phe Ile Ser
                420                 425                 430

<210> SEQ ID NO 9
<211> LENGTH: 461
<212> TYPE: PRT
<213> ORGANISM: Homo sapiens

<400> SEQUENCE: 9

Met Ser Arg Gln Val Val Arg Ser Ser Lys Phe Arg His Val Phe Gly
1                5                   10                  15

Gln Pro Ala Lys Ala Asp Gln Cys Tyr Glu Asp Val Arg Val Ser Gln
                20                  25                  30

Thr Thr Trp Asp Ser Gly Phe Cys Ala Val Asn Pro Lys Phe Val Ala
                35                  40                  45

Leu Ile Cys Glu Ala Ser Gly Gly Gly Ala Phe Leu Val Leu Pro Leu
        50                  55                  60

Gly Lys Thr Gly Arg Val Asp Lys Asn Ala Pro Thr Val Cys Gly His
65                  70                  75                  80

Thr Ala Pro Val Leu Asp Ile Ala Trp Cys Pro His Asn Asp Asn Val
                85                  90                  95

Ile Ala Ser Gly Ser Glu Asp Cys Thr Val Met Val Trp Glu Ile Pro
                100                 105                 110

Asp Gly Gly Leu Met Leu Pro Leu Arg Glu Pro Val Val Thr Leu Glu
                115                 120                 125

Gly His Thr Lys Arg Val Gly Ile Val Ala Trp His Thr Thr Ala Gln
                130                 135                 140
```

```
Asn Val Leu Leu Ser Ala Gly Cys Asp Asn Val Ile Met Val Trp Asp
145                 150                 155                 160

Val Gly Thr Gly Ala Ala Met Leu Thr Leu Gly Pro Glu Val His Pro
                165                 170                 175

Asp Thr Ile Tyr Ser Val Asp Trp Ser Arg Asp Gly Leu Ile Cys
            180                 185                 190

Thr Ser Cys Arg Asp Lys Arg Val Arg Ile Ile Glu Pro Arg Lys Gly
        195                 200                 205

Thr Val Val Ala Glu Lys Asp Arg Pro His Gly Thr Arg Pro Val
    210                 215                 220

Arg Ala Val Phe Val Ser Glu Gly Lys Ile Leu Thr Thr Gly Phe Ser
225                 230                 235                 240

Arg Met Ser Glu Arg Gln Val Ala Leu Trp Asp Thr Lys His Leu Glu
                245                 250                 255

Glu Pro Leu Ser Leu Gln Glu Leu Asp Thr Ser Ser Gly Val Leu Leu
            260                 265                 270

Pro Phe Phe Asp Pro Asp Thr Asn Ile Val Tyr Leu Cys Gly Lys Gly
        275                 280                 285

Asp Ser Ser Ile Arg Tyr Phe Glu Ile Thr Ser Glu Ala Pro Phe Leu
    290                 295                 300

His Tyr Leu Ser Met Phe Ser Ser Lys Glu Ser Gln Arg Gly Met Gly
305                 310                 315                 320

Tyr Met Pro Lys Arg Gly Leu Glu Val Asn Lys Cys Glu Ile Ala Arg
                325                 330                 335

Phe Tyr Lys Leu His Glu Arg Arg Cys Glu Pro Ile Ala Met Thr Val
            340                 345                 350

Pro Arg Lys Ser Asp Leu Phe Gln Glu Asp Leu Tyr Pro Pro Thr Ala
        355                 360                 365

Gly Pro Asp Pro Ala Leu Thr Ala Glu Glu Trp Leu Gly Gly Arg Asp
    370                 375                 380

Ala Gly Pro Leu Leu Ile Ser Leu Lys Asp Gly Tyr Val Pro Pro Lys
385                 390                 395                 400

Ser Arg Glu Leu Arg Val Asn Arg Gly Leu Asp Thr Gly Arg Arg
                405                 410                 415

Ala Ala Pro Glu Ala Ser Gly Thr Pro Ser Ser Asp Ala Val Ser Arg
            420                 425                 430

Leu Glu Glu Glu Met Arg Lys Leu Gln Ala Thr Val Gln Glu Leu Gln
        435                 440                 445

Lys Arg Leu Asp Arg Leu Glu Glu Thr Val Gln Ala Lys
    450                 455                 460

<210> SEQ ID NO 10
<211> LENGTH: 32
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is Ala, Leu, Ile, or Val
<220> FEATURE:
<221> NAME/KEY: MISC_FEATURE
<222> LOCATION: (4)..(4)
<223> OTHER INFORMATION: Xaa is Ala, Leu, Ile, or Val
<220> FEATURE:
<221> NAME/KEY: MISC_FEATURE
<222> LOCATION: (8)..(8)
<223> OTHER INFORMATION: Xaa is Ala, Leu, Ile, or Val
```

```
<220> FEATURE:
<221> NAME/KEY: MISC_FEATURE
<222> LOCATION: (11)..(11)
<223> OTHER INFORMATION: Xaa is Ala, Leu, Ile, or Val
<220> FEATURE:
<221> NAME/KEY: MISC_FEATURE
<222> LOCATION: (15)..(15)
<223> OTHER INFORMATION: Xaa is Ala, Leu, Ile, or Val
<220> FEATURE:
<221> NAME/KEY: MISC_FEATURE
<222> LOCATION: (22)..(22)
<223> OTHER INFORMATION: Xaa is Ala, Leu, Ile, or Val

<400> SEQUENCE: 10

Xaa Ser Arg Xaa Glu Glu Glu Xaa Arg Lys Xaa Gln Ala Thr Xaa Gln
1               5                   10                  15

Glu Leu Gln Lys Arg Xaa Asp Arg Leu Glu Glu Thr Val Gln Ala Lys
            20                  25                  30

<210> SEQ ID NO 11
<211> LENGTH: 32
<212> TYPE: PRT
<213> ORGANISM: Homo sapiens

<400> SEQUENCE: 11

Val Ser Arg Leu Glu Glu Glu Met Arg Lys Leu Gln Ala Thr Val Gln
1               5                   10                  15

Glu Leu Gln Lys Arg Leu Asp Arg Leu Glu Glu Thr Val Gln Ala Lys
            20                  25                  30

<210> SEQ ID NO 12
<211> LENGTH: 32
<212> TYPE: PRT
<213> ORGANISM: Artificial
<220> FEATURE:
<223> OTHER INFORMATION: synthetic

<400> SEQUENCE: 12

Val Ser Arg Leu Glu Glu Glu Ile Arg Lys Leu Gln Ala Thr Val Gln
1               5                   10                  15

Glu Leu Gln Lys Arg Leu Asp Arg Leu Glu Glu Thr Val Gln Ala Lys
            20                  25                  30

<210> SEQ ID NO 13
<211> LENGTH: 32
<212> TYPE: PRT
<213> ORGANISM: Artificial
<220> FEATURE:
<223> OTHER INFORMATION: synthetic

<400> SEQUENCE: 13

Val Ser Arg Ile Glu Glu Glu Ile Arg Lys Leu Gln Ala Thr Val Gln
1               5                   10                  15

Glu Leu Gln Lys Arg Leu Asp Arg Leu Glu Glu Thr Val Gln Ala Lys
            20                  25                  30

<210> SEQ ID NO 14
<211> LENGTH: 32
<212> TYPE: PRT
<213> ORGANISM: Artificial
<220> FEATURE:
<223> OTHER INFORMATION: synthetic

<400> SEQUENCE: 14

Ile Ser Arg Ile Glu Glu Glu Ile Arg Lys Leu Gln Ala Thr Val Gln
1               5                   10                  15
```

-continued

Glu Leu Gln Lys Arg Leu Asp Arg Leu Glu Glu Thr Val Gln Ala Lys
            20                  25                  30

<210> SEQ ID NO 15
<211> LENGTH: 32
<212> TYPE: PRT
<213> ORGANISM: Artificial
<220> FEATURE:
<223> OTHER INFORMATION: synthetic

<400> SEQUENCE: 15

Ile Ser Arg Ile Glu Glu Glu Ile Arg Lys Ile Gln Ala Thr Val Gln
1               5                   10                  15

Glu Leu Gln Lys Arg Leu Asp Arg Leu Glu Glu Thr Val Gln Ala Lys
            20                  25                  30

<210> SEQ ID NO 16
<211> LENGTH: 32
<212> TYPE: PRT
<213> ORGANISM: Artificial
<220> FEATURE:
<223> OTHER INFORMATION: synthetic

<400> SEQUENCE: 16

Ile Ser Arg Ile Glu Glu Glu Ile Arg Lys Ile Gln Ala Thr Val Gln
1               5                   10                  15

Glu Leu Gln Lys Arg Ile Asp Arg Leu Glu Glu Thr Val Gln Ala Lys
            20                  25                  30

<210> SEQ ID NO 17
<211> LENGTH: 32
<212> TYPE: PRT
<213> ORGANISM: Artificial
<220> FEATURE:
<223> OTHER INFORMATION: synthetic

<400> SEQUENCE: 17

Ile Ser Arg Ile Glu Glu Glu Ile Arg Lys Ile Asn Ala Thr Val Gln
1               5                   10                  15

Glu Leu Gln Lys Arg Ile Asp Arg Leu Glu Glu Thr Val Gln Ala Lys
            20                  25                  30

<210> SEQ ID NO 18
<211> LENGTH: 32
<212> TYPE: PRT
<213> ORGANISM: Artificial
<220> FEATURE:
<223> OTHER INFORMATION: synthetic

<400> SEQUENCE: 18

Ile Ser Arg Ile Glu Glu Glu Ile Arg Lys Ile Asn Ala Thr Ile Gln
1               5                   10                  15

Glu Leu Gln Lys Arg Ile Asp Arg Leu Glu Glu Thr Val Gln Ala Lys
            20                  25                  30

<210> SEQ ID NO 19
<211> LENGTH: 5
<212> TYPE: PRT
<213> ORGANISM: Artificial
<220> FEATURE:
<223> OTHER INFORMATION: synthetic

<400> SEQUENCE: 19

Gly Gly Gly Gly Ser

<210> SEQ ID NO 20
<211> LENGTH: 25
<212> TYPE: PRT
<213> ORGANISM: Artificial
<220> FEATURE:
<223> OTHER INFORMATION: synthetic

<400> SEQUENCE: 20

```
Gly Gly Gly Gly Ser Gly Gly Gly Ser Gly Gly Gly Gly Ser Gly
1               5                   10                  15
Gly Gly Gly Ser Gly Gly Gly Gly Ser
            20                  25
```

<210> SEQ ID NO 21
<211> LENGTH: 228
<212> TYPE: PRT
<213> ORGANISM: Artificial
<220> FEATURE:
<223> OTHER INFORMATION: synthetic

<400> SEQUENCE: 21

```
Leu Asp Lys Thr His Thr Cys Pro Pro Cys Pro Ala Pro Glu Leu Leu
1               5                   10                  15
Gly Gly Pro Ser Val Phe Leu Phe Pro Pro Lys Pro Lys Asp Thr Leu
            20                  25                  30
Met Ile Ser Arg Thr Pro Glu Val Thr Cys Val Val Val Asp Val Ser
        35                  40                  45
His Glu Asp Pro Glu Val Lys Phe Asn Trp Tyr Val Asp Gly Val Glu
    50                  55                  60
Val His Asn Ala Lys Thr Lys Pro Arg Glu Glu Gln Tyr Asn Ser Thr
65                  70                  75                  80
Tyr Arg Val Val Ser Val Leu Thr Val Leu His Gln Asp Trp Leu Asn
                85                  90                  95
Gly Lys Glu Tyr Lys Cys Lys Val Ser Asn Lys Ala Leu Pro Ala Pro
            100                 105                 110
Ile Glu Lys Thr Ile Ser Lys Ala Lys Gly Gln Pro Arg Glu Pro Gln
        115                 120                 125
Val Tyr Thr Leu Pro Pro Ser Arg Glu Glu Met Thr Lys Asn Gln Val
    130                 135                 140
Ser Leu Thr Cys Leu Val Lys Gly Phe Tyr Pro Ser Asp Ile Ala Val
145                 150                 155                 160
Glu Trp Glu Ser Asn Gly Gln Pro Glu Asn Asn Tyr Lys Thr Thr Pro
                165                 170                 175
Pro Val Leu Asp Ser Asp Gly Ser Phe Phe Leu Tyr Ser Lys Leu Thr
            180                 185                 190
Val Asp Lys Ser Arg Trp Gln Gln Gly Asn Val Phe Ser Cys Ser Val
        195                 200                 205
Met His Glu Ala Leu His Asn His Tyr Thr Gln Lys Ser Leu Ser Leu
    210                 215                 220
Ser Pro Gly Lys
225
```

<210> SEQ ID NO 22
<211> LENGTH: 6
<212> TYPE: PRT
<213> ORGANISM: Artificial
<220> FEATURE:

```
<223> OTHER INFORMATION: synthetic

<400> SEQUENCE: 22

Ser Gly Gly Gly Gly Ser
1               5

<210> SEQ ID NO 23
<211> LENGTH: 17
<212> TYPE: PRT
<213> ORGANISM: Artificial
<220> FEATURE:
<223> OTHER INFORMATION: synthetic

<400> SEQUENCE: 23

Gly Gly Gly Gly Ser Gly Gly Gly Ser Gly Gly Gly Gly Ser Ala
1               5                   10                  15

Leu

<210> SEQ ID NO 24
<211> LENGTH: 16
<212> TYPE: PRT
<213> ORGANISM: Artificial
<220> FEATURE:
<223> OTHER INFORMATION: synthetic

<400> SEQUENCE: 24

Gly Gly Gly Gly Ser Gly Gly Gly Gly Ser Gly Gly Gly Gly Ser Ala
1               5                   10                  15

<210> SEQ ID NO 25
<211> LENGTH: 15
<212> TYPE: PRT
<213> ORGANISM: Artificial
<220> FEATURE:
<223> OTHER INFORMATION: synthetic

<400> SEQUENCE: 25

Gly Gly Gly Gly Ser Gly Gly Gly Gly Ser Gly Gly Gly Gly Ser
1               5                   10                  15

<210> SEQ ID NO 26
<211> LENGTH: 14
<212> TYPE: PRT
<213> ORGANISM: Artificial
<220> FEATURE:
<223> OTHER INFORMATION: synthetic

<400> SEQUENCE: 26

Gly Gly Gly Gly Ser Gly Gly Gly Gly Ser Gly Gly Gly Gly
1               5                   10

<210> SEQ ID NO 27
<211> LENGTH: 28
<212> TYPE: PRT
<213> ORGANISM: Saccharomyces cerevisiae

<400> SEQUENCE: 27

Ile Lys Gln Ile Glu Asp Lys Ile Glu Glu Ile Leu Ser Lys Ile Tyr
1               5                   10                  15

His Ile Glu Asn Glu Ile Ala Arg Ile Lys Lys Leu
            20                  25

<210> SEQ ID NO 28
<211> LENGTH: 39
<212> TYPE: PRT
```

<213> ORGANISM: Homo sapiens

<400> SEQUENCE: 28

Cys Ala Cys Glu Ser Leu Val Lys Phe Gln Ala Lys Val Glu Gly Leu
1               5                   10                  15
Leu Gln Ala Leu Thr Arg Lys Leu Glu Ala Val Ser Lys Arg Leu Ala
            20                  25                  30
Ile Leu Glu Asn Thr Val Val
        35

<210> SEQ ID NO 29
<211> LENGTH: 39
<212> TYPE: PRT
<213> ORGANISM: Artificial
<220> FEATURE:
<223> OTHER INFORMATION: synthetic

<400> SEQUENCE: 29

Cys Ala Cys Glu Ser Leu Val Lys Phe Gln Ala Lys Val Glu Gly Leu
1               5                   10                  15
Ile Gln Ala Leu Thr Arg Lys Leu Glu Ala Val Ser Lys Arg Ile Ala
            20                  25                  30
Ile Leu Glu Asn Thr Val Val
        35

<210> SEQ ID NO 30
<211> LENGTH: 70
<212> TYPE: PRT
<213> ORGANISM: Homo sapiens

<400> SEQUENCE: 30

Glu Ala Glu Ala Glu Val Thr Leu Arg Glu Leu Gln Glu Ala Leu Glu
1               5                   10                  15
Glu Glu Val Leu Thr Arg Gln Ser Leu Ser Arg Glu Met Glu Ala Ile
            20                  25                  30
Arg Thr Asp Asn Gln Asn Phe Ala Ser Gln Leu Arg Glu Ala Glu Ala
        35                  40                  45
Arg Asn Arg Asp Leu Glu Ala His Val Arg Gln Leu Gln Glu Arg Met
    50                  55                  60
Glu Leu Leu Gln Ala Glu
65                  70

<210> SEQ ID NO 31
<211> LENGTH: 70
<212> TYPE: PRT
<213> ORGANISM: Artificial
<220> FEATURE:
<223> OTHER INFORMATION: synthetic

<400> SEQUENCE: 31

Ile Ala Glu Ile Glu Val Thr Ile Arg Glu Leu Gln Glu Ala Ile Glu
1               5                   10                  15
Glu Glu Val Leu Thr Arg Gln Ser Leu Ser Arg Glu Ile Glu Ala Ile
            20                  25                  30
Arg Thr Asp Ile Gln Asn Ile Ala Ser Gln Leu Arg Glu Ile Glu Ala
        35                  40                  45
Arg Ile Arg Asp Leu Glu Ala His Val Arg Gln Leu Gln Glu Arg Met
    50                  55                  60
Glu Leu Leu Gln Ala Glu
65                  70

<210> SEQ ID NO 32
<211> LENGTH: 33
<212> TYPE: PRT
<213> ORGANISM: Homo sapiens

<400> SEQUENCE: 32

Ala Ser Ala Leu Asn Thr Lys Ile Arg Ala Leu Gln Gly Ser Leu Glu
1               5                   10                  15

Asn Met Ser Lys Leu Leu Lys Arg Gln Asn Asp Ile Leu Gln Val Val
            20                  25                  30

Ser

<210> SEQ ID NO 33
<211> LENGTH: 33
<212> TYPE: PRT
<213> ORGANISM: Artificial
<220> FEATURE:
<223> OTHER INFORMATION: synthetic

<400> SEQUENCE: 33

Ile Ser Ala Leu Asn Thr Lys Ile Arg Ala Ile Gln Gly Ser Ile Glu
1               5                   10                  15

Asn Met Ser Lys Leu Ile Lys Arg Gln Asn Asp Ile Ile Gln Val Val
            20                  25                  30

Ser

<210> SEQ ID NO 34
<211> LENGTH: 128
<212> TYPE: PRT
<213> ORGANISM: Homo sapiens

<400> SEQUENCE: 34

Gln Leu Glu Thr Ala Lys Glu Pro Cys Met Ala Lys Phe Gly Pro Leu
1               5                   10                  15

Pro Ser Lys Trp Gln Met Ala Ser Ser Glu Pro Pro Cys Val Asn Lys
            20                  25                  30

Val Ser Asp Trp Lys Leu Glu Ile Leu Gln Asn Gly Leu Tyr Leu Ile
        35                  40                  45

Tyr Gly Gln Val Ala Pro Asn Ala Asn Tyr Asn Asp Val Ala Pro Phe
    50                  55                  60

Glu Val Arg Leu Tyr Lys Asn Lys Asp Met Ile Gln Thr Leu Thr Asn
65                  70                  75                  80

Lys Ser Lys Ile Gln Asn Val Gly Gly Thr Tyr Glu Leu His Val Gly
                85                  90                  95

Asp Thr Ile Asp Leu Ile Phe Asn Ser Glu His Gln Val Leu Lys Asn
            100                 105                 110

Asn Thr Tyr Trp Gly Ile Ile Leu Leu Ala Asn Pro Gln Phe Ile Ser
        115                 120                 125

<210> SEQ ID NO 35
<211> LENGTH: 128
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (3)..(3)
<223> OTHER INFORMATION: Xaa is Glu or Ala
<220> FEATURE:

```
<221> NAME/KEY: MISC_FEATURE
<222> LOCATION: (13)..(13)
<223> OTHER INFORMATION: Xaa is Ser or Phe
<220> FEATURE:
<221> NAME/KEY: MISC_FEATURE
<222> LOCATION: (17)..(17)
<223> OTHER INFORMATION: Xaa is Thr or Pro
<220> FEATURE:
<221> NAME/KEY: MISC_FEATURE
<222> LOCATION: (18)..(18)
<223> OTHER INFORMATION: Xaa is Leu or Ser
<220> FEATURE:
<221> NAME/KEY: MISC_FEATURE
<222> LOCATION: (22)..(22)
<223> OTHER INFORMATION: Xaa is Thr or Met
<220> FEATURE:
<221> NAME/KEY: MISC_FEATURE
<222> LOCATION: (28)..(28)
<223> OTHER INFORMATION: Xaa is Leu or Pro
<220> FEATURE:
<221> NAME/KEY: MISC_FEATURE
<222> LOCATION: (30)..(30)
<223> OTHER INFORMATION: Xaa is Met or Val
<220> FEATURE:
<221> NAME/KEY: MISC_FEATURE
<222> LOCATION: (34)..(34)
<223> OTHER INFORMATION: Xaa is Thr, Phe, or Ser
<220> FEATURE:
<221> NAME/KEY: MISC_FEATURE
<222> LOCATION: (50)..(50)
<223> OTHER INFORMATION: Xaa is Ser or Gly
<220> FEATURE:
<221> NAME/KEY: MISC_FEATURE
<222> LOCATION: (63)..(63)
<223> OTHER INFORMATION: Xaa is Arg or Pro
<220> FEATURE:
<221> NAME/KEY: MISC_FEATURE
<222> LOCATION: (67)..(67)
<223> OTHER INFORMATION: Xaa is Trp or Arg
<220> FEATURE:
<221> NAME/KEY: MISC_FEATURE
<222> LOCATION: (74)..(74)
<223> OTHER INFORMATION: Xaa is Leu or Met
<220> FEATURE:
<221> NAME/KEY: MISC_FEATURE
<222> LOCATION: (104)..(104)
<223> OTHER INFORMATION: Xaa is Ser or Asn
<220> FEATURE:
<221> NAME/KEY: MISC_FEATURE
<222> LOCATION: (109)..(109)
<223> OTHER INFORMATION: Xaa is Phe or Val
<220> FEATURE:
<221> NAME/KEY: MISC_FEATURE
<222> LOCATION: (112)..(112)
<223> OTHER INFORMATION: Xaa is Xaa is any amino acid other than Asn
<220> FEATURE:
<221> NAME/KEY: MISC_FEATURE
<222> LOCATION: (118)..(118)
<223> OTHER INFORMATION: Xaa is Val or Ile
<220> FEATURE:
<221> NAME/KEY: MISC_FEATURE
<222> LOCATION: (119)..(119)
<223> OTHER INFORMATION: Xaa is Leu or Ile

<400> SEQUENCE: 35

Gln Leu Xaa Thr Ala Lys Glu Pro Cys Met Ala Lys Xaa Gly Pro Leu
1               5                   10                  15

Xaa Xaa Lys Trp Gln Xaa Ala Ser Ser Glu Pro Xaa Cys Xaa Asn Lys
            20                  25                  30

Val Xaa Asp Trp Lys Leu Glu Ile Leu Gln Asn Gly Leu Tyr Leu Ile
        35                  40                  45

Tyr Xaa Gln Val Ala Pro Asn Ala Asn Tyr Asn Asp Val Ala Xaa Phe
    50                  55                  60

Glu Val Xaa Leu Tyr Lys Asn Lys Asp Xaa Ile Gln Thr Leu Thr Asn
```

```
                65                  70                  75                  80
Lys Ser Lys Ile Gln Asn Val Gly Gly Thr Tyr Glu Leu His Val Gly
                    85                  90                  95

Asp Thr Ile Asp Leu Ile Phe Xaa Ser Glu His Gln Xaa Leu Lys Xaa
                100                 105                 110

Asn Thr Tyr Trp Gly Xaa Xaa Leu Leu Ala Asn Pro Gln Phe Ile Ser
                115                 120                 125
```

<210> SEQ ID NO 36
<211> LENGTH: 128
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (112)..(112)
<223> OTHER INFORMATION: Xaa is any amino acid other than Asn

<400> SEQUENCE: 36

```
Gln Leu Glu Thr Ala Lys Glu Pro Cys Met Ala Lys Phe Gly Pro Leu
1               5                   10                  15

Pro Ser Lys Trp Gln Met Ala Ser Ser Glu Pro Pro Cys Val Asn Lys
                20                  25                  30

Val Ser Asp Trp Lys Leu Glu Ile Leu Gln Asn Gly Leu Tyr Leu Ile
            35                  40                  45

Tyr Gly Gln Val Ala Pro Asn Ala Asn Tyr Asn Asp Val Ala Pro Phe
        50                  55                  60

Glu Val Arg Leu Tyr Lys Asn Lys Asp Met Ile Gln Thr Leu Thr Asn
65                  70                  75                  80

Lys Ser Lys Ile Gln Asn Val Gly Gly Thr Tyr Glu Leu His Val Gly
                    85                  90                  95

Asp Thr Ile Asp Leu Ile Phe Asn Ser Glu His Gln Val Leu Lys Xaa
                100                 105                 110

Asn Thr Tyr Trp Gly Ile Ile Leu Leu Ala Asn Pro Gln Phe Ile Ser
                115                 120                 125
```

<210> SEQ ID NO 37
<211> LENGTH: 128
<212> TYPE: PRT
<213> ORGANISM: Artificial
<220> FEATURE:
<223> OTHER INFORMATION: synthetic

<400> SEQUENCE: 37

```
Gln Leu Glu Thr Ala Lys Glu Pro Cys Met Ala Lys Phe Gly Pro Leu
1               5                   10                  15

Pro Ser Lys Trp Gln Met Ala Ser Ser Glu Pro Pro Cys Val Asn Lys
                20                  25                  30

Val Ser Asp Trp Lys Leu Glu Ile Leu Gln Asn Gly Leu Tyr Leu Ile
            35                  40                  45

Tyr Gly Gln Val Ala Pro Asn Ala Asn Tyr Asn Asp Val Ala Pro Phe
        50                  55                  60

Glu Val Arg Leu Tyr Lys Asn Lys Asp Met Ile Gln Thr Leu Thr Asn
65                  70                  75                  80

Lys Ser Lys Ile Gln Asn Val Gly Gly Thr Tyr Glu Leu His Val Gly
                    85                  90                  95

Asp Thr Ile Asp Leu Ile Phe Asn Ser Glu His Gln Val Leu Lys Asp
                100                 105                 110
```

```
Asn Thr Tyr Trp Gly Ile Ile Leu Leu Ala Asn Pro Gln Phe Ile Ser
        115                 120                 125
```

```
<210> SEQ ID NO 38
<211> LENGTH: 229
<212> TYPE: PRT
<213> ORGANISM: Artificial
<220> FEATURE:
<223> OTHER INFORMATION: synthetic

<400> SEQUENCE: 38

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
210                 215                 220

Leu Ser Leu Gly Lys
225

<210> SEQ ID NO 39
<211> LENGTH: 1254
<212> TYPE: DNA
<213> ORGANISM: Artificial
<220> FEATURE:
<223> OTHER INFORMATION: synthetic

<400> SEQUENCE: 39
gagtctaagt acggccctcc ttgtcctcct tgccctgccc ctgagtttct gggcggacct      60
tccgtgttcc tgttcccccc aaagcccaag acaccctga tgatctcccg gaccccgaa      120 gtgacctgcg tggtggtgga tgtgtcccag gaagatcccg aggtgcagtt caattggtac     180
gtggacggcg tggaagtgca caacgccaag accaagccca gagaggaaca gttcaactcc     240
acctaccggg tggtgtccgt gctgaccgtg ctgcaccagg attggctgaa cggcaaagag     300
```

```
tacaagtgca aggtgtccaa caagggcctg ccctccagca tcgaaaagac catctccaag    360
gccaagggcc agccccggga accccaggtg tacacactgc ctccaagcca ggaagagatg    420
accaagaacc aggtgtccct gacctgtctc gtgaagggct ctacccctc cgatatcgcc     480
gtggaatggg agtccaacgg ccagcctgag aacaactaca agaccacccc ccctgtgctg    540
gactccgacg gctccttctt cctgtactcc cgcctgaccg tggacaagtc cagatggcag    600
gaaggcaacg tgttctcctg ctccgtgatg cacgaggccc tgcacaacca ctacacccag    660
aagtccctgt ccctgtctct gggcaagggc ggcggaggat ctggcggagg cggttctggt    720
ggtggtggat ctggtggcgg aggaagtggg ggaggggggat ctgtgtctcg gctggaagag   780
gaaatgcgga agctgcaggc caccgtgcag gaactgcaga gcggctgga cagactggaa     840
gagacagtgc aggctaaggg cggtggcgga cagctcgaga cagccaaaga accctgcatg    900
gccaagttcg ccccctgcc ttccaagtgg cagatggcct cttccgagcc ccctgcgtg     960
aacaaagtgt ccgactggaa gctggaaatc ctgcagaacg gcctgtacct gatctacggc   1020
caggtggccc ccaacgccaa ctacaacgat gtggcccct tcgaagtgcg gctgtacaag    1080
aacaaggaca tgatccagac cctgaccaac aagagcaaga tccagaacgt gggcggcacc   1140
tacgagctgc acgtgggcga taccatcgac ctgatcttca actccgagca ccaggtgctg   1200
aaggacaaca cctactgggg catcatcctg ctggccaacc cccagttcat ctcc         1254
```

<210> SEQ ID NO 40
<211> LENGTH: 418
<212> TYPE: PRT
<213> ORGANISM: Artificial
<220> FEATURE:
<223> OTHER INFORMATION: synthetic

<400> SEQUENCE: 40

```
Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
```

|  |  |  | 195 |  |  |  | 200 |  |  |  | 205 |  |
|---|---|---|---|---|---|---|---|---|---|---|---|---|

Val Met His Glu Ala Leu His Asn His Tyr Thr Gln Lys Ser Leu Ser
210                215                    220

Leu Ser Leu Gly Lys Gly Gly Gly Ser Gly Gly Gly Ser Gly
225              230                235                240

Gly Gly Gly Ser Gly Gly Gly Ser Gly Gly Gly Ser Val Ser
                 245            250                 255

Arg Leu Glu Glu Glu Met Arg Lys Leu Gln Ala Thr Val Gln Glu Leu
            260                265                270

Gln Lys Arg Leu Asp Arg Leu Glu Glu Thr Val Gln Ala Lys Gly Gly
        275                280                285

Gly Gly Gln Leu Glu Thr Ala Lys Glu Pro Cys Met Ala Lys Phe Gly
        290                295                300

Pro Leu Pro Ser Lys Trp Gln Met Ala Ser Ser Glu Pro Pro Cys Val
305                310                315                320

Asn Lys Val Ser Asp Trp Lys Leu Glu Ile Leu Gln Asn Gly Leu Tyr
                325                330                335

Leu Ile Tyr Gly Gln Val Ala Pro Asn Ala Asn Tyr Asn Asp Val Ala
                340                345                350

Pro Phe Glu Val Arg Leu Tyr Lys Asn Lys Asp Met Ile Gln Thr Leu
                355                360                365

Thr Asn Lys Ser Lys Ile Gln Asn Val Gly Gly Thr Tyr Glu Leu His
            370                375                380

Val Gly Asp Thr Ile Asp Leu Ile Phe Asn Ser Glu His Gln Val Leu
385                390                395                400

Lys Asp Asn Thr Tyr Trp Gly Ile Ile Leu Leu Ala Asn Pro Gln Phe
                    405                410                415

Ile Ser

```
<210> SEQ ID NO 41
<211> LENGTH: 1299
<212> TYPE: DNA
<213> ORGANISM: Artificial
<220> FEATURE:
<223> OTHER INFORMATION: synthetic

<400> SEQUENCE: 41
```

| atggccatca | tctacctgat | cctgctgttc | accgccgtgc | ggggcgagtc | taagtacggc | 60 |
|---|---|---|---|---|---|---|
| cctccttgtc | ctccttgccc | tgcccctgag | tttctgggcg | gaccttccgt | gttcctgttc | 120 |
| cccccaaagc | ccaaggacac | cctgatgatc | tcccggaccc | ccgaagtgac | ctgcgtggtg | 180 |
| gtggatgtgt | cccaggaaga | tcccgaggtg | cagttcaatt | ggtacgtgga | cggcgtggaa | 240 |
| gtgcacaacg | ccaagaccaa | gcccagagag | gaacagttca | actccaccta | ccgggtggtg | 300 |
| tccgtgctga | ccgtgctgca | ccaggattgg | ctgaacggca | agagtacaa | gtgcaaggtg | 360 |
| tccaacaagg | cctgcccctc | cagcatcgaa | aagaccatct | ccaaggccaa | gggccagccc | 420 |
| cgggaacccc | aggtgtacac | actgcctcca | agccaggaag | agatgaccaa | gaaccaggtg | 480 |
| tccctgacct | gtctcgtgaa | gggcttctac | ccctccgata | tcgccgtgga | atgggagtcc | 540 |
| aacggccagc | ctgagaacaa | ctacaagacc | accccccctg | tgctggactc | cgacggctcc | 600 |
| ttcttcctgt | actcccgcct | gaccgtggac | aagtccagat | ggcaggaagg | caacgtgttc | 660 |
| tcctgctccg | tgatgcacga | ggccctgcac | aaccactaca | cccagaagtc | cctgtccctg | 720 |
| tctctgggca | agggcggcgg | aggatctggc | ggaggcggtt | ctggtggtgg | tggatctggt | 780 |

```
ggcggaggaa gtgggggagg gggatctgtg tctcggctgg aagaggaaat gcggaagctg    840
caggccaccg tgcaggaact gcagaagcgg ctggacagac tggaagagac agtgcaggct    900
aagggcggtg gcggacagct cgagacagcc aaagaaccct gcatggccaa gttcggcccc    960
ctgccttcca gtggcagat ggcctcttcc gagcccccct gcgtgaacaa agtgtccgac   1020
```
(ctgccttcca agtggcagat ggcctcttcc gagcccccct gcgtgaacaa agtgtccgac) 1020
```
tggaagctgg aaatcctgca gaacggcctg tacctgatct acggccaggt ggcccccaac   1080
gccaactaca acgatgtggc cccttcgaa gtgcggctgt acaagaacaa ggacatgatc    1140
```
(gccaactaca acgatgtggc ccccttcgaa gtgcggctgt acaagaacaa ggacatgatc) 1140
```
cagaccctga ccaacaagag caagatccag aacgtgggcg gcacctacga gctgcacgtg   1200
ggcgatacca tcgacctgat cttcaactcc gagcaccagg tgctgaagga caacacctac   1260 tgggcatca tcctgctggc caaccccag ttcatctcc                            1299
```
(tggggcatca tcctgctggc caaccccag ttcatctcc) 1299

<210> SEQ ID NO 42
<211> LENGTH: 433
<212> TYPE: PRT
<213> ORGANISM: Artificial
<220> FEATURE:
<223> OTHER INFORMATION: synthetic

<400> SEQUENCE: 42

Met Ala Ile Ile Tyr Leu Ile Leu Leu Phe Thr Ala Val Arg Gly Glu
1               5                   10                  15

Ser Lys Tyr Gly Pro Pro Cys Pro Cys Pro Ala Pro Glu Phe Leu
            20                  25                  30

Gly Gly Pro Ser Val Phe Leu Phe Pro Pro Lys Pro Lys Asp Thr Leu
        35                  40                  45

Met Ile Ser Arg Thr Pro Glu Val Thr Cys Val Val Val Asp Val Ser
    50                  55                  60

Gln Glu Asp Pro Glu Val Gln Phe Asn Trp Tyr Val Asp Gly Val Glu
65                  70                  75                  80

Val His Asn Ala Lys Thr Lys Pro Arg Glu Glu Gln Phe Asn Ser Thr
                85                  90                  95

Tyr Arg Val Val Ser Val Leu Thr Val Leu His Gln Asp Trp Leu Asn
            100                 105                 110

Gly Lys Glu Tyr Lys Cys Lys Val Ser Asn Lys Gly Leu Pro Ser Ser
        115                 120                 125

Ile Glu Lys Thr Ile Ser Lys Ala Lys Gly Gln Pro Arg Glu Pro Gln
    130                 135                 140

Val Tyr Thr Leu Pro Pro Ser Gln Glu Glu Met Thr Lys Asn Gln Val
145                 150                 155                 160

Ser Leu Thr Cys Leu Val Lys Gly Phe Tyr Pro Ser Asp Ile Ala Val
                165                 170                 175

Glu Trp Glu Ser Asn Gly Gln Pro Glu Asn Asn Tyr Lys Thr Thr Pro
            180                 185                 190

Pro Val Leu Asp Ser Asp Gly Ser Phe Phe Leu Tyr Ser Arg Leu Thr
        195                 200                 205

Val Asp Lys Ser Arg Trp Gln Glu Gly Asn Val Phe Ser Cys Ser Val
    210                 215                 220

Met His Glu Ala Leu His Asn His Tyr Thr Gln Lys Ser Leu Ser Leu
225                 230                 235                 240

Ser Leu Gly Lys Gly Gly Gly Ser Gly Gly Gly Ser Gly Gly
                245                 250                 255

Gly Gly Ser Gly Gly Gly Ser Gly Gly Gly Ser Val Ser Arg
            260                 265                 270

-continued

```
Leu Glu Glu Glu Met Arg Lys Leu Gln Ala Thr Val Gln Glu Leu Gln
            275                 280                 285

Lys Arg Leu Asp Arg Leu Glu Glu Thr Val Gln Ala Lys Gly Gly Gly
    290                 295                 300

Gly Gln Leu Glu Thr Ala Lys Glu Pro Cys Met Ala Lys Phe Gly Pro
305                 310                 315                 320

Leu Pro Ser Lys Trp Gln Met Ala Ser Ser Glu Pro Pro Cys Val Asn
                325                 330                 335

Lys Val Ser Asp Trp Lys Leu Glu Ile Leu Gln Asn Gly Leu Tyr Leu
            340                 345                 350

Ile Tyr Gly Gln Val Ala Pro Asn Ala Asn Tyr Asn Asp Val Ala Pro
        355                 360                 365

Phe Glu Val Arg Leu Tyr Lys Asn Lys Asp Met Ile Gln Thr Leu Thr
    370                 375                 380

Asn Lys Ser Lys Ile Gln Asn Val Gly Gly Thr Tyr Glu Leu His Val
385                 390                 395                 400

Gly Asp Thr Ile Asp Leu Ile Phe Asn Ser Glu His Gln Val Leu Lys
                405                 410                 415

Asp Asn Thr Tyr Trp Gly Ile Ile Leu Leu Ala Asn Pro Gln Phe Ile
            420                 425                 430

Ser

<210> SEQ ID NO 43
<211> LENGTH: 9
<212> TYPE: PRT
<213> ORGANISM: Homo sapiens

<400> SEQUENCE: 43

Glu Glu Gln Tyr Asn Ser Thr Tyr Arg
1               5

<210> SEQ ID NO 44
<211> LENGTH: 9
<212> TYPE: PRT
<213> ORGANISM: Homo sapiens

<400> SEQUENCE: 44

Asp Met Ile Gln Thr Leu Thr Asn Lys
1               5

<210> SEQ ID NO 45
<211> LENGTH: 45
<212> TYPE: PRT
<213> ORGANISM: Homo sapiens

<400> SEQUENCE: 45

Ile Gln Asn Val Gly Gly Thr Tyr Glu Leu His Val Gly Asp Thr Ile
1               5                   10                  15

Asp Leu Ile Phe Asn Ser Glu His Gln Val Leu Lys Asn Asn Thr Tyr
            20                  25                  30

Trp Gly Ile Ile Leu Leu Ala Asn Pro Gln Phe Ile Ser
        35                  40                  45

<210> SEQ ID NO 46
<211> LENGTH: 17
<212> TYPE: PRT
<213> ORGANISM: Artificial
<220> FEATURE:
<223> OTHER INFORMATION: synthetic
```

```
<400> SEQUENCE: 46

Asp Asn Thr Tyr Trp Gly Ile Ile Leu Leu Ala Asn Pro Gln Phe Ile
1               5                   10                  15
Ser

<210> SEQ ID NO 47
<211> LENGTH: 241
<212> TYPE: PRT
<213> ORGANISM: Homo sapiens

<400> SEQUENCE: 47

Met Ala Gln His Gly Ala Met Gly Ala Phe Arg Ala Leu Cys Gly Leu
1               5                   10                  15

Ala Leu Leu Cys Ala Leu Ser Leu Gly Gln Arg Pro Thr Gly Gly Pro
                20                  25                  30

Gly Cys Gly Pro Gly Arg Leu Leu Leu Gly Thr Gly Thr Asp Ala Arg
            35                  40                  45

Cys Cys Arg Val His Thr Thr Arg Cys Cys Arg Asp Tyr Pro Gly Glu
        50                  55                  60

Glu Cys Cys Ser Glu Trp Asp Cys Met Cys Val Gln Pro Glu Phe His
65                  70                  75                  80

Cys Gly Asp Pro Cys Cys Thr Thr Cys Arg His His Pro Cys Pro Pro
                85                  90                  95

Gly Gln Gly Val Gln Ser Gln Gly Lys Phe Ser Phe Gly Phe Gln Cys
            100                 105                 110

Ile Asp Cys Ala Ser Gly Thr Phe Ser Gly Gly His Glu Gly His Cys
        115                 120                 125

Lys Pro Trp Thr Asp Cys Thr Gln Phe Gly Phe Leu Thr Val Phe Pro
    130                 135                 140

Gly Asn Lys Thr His Asn Ala Val Cys Val Pro Gly Ser Pro Pro Ala
145                 150                 155                 160

Glu Pro Leu Gly Trp Leu Thr Val Val Leu Leu Ala Val Ala Ala Cys
                165                 170                 175

Val Leu Leu Leu Thr Ser Ala Gln Leu Gly Leu His Ile Trp Gln Leu
            180                 185                 190

Arg Ser Gln Cys Met Trp Pro Arg Glu Thr Gln Leu Leu Leu Glu Val
        195                 200                 205

Pro Pro Ser Thr Glu Asp Ala Arg Ser Cys Gln Phe Pro Glu Glu Glu
    210                 215                 220

Arg Gly Glu Arg Ser Ala Glu Glu Lys Gly Arg Leu Gly Asp Leu Trp
225                 230                 235                 240

Val
```

GITRL FUSION PROTEINS COMPRISING A HUMAN CORONIN 1A DERIVED TRIMERIZATION DOMAIN

This application claims benefit under 35 U.S.C. § 119(e) of the following U.S. Provisional Application No. 62/204,212 filed Aug. 12, 2015; and U.S. Provisional Application No. 62/350,447, filed Jun. 15, 2016. Each of the above listed applications is incorporated by reference herein in its entirety for all purposes.

REFERENCE TO SEQUENCE LISTING SUBMITTED ELECTRONICALLY

The content of the electronically submitted sequence listing in ASCII text file (Name GITRLF-100P2_ST25.txt; Size: 56,159 bytes; and Date of Creation: Jun. 15, 2016) filed with the application is incorporated herein by reference in its entirety.

BACKGROUND

Glucocorticoid-induced tumor necrosis factor receptor (TNFR)-related protein (GITR), also known as TNFRSF18, AITR or CD357, is expressed on regulatory T cells and is up-regulated on antigen experienced CD4$^+$ helper cells and CD8$^+$ cytotoxic T cells as well as activated NK cells (Stephens et al. J. Immunol. (2004) 173(8): 5008-5020; Clothier and Watts, *Cytokine Growth Factor Rev.* (2014)). GITR is part of a complex system of receptors and ligands that are involved in controlling T-cell activation by antigen exposure. GITR has one known endogenous ligand, GITR ligand (GITRL), that exists in a loosely trimeric form and can cluster GITR resulting in potent cell signaling events within T cells (Chattopadhyay et al. (2007) *Proc. Natl. Acad. Sci. USA* 104(49): 19452-19457). The interaction between GITR and GITRL results in delivery of positive co-stimulatory signals to T cells, which enhance their proliferation and activation by antigen exposure, help to promote memory cell generation and reprogram regulatory T cells; reducing their suppressive functions (Clothier and Watts, *Cytokine Growth Factor Rev.* (2014) January 4; Schaer et al. *Curr Opin Immunol.* (2012)).

SUMMARY

This disclosure relates to polypeptide subunits, each including, as a fusion polypeptide, the receptor-binding domain of GITR Ligand (GITRL), a multimerization domain, e.g. trimerization domain, and an IgG Fc domain, which are capable of forming stable multimeric, e.g., hexameric proteins. Compositions and methods are provided that are useful for cancer immunotherapy and treatment of viral infections.

In certain aspects, isolated single-chain polypeptide subunits that include: an IgG Fc domain; a functional multimerization domain; and a receptor binding domain of a Glucocorticoid-Induced TNF Receptor Ligand (GITRL), wherein the polypeptide subunit can self-assemble into a trimeric or a hexameric protein are provided.

In certain aspects, trimeric proteins that include three single-chain polypeptide subunits that each include: an IgG Fc domain; a functional multimerization domain; and a receptor binding domain of a Glucocorticoid-Induced TNF Receptor Ligand (GITRL), are provided.

In certain aspects, hexameric proteins that include six single-chain polypeptide subunits that each include: an IgG Fc domain; a functional multimerization domain; and a receptor binding domain of a Glucocorticoid-Induced TNF Receptor Ligand (GITRL), are provided.

In certain aspects, compositions that include the hexameric proteins and a carrier are provided.

In certain aspects, polynucleotides that include a nucleic acid that encodes the single chain polypeptide subunits or the hexameric proteins are provided.

In certain aspects, vectors that include the polynucleotides that encode the single chain polypeptide subunits or the hexameric proteins are provided.

In certain aspects, host cells that include the polynucleotides that encode the single chain polypeptide subunits or the hexameric proteins or that include the vectors that include the polynucleotides are provided.

In certain aspects, methods of producing the polypeptide subunits or of producing the hexameric proteins are provided, where the methods include culturing the host cells that include polynucleotides or vectors that encode the polypeptide subunits or hexameric proteins under conditions in which the polypeptide subunit or hexameric protein encoded by the polynucleotide or vector is expressed, and recovering the polypeptide subunit or hexameric protein.

In certain aspects, methods to promote survival or proliferation of antigen experienced T cells and/or activated NK cells are provided, where the methods include contacting antigen experienced T cells and/or activated NK cells with the hexameric protein or the composition, wherein the hexameric protein can specifically bind to GITR on the surface of the T cells and/or NK cells.

In certain aspects, methods of inducing cytokine release from activated GITR expressing immune cells are provided, where the methods include contacting these cells with the hexameric protein or the composition, wherein the hexameric protein can specifically bind to GITR on the surface of these cells.

In certain aspects, methods of promoting T cell or NK cell activation are provided, where the methods include contacting T cells or NK cells with the hexameric protein or the composition, wherein the hexameric protein can specifically bind to GITR on the surface of the T cells or NK cells.

In certain aspects, methods of treating cancer in a subject are provided, where the methods include administering to a subject in need of treatment an effective amount of the hexameric protein, or the composition, are provided.

In certain aspects, methods of enhancing an immune response in a subject, where the methods include administering to a subject in need thereof a therapeutically effective amount of the hexameric protein, or the composition, are provided.

In certain aspects, methods of treating a solid tumor in a subject, comprising administering the isolated single-chain polypeptide subunit diclosed above and an OX40 agonist to the subject, are provided.

In another aspect, methods of treating a solid tumor in a subject, comprising administering the isolated single-chain polypeptide subunit diclosed above and a T-cell priming agent to the subject, are provided.

BRIEF DESCRIPTION OF THE DRAWINGS

FIG. 2A-D. Graph showing binding profile of the hexameric GITRL FP variants to GITR expressing CHO cells.

FIG. 12. Hexameric GITRL FP enhances the proliferation of primary human T cells in response to anti-CD3 and anti-CD28. The proliferation of primary human T cells in response to anti-CD3 and anti-CD28 was increased by addition of plate bound hexameric GITRL IgG1 FP comprising monomeric subunits having the amino acid sequence set forth in SEQ ID NO:6 or hexameric GITRL IgG4P FP comprising monomeric subunits having an amino acid sequence set forth in SEQ ID NO: 40. The effect was concentration dependent, with an $EC_{50}$ of 0.3 nM for the GITRL IgG1 FP and an $EC_{50}$ of 0.5 nM for the GITRL IgG4P FP. The addition of an isotype control antibody had no effect. Experiments were conducted in triplicate wells. Error bars represent standard error of the mean.

FIG. 13. The release of IFN-γ by primary human T cells in response to anti-CD3 and anti-CD28 was increased by addition of plate bound hexameric GITRL IgG1 FP comprising monomeric subunits having the amino acid sequence set forth in SEQ ID NO: 6 or hexameric GITRL IgG4P FP comprising monomeric subunits having the amino acid sequence set forth in SEQ ID NO: 40. The effect was concentration dependent, with an $EC_{50}$ of 0.6 nM for the GITRL IgG1 FP and an $EC_{50}$ of 0.8 nM for the GITRL IgG4P FP. The addition of an isotype control antibody had no effect. Experiments were conducted in triplicate wells. Error bars represent standard error of the mean.

FIG. 34 (A)-(D). Murine GITRL-FP mIgG2a mediates PD changes in T-cell proliferation and activation in a dose and schedule dependent manner. Frequency of (A) Ki67, (B) ICOS, (C) PD-1 and (D) OX40 positive CD4+ T-cells in the tumor draining lymph node of CT26 tumor bearing mice 7 days following treatment with 0.2 or 1 mg/kg mIgG2a mGITRL-FP once, every three days [Q3D] or every day [Q1D]. Error bars represent the standard error of the mean from 7-8 mice per group. *p<0.05, p<0.01*p<0.001, ****0<0.0001, as calculated by one way ANOVA.

FIG. 35 (A)-(B). Binding and potency profile of a mouse OX40 ligand fusion protein. (A) Binding ELISA showing that mGITRL-FP mIgG1 and mIgG2a each binds specifically to recombinant mouse GITR-Fc (black bars) and not to recombinant mouse OX40-Fc and that mOX40L-FP mIgG1 and mIgG2a each binds specifically to recombinant mouse OX40 (grey bars) and not recombinant mouse GITR. mOX40L-FP Y182A isotype control binds minimally to recombinant mouse OX40-Fc. (B) Binding of mOX40L-FP mIgG1 (black circles) or Y182A isotype control (open circles) to human OX40 on Jurkat human OX40 NF-κB reporter cell line. Mouse OX40L FP mIgG1 induced NF KB signalling in the reporter assay but this was not evident for the mOX40L-FP Y182A isotype control.

FIG. 38 (A)-(I). Combination of mGITRL-FP mIgG2a and mOX40L-FP mIgG1 synergise to induce increased antitumor activity in B16F10-Luc2 and CT26 tumor bearing mice. Tumor growth in B16F10-Luc2 and CT26 tumor bearing mice. (A)-(E) B16F10-Luc2 tumor bearing mice were dosed i.p. with saline, 25 mg/kg mGITRL-FP mIgG2a biweekly for two weeks, 15 mg/kg mOX40L-FP mIgG1 biweekly for three weeks or a combination of both molecules and tumor growth measured. (F)-(I) CT26 tumor bearing mice were untreated or treated by i.p. injection of isotype control, 7.5 mg/kg of mOX40L-FP mIgG1 twice weekly for two doses, a single suboptimal dose of mGITRL-FP mIgG2a at 0.1 mg/kg or the combination of both molecules. Number of total regressions are indicated next to each individual graph.

FIG. 39. Combination of mGITRL-FP mIgG2a and mOX40L-FP mIgG1 induces increased survival of mice bearing B16F10-Luc2 tumors compared to monotherapy treatment. B16F10-Luc2 tumor bearing mice were dosed i.p. with saline, 25 mg/kg mGITRL-FP mIgG2a biweekly for two weeks, 15 mg/kg mOX40L-FP mIgG1 bi weekly for three weeks or a combination of both molecules and survival measured. Log Rank test, where * indicates a P-value <0.001,  indicates a P-value <0.01 and * indicates a P-value of <0.05.

FIG. 43 (A)-(D). (A)-(B) TC-1 cells were implanted into the footpad of C57BL/6 mice, 2×104 cells/mouse. The mice were randomized by tumor volume on day 14 and dosing was initiated. The mice were dosed IP with mGITRL-FP IgG2a biweekly for 4 total doses. On day 24, untreated mice were sacrificed to examine (C) GITR expression on Tregs and (D) GITR expression on CD8 T-cells. Mice were evaluated for E7 specific T-cells, and none were detected by E7 restim or by dextramer.

DETAILED DESCRIPTION

Figure 1:
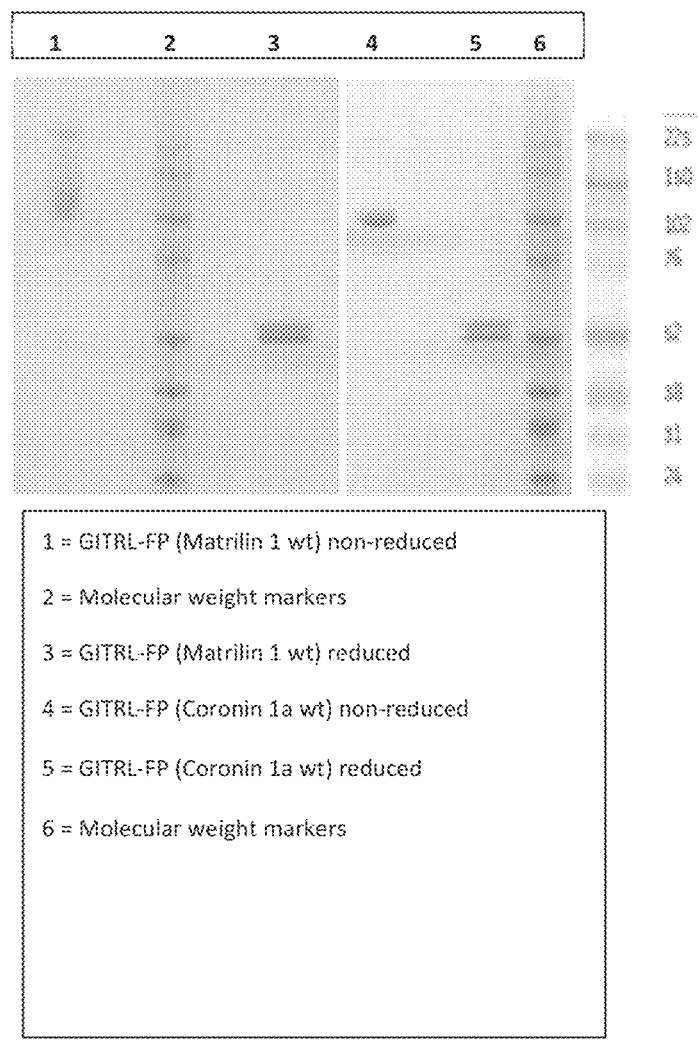
FIG. 1. SDS-PAGE analysis of recombinant GITRL fusion protein (FP) (Matrilin 1 wt) and GITRL FP (Coronin 1a wt) proteins purified using Protein G and size exclusion chromatography.
Figure 3A:
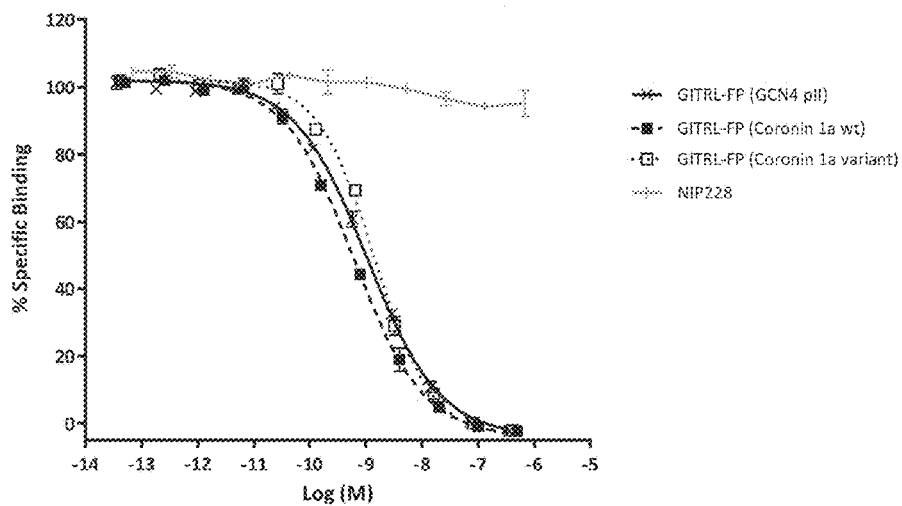
FIG. 3A-D. Graph showing the inhibition profile of the hexameric GITRL FP variants competing for binding of trimeric GITRL to GITR-Fc.
Figure 3B:
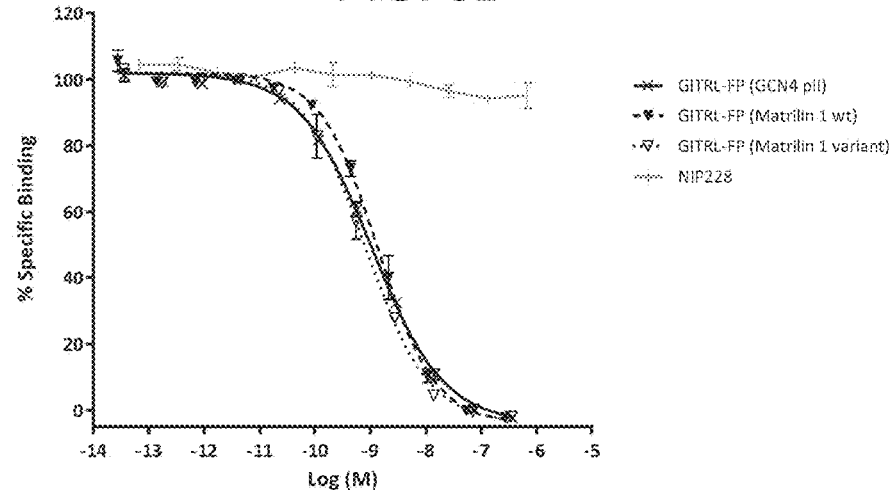
Figure 3C:
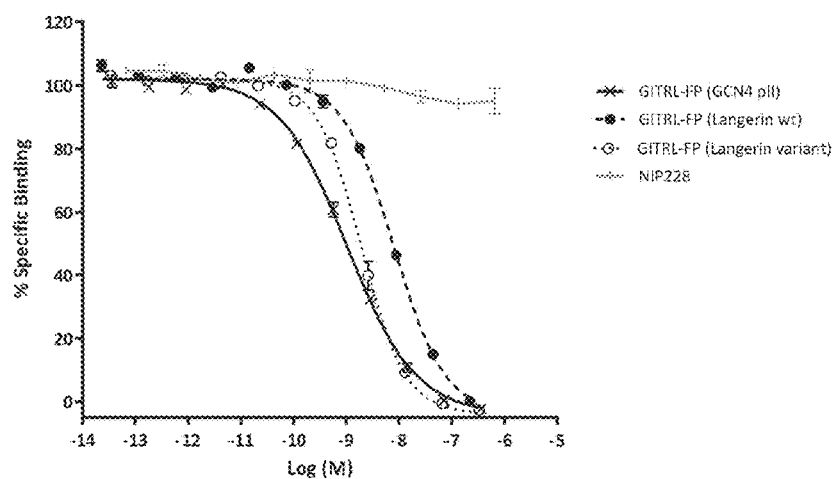
Figure 3D:
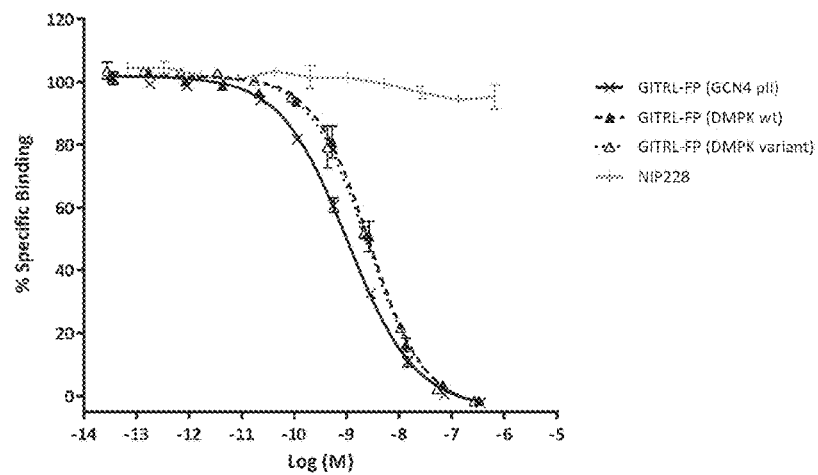
Figure 4A:
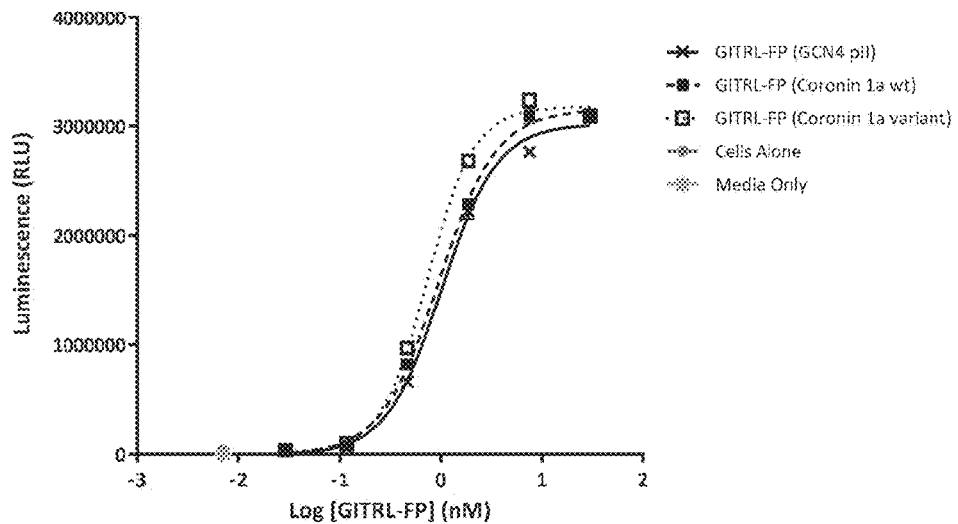
FIG. 4A-D. Graph showing the relative potency of the GITRL FP molecules using a human GITR transfected NF-κB luciferase gene reporter cell line.
Figure 4B:
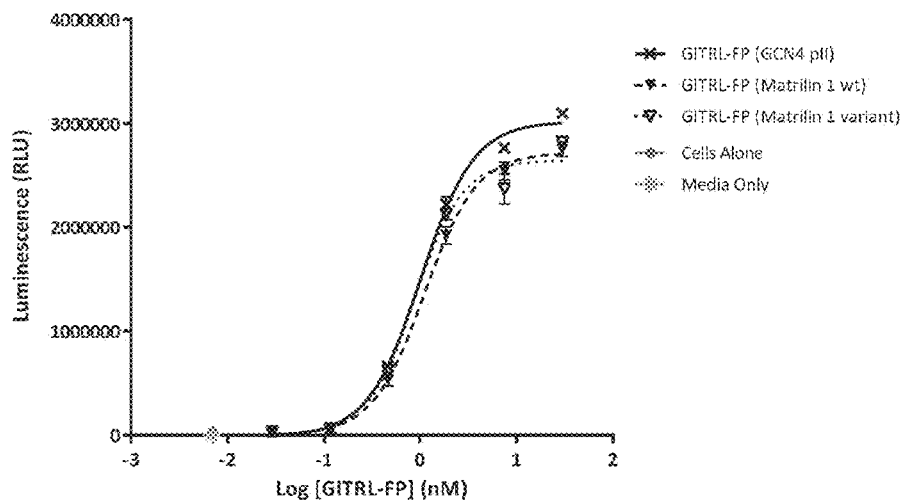
Figure 4C:
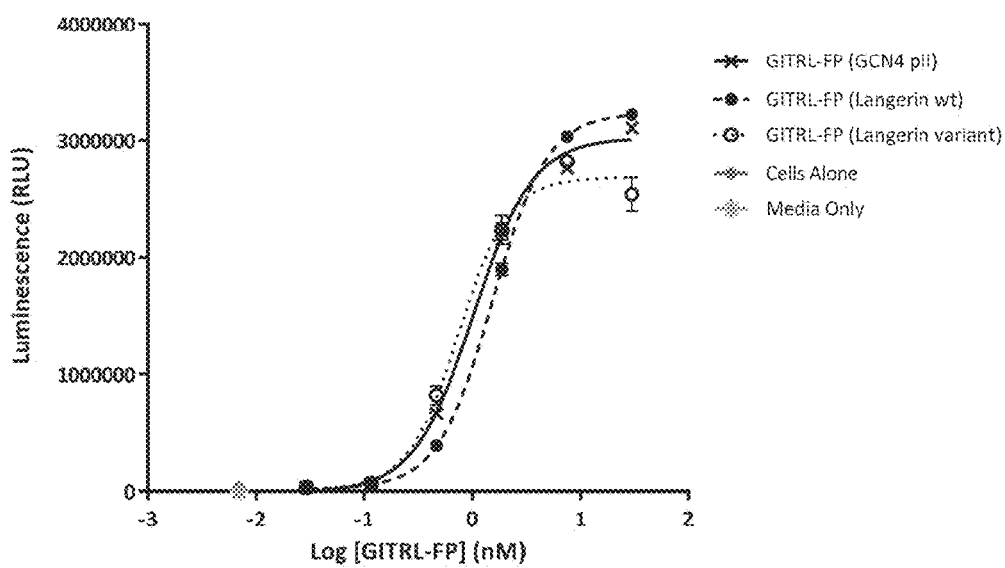
Figure 4D:
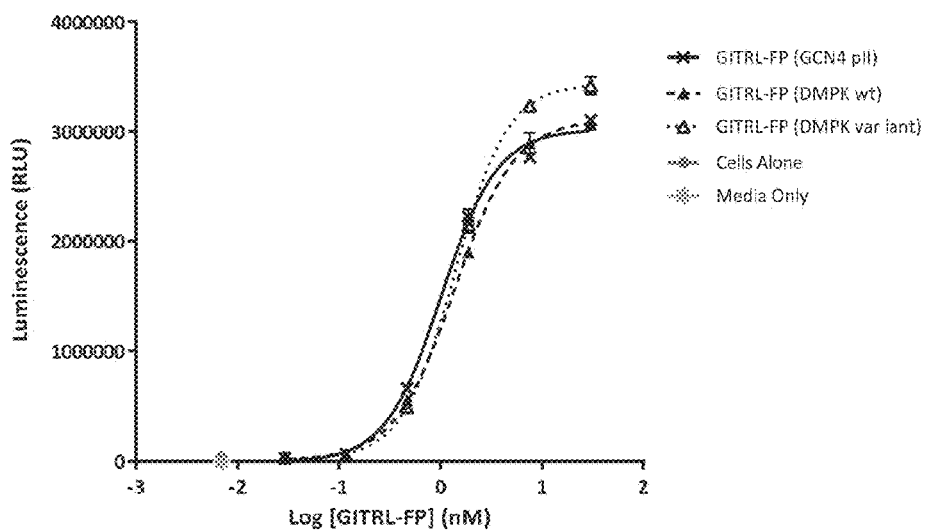

Engagement of the GITR receptor on T cells, e.g., $CD4^+$ T cells or $CD8^+$ T cells during, or shortly after, priming by an antigen results in an increased response of the T cells, e.g., $CD4^+$ T cells or $CD8^+$ T cells to the antigen. Engagement of the GITR receptor on NK cells or B cells, e.g., during, or shortly after, priming by an activating signal (e.g., antigen exposure) results in an increased response of the NK cells or B cells. In the context of the present disclosure, the term "engagement" refers to binding to and stimulation of at least one activity mediated by the GITR receptor. For example, engagement of the GITR receptor on antigen specifics, e.g., $CD4^+$ T cells or $CD8^+$ T cells results in increased T-cell proliferation and increased cytokine production, as compared to the response to antigen alone. The elevated response to the antigen can be maintained for a period of time substantially longer than in the absence of GITR receptor engagement. Thus, stimulation via the GITR receptor enhances the antigen specific immune response by boosting T-cell, NK-cell, or B-cell recognition of non-self, e.g., tumor antigens or viral antigens. GITR has been implicated in T-cell mediated control of certain chronic viral infections (Pascutti, et al., PLoS Pathog. 2015 Mar. 4; 11(3); Clouthier, et al., PLoS Pathog. 2015 Jan. 15; 11(1)).

GITR agonists can enhance antigen specific immune responses in a subject, such as a human subject, when administered to the subject during or shortly after priming of T cells by an antigen. GITR agonists include GITR ligand ("GITRL"), such as soluble GITRL fusion proteins and anti-GITR antibodies or fragments thereof. A specific example is a fusion polypeptide subunit comprising the receptor binding domain of GITRL, a multimerization domain, e.g., trimerization domain, e.g., an alpha helical coiled coil domain derived from Coronin 1a, and a IgG Fc domain, where the polypeptide subunit self-assembles into a multimeric (e.g., trimeric or hexameric) fusion protein. Also described herein are nucleic acids including polynucleotide sequences that encode such fusion polypeptides. This disclosure also provides methods for enhancing an antigen specific immune response in a subject using the multimeric GITRL fusion proteins. The compositions and methods disclosed herein with respect to GITRL fusion proteins can be more generally applied to the production and use of multimeric (e.g., trimeric and hexameric) receptor-binding fusion proteins, for example, in a method of treating cancer, a method of treating a viral infection, or a method of enhancing an immune response in a subject.

Definitions

The term "a" or "an" entity refers to one or more of that entity; for example, "polypeptide subunit" is understood to represent one or more polypeptide subunits. As such, the terms "a" (or "an"), "one or more," and "at least one" can be used interchangeably herein.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various aspects or aspects of the disclosure, which can be had by reference to the specification as a whole. Accordingly, the terms defined immediately below are more fully defined by reference to the specification in its entirety.

As used herein, the phrase "antigen experienced" is used to describe a cell that has been exposed to an antigen where the exposure to that antigen has elicited a response in the cell.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids are included within the definition of "polypeptide," and the term "polypeptide" can be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-standard amino acids. A polypeptide can be derived from a natural biological source or produced by recombinant technology, but is not necessarily translated from a designated nucleic acid sequence. It can be generated in any manner, including by chemical synthesis.

A "protein" as used herein can refer to a single polypeptide, i.e., a single amino acid chain as defined above, but can also refer to two or more polypeptides that are associated, e.g., by disulfide bonds, hydrogen bonds, or hydrophobic interactions, to produce a multimeric protein. As used herein, the term "polypeptide subunit" refers to a polypeptide chain of amino acids which can interact with other polypeptide subunits, either identical or different, to form a multimeric protein, e.g., a hexameric protein as described herein.

A polypeptide as disclosed herein can be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides can have a defined three-dimensional structure, although they do not necessarily have such structure. Polypeptides with a defined three-dimensional structure are referred to as folded, and polypeptides that do not possess a defined three-dimensional structure, but rather can adopt a large number of different conformations, and are referred to as unfolded.

An "isolated" substance, composition, entity, and/or any combination of substances, compositions, or entities, or any grammatical variants thereof, e.g., isolated biological material, is a substance that is not in its natural milieu. No particular level of purification is required. For example, an isolated antibody is an antibody that is not produced or situated in its native or natural environment. Recombinantly produced biological materials are considered isolated as disclosed herein, as are materials that are produced in a non-native cell, such as a hybridoma. A substance, e.g., biological material, is also considered "isolated" if it has been separated, fractionated, or partially or substantially purified by any suitable technique. In certain aspects, an isolated substance, e.g., isolated biological material, can be "non-naturally occurring."

As used herein, the term "non-naturally occurring" substance, composition, entity, and/or any combination of substances, compositions, or entities, or any grammatical variants thereof, is a conditional term that explicitly excludes, but only excludes, those forms of the substance, composition, entity, and/or any combination of substances, compositions, or entities that are well-understood by persons of ordinary skill in the art as being "naturally-occurring," or that are, or might be at any time, determined or interpreted by a judge or an administrative agency such as the United States Patent and Trademark Office, or judicial body to be, "naturally-occurring." For example, the term "a non-naturally occurring antibody explicitly excludes those antibodies that exist in nature, e.g., an antibody that would naturally be present in the immune system of a mouse exposed to a normal milieu of antigenic stimulus, or an antibody finally determined by an administrative body, e.g., the United States Patent and Trademark Office, or a judicial body, e.g., a federal court, to be "naturally-occurring."

Other polypeptides disclosed herein are fragments, derivatives, analogs, or variants of the foregoing polypeptides, and any combination thereof. The terms "fragment," "variant," "derivative" and "analog" when referring to polypeptide subunit or multimeric protein as disclosed herein can include any polypeptide or protein that retain at least some of the activities of the complete polypeptide or protein, but which is structurally different. Fragments of polypeptides include, for example, proteolytic fragments, as well as deletion fragments. Variants include fragments as described above, and also polypeptides with altered amino acid sequences due to amino acid substitutions, deletions, or insertions. Variants can occur spontaneously or be intentionally constructed. Intentionally constructed variants can be produced using art-known mutagenesis techniques. Variant polypeptides can comprise conservative or non-conservative amino acid substitutions, deletions or additions. Derivatives are polypeptides that have been altered so as to exhibit additional features not found on the native polypeptide. Examples include fusion proteins. Variant polypeptides can also be referred to herein as "polypeptide analogs." As used herein a "derivative" refers to a subject polypeptide having one or more amino acids chemically derivatized by reaction of a functional side group. Also included as "derivatives" are those peptides that contain one or more standard or synthetic amino acid derivatives of the twenty standard amino acids. For example, 4-hydroxyproline can be substituted for proline; 5-hydroxylysine can be substituted for lysine; 3-methylhistidine can be substituted for histidine; homoserine can be substituted for serine; and ornithine can be substituted for lysine.

A "conservative amino acid substitution" is one in which one amino acid is replaced with another amino acid having a similar side chain. Families of amino acids having similar side chains have been defined in the art, including basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. Methods of identifying nucleotide and amino acid conservative substitutions which do not eliminate protein activity are well-known in the art (see, e.g., Brummell et al., *Biochem.* 32: 1180-1 187 (1993); Kobayashi et al., *Protein Eng.* 12(10):879-884 (1999); and Burks et al., *Proc. Natl. Acad. Sci. USA* 94:412-417 (1997)).

As used herein, the term "antibody" (or a fragment, variant, or derivative thereof) refers to at least the minimal portion of an antibody which is capable of binding to antigen, e.g., at least the variable domain of a heavy chain (VH) and the variable domain of a light chain (VL) in the context of a typical antibody produced by a B cell. Basic antibody structures in vertebrate systems are relatively well understood. See, e.g., Harlow et al., Antibodies: A Laboratory Manual, (Cold Spring Harbor Laboratory Press, 2nd ed. 1988).

Antibodies or antigen-binding fragments, variants, or derivatives thereof include, but are not limited to, polyclonal, monoclonal, human, humanized, or chimeric antibodies, single chain antibodies, epitope-binding fragments, e.g., Fab, Fab' and F(ab')2, Fd, Fvs, single-chain Fvs (scFv), single-chain antibodies, disulfide-linked Fvs (sdFv), fragments comprising either a VL or VH domain, and fragments produced by a Fab expression library. ScFv molecules are known in the art and are described, e.g., in U.S. Pat. No. 5,892,019. Immunoglobulin or antibody molecules encompassed by this disclosure can be of any type (e.g., IgG, IgE, IgM, IgD, IgA, and IgY), class (e.g., IgG1, IgG2, IgG3, IgG4, IgA1 and IgA2) or subclass of immunoglobulin molecule.

The term "polynucleotide" is intended to encompass a singular nucleic acid as well as plural nucleic acids, and refers to an isolated nucleic acid molecule or construct, e.g., messenger RNA (mRNA) or plasmid DNA (pDNA). A polynucleotide can comprise a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. By "isolated" nucleic acid or polynucleotide is intended a nucleic acid molecule, DNA or RNA, which has been removed from its native environment. For example, a recombinant polynucleotide encoding a polypeptide subunit contained in a vector is considered isolated as disclosed herein. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides. Isolated polynucleotides or nucleic acids further include such molecules produced synthetically. In addition, polynucleotide or a nucleic acid can be or can include a regulatory element such as a promoter, ribosome binding site, or a transcription terminator.

As used herein, a "coding region" is a portion of nucleic acid comprising codons translated into amino acids. Although a "stop codon" (TAG, TGA, or TAA) is not translated into an amino acid, it can be considered to be part of a coding region, but any flanking sequences, for example promoters, ribosome binding sites, transcriptional terminators, introns, and the like, are not part of a coding region. Two or more coding regions can be present in a single polynucleotide construct, e.g., on a single vector, or in separate polynucleotide constructs, e.g., on separate (different) vectors. Furthermore, any vector can contain a single coding region, or can comprise two or more coding regions, e.g., a single vector can separately encode an immunoglobulin heavy chain variable region and an immunoglobulin light chain variable region. In addition, a vector, polynucleotide, or nucleic acid can encode heterologous coding regions, either fused or unfused to a nucleic acid encoding a polypeptide subunit or fusion protein as provided herein. Heterologous coding regions include without limitation specialized elements or motifs, such as a secretory signal peptide or a heterologous functional domain.

In certain embodiments, the polynucleotide or nucleic acid is DNA. In the case of DNA, a polynucleotide comprising a nucleic acid that encodes a polypeptide normally can include a promoter and/or other transcription or translation control elements operably associated with one or more coding regions. An operable association or linkage is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" or "operably linked" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter can be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein.

A variety of transcription control regions are known to those skilled in the art. These include, without limitation, transcription control regions that function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

In other embodiments, a polynucleotide can be RNA, for example, in the form of messenger RNA (mRNA).

Polynucleotide and nucleic acid coding regions can be associated with additional coding regions that encode secretory or signal peptides, which direct the secretion of a polypeptide encoded by a polynucleotide as disclosed herein, e.g., a polynucleotide encoding a polypeptide subunit provided herein. According to the signal hypothesis, proteins secreted by mammalian cells have a signal peptide or secretory leader sequence that is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the complete or "full length" polypeptide to produce a secreted or "mature" form of the polypeptide. In certain embodiments, the native signal peptide, e.g., an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, can be used. For example, the wild-type leader sequence can be substituted with the leader sequence of influenza A virus haemaglutinin, human tissue plasminogen activator (TPA) or mouse β-glucuronidase.

A "vector" is a nucleic acid molecule as introduced into a host cell, thereby producing a transformed host cell. A vector can include nucleic acid sequences that permit it to replicate in a host cell, such as an origin of replication. A vector can also include one or more selectable marker gene and other genetic elements known in the art.

A "transformed" cell, or a "host" cell, is a cell into which a nucleic acid molecule has been introduced by molecular biology techniques. As used herein, the term transformation encompasses all techniques by which a nucleic acid molecule can be introduced into such a cell, including transfection with viral vectors, transformation with plasmid vectors, and introduction of naked DNA by electroporation, lipofection, and particle gun acceleration. A transformed cell or a host cell can be a bacterial cell or a eukaryotic cell.

By "specifically binds," it is generally meant that a molecule, e.g., a GITRL or receptor-binding fragment thereof, binds to another molecule, e.g., GITR, via its receptor-binding domain, and that the binding entails some complementarity between the ligand and its receptor. According to this definition, a ligand is said to "specifically bind" to a receptor when it binds to that receptor, via its receptor-binding domain more readily than it would bind to a random, unrelated molecule. The term "specificity" is used herein to qualify the relative affinity by which a certain ligand binds to a certain receptor. For example, ligand "A" may be deemed to have a higher specificity for a given receptor than ligand "B," or ligand "A" may be said to bind to receptor "C" with a higher specificity than it has for related receptor "D."

By "a receptor-binding domain," it is intended a binding domain comprised in a ligand, e.g., a GITRL as disclosed herein.

A ligand, e.g., a GITRL fusion polypeptide subunit or multimeric GITRL fusion protein as disclosed herein can bind to a receptor, e.g., GITR, with an off rate (k(off)) of less than or equal to $5\times10^{-2}$ sec$^{-1}$, $10^{-2}$ sec$^{-1}$, $5\times10^{-3}$ sec$^{-1}$ or $10^{-3}$ sec$^{-1}$. A ligand, e.g., a GITRL fusion polypeptide subunit or multimeric GITRL fusion protein as disclosed herein can bind to a receptor, e.g., GITR, with an off rate (k(off)) less than or equal to $5\times10^{-4}$ sec$^{-1}$, $10^{-4}$ sec$^{-1}$, $5\times10^{-5}$ sec$^{-1}$, or $10^{-5}$ sec$^{-1}$ $5\times10^{-6}$ sec$^{-1}$, $10^{-6}$ sec$^{-1}$, $5\times10^{-7}$ sec$^{-1}$ or $10^{-7}$ sec$^{1}$.

The terms "inhibit," "block," and "suppress" are used interchangeably herein and refer to any statistically significant decrease in biological activity, including full blocking of the activity. For example, "inhibition" can refer to a decrease of about 10%, 20%, 30%, 40%, 50%, 60%, 70%, 80%, 90% or 100% in biological activity.

As used herein, the term "affinity" refers to a measure of the strength of the binding of a ligand to its cognate receptor. As used herein, the term "avidity" refers to the overall stability of the complex between a population of ligands and receptors, that is, the functional combining strength of a combination of ligands and receptors, e.g., interaction of a hexameric GITRL IgG Fusion Protein (GITRL FP) to cell surface GITR. Avidity is related to both the affinity of individual receptor binding domains in the population with specific receptors, and also the valencies of the ligands and the receptors.

A ligand, e.g., a GITRL fusion polypeptide subunit or multimeric GITRL fusion protein as disclosed herein can also be described or specified in terms of its binding affinity to a ligand. For example, a ligand can bind to a receptor with a dissociation constant or $K_D$ no greater than $5\times10^{-2}$ M, $10^{-2}$ M, $5\times10^{-3}$M, $10^{-3}$M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$M, $5\times10^{-8}$ M, $10^{-8}$ M, $5\times10^{-9}$ M, $10^{-9}$ M, $5\times10^{-10}$ M, $10^{-10}$ M, $5\times10^{-11}$M, $10^{-11}$M, $5\times10^{-12}$M, $10^{-12}$ M, $5\times10^{-13}$M, $10^{-13}$M, $5\times10^{-14}$ M, $10^{-14}$ M, $5\times10^{-15}$ M, or $10^{-15}$ M.

A ligand, e.g., a GITRL fusion polypeptide subunit or multimeric GITRL fusion protein as disclosed herein can bind to a receptor, e.g., GITR, with an on rate (k(on)) of greater than or equal to $10^3$ M$^{-1}$ sec$^{-1}$, $5\times10^3$ M$^{-1}$ sec$^{-1}$, $10^4$ M$^{-1}$ sec$^{-1}$ or $5\times10^4$ M$^{-1}$ sec$^{-1}$. A ligand, e.g., a GITRL fusion polypeptide subunit or multimeric GITRL fusion protein as disclosed herein can bind to a receptor, e.g., GITR, with an on rate (k(on)) greater than or equal to $10^5$ M$^{-1}$ sec$^{-1}$, $5\times10^5$ M$^{-1}$ sec$^{-1}$, $10^6$ M$^{-1}$ sec$^{-1}$, or $5\times10^6$ M$^{-1}$ sec$^{-1}$ or $10^7$ M$^{-1}$ sec$^{-1}$.

GITR, or "GITR receptor" is a protein, also variously termed glucocorticoid-induced TNF-related protein, tumor necrosis factor ligand superfamily member 18, TNSF 18, activation-inducible TNF-related receptor, AITR, CD357, and RP5-902P8.2, is expressed on the surface of activated NK cells and antigen experienced T-cells, e.g., CD4$^+$ and CD8$^+$ T cells, as well as on CD4$^+$ CD25$^+$FOXP3$^+$ regulatory T-cells (Tregs; Stephens et al. *J. Immunol.* (2004) 173(8): 5008-5020). GITR is, e.g., the protein of SEQ ID NO: 47. "GITR ligand" ("GITRL"), also variously termed glucocorticoid-induced TNF-related ligand, tumor necrosis factor ligand superfamily member 18 ligand, TNFSF18 ligand, TL6, activation-inducible TNF-related ligand, AITR ligand, AITRL, and RP1-15D23, is found largely on antigen presenting cells (APCs; Stephens et al. *J. Immunol.* (2004) 173(8): 5008-5020). GITRL is expressed on the surface of cells and includes an intracellular, a transmembrane and an extracellular receptor-binding domain.

As used herein, the term "GITRL" refers to the entire GITR ligand, soluble GITR ligand, and functionally active portions of the GITR ligand. Also included within the definition of GITRL are both naturally occurring allelic variants of GITRL, GITR ligand variants which vary in amino acid sequence from naturally occurring GITR ligand molecules, and combinations of such variants, where the variants retain the ability to specifically bind to a GITR receptor. Certain variants of GITRL comprising amino acid residue substitutions are identified herein by residue number in the mature GITRL protein of SEQ ID NO: 1. For example, N161D refers to a substitution of an asparagyl residue at position 161 of a mature human GITRL of SEQ ID NO: 1 with an aspartyl residue and also to that same substitution in the equivalent position in the extracellular domain of a human GITRL of SEQ ID NO: 6 and SEQ ID NO: 8. In referring to various substitutions in the GITRL sequence of SEQ ID NO: 1, equivalent substitutions of the corresponding residues in GITRL polypeptides other than the GITRL polypeptide of SEQ ID NO: 1 are also provided herein. Such corresponding residues can be readily identified by aligning the SEQ ID NO: 1 sequence with the GITRL sequence to be substituted. For example, a GITRL peptide having a single amino acid N-terminal addition to SEQ ID NO: 1 could have a substitution of an asparagyl residue at position 162 that would be equivalent to a substitution of an asparagyl residue at position 161 of SEQ ID NO: 1.

As used herein, the term "GITRL fusion polypeptide subunit" or "GITRL FP subunit" refers to a single-chain polypeptide subunit comprising: a human IgG Fc domain; a functional trimerization domain; and a receptor binding domain of a Glucocorticoid-Induced TNF Receptor Ligand (GITRL), wherein the polypeptide subunit can self-assemble into a multimeric e.g. a trimeric or a hexameric protein. The terms "multimeric GITRL fusion protein" or "multimeric GITRL FP" refer to self-assembled multimers of a GITRL fusion polypeptide subunit including, e.g., trimers and hexamers. When an IgG Fc domain of a certain isotype is used in a GITRL FP subunit, the GITRL FP having that isotype is described as a "GITRL IgGX FP", where X can be 1, 2, 2a, 3, 4, or 4P, e.g., GITRL IgG1 FP, GITRL IgG2 FP, GITRL IgG2a FP, GITRL IgG3 FP, GITRL IgG4 FP, and GITRL IgG4P FP.

As used herein, "OX40 polypeptide" means a polypeptide or fragment thereof having at least about 85% amino acid identity to NCBI Accession No. NP_003318. OX40 is a member of the TNFR-superfamily of receptors that is expressed on the surface of antigen-activated mammalian CD4+ and CD8+ T lymphocytes. See, for example, Paterson et al., Mol Immunol 24, 1281-1290 (1987); Mallett et al., EMBO J 9, 1063-1068 (1990); and Calderhead et al., J Immunol 151, 5261-5271 (1993)). OX40 is also referred to as CD134, ACT-4, and ACT35. OX40 receptor sequences are known in the art and are provided, for example, at GenBank Accession Numbers: AAB33944 or CAE11757.

An exemplary human OX40 amino acid sequence is provided below:

(SEQ ID NO: 52)

```
  1    mcvgarrlgr gpcaallllg lglstvtglh cvgdtypsnd rcchecrpgn gmvsrcsrsq
 61    ntvcrpcgpg fyndvvsskp ckpctwcnlr sgserkqlct atqdtvcrcr agtqpldsyk
121    pgvdcapcpp ghfspgdnqa ckpwtnctla gkhtlqpasn ssdaicedrd ppatqpqetq
181    gpparpitvq pteawprtsq gpstrpvevp ggravaailg lglvlgllgp laillalyll
241    rrdqrlppda hkppgggsfr tpigeeqada hstlaki
```

By "OX40 ligand" is meant a polypeptide or fragment thereof having at least about 85% amino acid identity to NCBI Accession No. NP_003317 and that specifically binds the OX40 receptor. See, for example, Baum P. R., et al. EMBO J. 13:3992-4001(1994)). The term OX40L includes the entire OX40 ligand, soluble OX40 ligand, and fusion proteins comprising a functionally active portion of OX40 ligand covalently linked to a second moiety, e.g., a protein domain. Also included within the definition of OX40L are variants which vary in amino acid sequence from naturally occurring OX4L but which retain the ability to specifically bind to the OX40 receptor. Further included within the definition of OX40L are variants which enhance the biological activity of OX40. OX40 ligand sequences are known in the art and are provided, for example, at GenBank Accession Numbers: NP_003318.

An exemplary human OX40 ligand amino acid sequence is provided below:

(SEQ ID NO: 53)
MERVQPLEENVGNAARPRFERNKLLLVASVIQGLGLLLCFTYICLHFSA

LQVSHRYPRIQSIKVQFTEYKKEKGFILTSQKEDEIMKVQNNSVIINCD

GFYLISLKGYFSQEVNISLHYQKDEEPLFQLKKVRSVNSLMVASLTYKD

KVYLNVTIDNISLDDFHVNGGELILIHQNPGEFCVL

As used herein, "OX40 agonist" means an OX40 ligand that specifically interacts with and increases the biological activity of the OX40 receptor. Desirably, the biological activity is increased by at least about 10%, 20%, 30%, 50%, 70%, 80%, 90%, 95%, or even 100%. In certain aspects, OX40 agonists as disclosed herein include OX40 binding polypeptides, such as anti-OX40 antibodies (e.g., OX40 agonist antibodies), OX40 ligands, or fragments or derivatives of these molecules.

As used herein, "OX40 antibody" means an antibody that specifically binds OX40. OX40 antibodies include monoclonal and polyclonal antibodies that are specific for OX40 and antigen-binding fragments thereof. In certain aspects, anti-OX40 antibodies as described herein are monoclonal antibodies (or antigen-binding fragments thereof), e.g., murine, humanized, or fully human monoclonal antibodies. In one particular embodiment, the OX40 antibody is an OX40 receptor agonist, such as the mouse anti-human OX40 monoclonal antibody (9B12) described by Weinberg et al., J Immunother 29, 575-585 (2006). In other embodiments, the antibody which specifically binds to OX40, or an antigen-binding fragment thereof binds to the same OX40 epitope as mAb 9B12. In another aspect, the antibody is MEDI0562. See, for example, US Pub. No. 2016/0137740.

As used herein, "OX40 ligand fusion protein (OX40L FP)" means a protein that specifically binds the OX40 receptor and increases an immune response. In one embodiment, binding of an OX40 ligand fusion protein to the OX40 receptor enhances a tumor antigen specific immune response by boosting T-cell recognition. Exemplary OX40 ligand fusion proteins are described in U.S. Pat. No. 7,959,925, entitled, "Trimeric OX40 Immunoglobulin Fusion Protein and Methods of Use." Other OX40 ligand fusion proteins are described, for example, in U.S. Pat. No. 6,312,700. In one embodiment, an OX40 ligand fusion protein enhances tumor-specific T-cell immunity. In one embodiment, the OX40 ligand fusion protein is MEDI6383 (SEQ ID NO: 50). See, for example, US Pub. No. 2016/0024176.

A "trimerization domain" is an amino acid sequence within a polypeptide that promotes assembly of the polypeptide into trimers. For example, a trimerization domain can promote assembly into trimers via associations with other trimerization domains (of additional polypeptides with the same or a different amino acid sequence). The term is also used to refer to a polynucleotide that encodes such a peptide or polypeptide.

The term "Fc" domain refers to a portion of an antibody constant region. Traditionally, the term Fc domain refers to a protease (e.g., papain) cleavage product encompassing the paired CH2, CH3 and hinge regions of an antibody. In the context of this disclosure, the term Fc domain or Fc refers to any polypeptide (or nucleic acid encoding such a polypeptide), regardless of the means of production, that includes all or a portion of the CH2, CH3 and hinge regions of an immunoglobulin polypeptide.

As used herein, the term "IgG Fc domain" refers to an Fc domain of an IgG1, IgG2, IgG3, or IgG4 immunoglobulin, and variants of such Fc domains. Variants of an IgG4 Fc domain include, but are not limited to, an IgG4P Fc domain.

As used herein the term "CH2 domain" includes the portion of the Fc domain of a heavy chain molecule that extends, e.g., from about amino acid 244 to amino acid 360 of an antibody using conventional numbering schemes (amino acids 244 to 360, Kabat numbering system; and amino acids 231-340, EU numbering system). It is also well documented that the CH3 domain extends from the CH2 domain to the C-terminal of the IgG molecule and comprises approximately 108 amino acids.

As used herein, the term "linker region" includes any peptide that is used to fuse or join two protein domains. Such linkers include, but are not limited to, peptides that comprise (Gly4)n motif(s), a (Gly$_4$Ser)n motif(s) (SEQ ID NO: 19), and Ser(Gly$_4$Ser)n motif(s) (SEQ ID NO: 22).

As used herein, the term "IgG hinge region" includes the portion of the Fc domain of a heavy chain IgG molecule that joins the CH1 domain to the CH2 domain. This hinge region comprises approximately 25 amino acids and is flexible, thus allowing the two N-terminal antigen binding regions to move independently. Hinge regions can be subdivided into three distinct domains: upper, middle, and lower hinge domains (Roux et al., J. Immunol. 161:4083 (1998)).

As used herein the term "disulfide bond" includes the covalent bond formed between two sulfur atoms. The amino acid cysteine comprises a thiol group that can form a disulfide bond or bridge with a second thiol group. In certain aspects provided herein, a human IgG4 Fc domain can be mutated in the hinge region to insure disulfide bond formation between two hinge regions, specifically, a serine to proline mutation at position 228 (according to EU numbering). Human IgG4 Fc domains comprising the S228P mutation are referred to herein as "IgG4P Fc domains."

As used herein, the terms "linked," "fused" or "fusion" can be used interchangeably. These terms refer to the joining together of two more elements or components, by whatever means including chemical conjugation or recombinant means. An "in-frame fusion" refers to the joining of two or more polynucleotide open reading frames (ORFs) to form a continuous longer ORF, in a manner that maintains the correct translational reading frame of the original ORFs. Thus, a recombinant fusion protein is a single protein containing two or more segments that correspond to polypeptides encoded by the original ORFs (which segments are not normally so joined in nature), e.g., a GITRL fusion polypeptide subunit as provided herein. Although the reading frame is thus made continuous throughout the fused segments, the segments can be physically or spatially separated by, for example, in-frame linker sequence.

In the context of polypeptides, a "linear sequence" or a "sequence" is an order of amino acids in a polypeptide in an amino to carboxyl terminal direction in which amino acids that neighbor each other in the sequence are contiguous in the primary activated structure of the polypeptide.

The term "expression" as used herein refers to a process by which a gene produces a biochemical, for example, a polypeptide. The process includes any manifestation of the functional presence of the gene within the cell including, without limitation, gene knockdown as well as both transient expression and stable expression. It includes without limitation transcription of the gene into messenger RNA (mRNA), and the translation of such mRNA into polypeptide(s). If the final desired product is a biochemical, expression includes the creation of that biochemical and any precursors. Expression of a gene produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

As used herein the terms "treat," "treatment," or "treatment of" when used in the context of treating cancer (e.g., in the phrase "treating a cancer patient") refers to reducing the potential for disease pathology, reducing the occurrence of disease symptoms, e.g., to an extent that the subject has a longer survival rate or reduced discomfort. For example, treating can refer to the ability of a therapy when administered to a subject, to reduce disease symptoms, signs, or causes. Treating also refers to mitigating or decreasing at least one clinical symptom and/or inhibition or delay in the progression of the condition and/or prevention or delay of the onset of a disease or illness.

As used herein the terms "treat," "treatment," or "treatment of" when used in the context of treating a viral infection (e.g., in the phrase "treating a viral infection") refers to reducing the pathological conditions and/or symptoms associated with the viral infection.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, sports animals, and zoo animals, including, e.g., humans, non-human primates, dogs, cats, guinea pigs, rabbits, rats, mice, horses, cattle, bears, and so on.

The term "pharmaceutical composition" refers to a preparation that is in such form as to permit the biological activity of the active ingredient to be effective, and that contains no additional components that are unacceptably toxic to a subject to which the composition would be administered. Such composition can be sterile.

An "effective amount" of an antibody as disclosed herein is an amount sufficient to carry out a specifically stated purpose. An "effective amount" can be determined empirically and in a routine manner, in relation to the stated purpose.

GITRL Fusion Polypeptide Subunits

The present disclosure relates to a GITRL fusion polypeptide subunit that can assemble into a multimeric, e.g., trimeric or hexameric protein with improved properties that include, but are not limited to, improved yield when expressed in transfected mammalian cell cultures; improved binding affinity for GITR; improved activity in various biological assays and/or improved homogeneity when purified or partially purified in comparison to previously disclosed polypeptides containing GITRL (See, e.g., Wyzgol et al., J Immunol 2009; 183:1851-1861). GITRL fusion polypeptide subunits provided herein can comprise an IgG Fc domain, e.g., a human IgG Fc domain, a trimerization domain, and the receptor binding domain of human GITRL. An exemplary embodiment is illustrated schematically in FIG. 7. Typically, the IgG Fc domain, the trimerization domain and the GITRL receptor binding domain are arranged in an N-terminal to C-terminal direction. An exemplary GITRL IgG1 fusion polypeptide subunit is represented by SEQ ID NO: 6.

In certain embodiments, the GITRL receptor binding domain is an extracellular domain of a human GITRL. The sequence of one such domain is represented by SEQ ID NO: 37.

In certain aspects, the GITRL receptor binding domain is a GITRL variant extracellular domain. GITRL variant extracellular domains that can be used include, but are not limited to, polypeptides having at least 70%, 75%, 80%, 85%, 90%, 95%, 97%, 98%, 99%, or 100% sequence identity across the entire length of SEQ ID NO: 37. In certain aspects, the GITRL variant extracellular domain is a polypeptide having at least 70%, 75%, 80%, 85%, 90%, 95%, 97%, 98%, 99%, or 100% sequence identity across the entire length of SEQ ID NO: 34. In certain aspects, the GITRL variant extracellular domain residue corresponding to asparagyl 161 of SEQ ID NO: 1 is substituted with any amino acid or with an aspartyl residue. GITRL variant extracellular domains where the residue corresponding to asparagyl 161 of SEQ ID NO: 1 is substituted with any amino acid or with an aspartyl residue include, but are not limited to, polypeptides having at least 70%, 75%, 80%, 85%, 90%, 95%, 97%, 98%, or 99%, sequence identity across the entire length of SEQ ID NO: 35, SEQ ID NO: 36, and SEQ ID NO: 37. Such substitutions can reduce or eliminate N-linked glycosylation of this site in the GITRL variant extracellular domain. In certain aspects, the GITRL variant extracellular domain residue corresponding to asparagyl 106 of SEQ ID NO: 1 is substituted with an alanyl residue. In certain contexts, N106A substitutions of hGITRL can result in increased binding to GITR and an improved T-cell proliferation response (Chattopadhyay et al. (2007) Proc. Natl. Acad. Sci. USA 104(49):19452-19457). In certain aspects, GITRL variant extracellular domain residues corresponding to Glu 52, Phe 62, Pro 66, Pro 67, Met 71, Pro 77, Val 79, Asn 92, Ser 83, Gly 99, Asn 104, Pro 112, Arg 116, Met 123, Asn 153, Val 158, Asn 161, Iso 167, Iso 168, and combinations thereof are independently substituted with a non-naturally occurring amino acid residue or an amino acid residue of an allelic variant. A non-limiting example of a GITRL variant extracellular domain is provided in SEQ ID NO: 35, where $X_1$=Glu or Ala, $X_2$=Ser or Phe, $X_3$=Thr or Pro, $X_4$=Leu or Ser, $X_5$=Thr or Met, $X_6$=Leu or Pro, $X_7$=Met or Val, $X_8$=Thr, Phe, or Ser, $X_9$=Ser or Gly, $X_{10}$=Arg or Pro, $X_{11}$=Trp or Arg, $X_{12}$=Leu or Met, $X_{13}$=Ser or Asn, $X_{14}$=Phe or Val, $X_{15}$=any amino acid other than Asn or Asp, $X_{16}$=Val or Ile, $X_{17}$=Leu or Ile, and where $X_1$-$X_{17}$ are independently selected and can be present in any combination.

Any GITRL polypeptide sequence that retains the desired property of binding to the GITR receptor is suitable in the fusion polypeptides and methods described herein.

Adjacent to the GITRL receptor binding domain is a trimerization domain. The term "adjacent" includes, for example, contiguous with, or associated via a linker region or heterologous agent. Such domains, when contiguous to one another, are domains that are fused directly to one another. The trimerization domain serves to promote self-assembly of individual GITRL fusion polypeptide subunits into a trimeric protein or into a hexameric protein. In certain embodiments, a GITRL fusion polypeptide subunit with a trimerization domain self-assembles into a hexameric GITRL fusion protein. In one embodiment, the trimerization domain is a coiled coil domain, e.g., a leucine zipper domain. An exemplary trimeric leucine zipper domain is the engineered yeast GCN4 pII variant described by Harbury et al. (1993) Science 262:1401-1407, the disclosure of which is incorporated herein for all purposes. Exemplary trimerization domains include: TNF receptor-associated factor-2 (TRAF2) (GENBANK® Accession No. Q12933 [gi: 23503103]; amino acids 310-349); Thrombospondin 1 (Accession No. PO7996 [gi:135717]; amino acids 291-314); Matrilin-4 (Accession No. 095460 [gi:14548117]; amino acids 594-618; cartilage matrix protein (matrilin-1) (Accession No. NP002370 [gi:4505111]; amino acids 463-496; Heat shock transcription factor (HSF) (Accession No. AAX42211 [gi:61362386]; amino acids 165-191; and Cubilin (Accession No. NP001072 [gi:4557503]; amino acids 104-138.

In certain aspects, the trimerization domain comprises an alpha-helical coiled coil domain. Useful alpha-helical coiled coil domains include, but are not limited to those derived from Matrilin 1, Coronin 1a, dystrophia myotonica kinase (DMPK), Langerin, and combinations thereof. Such derivatives include, but are not limited to, coiled coil domains with wild type sequences as well as variants comprising one or more amino acid substitutions in the coiled coil domain wild type sequence. Coronin 1a proteins containing Coronin 1a trimerization domains are also sometimes synonymously referred to as any of Coronin-like protein A, Clipin-A, Coronin-like protein p57, Tryptophan aspartate-containing coat protein and the HUGO name CORO1A. Non-limiting examples of wild-type coiled coil domains derived from various proteins that can be used include Matrilin 1 (SEQ ID NO: 28), DMPK (SEQ ID NO: 30), Langerin (SEQ ID NO: 32), and Coronin 1a (SEQ ID NO: 11). Variants of the alpha-helical coiled coil domains can include allelic variants, engineered variants, and combinations thereof. Alpha-helical coiled coil domains are typically organized in heptad sequence repeats "hpphcpc" (or abcdefg) that can be independently substituted at one or more of the "h" positions ("a" and/or "d" positions) in one or more of the repeats with Alanine, Leucine, Isoleucine, or Valine residues. In such "hpphcpc" heptad repeats, h represents hydrophobic residues, c represents, typically, charged residues, and p represents polar (and, therefore, hydrophilic) residues. Alpha-helical coiled coil domain variants of Matrilin 1, Coronin 1a, dystrophia myotonica kinase (DMPK), and Langerin where one or more of the "a" and/or "d" positions in one or more of the heptad repeats of those trimerization domains are substituted with Alanine, Leucine, Isoleucine, or Valine residues are provided. Non-limiting examples of alpha-helical coiled coil domain variants that can be used include Matrilin 1 (SEQ ID NO: 29), DMPK (SEQ ID NO: 31), Langerin (SEQ ID NO: 32), and Coronin 1a (SEQ ID NO: 12-18). In certain aspects, a variant Matrilin 1 trimerization domain used in the GITRL fusion polypeptide subunit can include, but is not limited to, a polypeptide having at least 70%, 75%, 80%, 85%, 90%, 95%, 97%, 98%, or 99% sequence identity across the entire length of SEQ ID NO: 29. In certain aspects, a variant DMPK trimerization domain used in the GITRL fusion polypeptide subunit can include, but is not limited to, a polypeptide having at least 70%, 75%, 80%, 85%, 90%, 95%, 97%, 98%, or 99% sequence identity across the entire length of SEQ ID NO: 31. In certain aspects, a variant Langerin trimerization domain used in the GITRL fusion polypeptide subunit can include, but is not limited to, a polypeptide having at least 70%, 75%, 80%, 85%, 90%, 95%, 97%, 98%, or 99% sequence identity across the entire length of SEQ ID NO: 33. In certain aspects, a Coronin 1a trimerization domain used in the GITRL fusion polypeptide subunit can include, but is not limited to, a polypeptide having at least 70%, 75%, 80%, 85%, 90%, 95%, 97%, 98%, or 99% sequence identity across the entire length of SEQ ID NO: 11. In certain aspects, a Coronin 1a trimerization domain variant consensus sequence where one or more of the "A" and/or "D" positions in one or more of the heptad repeats of those trimerization domains are substituted with Alanine, Leucine, Isoleucine, or Valine residues that can be used in the GITRL fusion polypeptide subunits is provided as SEQ ID NO: 10. Exemplary coronin 1a wt and variant sequences that can be used in a GITRL fusion polypeptide subunit are presented in Table A.

TABLE A

Coronin 1a Coiled Coil domains and variants thereof

| Trimerization Domain | Sequence | SEQ ID NO: | ProCoil prediction score | Predicted oligomeric state |
|---|---|---|---|---|
| heptad sequence repeat | hpphcpc-hpphcpc-hpphcpc-hpphcpc-hpph; where h represents hydrophobic residues, c represents, typically, charged residues, and p represents polar (and, therefore, hydrophilic) residues. The positions of the heptad repeat can also be denoted by the lowercase letters abcdefg. | NA | | |
| hCor1a Consensus (X = Ala, Leu, Ile, or Val) | XSRXEEEXRKXQATXQELQKRXDRLEETVQAK | 10 | | |
| hCor1a wt | VSRLEEEMRKLQATVQELQKRLDRLEETVQAK | 11 | 0.101544216 | TRIMER |
| hCor1a variant 1 | VSRLEEEIRKLQATVQELQKRLDRLEETVQAK | 12 | 0.205919088 | TRIMER |
| hCor1a variant 2 | VSRIEEEIRKLQATVQELQKRLDRLEETVQAK | 13 | 0.386363142 | TRIMER |
| hCor1a variant 3 | ISRIEEEIRKLQATVQELQKRLDRLEETVQAK | 14 | 0.431631235 | TRIMER |
| hCor1a variant 4 | ISRIEEEIRKIQATVQELQKRLDRLEETVQAK | 15 | 0.509021117 | TRIMER |
| hCor1a variant 5 | ISRIEEEIRKIQATVQELQKRIDRLEETVQAK | 16 | 0.668080151 | TRIMER |
| hCor1a variant 6 | ISRIEEEIRKINATVQELQKRIDRLEETVQAK | 17 | 0.785463418 | TRIMER |
| hCor1a variant 7 | ISRIEEEIRKINATIQELQKRIDRLEETVQAK | 18 | 0.729421966 | TRIMER |

A GITRL fusion polypeptide subunit having certain trimerization domains provided herein (e.g. a coronin 1a trimerization domain or variant thereof) can exhibit improved properties when compared to other GITRL fusion polypeptide subunits having distinct trimerization domains. More specifically, a GITRL fusion polypeptide subunit having a coronin 1a trimerization domain or variant thereof can exhibit improved properties that include, but are not limited to, improved yield when expressed in transformed mammalian cell cultures; e.g. CHO cells; improved binding affinity for GITR; improved activity in various biological assays (e.g. activation of the NF-κB signaling pathway); and/or improved homogeneity when purified or partially purified. Without seeking to be limited by theory, it is believed that such improved properties of a GITRL fusion polypeptide subunit having a coronin 1a trimerization domain or variant thereof can facilitate the manufacture of GITRL fusion polypeptide subunits and/or improve the efficacy of multimeric GITRL fusion proteins in various therapeutic applications.

In addition to the GITRL receptor binding domain and the trimerization domain, a GITRL fusion polypeptide subunit as provided herein includes an immunoglobulin domain, such as a constant region or "Fc" domain. In certain aspects the present disclosure provides both a human IgG1 and IgG4 Fc domain including at least the hinge region. In certain aspects the human IgG1 or IgG4 Fc domain further includes the CH2 domain. In certain aspects the human IgG1 or IgG4 Fc domain further includes the CH3 domain. In certain aspects, the Fc domain is a human IgG1 Fc domain or variant thereof. A human IgG Fc domain can comprise a peptide having an amino acid sequence having at least 70%, 80%, 85%, 90%, 95%, 96%, 97%, 98%, 99%, or 100% sequence identity to SEQ ID NO: 21. Variants of an IgG Fc domain (e.g. an IgG1 Fc domain) that can be used include, but are not limited to, the IgG Fc domain containing one or more amino acid residues independently selected from the group consisting of 252Y, 254T, 256E, and combinations thereof, wherein the residues are numbered according to EU numbering. In certain aspects the hinge region of an IgG4 Fc region can comprise a serine to proline mutation at position 228 (according to EU numbering) which confers complete inter-heavy chain disulfide bond formation. In certain aspects the IgG4 hinge region comprises amino acids 1 to 12 of SEQ ID NO: 40. In certain aspects the human IgG4 Fc domain is an IgG4P-Fc domain with the S228P mutation of SEQ ID NO: 38.

Figure 7:
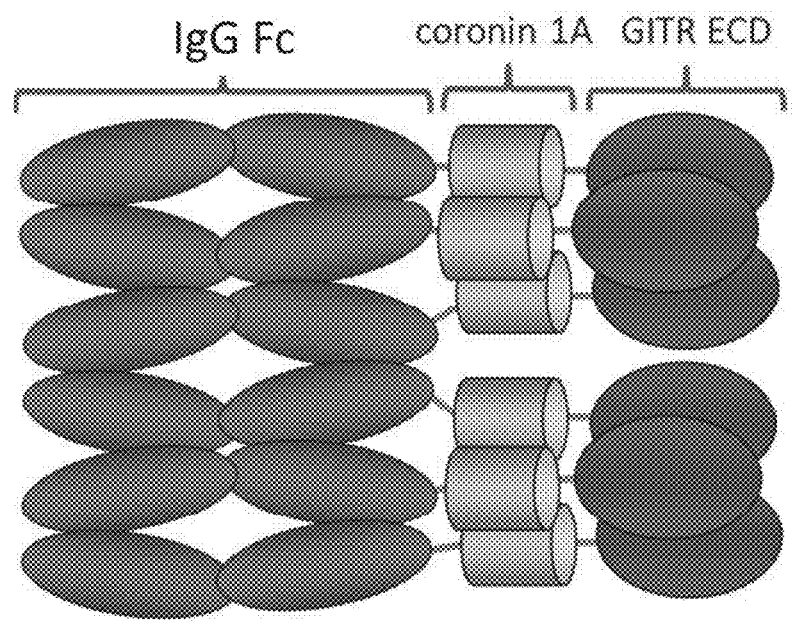
FIG. 7. Schematic of a hexameric GITRL FP molecule.

In combination with the trimerization domain which brings together three GITRL receptor binding domains, the disulfide bond formation between two IgG Fc domains results in the formation of a hexameric protein (FIG. 7). Thus, the immunoglobulin domain serves as a dimerization domain that promotes assembly between two trimeric GITRL fusion proteins into a stable hexamer (that is a multimer that contains six GITRL fusion polypeptide subunits) via interactions between unpaired immunoglobulin domains. In certain aspects, a human IgG4 Fc domain provides stability to the hexameric protein without promoting effector functions such as antibody dependent cellular cytotoxicity (ADCC) or complement-dependent cellular cytotoxicity. In other aspects, a human IgG1 Fc domain provides stability to the hexameric protein while promoting effector functions such as antibody dependent cellular cytotoxicity (ADCC) or complement-dependent cellular cytotoxicity.

In certain aspects, this disclosure provides a single-chain polypeptide subunit that self-assembles to form a hexameric protein that can specifically bind to GITR. An exemplary polypeptide subunit comprises a human IgG Fc domain, a functional trimerization domain, and a receptor binding domain of GITRL. In specific aspects the polypeptide subunit can self-assemble into a hexameric protein. In certain aspects, the polypeptide subunit is arranged, from the amino terminus to the carboxy terminus, as follows: the human IgG Fc domain, followed by the trimerization domain, followed by the GITRL receptor binding domain. The three domains can be immediately adjacent. For example, in certain aspects the carboxy terminus of the human IgG Fc domain is fused directly to the amino terminus of the trimerization domain, and the carboxy terminus of the trimerization domain is fused directly to the amino terminus of the GITRL receptor binding domain. Alternatively, two or three domains can be separated by one or more linkers, spacers, or other heterologous polypeptides. Useful linkers include, but are not limited to, a (Gly$_4$)n motif, a (Gly$_4$Ser)n motif (SEQ ID NO: 19), Ser(Gly$_4$Ser)n motif (SEQ ID NO: 22), GGGGSGGGGSGGGGSAL (SEQ ID NO: 23), or GGGGSGGGGSGGGGSA (SEQ ID NO: 24), and combinations thereof, where n is a positive integer selected from the group consisting of 1, 2, 3, 4, 5, 6, 7, 8, 9 and 10.

In certain aspects, a GITRL fusion polypeptide subunit as provided herein can specifically bind to human GITR. In certain aspects, a GITRL fusion polypeptide subunit as provided herein can specifically bind to a non-human primate GITR, e.g., cynomolgus monkey GITR or rhesus monkey GITR. In certain aspects, a GITRL fusion polypeptide subunit as provided herein does not bind to mouse GITR or to rat GITR.

A GITRL fusion polypeptide subunit as provided herein can contain one or more conservative amino acid changes, e.g., up to ten conservative changes (e.g., two substituted amino acids, three substituted amino acids, four substituted amino acids, or five substituted amino acids, etc.), provided that the changes can be made in the polypeptide without changing a biochemical function of the GITRL fusion polypeptide subunit or multimeric GITRL FP.

For example, one or more conservative changes can be made in a GITRL receptor binding domain without changing its ability to bind to GITR. Similarly, one or more conservative changes can be made in trimerization domain without altering its ability to trimerize.

GITRL fusion polypeptide subunits provided herein can also contain one or more amino acid substitutions, insertions, or deletions that block or reduce N-linked glycosylation of asparagyl residue 161 of GITRL. In certain aspects, asparagyl residue 161 of GITRL is substituted with any amino acid other than an asparagyl residue to block or reduce glycosylation. In certain aspects, asparagyl residue 161 of GITRL is substituted with an aspartyl residue, e.g., is a N161D variant of GITRL as shown in SEQ ID NO: 4. In certain aspects, N-linked glycosylation of asparagyl residue 161 of GITRL is blocked or reduced by amino acid substitutions, insertions, or deletions that disrupt the N-linked glycosylation site sequence NNT of GITRL residues 161-163 such that this sequence no longer conforms to the canonical N-linked glycosylation site sequence NX(T, S, or C). In certain embodiments, substitution of threonyl residue 163 with an amino acid residue other than serinyl or cysteinyl can be used to block or reduce N-linked glycosylation of asparagyl residue 161 of GITRL, provided that the changes can be made in the polypeptide without changing a biochemical function of the GITRL fusion polypeptide subunit or multimeric GITRL fusion protein.

Additionally, part of a polypeptide domain can be deleted without impairing or eliminating all of its functions. Similarly, insertions or additions can be made in the polypeptide chain, for example, adding epitope tags, without impairing or eliminating its functions, as described below. Other modifications that can be made without materially impairing one or more functions of a polypeptide include, for example, in vivo or in vitro chemical and biochemical modifications that incorporate unusual amino acids. Such modifications include, for example, acetylation, carboxylation, phosphorylation, glycosylation, labeling, e.g., with radionuclides, and various enzymatic modifications, as will be readily appreciated by those of ordinary skill in the art. A variety of methods for labeling polypeptides, and labels useful for such purposes, are well known in the art, and include radioactive isotopes such as $^{32}$P, fluorophores, chemiluminescent agents, enzymes, and antiligands.

The fusion polypeptide subunit can further include a heterologous agent, e.g., a stabilizing agent, an immune response modifier, or a detectable agent. In certain aspects the heterologous agent comprises one or more additional polypeptide sequences fused to the polypeptide subunit via a peptide bond, such as a signal sequence (e.g., a secretory signal sequence), a linker sequence, an amino acid tag or label, or a peptide or polypeptide sequence that facilitates purification. In certain aspects, the heterologous polypeptide can be fused to the N-terminus of the IgG-Fc domain, the heterologous polypeptide can be fused to the C-terminus of the receptor binding domain of GITRL, the heterologous polypeptide can be fused to the C-terminus of the IgG-Fc domain and to the N-terminus of the trimerization domain, or the heterologous polypeptide can be fused to the C-terminus of the trimerization domain and to the N-terminus of the receptor binding domain of GITRL. Alternatively the heterologous polypeptide can be fused internally within any of the IgG Fc domain, the trimerization domain, or the GITRL receptor binding domain, as long as the functional characteristics of the domains are maintained.

In certain aspects, the heterologous agent can be chemically conjugated to the polypeptide subunit. Exemplary heterologous agents that can be chemically conjugated to the polypeptide subunit include, without limitation, linkers, drugs, toxins, imaging agents, radioactive compounds, organic and inorganic polymers, and any other compositions which might provide a desired activity that is not provided by the polypeptide subunit itself. Specific agents include, without limitation, polyethylene glycol (PEG), a cytotoxic agent, a radionuclide, an imaging agent, biotin.

In certain aspects, the GITRL fusion polypeptide subunits as well as any trimers or hexameric proteins comprising those subunits can be used as controls, reference standards for developing or executing diagnostic assays (e.g. for dosing determinations), or research tools. For example, the disclosure provides a GITRL fusion polypeptide subunit as described above, where the GITRL receptor binding domain comprises any of SEQ ID NOs: 34, 35, 36, or 37. In certain aspects, the control, reference standard, or tool can comprise a GITRL fusion polypeptide subunit having at least 70%, 80%, 85%, 90%, 95%, 96%, 97%, 98%, 99%, 99.5%, or 100% sequence identity to SEQ ID NO: 6. In another example, the disclosure provides GITRL fusion polypeptide subunits that can form a multimeric protein as described above, but where the GITRL receptor binding domain is a mouse or rat GITRL receptor binding domain, and the Fc domain is an Fc domain of human or murine origin, and the multimerisation domain is, e.g., a trimerization domain, e.g., coronin 1a trimerization domain. This fusion protein can be used to conduct in vivo experiments in rodents. Without seeking to be limited by theory, IgG Fc domain effector functions conferred by distinct IgG isotypes in mice generally differ from those conferred by the same IgG isotype in humans. However, it has been previously shown that specific mouse IgG isotypes are considered analogous or comparable to alternative IgG isotypes in human, for example mouse IgG2a is considered analogous to human IgG1 and mouse IgG1 is considered comparable to human IgG4. As such, results obtained in mice with a given mouse IgG Fc domain isotype can be used to predict results obtained in humans with analogous or comparable human IgG isotypes.

Multimeric GITRL Fusion Proteins

A GITRL fusion polypeptide subunit as described above can self-assemble into a hexameric GITRL FP. Accordingly, the disclosure provides a hexameric protein comprising six polypeptide subunits as described above. An exemplary polypeptide subunit described in the Examples self-assembles into a hexameric protein designated herein as a "hexameric GITRL FP." A non-limiting example of an amino acid sequence of a GITRL fusion polypeptide subunit that self-assembles into a hexameric GITRL FP is provided in SEQ ID NO: 6. Nonetheless, one of ordinary skill in the art will recognize in light of the instant disclosure that numerous other sequences also fulfill the criteria set forth herein for hexameric GITRL FPs. Hexameric GITRL FPs comprising six GITRL fusion polypeptide subunits with at least 70%, 80%, 85%, 90%, 95%, 96%, 97%, 98%, 99%, 99.5%, or 100% sequence identity to SEQ ID NO: 6 are also provided herein.

In certain aspects, certain GITRL fusion polypeptide subunits provided herein can also self-assemble into a trimeric GITRL FP comprising three GITRL fusion polypeptide subunits. This could occur, for example, where an Fc domain that cannot dimerize is used in a GITRL FP to generate a trimeric protein. Examples of Fc domains that cannot dimerize and are thus suitable for production of trimeric GITRL FP include, but are not limited to, monomeric IgG1 Fc molecules (Ying et al. J Biol Chem. Jun. 1, 2012; 287(23): 19399-19408) and monovalent IgG4 molecules (Wilkinson, et al. MAbs. May 1, 2013; 5(3): 406-417).

A multimeric GITRL fusion protein as provided herein, e.g., a hexameric GITRL FP, can specifically bind to GITR as expressed on primary antigen experienced T-cells, e.g., primary antigen experienced T-cells, from human, cynomolgus monkey, rhesus monkey, or any combination thereof.

A hexameric protein as provided herein, e.g., a hexameric GITRL FP, can specifically bind to recombinant GITR. In certain aspects a hexameric protein as provided herein, e.g., a hexameric GITRL FP, can bind to recombinant human GITR with a binding affinity of about 1 nM to about 120 nM, e.g., about 10 nM to about 100 nM, e.g., about 20 nM to about 100 nM, e.g., about 60 nM to about 100 nM, all as measured by kinetic exclusion assay. For example, a hexameric protein as provided herein, e.g., a hexameric GITRL FP, can bind to recombinant human GITR with a binding affinity of about 0.1 nM, about 0.5 nM, about 1 nM, about 2 nM, about 3 nM, about 4 nM, about 5 nM, about 6 nM, about 7 nM, about 8 nM, about 9 nM, about 10 nM, about 20 nM, about 30 nM, about 40 nM, about 50 nM, about 60 nM, about 70 nM, about 80 nM, about 90 nM, about 100 nM, about 120 nM, about 250 nM or about 500 nM, all as measured by a kinetic exclusion assay. In certain aspects, a hexameric protein as provided herein, e.g., a hexameric GITRL FP, can bind to recombinant human GITR with a binding affinity of any of about 0.1 nM, about 0.5 nM, about 1 nM, about 2 nM, about 3 nM, about 4 nM, about 5 nM, about 6 nM, about 7 nM, about 8 nM, about 9 nM, about 10 nM, about 20 nM, about 30 nM, about 40 nM, about 50 nM, about 60 nM, or about 70 nM to any of about 90 nM, about 100 nM, about 120 nM, about 250 nM, or about 500 nM, all as measured by kinetic exclusion assay. In certain aspects, a hexameric protein as provided herein, e.g., a hexameric GITRL FP, can bind to recombinant human GITR with a binding affinity of about 82 nM as measured by kinetic exclusion assay. Binding affinity can be measured by a number of different methods and/or instruments, and the relative binding affinities can vary depending on the method or instrument, as is well understood by persons or ordinary skill in the art.

In another example, a hexameric protein as provided herein, e.g., GITRL FP, can bind to cynomolgus monkey GITR expressed on primary antigen experienced cynomolgus monkey T cells, for example CD4$^+$ or CD8$^+$ T cells.

In certain aspects, a hexameric protein as provided herein, e.g., GITRL FP, can induce dose-dependent proliferation of antigen experienced CD3$^+$ T cells in a plate-based assay. For example, in an in vitro assay using a hexameric protein as provided herein, e.g., GITRL, a 20% maximal proliferation response (EC$_{20}$) can be achieved in primary antigen experienced human CD3$^+$ T cells at a hexameric protein concentration of about 0.03 nM to about 0.2 nM, e.g., about 0.16 nM, a 50% maximal proliferation response (EC$_{50}$) can be achieved in primary antigen experienced human CD3$^+$ T cells at a hexameric protein concentration of about 0.2 nM to about 1 nM, e.g., about 0.4 nM, and a 90% maximal proliferation response (EC$_{90}$) can be achieved in primary antigen experienced human CD3$^+$ T cells at a hexameric protein concentration of about 0.7 nM to about 5 nM, e.g., about 1.8 nM, all as measured by thymidine incorporation.

In certain aspects, a hexameric protein as provided herein, e.g., GITRL IgG Fusion Protein, can induce dose-dependent cytokine release from antigen experienced T cells, e.g., human primary antigen experienced CD3$^+$ T cells. In certain aspects, the released cytokine is IFNγ, TNFα, IL-5, IL-10, IL-2, IL-4, IL-13, IL-8, IL-12 p70, IL-1β, or any combination thereof. In certain aspects, the cytokine is IFNγ, TNFα, IL-5, IL-10, or any combination thereof. Similarly, a hexameric protein as provided herein, e.g., GITRL FP, can enhance Tcell proliferation and cytokine release in primary antigen experienced cynomolgus monkey T cells and in primary antigen experienced rhesus monkey T cells.

In additional aspects, a hexameric protein as provided herein, e.g., GITRL FP can activate the NFκB pathway in GITR expressing T cells. For example, a hexameric protein as provided herein, e.g., GITRL FP can activate the NFκB pathway in GITR-expressing Jurkat NFκB-luciferase reporter cells that produce luciferase in response to stimulation of the NFκB signaling pathway, with an EC$_{50}$ of about 20 pM to about 300 pM, e.g., about 182 pM for hexameric GITRL IgG1FP, and 289 pM for hexameric GITRL IgG4FP. Alternatively, a hexameric protein as provided herein, e.g., GITRL FP can activate the NFκB pathway in cells expressing human GITR, cynomolgus monkey GITR or rhesus monkey GITR.

In yet another aspect a hexameric protein as provided herein, e.g., GITRL FP can facilitate cancer treatment, e.g., by slowing tumor growth, stalling tumor growth, or reducing the size of existing tumors, when administrated as an effective dose to a subject in need of cancer treatment. In certain aspects the facilitation of cancer treatment can be achieved in the presence of T cells. In certain aspects, a hexameric protein as provided herein, e.g., GITRL FP, when administered as an effective dose to a subject in need of treatment, can reduce tumor growth by at least 10%, at least 20%, at least 30%, at least 40%, at least 50%, at least 60%, at least 70%, at least 80%, at least 90%, at least 95%, at least 98%, or at least 100% compared to administration of an isotype-matched control molecule.

In yet another aspect a hexameric protein as provided herein, e.g., GITRL FP can facilitate treatment of viral infections, e.g., by slowing viral multiplication, stalling viral multiplication, or reducing infection reoccurrance or infection reoccurance frequency, when administrated as an effective dose to a subject in need of the treatment, e.g. a subject infected with the virus. Such subjects can have either a chronic or a latent viral infection. In certain aspects, the treatments are of subjects having latent viral infections and reduce infection reoccurrence or infection reoccurrence frequency in comparison to subjects treated with a placebo. In certain aspects the facilitation of treatment of the viral infection can be achieved in the presence of T cells. In certain aspects, a hexameric protein as provided herein, e.g., GITRL FP, when administered as an effective dose to a subject in need of treatment, can reduce viral load by at least 10%, at least 20%, at least 30%, at least 40%, at least 50%, at least 60%, at least 70%, at least 80%, at least 90%, at least 95%, at least 98% or at least 100% compared to administration of an isotype-matched control molecule. In certain aspects, a hexameric protein as provided herein, e.g., GITRL FP, when administered as an effective dose to a subject in need of treatment, can reduce the reoccurrence of the viral infection by at least 10%, at least 20%, at least 30%, at least 40%, at least 50%, at least 60%, or at least 70%, at least 80%, at least 90%, at least 95%, at least 98% or at least 100% compared to administration of an isotype-matched control molecule.

In yet further aspects, a hexameric protein as provided herein, e.g., a GITRL IgG4 Fusion Protein, can induce proliferation of antigen experienced, GITR-expressing T cells through binding to GITR, but does not substantially trigger complement-dependent or antibody-dependent cytotoxicity against the antigen experienced T cells. Moreover in certain aspects, a hexameric protein as provided herein, e.g., a multimeric GITRL IgG1 Fusion Protein, can induce proliferation of antigen experienced, GITR-expressing T cells through binding to GITR, but does bind to C1q and trigger Fc receptor-mediated antibody-dependent cellular cytotoxicity or phagocytosis of antigen experienced $CD4^+$ T cells, in particular $FOXP3^+$ $CD4^+$ regulatory T cells.

Polynucleotides Encoding GITRL IgG Fusion Polypeptide Subunits

The disclosure further provides a polynucleotide comprising a nucleic acid that encodes a GITRL fusion polypeptide subunit or a hexameric protein as provided herein, e.g., GITRL FP. An exemplary polynucleotide sequence that encodes a GITRL fusion polypeptide subunit is represented by SEQ ID NO: 5. In certain aspects, nucleic acid sequences encoding the IgG Fc domain, the trimerization domain and the GITRL receptor binding domains are joined in a 5' to 3' orientation, e.g., contiguously linked in a 5' to 3' orientation. In other aspects, the provided polynucleotide can further comprise a signal sequence encoding, e.g., a secretory signal peptide or membrane localization sequence. Polynucleotides encoding any and all GITRL fusion polypeptide subunits or multimeric, e.g., hexameric proteins comprising the subunits, are provided by this disclosure.

In certain aspects, the disclosure provides a polynucleotide comprising a nucleic acid that encodes GITRL fusion polypeptide subunit. In certain aspects the nucleic acid sequence comprises SEQ ID NO: 5.

Polynucleotides encoding a GITRL fusion polypeptide subunit, or a hexameric protein as provided herein, e.g., GITRL FP include deoxyribonucleotide (DNA, cDNA) or ribodeoxyribonucleotide (RNA) sequences, or modified forms of either nucleotide, which encode the fusion polypeptides described herein. The term includes single and double stranded forms of DNA and/or RNA.

Also provided are polynucleotides comprising nucleic acid sequences comprising one or a small number of deletions, additions and/or substitutions. Such changes can be contiguous or can be distributed at different positions in the nucleic acid. A substantially identical nucleic acid sequence can, for example, have 1, or 2, or 3, or 4, or even more nucleotide deletions, additions and/or substitutions. In certain aspects, the one or more deletions, additions and/or substitutions do not alter the reading frame encoded by the polynucleotide sequence, such that a modified ("mutant") but substantially identical polypeptide is produced upon expression of the nucleic acid.

The similarity between amino acid (and/or nucleic acid) sequences is expressed in terms of the similarity between the sequences, otherwise referred to as sequence identity. Sequence identity is frequently measured in terms of percentage identity (or similarity); the higher the percentage, the more similar are the primary activated structures of the two sequences. "Percent (%) identity" is defined herein as the percentage of amino acid residues in a candidate sequence that are identical with the amino acid residues in a selected sequence, after aligning the sequences and introducing gaps in the candidate and/or selected sequence, if necessary, to achieve the maximum percent sequence identity, and not considering any conservative amino acid substitutions as part of the sequence identity.

Thus, a polynucleotide comprising a nucleic acid that encodes a GITRL fusion polypeptide subunit, or a hexameric protein as provided herein, e.g., GITRL FP, can be at least about 70%, at least about 75%, at least about 80%, at least about 85%, at least about 90%, at least about 95%, or at least 96%, frequently at least 97%, 98%, or 99% identical to SEQ ID NO: 5 or to at least one sub sequence thereto. Alignment for purposes of determining percent homology (i.e., sequence similarity) or percent identity can be achieved in various ways that are within the skill in the art, for instance, using publicly or proprietary algorithms. For instance, sequence similarity can be determined using pairwise alignment methods, e.g., BLAST, BLAST-2, ALIGN, or ALIGN-2 or multiple sequence alignment methods such as Megalign (DNASTAR), ClustalW or T-Coffee software. Those skilled in the art can determine appropriate scoring functions, e.g., gap penalties or scoring matrices for measuring alignment, including any algorithms needed to achieve optimal alignment quality over the full-length of the sequences being compared. In addition, sequence alignment can be achieved using structural alignment methods (e.g., methods using secondary or tertiary structure information to align two or more sequences), or hybrid methods combining sequence, structural, and phylogenetic information to identify and optimally align candidate protein sequences.

The NCBI Basic Local Alignment Search Tool (BLAST) (Altschul et al., J. Mol. Biol. (1990) 215:403) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Thus, a nucleic acid sequence that is substantially identical, or substantially similar to SEQ ID NO: 5 is encompassed within the present disclosure. A sequence is substantially identical to SEQ ID NO: 5 if the sequence is identical, on a nucleotide by nucleotide basis, with at least a subsequence of the reference sequence (e.g., SEQ ID NO: 4). Such nucleic acids can include, e.g., insertions, deletions, and substitutions relative to SEQ ID NO: 4. For example, such nucleic acids can be at least about 70%, 80%, 90%, 95%, 96%, 97%, 98% or even 99% identical to a reference nucleic acid, or encode a polypeptide at least about 70%, 80%, 90%, 95%, 96%, 97%, 98% or even 99% identical to the reference polypeptide sequence, e.g., SEQ ID NO: 4.

Additionally, a polynucleotide comprising a nucleic acid encoding a GITRL fusion polypeptide subunit, or a hexameric protein as provided herein, e.g., GITRL FP, can also include polynucleotide sequences, such as expression regulatory sequences and/or vector sequences that facilitate the expression or replication of the nucleic acids. Similarly, a polynucleotide comprising a nucleic acid encoding a GITRL fusion polypeptide subunit, or a hexameric protein as provided herein, e.g., GITRL FP, can include additional coding sequences that confer functional attributes on the encoded polypeptide. Such sequences include, but are not limited to, secretory signal sequences and membrane localization signals. A non-limiting example of a nucleic acid encoding a signal peptide that is operably linked to a nucleic acid encoding a GITRL fusion polypeptide subunit is provided in SEQ ID NO: 7.

A polynucleotide comprising a nucleic acid encoding a GITRL fusion polypeptide subunit, or a hexameric protein as provided herein, e.g., GITRL FP, can be introduced into a vector, such as a eukaryotic expression vector, by conventional techniques. Accordingly, the disclosure provides a vector comprising a polynucleotide as provided herein. An expression vector is designed to permit the transcription of the polynucleotide sequence encoding a GITRL fusion polypeptide subunit, or a hexameric protein as provided herein, e.g., GITRL FP in cells by providing regulatory sequences that initiate and enhance the transcription of the cDNA and ensure its proper splicing and polyadenylation. Numerous expression vectors are known to those of skill in the art, and are available commercially, or can be assembled from individual components according to conventional molecular biology procedures.

The choice of expression control sequence and expression vector will depend upon the choice of host cell. A wide variety of expression host/vector combinations can be employed. Useful expression vectors for eukaryotic hosts include, for example, vectors comprising expression control sequences from SV40, bovine papilloma virus, adenovirus and cytomegalovirus. Useful expression vectors for bacterial hosts include known bacterial plasmids, such as plasmids from E. coli, including pCR 1, pBR322, pMB9 and their derivatives, wider host range plasmids, such as M13 and filamentous single-stranded DNA phages.

Suitable host cells for expression of a GITRL fusion polypeptide subunit, or a hexameric protein as provided herein, e.g., GITRL FP include prokaryotes, yeast, insect or higher eukaryotic cells under the control of appropriate promoters. Prokaryotes include gram negative or gram positive organisms, for example E. coli or bacilli. Higher eukaryotic cells include established cell lines of mammalian origin as described below. Cell-free translation systems could also be employed. Additional information regarding methods of protein production, including antibody production, can be found, e.g., in U.S. Patent Publication No. 2008/0187954, U.S. Pat. Nos. 6,413,746 and 6,660,501, and International Patent Publication No. WO 2004/009823, each of which is hereby incorporated by reference herein in its entirety.

Also provided is a host cell comprising a polynucleotide or vector as provided herein. Various mammalian or insect cell culture systems can be advantageously employed to express polypeptide subunits or hexameric proteins provided herein. Expression of recombinant proteins in mammalian cells can be performed because such proteins are generally correctly folded, appropriately modified and completely functional. Examples of suitable mammalian host cell lines include HEK-293 and HEK-293T, the COS-7 lines of monkey kidney cells, described by Gluzman (Cell 23:175, 1981), and other cell lines including, for example, L cells, C127, 3T3, Chinese hamster ovary (CHO), HeLa and BHK cell lines. Mammalian expression vectors can comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences. Baculovirus systems for production of heterologous proteins in insect cells are reviewed by Luckow and Summers, BioTechnology 6:47 (1988).

The expression and purification of proteins, such as a GITRL fusion polypeptide subunit, or a hexameric protein as provided herein, e.g., GITRL FP, can be performed using standard laboratory techniques. Examples of such methods are discussed or referenced herein. After expression, purified proteins have many uses, including for instance functional analyses, antibody production, and diagnostics, as well as the prophylactic and therapeutic uses described below. For example, polypeptide subunits or hexameric proteins provided herein can be used to produce pharmaceutical compositions, including vaccine compositions suitable for prophylactic and/or therapeutic administration.

A GITRL fusion polypeptide subunit, or a hexameric protein as provided herein, e.g., GITRL FP produced by a transformed host, can be purified according to any suitable method. Such standard methods include chromatography (e.g., ion exchange, affinity and sizing column chromatography), centrifugation, differential solubility, or by any other standard technique for protein purification. Affinity tags such as hexahistidine, maltose binding domain, influenza coat sequence and glutathione-S-transferase can be attached to the protein to allow easy purification by passage over an appropriate affinity column. Isolated proteins can also be physically characterized using such techniques as proteolysis, nuclear magnetic resonance and x-ray crystallography.

For example, supernatants from systems that secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Finally, one or more reversed-phase high performance liquid chromatography (RP-HPLC) steps employing hydrophobic RP-HPLC media, e.g., silica gel having pendant methyl or other aliphatic groups, can be employed to further purify an influenza B/Yamagata virus-binding molecule. Some or all of the foregoing purification steps, in various combinations, can also be employed to provide a homogeneous recombinant protein.

A GITRL fusion polypeptide subunit, or a hexameric protein as provided herein, e.g., GITRL FP produced in bacterial culture, can be isolated, for example, by initial extraction from cell pellets, followed by one or more concentration, salting-out, aqueous ion exchange or size exclusion chromatography steps. High performance liquid chromatography (HPLC) can be employed for final purification steps. Microbial cells employed in expression of a recombinant protein can be disrupted by any convenient method, including freeze-thaw cycling, sonication, mechanical disruption, or use of cell lysing agents.

Pharmaceutical Compositions and Administration Methods

Methods of preparing and administering a hexameric protein as provided herein, e.g., GITRL FP as provided herein, to a subject in need thereof, e.g., to enhance an immune response in a cancer patient, e.g., to inhibit or reduce tumor growth, or patient having a viral infection, e.g., to reduce viral load or to reduce reoccurance of viral infection, are well known to or can be readily determined by those skilled in the art. The route of administration of a hexameric protein as provided herein, e.g., GITRL FP can be, for example, oral, parenteral, by inhalation or topical. The term parenteral as used herein includes, e.g., intravenous, intraarterial, intraperitoneal, intramuscular, subcutaneous, rectal, or vaginal administration. While all these forms of administration are clearly contemplated as suitable forms, another example of a form for administration would be a solution for injection, in particular for intravenous or intraarterial injection or drip. Usually, a suitable pharmaceutical composition can comprise, without limitation, a buffer (e.g. acetate, phosphate or citrate buffer), a surfactant (e.g. polysorbate), a stabilizer agent (e.g. human albumin), etc. In other methods compatible with the teachings herein, a hexameric protein as provided herein, e.g., GITRL FP as provided herein can be delivered directly to the site of the adverse cellular population thereby increasing the exposure of the diseased tissue to the therapeutic agent.

Certain pharmaceutical compositions provided herein can be orally administered in an acceptable dosage form including, e.g., capsules, tablets, aqueous suspensions or solutions. Certain pharmaceutical compositions also can be administered by nasal aerosol or inhalation. Such compositions can be prepared as solutions in saline, employing benzyl alcohol or other suitable preservatives, absorption promoters to enhance bioavailability, and/or other conventional solubilizing or dispersing agents.

The amount of a hexameric protein as provided herein, e.g., GITRL FP that can be combined with carrier materials to produce a single dosage form will vary depending upon the subject treated and the particular mode of administration. The composition can be administered as a single dose, multiple doses or over an established period of time in an infusion. Dosage regimens also can be adjusted to provide the optimum desired response (e.g., a therapeutic or prophylactic response).

By "therapeutically effective dose or amount" or "effective amount" is intended an amount of a hexameric protein as provided herein, e.g., GITRL FP, that when administered brings about a positive therapeutic response with respect to treatment of a patient with a disease or condition to be treated.

Kits

This disclosure further provides kits that comprise a hexameric protein as provided herein, e.g., GITRL FP described herein and that can be used to perform the methods described herein. In certain embodiments, a kit comprises at least one purified a hexameric protein as provided herein, e.g., GITRL FP, in one or more containers. One skilled in the art will readily recognize that the disclosed hexameric protein as provided herein, e.g., GITRL FP, can be readily incorporated into one of the established kit formats that are well known in the art.

Immunoassays

A hexameric protein as provided herein, e.g., GITRL FP can be assayed for specific and/or selective binding by any method known in the art. The immunoassays that can be used include but are not limited to competitive and non-competitive assay systems using techniques such as Western blots, radioimmunoassays, ELISA (enzyme linked immunosorbent assay), fluorescent focus assay (FFA), microneutralization assay, hemagglutination inhibition assay (HAI), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, to name but a few. Such assays are routine and well known in the art (see, e.g., Ausubel et al., eds, (1994) Current Protocols in Molecular Biology (John Wiley & Sons, Inc., NY) Vol. 1, which is incorporated by reference herein in its entirety). FFA, microneutralization assay, and HAI will be discussed in details in the Examples below.

Methods and reagents suitable for determination of binding characteristics of a hexameric protein as provided herein are known in the art and/or are commercially available. Equipment and software designed for such kinetic analyses are commercially available (e.g., BIAcore®, BIAevaluation® software, GE Healthcare; KINEXA® Software, Sapidyne Instruments).

Methods of Immune Enhancement and Treatment

The enhancement of an antigen-specific immune response in a subject (e.g., a mammalian subject, such as a human subject) by engaging GITR on antigen experienced T cells, e.g., antigen experienced $CD4^+$ or $CD8^+$ T cells during or after antigen activation can be accomplished using a wide variety of methods. The method of choice will primarily depend upon the type of antigen against which it is desired to enhance the immune response, and various methods available are discussed below. Whatever method is selected, a hexameric protein as provided herein, e.g., GITRL FP, can be administered to a subject, e.g., a human patient such that it is presented to T cells of the subject during or shortly after priming of the T cells by antigen. Exemplary methods of activating an immune response in a subject, e.g., a human subject using an OX40 hexameric protein, are presented in US Pub. No. 2016/0024176, which is incorporated by reference herein in its entirety, and can be adapted for use with the GITRL FPs provided herein.

In certain aspects, the disclosure provides a method to promote survival or proliferation of antigen experienced T cells, e.g., antigen experienced $CD4^+$ or $CD8^+$ T cells, comprising contacting the antigen experienced T cells, e.g., antigen experienced $CD4^+$ or $CD8^+$ T cells, with a hexameric protein as provided herein, e.g., GITRL FP, under conditions where the hexameric protein can specifically bind to GITR on the surface of the T cells, e.g., antigen experienced $CD4^+$ or $CD8^+$ T cells. In certain aspects the contacting is in vitro. In certain aspects the contacting is in vivo, e.g. via administration of an effective dose of the hexameric protein to a subject in need of treatment. In certain aspects the contacting can occur at the same time as T-cell activation, e.g., antigen activation, in certain aspects the contacting can occur after T-cell activation.

In further aspects, the disclosure provides a method of enhancing cytokine release from antigen experienced T cells, e.g., antigen experienced CD4$^+$ or CD8$^+$ T cells, comprising contacting the antigen experienced T cells, e.g., antigen experienced CD4$^+$ or CD8$^+$ T cells, with a hexameric protein as provided herein, e.g., GITRL FP, wherein the hexameric protein can specifically bind to GITR on the surface of the antigen experienced T cells, e.g., antigen experienced CD4$^+$ or CD8$^+$ T cells. In certain aspects the contacting is in vitro. In certain aspects the contacting is in vivo, e.g. via administration of an effective dose of the hexameric protein to a subject in need of treatment. In certain aspects the contacting can occur at the same time as T-cell-activation, e.g., antigen activation, in certain aspects the contacting can occur after T-cell activation. In certain aspects the cytokine can be IFNγ, TNFα, IL-5, IL-10, IL-2, IL-4, IL-13, IL-8, IL-12 p70, IL-1β, GM-CSF, or any combination thereof. In certain aspects the cytokine is IFNγ, TNFα, IL-5, IL-10, IL-4, IL-13, GM-CSF, or any combination thereof.

In certain aspects, the antigen experienced T cells, e.g., antigen experienced CD4$^+$ or CD8$^+$ T cells are human CD4$^+$ or CD8$^+$ T cells, cynomolgus monkey CD4$^+$ or CD8$^+$ T cells, rhesus monkey CD4$^+$ or CD8$^+$ T cells, or a combination thereof.

The disclosure further provides a method of promoting T-cell activation, comprising contacting T cells with a hexameric protein as provided herein, e.g., GITRL Fusion Protein, wherein the hexameric protein can specifically bind to GITR on the surface of the T cells. In certain aspects the contacting occurs in the presence of antigen, e.g., a tumor antigen. In certain aspects the method further comprises cross-linking of the hexameric GITRL Fusion Protein through interaction of the IgG-Fc domain of the GITRL FP with a cell expressing FcγR, e.g., a B cell, monocyte, macrophage, myeloid or plasmacytoid dendritic cell, follicular dendritic cell, Langerhans cell, endothelial cell, NK cell, neutrophil, eosinophil, platelet, mast cell, a CD45$^+$ cell from a primary human tumor or tumor-draining or non-draining lymph node, a CD45$^+$ cell from other secondary or tertiary lymphoid structures, or a combination thereof. In certain aspects, the T-cell activation can be measured as stimulation of the NFκB signal transduction pathway. In certain aspects, the GITRL FP that promotes T-cell activation is a GITRL IgG1 FP, a GITRL IgG4 FP, or variant thereof. In certain aspects the contacting is in vitro. In certain aspects the contacting is in vivo, e.g. via administration of an effective dose of the hexameric protein to a subject in need of treatment.

Also provided herein are methods for treating cancer, comprising administration of GITRL FP, and an OX40 agonist (e.g., an OX40 ligand fusion protein or OX40 agonist antibody). Administration of GITRL FP and OX40 ligand fusion protein resulted in a reduction in tumor volume and increased survival in a mouse tumor model. In certain aspects, a patient presenting with a solid tumor is administered GITRL FP and an OX40 ligand fusion protein (e.g., MEDI6383).

Effective treatment with a cancer therapy including GITRL FP and OX40 agonist includes, for example, reducing the rate of progression of the cancer, retardation or stabilization of tumor or metastatic growth, tumor shrinkage and/or tumor regression, either at the site of a primary tumor, or in one or more metastases. In some aspects the reduction or retardation of tumor growth can be statistically significant. A reduction in tumor growth can be measured by comparison to the growth of patient's tumor at baseline, against an expected tumor growth, against an expected tumor growth based on a large patient population, or against the tumor growth of a control population. In other embodiments, the methods of the invention increase survival.

Clinical response to administration of a cancer therapy including GITRL FP and OX40 agonist can be assessed using diagnostic techniques known to clinicians, including but not limited to magnetic resonance imaging (MRI) scan, x-radiographic imaging, computed tomographic (CT) scan, flow cytometry or fluorescence-activated cell sorter (FACS) analysis, histology, gross pathology, and blood chemistry, including but not limited to changes detectable by ELISA, RIA, and chromatography.

The disclosure further provides methods of treating cancer or viral infections in a subject, comprising administering to a subject in need of treatment an effective amount of a hexameric protein as provided herein, e.g., GITRL FP, or a composition or formulation comprising the hexameric protein. In certain aspects, the cancer is a solid tumor. According to this method, administration of the hexameric protein or composition can inhibit tumor growth; can promote tumor reduction, or both. In certain aspects, the tumor growth inhibition is achieved in the presence of T cells.

The terms "cancer", "tumor", "cancerous", and "malignant" refer to or describe the physiological condition in mammals that is typically characterized by unregulated cell growth. Examples of cancers include but are not limited to, carcinoma including adenocarcinomas, lymphomas, blastomas, melanomas, sarcomas, and leukemias. More particular examples of such cancers include squamous cell cancer, small-cell lung cancer, non-small cell lung cancer, gastrointestinal cancer, Hodgkin's and non-Hodgkin's lymphoma, pancreatic cancer, glioblastoma, glioma, cervical cancer, ovarian cancer, liver cancer such as hepatic carcinoma and hepatoma, bladder cancer, breast cancer (including hormonally mediated breast cancer, see, e.g., Innes et al. (2006) Br. J. Cancer 94:1057-1065), colon cancer, colorectal cancer, endometrial carcinoma, myeloma (such as multiple myeloma), salivary gland carcinoma, kidney cancer such as renal cell carcinoma and Wilms' tumors, basal cell carcinoma, melanoma, prostate cancer, vulval cancer, thyroid cancer, testicular cancer, esophageal cancer, haematological cancers including, but not limited to, acute myeloid leukemia (AML) and multiple myeloma (MM), various types of head and neck cancer including, but not limited to, squamous cell cancers, and cancers of mucinous origins, such as, mucinous ovarian cancer, cholangiocarcinoma (liver) and renal papillary carcinoma. In certain embodiments, the haematological cancer is selected from the group consisting of Hodgkins lymphoma, non-Hodgkins lymphoma, multiple myeloma, acute lymphoblastic leukemia, acute myelogenous leukemia, chronic lymphocytic leukemia, and chronic myelogenous leukemia.

Some embodiments are directed to a method of preventing or treating a cancer or a viral infection in a subject in need thereof, comprising administering to the subject an effective amount of a hexameric protein as provided herein, e.g., GITRL FP, a composition or formulation comprising the hexameric protein, or a polynucleotide, a vector, or a host cell as described herein.

Methods of treating viral infections in subjects in need thereof comprising administering to the subject an effective amount of the hexameric protein or a composition comprising the hexameric protein are also provided. In certain embodiments, the viral infection can be a chronic or a latent viral infection. Such chronic viral infections are viral infections characterized by weeks, months, or years of viral infection where virion multiplication occurs. Such latent viral infections are viral infections characterized by a period where virions are not multiplying. Subjects in need thereof can in certain embodiments be identified by performing an assay diagnostic for the presence of the virus in the subject or in a sample obtained from the subject. In certain embodiments, the treatment can provide for a decrease in viral load, decrease in viral reactivation, amelioration of symptoms associated with said infection, or the combination thereof. In certain embodiments, the decrease in viral load, reactivation, or symptoms is in comparison to control subject treated with a placebo. In certain embodiments of any of the aforementioned methods, the viral infection is by a virus selected from the group consisting of Human Immunodeficiency Virus (HIV), Hepatitis B virus, Hepatitis C virus, measles, Epstein-Barr virus (EBV), Cytomegalovirus (CMV), adenovirus (AdV), Human Papillomavirus (HPV), Herpes Simplex Virus (HSV), Varicella-Zoster virus (VZV), and combinations thereof.

The compositions of the disclosure can be administered by any suitable method, e.g., parenterally, intraventricularly, orally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

The disclosure further provides a method of enhancing an immune response in a subject comprising administering to a subject in need thereof a therapeutically effective amount of a hexameric protein as provided herein, e.g., GITRL FP, or a composition or formulation comprising the hexameric protein.

The subject to be treated can be any animal, e.g., mammal, in need of treatment, in certain aspects, subject is a human subject.

In its simplest form, a preparation to be administered to a subject is a hexameric protein as provided herein, e.g., GITRL FP, administered in conventional dosage form, and preferably combined with a pharmaceutical excipient, carrier or diluent as described elsewhere herein.

A hexameric protein as provided herein, e.g., GITRL FP, can be administered by any suitable method as described elsewhere herein, e.g., via IV infusion. In certain aspects, a hexameric protein as provided herein, e.g., GITRL FP, can be introduced into a tumor, or in the vicinity of a tumor cell.

All types of tumors are potentially amenable to treatment by this approach including, without limitation, carcinoma of the breast, lung, pancreas, ovary, kidney, colon and bladder, as well as melanomas, sarcomas and lymphomas.

T Cell Priming Agents

Methods of treating cancer in subjects in need thereof comprising administering to the subject an effective amount of the hexameric protein or a composition comprising the hexameric protein in combination with a T cell priming agent are also provided. In certain aspects, the T-cell priming agent is a DNA vaccine plus an adjvant. In specific aspects, this combination is, e.g., E7 Synthetic Loing Peptide (SLP) and CpG Oligodeoxynucleotide. In further aspects, the T cell priming agent is an epigenetic modifier, e.g, 5-aza-2'-deoxycytidine or histone modifiers such as HDAC inhibitors. In additional aspects, the T cell priming agent is a virus, e.g., Vaccinia, Listeria, or Newcastle Disease Virus.

* * *

This disclosure employs, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Sambrook et al., ed. (1989) Molecular Cloning A Laboratory Manual (2nd ed.; Cold Spring Harbor Laboratory Press); Sambrook et al., ed. (1992) Molecular Cloning: A Laboratory Manual, (Cold Springs Harbor Laboratory, NY); D. N. Glover ed., (1985) DNA Cloning, Volumes I and II; Gait, ed. (1984) Oligonucleotide Synthesis; Mullis et al. U.S. Pat. No. 4,683,195; Hames and Higgins, eds. (1984) Nucleic Acid Hybridization; Hames and Higgins, eds. (1984) Transcription And Translation; Freshney (1987) Culture Of Animal Cells (Alan R. Liss, Inc.); Immobilized Cells And Enzymes (IRL Press) (1986); Perbal (1984) A Practical Guide To Molecular Cloning; the treatise, Methods In Enzymology (Academic Press, Inc., N.Y.); Miller and Calos eds. (1987) Gene Transfer Vectors For Mammalian Cells, (Cold Spring Harbor Laboratory); Wu et al., eds., Methods In Enzymology, Vols. 154 and 155; Mayer and Walker, eds. (1987) Immunochemical Methods In Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor, N.Y., (1986); and in Ausubel et al. (1989) Current Protocols in Molecular Biology (John Wiley and Sons, Baltimore, Md.).

General principles of antibody engineering are set forth in Borrebaeck, ed. (1995) Antibody Engineering (2nd ed.; Oxford Univ. Press). General principles of protein engineering are set forth in Rickwood et al., eds. (1995) Protein Engineering, A Practical Approach (IRL Press at Oxford Univ. Press, Oxford, Eng.). General principles of antibodies and antibody-hapten binding are set forth in: Nisonoff (1984) Molecular Immunology (2nd ed.; Sinauer Associates, Sunderland, Mass.); and Steward (1984) Antibodies, Their Structure and Function (Chapman and Hall, New York, N.Y.). Additionally, standard methods in immunology known in the art and not specifically described are generally followed as in Current Protocols in Immunology, John Wiley & Sons, New York; Stites et al., eds. (1994) Basic and Clinical Immunology (8th ed; Appleton & Lange, Norwalk, Conn.) and Mishell and Shiigi (eds) (1980) Selected Methods in Cellular Immunology (W.H. Freeman and Co., NY).

Standard reference works setting forth general principles of immunology include Current Protocols in Immunology, John Wiley & Sons, New York; Klein (1982) J., Immunology: The Science of Self-Nonself Discrimination (John Wiley & Sons, NY); Kennett et al., eds. (1980) Monoclonal Antibodies, Hybridoma: A New Dimension in Biological Analyses (Plenum Press, NY); Campbell (1984) "Monoclonal Antibody Technology" in Laboratory Techniques in Biochemistry and Molecular Biology, ed. Burden et al., (Elsevier, Amsterdam); Goldsby et al., eds. (2000) Kuby Immunology (4th ed.; H. Freemand & Co.); Roitt et al. (2001) Immunology (6th ed.; London: Mosby); Abbas et al. (2005) Cellular and Molecular Immunology (5th ed.; Elsevier Health Sciences Division); Kontermann and Dubel (2001) Antibody Engineering (Springer Verlag); Sambrook and Russell (2001) Molecular Cloning: A Laboratory Manual (Cold Spring Harbor Press); Lewin (2003) Genes VIII (Prentice Hall 2003); Harlow and Lane (1988) Antibodies: A Laboratory Manual (Cold Spring Harbor Press); Dieffenbach and Dveksler (2003) PCR Primer (Cold Spring Harbor Press).

All of the references cited above, as well as all references cited herein, are incorporated herein by reference in their entireties.

The following examples are offered by way of illustration and not by way of limitation.

EXAMPLES

TABLE B

List of Abbreviations and Definitions of Terms

| Abbreviation or Term | Definition |
|---|---|
| A | Alanine |
| ADCC | Antibody-dependent cellular cytotoxicity |
| ° C. | Degrees Celsius |
| CDC | Complement-dependent cytotoxicity |
| CR | complete response |
| Cyno | cynomolgus |
| F | Phenylalanine |
| FACS | Fluorescence Activated Cell Sorting |
| FBS | Fetal bovine serum |
| LC-QTOF MS | liquid chromatography coupled with quadruple time of flight mass spectrometry |
| M | Molarity |
| mAb | monoclonal antibody |
| hGITRL | human GITRL |
| μg | micrograms |
| MFI | Mean fluorescence intensity |
| min | Minutes |
| mL | Milliliter |
| Multimeric mGITRL FP | A multimeric mouse GITR ligand mouse IgG Fusion Protein |
| NIP228 | A human monoclonal antibody against 4-hydroxy-3-iodo-5-nitrophenylacetic acid |
| NK | Natural killer |
| PBS | Phosphate buffered saline |
| pM | Picomolar |
| RBD | receptor binding domain |
| Rh | Recombinant human |
| ROA | route of administration |
| rpm | Revolutions per minute |
| RT | Room temperature |
| SC | subcutaneous |
| SD | Standard Deviation |
| TCR | T cell receptor |
| TGI | tumor growth inhibition |
| TNFR | Tumor necrosis factor receptor |
| Treg | T regulatory |
| V | volume |

Example 1

Engineering of GITRL IgG Fc Fusion Protein

Identification of a Suitable Human Trimerization Motif that could be Utilized for Generating a Multimeric Human GITRL-FP Molecule Efforts to generate a human hexameric GITRL FP had originally focused on the use of the GCN4 pII trimerization motif to stabilize the GITRL trimer and form a hexameric protein. This motif, however, is derived from a yeast protein and the administration of GITRL FP containing a non-human motif to humans may result in immunogenicity. Therefore, it was considered desirable to generate an equivalent GITRL FP containing a trimerization motif derived from a human protein. Amino acid sequences from 51 proteins that form trimeric coiled-coil motifs, as demonstrated by their three-dimensional crystal structure or those of orthologs, were identified via the Protein Data Bank (PDB; accessible through the internet via the world wide web site "wwpdb.org") and a subset of 4 coiled-coil motifs were selected for incorporation into GITRL FP molecules for empirical experimental testing.

Methods

The three-dimensional crystal structures of coronin-1A (PDB code: 2akf), matrilin 1 (1aq5), langerin (3kqg) and dystrophia myotonica kinase DMPK (PDB code: 1wt6) coiled-coil motifs were analyzed using PyMol Visualisation Graphics software.

Results

Following a search of the Protein Data Bank (PDB) for trimeric coiled coil protein sequences that identified 51 candidate sequences, four sequences were selected for use in generating multimeric GITRL FPs (Table 1-1). These four sequences were coiled-coil sequences from human proteins coronin 1a, matrilin 1, langerin and DMPK. The structure of the coiled-coil motif from mouse coronin 1a (PDB code: 2akf) is reported to be stable trimer in solution (Kammerer, R. A. et al. PNAS, vol: 102, p13891-13896 (2005)). The human coronin 1a coiled-coil sequence shows high sequence identity to the mouse protein (78.1% sequence identity) so this sequence was predicted to form a trimeric coiled-coil structure. Similarly, the structure of the coiled-coil motif from chicken matrilin 1 (PDB code: 1aq5) is reported to be a trimer (Dames, S. A. et al. NAT. STRUCT. BIOL. 5:687-691 (1998); PDB code: 1aq5). The human matrilin 1 coiled-coil sequence was predicted to form a trimeric coiled-coil structure based on its high sequence identity (60.0% sequence identity) to the chicken ortholog. The human langerin (PDB code: 3kqg) and human DMPK (PDB code: 1wt6) coiled-coil sequences also are reported to be trimeric (Feinberg, H. et al., J. BIOL. CHEM. 285:13285-13293 (2010)) and were selected for use in generating multimeric human GITRL fusion proteins.

To provide additional coiled-coil sequences for use in the GITRL fusion proteins, variants of the wild-type coiled-coil sequences from human coronin-1A, matrilin-1, langerin and DMPK were produced. To generate these variant sequences the online implementation of the ProCoil algorithm (accessible through the internet via the world wide web site "bioinf.jku.at/software/procoil/") was used. This algorithm predicts the probabilities of given sequences to form dimeric and trimeric coiled-coil structures. Several variants of the wild-type coiled-coil sequences mentioned above were predicted to have higher probability scores for forming trimers compared to the wild-type sequences. The variant sequence with the highest probability for being a trimer was selected for use in generating hexameric GITRL FP.

The variant coiled-coil sequences chosen for all the above four human proteins are shown in Table 1-1.

TABLE 1-1

Sequences for use as trimeric coiled-coil motifs in GITRL FP constructs

| Trimerization Motif | Sequence and SEQ ID NO |
|---|---|
| GCN4 pII | IKQIEDKIEEILSKIYHIENEIARIKKL (SEQ ID NO: 27) |
| Matrilin 1 wt | CACESLVKFQAKVEGLLQALTRKLEAVS KRLAILENTVV (SEQ ID NO: 28) |

TABLE 1-1-continued

Sequences for use as trimeric coiled-coil motifs in GITRL FP constructs

| Trimerization Motif | Sequence and SEQ ID NO |
|---|---|
| Matrilin 1 variant | CACESLVKFQAKVEGLIQALTRKLEAVS KRIAILENTVV (SEQ ID NO: 29) |
| Coronin 1a wt | VSRLEEEMRKLQATVQELQKRLDRLEET VQAK (SEQ ID NO: 11) |
| Coronin 1a variant | ISRIEEEIRKINATVQELQKRIDRLEET VQAK (SEQ ID NO: 17) |
| DMPK wt | EAEAEVTLRELQEALEEEVLTRQSLSRE MEAIRTDNQNFASQLREAEARNRDLEAH VRQLQERMELLQAE (SEQ ID NO: 30) |
| DMPK variant | IAEIEVTIRELQEAIEEEVLTRQSLSRE IEAIRTDIQNIASQLREIEARIRDLEAH VRQLQERMELLQAE (SEQ ID NO: 31) |
| Langerin wt | ASALNTKIRALQGSLENMSKLLKRQNDI LQVVS (SEQ ID NO: 32) |

In Silico Analysis to Rank the Trimerization Motifs

In silico predictions of motifs that would generate a more stable GITRL trimers, and therefore a more stable multimeric GITRL FP, were made by analyzing the sequences in Table 1-1 with the algorithm (LOGICOIL) to predict their oligomeric state. In addition, the scores obtained for the formation of a parallel trimer were compared to those from coiled coils identified from the entire human proteome via the combination of two algorithms (MARCOIL and LOGICOIL).

Methods

The genome-wide prediction was performed on the human proteome downloaded from the ftp site "ftp.ncbi.nlm.nih.gov/refseq/H_sapiens/mRNA_Prot/human.protein.faa.gz." This version includes a total number of 71861 protein sequences. These sequences were scanned and the coiled-coil motifs were identified by executing the software MARCOIL, downloaded from the worldwide web site "bcf.isb-sib.ch/Delorenzi/Marcoil/Marcoilcode.tar.gz". All of the motifs that passed certain specific thresholds (i.e. 0.01, 0.10, 0.50, 0.90 and 0.99) were further analyzed using the LOGICOIL algorithm, downloaded from the internet via the world wide web site "coiledcoils.chm.bris.ac.uk/LOGICOIL/LOGICOIL_Source.zip", to predict the oligomerization state (parallel or anti-parallel dimer, trimer or tetramer) of coiled-coil sequences. This package was implemented in the R language (version 3.0.2-2013-09-25). An ad-hoc perl script was developed to convert the outputs from MARCOIL to the file format expected by LOGICOIL. The histograms were plotted in R using the lattice package (version 0.20-23).

Results

Coiled-coil motifs in all human sequences from Refseq were predicted (using MARCOIL). The number of coiled-coil motifs predicted by the MARCOIL algorithm for different thresholds is shown in Table 1-2. The oligomeric states of all the motifs from the 0.99 threshold were then predicted, using LOGICOIL, alongside the eight selected trimeric coiled coil domains in Table 1-2.

The distribution of these scores and the ranking of the motifs used in this study are shown in Table 1-3.

TABLE 1-2

The number of coiled-coil motifs predicted by the MARCOIL algorithm for different thresholds

| Threshold | Number of Motifs |
|---|---|
| 0.01 | 168583 |
| 0.10 | 68793 |
| 0.50 | 41762 |
| 0.90 | 34714 |
| 0.99 | 27240 |

TABLE 1-3

Ranking of the eight coiled-coil motifs in the context of the whole proteome, including LOGICOIL TRIM scores

| PROTEOME RANKING | SUBSET RANKING | SEQUENCE | LOGICOIL TRIM |
|---|---|---|---|
| 20 | 1 | GCN4 pII | 2.43 |
| 201 | 2 | hDMPK-mutant | 1.74 |
| 219 | 3 | hLangerin-wt | 1.71 |
| 241 | 4 | hLangerin-variant | 1.68 |
| 427 | 5 | hCor1a-wt | 1.58 |
| 1065 | 6 | hCor1a-mutant | 1.44 |
| 3620 | 7 | hDMPK-wt | 1.18 |
| 12473 | 8 | hMatrilin-variant | 0.96 |
| 18993 | 9 | hMatrilin-wt | 0.81 |

Generation of GITRL FP Variants that Contain Different Human Trimerization Motifs The sequences for each of the selected trimerization motifs, in addition to the GCN4 pII sequence, were cloned in an appropriate configuration, into DNA vectors that encoded the other elements of the GITRL FPs i.e., between a human Fc domain and the extracellular domain of human GITRL, separated by short flexible amino acid linker sequences. These vectors were used to transiently transfect mammalian cells, enabling the secretion and subsequent purification of the recombinant hexameric GITRL FP proteins.

Method

Suspension CHO cells were transiently transfected, using PEI, with DNA vectors encoding the different hexameric GITRL FPs and grown for eight days at 37° C., shaking at 140 rpm with 80% humidity. Forty milliliters of the conditioned media containing the secreted proteins was separated from cells and cell debris by centrifugation at 1,600×g and filtration. The proteins were purified using Mab SelectSure™ resin and their size and integrity was analyzed by reducing SDS-PAGE.

Larger scale expression and a two-step purification protocol were adopted subsequently for hexameric GITRL FP (coronin 1a wt) and hexameric GITRL FP (matrilin 1 wt). Here, a larger volume of the CHO conditioned (400 ml) was subjected to Protein G chromatography followed by a size-exclusion chromatography step (S200 16/60). These purified proteins were used for SEC-MALLS analysis.

Results

All recombinant hexameric GITRL FP proteins expressed at similar levels, but the hexameric GITRL-FP containing the coronin 1a wt motif did appear to provide a higher yield than the other proteins (Table 1-4: FIG. 1).

TABLE 1-4

Protein yields from transient expression in CHO cells for the eight GITRL FP proteins

| GITRL FP | Concentration (mg/ml) |
| --- | --- |
| Matrilin 1 wt | 0.51 |
| Matrilin 1 variant | 0.57 |
| Coronin 1a wt | 0.9 |
| Coronin 1a variant | 0.63 |
| DMPK wt | 0.66 |
| DMPK variant | 0.34 |
| Langerin wt | 0.37 |
| Langerin variant | 0.48 |

Characterization of GITRL FP Variants that Contain Different Human Trimerization Motifs Binding of GITRL FP Variants to Cells Expressing GITR In order to determine whether the hexameric GITRL FP molecules could bind to cell surface-expressed GITR, they were incubated with cells overexpressing GITR and their binding was detected via their Fc domain.

Method

A fixed concentration of a DyLight-649 conjugated anti-human IgG antibody buffer, followed by a 2-fold dilution of the purified hexameric GITRL FP proteins described above in section 1.3 and an isotype control antibody (NIP228) were added in duplicate wells to a 384 well black walled clear bottom plate. CHO cells stably expressing GITR were added to all wells and the plate incubated at room temperature for four hours. Binding to the CHO-GITR cells was determined using the Mirrorball™ plate cytometer with a 640 nm laser and the fluorescence measured.

Results

Results are presented in FIGS. 2A-D. The binding profile obtained demonstrates a "hook effect" which is observed when the concentration of the hexameric GITRL FP exceeds the concentration of the DyLight-649 conjugated detection antibody, resulting in less binding being detected at the higher concentrations of hexameric GITRL FP; thus a bell-shaped binding profile is produced. Despite this phenomenon, the different hexameric GITRL FP molecules produce a very similar binding profile.

Competition of GITRL Competition of GITRL FP Variants with Recombinant Trimeric Ligand for Binding to GITR The effect of the hexameric GITRL FP molecules on human GITRL binding to human GITR was determined using a Homogeneous Time Resolved Fluorescence (HTRF) assay.

Method

The hexameric GITRL FP molecules were titrated into an HTRF assay in which binding of GITRL-HA (hemagglutinin tag) to GITR-Fc was measured. The human GITR Fc was conjugated with europium cryptate and an anti-HA antibody conjugated with XL665 was used to detect the GITRL-HA protein. $IC_{50}$ values were determined by curve fitting the analyzed data to a four parameter logistic equation with Prism 5.01 software (GraphPad).

Results

Results are presented in FIGS. 3A-D and Table 1-5. The hexameric GITRL FP molecules with the different trimerization motifs are all potent inhibitors of trimeric GITRL-HA binding to GITR-Fc. The majority of GITRL FP variants produced similar inhibition profiles and $IC_{50}$ values with the exception of GITRL FP (Langerin wt) that demonstrated an 8-fold lower potency than GITRL FP (GCN4). GITRL FP (Coronin 1a) had the lowest $IC_{50}$ value at 0.61 nM.

TABLE 1-5

$IC_{50}$ (nM) values for GITRL FP proteins competing for binding of trimeric GITRL to GITR-Fc

| Test sample | IC50 (nM) |
| --- | --- |
| GITRL FP (GCN4 pII) | 1.06 |
| GITRL FP (Matrilin 1 wt) | 1.36 |
| GITRL FP (Matrilin 1 variant) | 0.83 |
| GITRL FP (Coronin 1a wt) | 0.61 |
| GITRL FP (Coronin 1a variant) | 1.44 |
| GITRL FP (DMPK wt) | 2.73 |
| GITRL FP (DMPK variant) | 2.43 |
| GITRL FP (Langerin wt) | 8.05 |
| GITRL FP (Langerin variant) | 2.0 |
| NIP228 IgG-TM | No Inhibition |

Activity of GITRL FP Variants in a Reporter Assay

The functional activity of the different GITRL FP molecules (hexameric GITRL IgG1 FP (SEQ ID NO: 6) and hexameric GITRL IgG4 FP (SEQ ID NO: 40) was determined in an assay using NFκB-luciferase reporter cells stably expressing GITR. Luminescence, driven by agonism of GITR and subsequent activation of the NFκB pathway, was measured.

Method

GITRL FP proteins were serially diluted 4-fold for a six-point data curve and added in triplicate to 96 well plates. Then Jurkat NF-κB luciferase reporter cells transfected with human GITR were added to all wells of the assay plates and incubated at 37° C. for three hours. Luciferase expression was detected by adding Steady-Glo reagent to all wells of the assay plates. The plates were incubated for five minutes at room temperature and then luminescence was measured and $EC_{50}$ values were generated using log (agonist) vs. response variable slope nonlinear curve fit in GraphPad Prism 5.01 (GraphPad).

Results

Results are presented in FIGS. 4A-D and Table 1-6. All the hexameric GITRL FP proteins trigger NF-κB signaling. The proteins generated similar potency profiles and $EC_{50}$ values to GITRL FP (GCN4).

TABLE 1-6

$EC_{50}$ (nM) values for GITRL FP variants using a human GITR transfected NF-κB luciferase gene reporter cell line

| # | Test sample | $EC_{50}$ (nM) |
| --- | --- | --- |
| 1 | GITRL FP (GCN4 pII) | 1.02 |
| 2 | GITRL FP (Matrilin 1 wt) | 1.12 |
| 3 | GITRL FP (Matrilin 1 variant) | 0.90 |
| 4 | GITRL FP (Coronin 1a wt) | 0.95 |
| 5 | GITRL FP (Coronin 1a variant) | 0.74 |
| 6 | GITRL FP (DMPK wt) | 1.37 |
| 7 | GITRL FP (DMPK variant) | 1.39 |
| 8 | GITRL FP (Langerin wt) | 1.54 |
| 9 | GITRL FP (Langerin variant) | 0.75 |

Melting Temperature of GITRL FP Variants

The melting temperature of the GITRL FP proteins was determined using a fluorescent dye (Sypro Orange) whose emission properties change in the presence of an unfolded protein.

Method

Thermostability of multimeric GITRL FP variants was assessed using a Sypro Orange-based assay to calculate melting temperatures (Tm). The different proteins were first diluted to 0.5 mg/mL in 2×PBS before dispensing into a 96 well PCR plate. Sypro Orange™ was added to each well on the plate, which was then sealed. Plates were read on a Real-Time™ PCR machine using a Chromo4™ continuous fluorescence detector. The temperature was set to increase from 20° C. to 90° C. with a read every 1° C. and a hold time of is. Unfolding transitions were determined by plotting the fluorescence intensity and fluorescence derivative as a function of temperature. Each multimeric GITRL-FP protein was analyzed in duplicate.

Results

Results are presented in FIGS. 5A-D. Melting temperatures for each of the nine multimeric GITRL-FP proteins are summarized in Table 1-7 below. All variants have a similar profile with the exception of GITRL FP (DMPK wt) which displays a single transition peak at 59° C. compared to 62-64° C. for the majority of the others, GITRL FP (Langerin wt) and GITRL FP (Langerin variant) which both display an additional transition peak at a low temperature (45-50° C.) suggesting some structural instability.

TABLE 1-7

Transition temperatures for the nine GITRL FP proteins

| # | Test sample | Tm1 (° C.) | Tm2 (° C.) |
|---|---|---|---|
| 1 | GITRL FP (GCN4 pII) | / | 63 |
| 2 | GITRL FP (Matrilin 1 wt) | / | 62.5 |
| 3 | GITRL FP (Matrilin 1 variant) | / | 63 |
| 4 | GITRL FP (Coronin 1a wt) | / | 63 |
| 5 | GITRL FP (Coronin 1a variant) | / | 63 |
| 6 | GITRL FP (DMPK wt) | / | 59 |
| 7 | GITRL FP (DMPK variant) | / | 63.5 |
| 8 | GITRL FP (Langerin wt) | 47.5 | 63 |
| 9 | GITRL FP (Langerin variant) | 45-50 | 62 |

In Silico Immunogenicity Analysis of GITRL FP Variants

The predicted immunogenicity of the 8 coiled coil domains and their surrounding sequences was determined using the ProPred algorithm.

Method

Using ProPred [Singh & Raghava (2001) Bioinformatics 17(12)], the T-score of the eight selected human trimerization motifs, and yeast GCN4 pII were evaluated. The T-score of an arbitrary amino acid sequence quantifies the number of strongly binding MHC class II epitopes relative to the total length of the amino acid sequence. A nine-mer subsequence is considered a strongly binding epitope, if ProPred returns a binding score that lies above the 95 percentile of scores obtained by evaluating a set of 10,000 randomly generated nine-mer sequences. The T-score was calculated for each motif, including the 2×[G4S] sequence preceding the motif and the [G4] sequence and first 4 amino acids of the GITRL domain following the motif, for the eight most common human alleles. The overall T-score was then formed as the sum of the individual allele T-scores.

Results

The overall T score for each trimerization motif and its surrounding sequence is shown in Table 1-8. Note that the maximal score is equal to eight, which corresponds to a case where every nine-mer in the sequence is a strongly binding epitope for all of the eight alleles that are tested. Interestingly this global analysis predicts that almost all candidates, except for DMPK wt have slightly stronger immunogenic profiles than GCN4. Matrilin wt and variant both have the highest overall T score.

TABLE 1-8

Overall T scores for the eight human trimerization motifs and GCN4 pII

| # | Coiled coil motif | T score |
|---|---|---|
| 1 | GCN4 pII | 0.131579 |
| 2 | Matrilin 1 | 0.270833 |
| 3 | Matrilin 1 variant | 0.270833 |
| 4 | Coronin 1a wt | 0.142857 |
| 5 | Coronin 1a variant | 0.166667 |
| 6 | DMPK wt | 0.0875 |
| 7 | DMPK variant | 0.175 |
| 8 | Langerin wt | 0.209302 |
| 9 | Langerin variant | 0.186047 |

SEC-MALLS Analysis of GITRL FP Variants

Method

Proteins were analyzed on a BioSep-Sec-S™ 4000 (void volume, V0=5.7 ml) and all runs were performed at the flow rate of 0.5 ml/min for 30 min. Elution was monitored with a UV280, refractive index and multi-angle laser light scattering detectors. Samples (at 1-2 mg/ml) were loaded on the column and the molar mass and particle diameter were then calculated.

Results

Multimeric GITRL FP (Matrilin 1 wt)

GITRL FP with the matrilin-1 trimerization motif yielded three distinct peaks on the gel-filtration column: peak 2 has the weight-average molar mass of 312 kDa in agreement with the expected molar mass of the glycosylated hexamer and constitutes 40.9% of the total protein mass, while peak 1 has weight-average molar mass corresponding to the dimer of hexamers (~610 kDa) and constitutes 41.3% of the total mass injected. Peak 3 has a lower than expected mass (~215 kDa) which could be either a result of fragmentation or a loss of a dimer from the hexamer. It constitutes 17.7% of the total protein mass. The composition of this protein preparation is therefore heterogeneous, with no single dominant oligomeric species.

Multimeric GITRL FP (Coronin 1a Wt)

Analysis of the overlay of UV280, refractive index and 900-laser scattering traces shows that 93.9% of this protein elutes at 16.4 min as a monodisperse species of 300 kDa. This observed mass is consistent with the predicted mass of the hexameric GITRL FP polypeptide (274.95 kDa). The difference between calculated and observed mass of 25 kDa is most likely caused by glycosylation. The minor peak at 14.7 min has the weight-average molar mass of 690 kDa which could be attributed to the dimer of hexamers.

Multimeric GITRL FP (GCN4 pII)

Similarly, analysis of the laser scattering and refractive index chromatograms of GITRL FP with the GCN4 pII trimerization motif demonstrates that 93.75% of this protein elutes as a monodisperse species of 330 kDa, consistent with the glycosylated hexamer. The peak eluting at 15 minutes contains only 6.25% of total protein and has the weight-average molar mass of approximately 700 kDa probably reflecting the presence of a dimer of hexamers.

Molar Mass Versus Time Profiles

Figure 6:
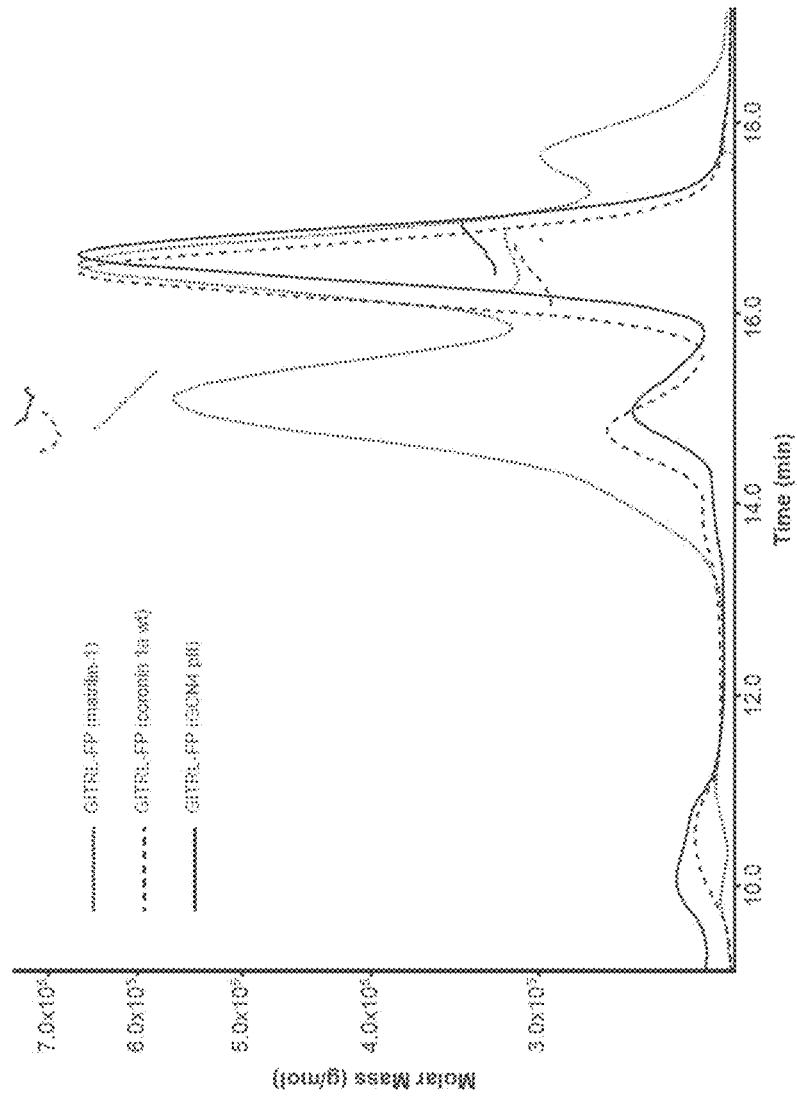
FIG. 6. The molar mass composition of eluted peaks. The graph shows that multimeric GITRL FP matrilin-1 protein (dotted line) in solution forms three species with weight-average molar mass (from left to right) of 612, 312 and 215 kDa with no easily identifiable major species. On the other hand, >90% of multimeric GITRL FP (coronin 1a wt; dashed line) and multimeric GITRL FP (GCN4 pII; solid line) protein mass elutes as a single protein species. These peaks are nevertheless not perfectly monodisperse most likely due to heterogeneity of glycans attached to the protein.

FIG. 6 shows the molar mass composition of eluted peaks for each of the three Multimeric GITRL FP proteins. For all three proteins, the molar mass across early peaks with ~15 min retention time is highly variable, particularly in the case of GITRL FP (Matrilin 1 wt) where the mass of molecules eluted at the beginning and at the end of the same peak differs by more than 100 kDa. Peaks eluting at ~17 minutes are less heterogeneous in their molecular composition, with the maximal molar mass variation in GITRL FP (coronin 1a wt) of less than 20 kDa. The variation in the weight-average molar mass is most likely caused by differences in the glycan content of the glycoproteins being eluted within the same peak.

Summary of Characterization Data

In analyzing the compiled data as shown in

Table 1-9 that compares the performance of various coiled coil trimerization domains in multimeric GITRL FP, the coronin 1a coiled coil domain provides improved expression yield. Comparison of the prediction scores of the coronin-1a coiled-coil motif and the motifs from human sequences classified as trimeric coiled-coil, however, shows that the coronin-1a wt had a LOGICOIL ranking of 5.

Expression and Purification of Recombinant Protein

CHO cells growing in suspension in a chemically defined media similar to CD-CHO™ (Life Technologies Ltd, Paisley, UK) in wavebag bioreactors, were transfected with DNA vectors encoding the different hexameric GITRL FPs. The cultures were maintained as a fed batch, using a nutrient feed similar to CHO CD-Efficient Feed A™ (Life Technologies Ltd, Paisley, UK), for 10-12 days at which point they were harvested using filtration for cell removal. The conditioned medium was then refrigerated prior to purification.

Protein was purified from conditioned media using Mab-SelectSure™ resin. The eluted peak was neutralized and filtered prior to further purification on Hydroxyapatite Type

TABLE 1-9

Summary of characterization data

| Trimerization Motif | LOGICOIL ranking | Expression yield (mg/ml) | Tm1 (Sypro Orange) | Receptor/ Ligand inhibition IC50 (HTRF) | Cell binding (Mirrorball) | Agonism EC$_{50}$ (NFkB Reporter) | In silico Immunogenicity |
|---|---|---|---|---|---|---|---|
| GCN4 | 1 | | 63 | 1.06 | Good | 0.89 | 0.132 |
| Matrilin 1 wt | 9 | 0.51 | 62.5 | 1.36 | Good | 0.92 | 0.271 |
| Matrilin 1 variant | 8 | 0.57 | 63 | 0.83 | Good | 0.89 | 0.271 |
| Coronin 1a wt | 5 | 0.9 | 63 | 0.61 | Good | 0.75 | 0.143 |
| Coronin 1a variant | 6 | 0.63 | 63 | 1.44 | Good | 0.71 | 0.167 |
| DMPK wt | 7 | 0.66 | 59 | 2.73 | Good | 0.96 | 0.088 |
| DMPK variant | 2 | 0.34 | 63.5 | 2.43 | Good | 1.38 | 0.175 |
| Langerin wt | 3 | 0.37 | 47.5 | 8.05 | Good | 1.17 | 0.209 |
| Langerin variant | 4 | 0.48 | 45-50 | 2 | Good | 0.57 | 0.186 |

Example 2

Figure 8:
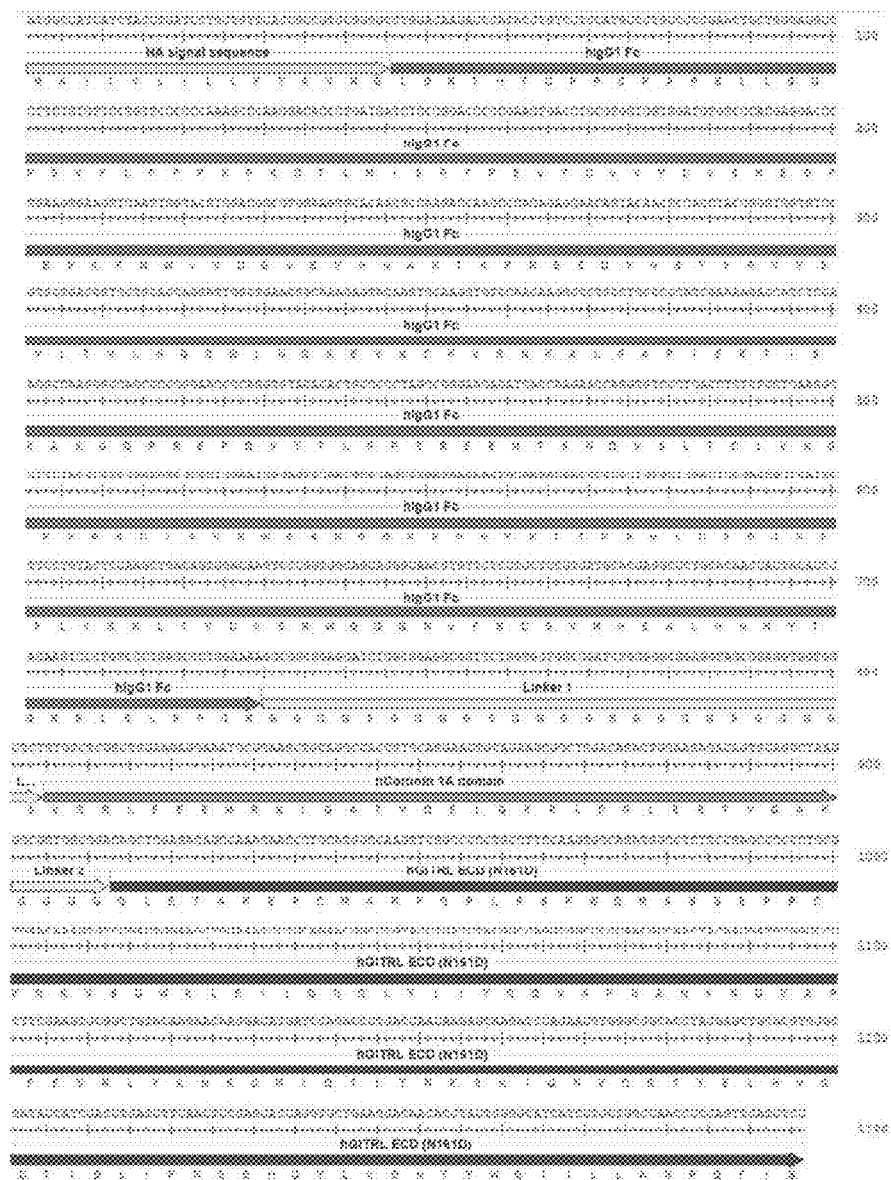
FIG. 8. Nucleotide and translated protein sequence of a representative GITRL IgG1 fusion polypeptide subunit. The individual domains are highlighted and annotated. ECD=extracellular domain; GITRL=glucocorticoid induced tumor necrosis factor receptor ligand; HA=hemagglutinin. The nucleic acid sequence of FIG. 8 is provided as SEQ ID NO: 7 and the encoded precursor protein sequence is provided as SEQ ID NO: 8.

Generation and Characterization of a GITRL Fusion Protein, Characterization of the Same, and Characterization of Mouse GITRL Fusion Proteins Derivation and Composition A hexameric GITRL IgG1 Fusion Protein comprising monomeric subunits having the amino acid sequence of SEQ ID NO: 6 was constructed. Each GITRL IgG1 FP monomeric subunit of SEQ ID NO: 6 comprises 3 distinct domains: 1) a human IgG1 Fc domain; 2) an alpha helical coiled coil trimerization domain derived from the human coronin 1A protein and 3) the human GITRL ECD, with a single point mutation (N161D) in the human GITRL ECD that eliminates the sole occupied glycosylation site. Each domain is separated by flexible glycine and serine-rich or glycine-rich, e.g., (Gly)$_4$ linkers (FIG. 8). The human GITRL ECD domain in each monomer forms weak non-covalent trimers with two further monomers in solution, and this association is strengthened through interactions between the human coronin 1A trimerization domains resulting in a stabilized trimeric structure. The interaction of the IgG1 Fc domains present in each trimer leads to subsequent formation of a dimer of GITRL trimers resulting in the final hexameric conformation.

The DNA molecule set forth in SEQ ID NO: 7, which encodes the precursor GITRL IgG1 FP polypeptide subunit having the amino acid sequence of SEQ ID NO: 8, was synthesized and cloned, using standard molecular biology techniques, into an expression vector that enabled efficient transient recombinant protein expression.

The nucleotide and deduced amino acid sequences of the subunit monomer of the GITRL IgG1 FP polypeptide subunit set forth in SEQ ID NO: 6, are shown in FIG. 8.

1 resin. Elution was carried out with a salt gradient. Purity was monitored by SEC HPLC throughout the process.

Glycosylation Analysis of GITRL IgG1 FP Polypeptide Subunit

Figure 9:
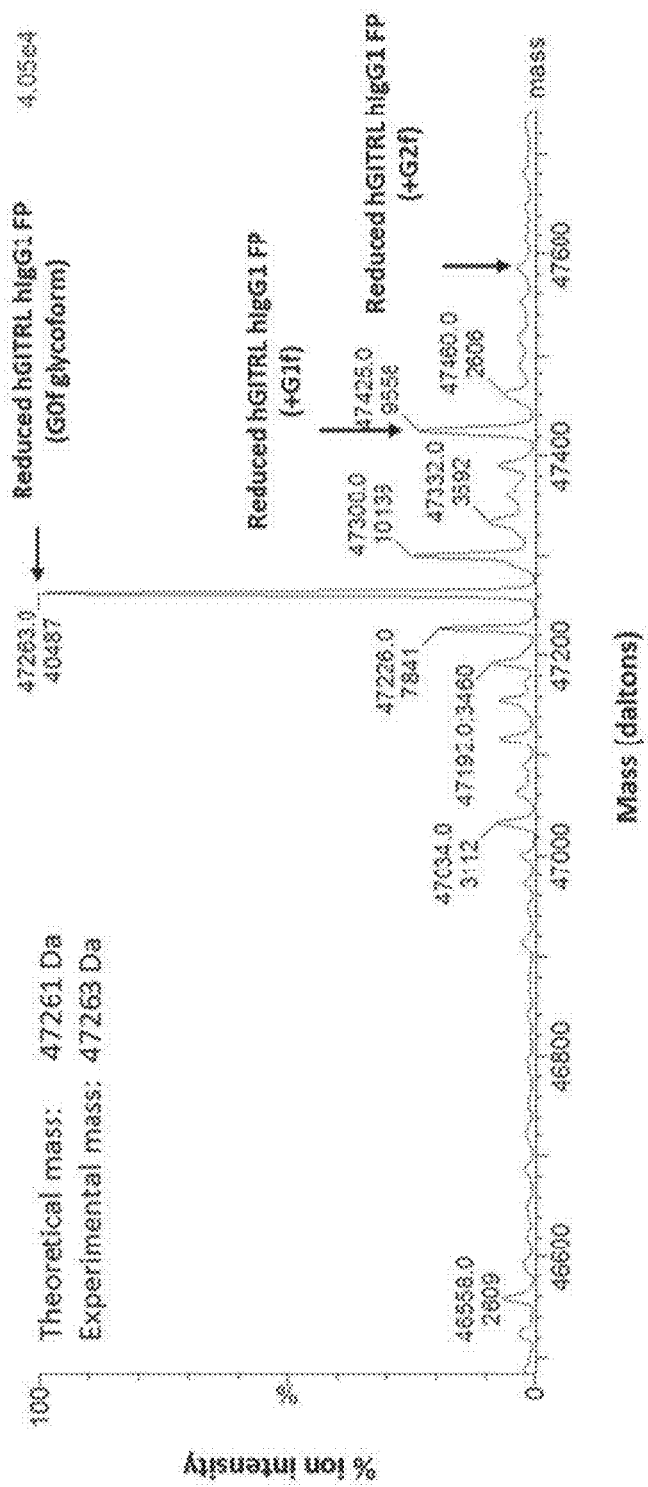
FIG. 9. Deconvoluted LC-QTOF MS spectrum for a reduced GITRL IgG1 FP subunit. The accurate mass of GITRL IgG1 FP monomeric subunit (SEQ ID NO: 6), as determined by liquid chromatography coupled with quadrupole time of flight (QTOF) mass spectrometry (LC-QTOF MS), is consistent with the expected amino acid sequence with the addition of one biantennary glycan (predominantly G0f) per chain at the canonical glycosylation site in the Fc domain.

The glycosylation status of the GITRL IgG1 FP polypeptide subunit of SEQ ID NO: 6 was determined using liquid chromatography coupled with quadrupole time of flight (QTOF) mass spectrometry (LC-QTOF MS), and peptide mapping with mass spectrometry. The results are shown in FIG. 9.

The accurate mass of the GITRL IgG1 FP polypeptide subunit of SEQ ID NO: 6, obtained by LC-QTOF MS analysis of the reduced polypeptide subunit, is consistent with the expected amino acid sequence with the addition of one biantennary glycan (predominantly G0f) per chain. The mass profile is consistent with Fc domain glycosylation with no N-glycan occupancy at N129 in the GITRL ECD (N369 in fusion protein) of the GITRL IgG1 FP polypeptide subunit of SEQ ID NO: 6 as confirmed by peptide mapping. These data also confirm that the N161D mutation in the GITRL ECD (N401 in the fusion protein) results in an aglycosylated GITRL ECD, with N-glycosylation present only at the canonical glycosylation site in the Fc domain.

In Vitro Characterization of a Hexameric GITRL IgG1 FP

Effect of a Hexameric GITRL IgG1 FP on Ligand-Receptor Binding

Figure 10:
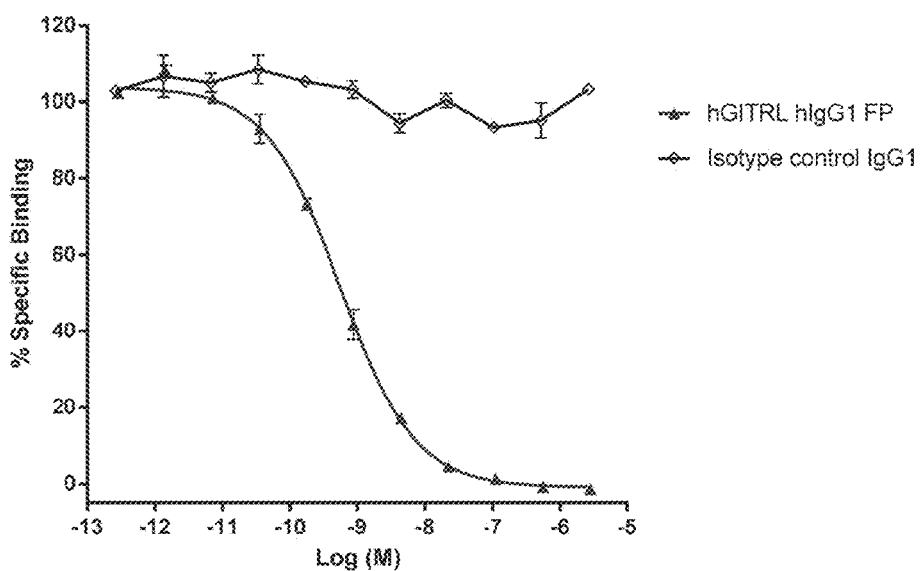
FIG. 10. Human GITR-Fc conjugated to europium cryptate binds to hGITRL-HA in a homogeneous time resolved fluorescence assay. A titration of the IgG1 isotype control antibody does not inhibit this binding. Hexameric GITRL IgG1 FP comprising monomeric subunits having the amino acid sequence set forth in SEQ ID NO: 6 inhibits binding between hGITR and hGITRL with a half-maximal inhibitory concentration (IC50) of 0.562 nM. Experiments were conducted in duplicate wells. Error bars represent standard error of the mean. GITR(L)=glucocorticoid induced tumor necrosis factor receptor (ligand).

The effect of a hexameric GITRL IgG1 FP having the monomeric GITRL IgG1 FP subunit sequence of SEQ ID NO: 6 on human GITRL binding to human GITR was determined using a Homogeneous Time Resolved Fluorescence (HTRF) assay. The GITRL IgG1 FP was titrated into an HTRF assay in which binding of GITRL-HA (hemagglutinin tag) to GITR-Fc was measured. The human GITR-Fc was conjugated with europium cryptate and an anti-HA antibody conjugated with XL665 was used to detect the GITRL-HA protein. $IC_{50}$ values were determined by curve fitting the analyzed data to a four parameter logistic equation with Prism 6.0x software (GraphPad). Representative results shown in FIG. 10 demonstrate that the GITRL IgG1 FP inhibits the binding of GITRL-HA to GITR with an $IC_{50}$ of 0.562 nM. No inhibition was observed with isotype control antibody NIP228.

GITR Agonism

The purpose of this experiment was to determine the ability of a GITRL fusion protein (FP) to deliver signals via the GITR receptor.

Method

Hexameric GITRL FP was added in solution to Jurkat cells transfected with hGITR and a luciferase reporter gene linked to a nuclear factor kappa B (NFκB) promoter. In this assay activation of the GITR receptor results in signaling via the NFκB pathway, which in turn results in an increase in luciferase activity that can be measured via luminescence.

Results

Figure 11:
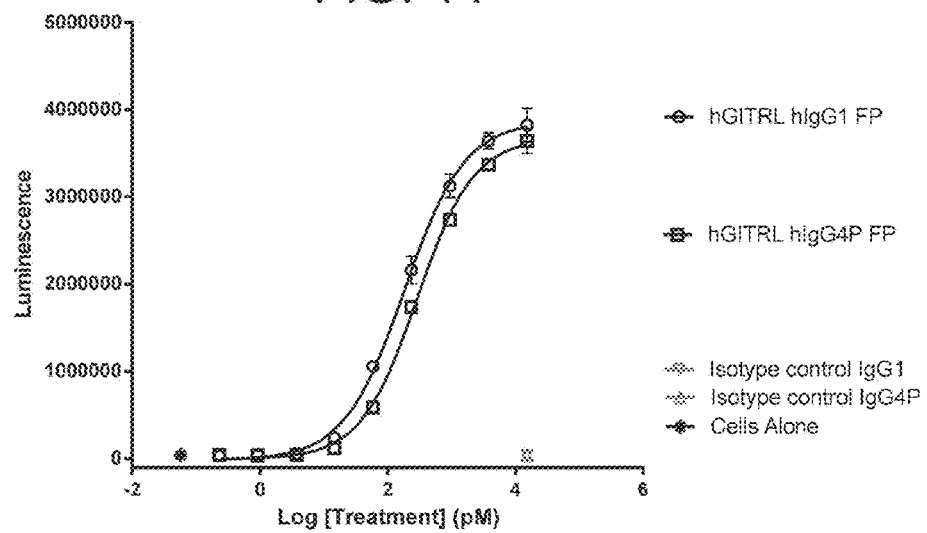
FIG. 11. Hexameric GITRL FPs are potent agonists of the GITR receptor. Test articles were added in solution, at the concentrations indicated, to Jurkat cells transfected with hGITR and a luciferase reporter gene linked to an NFκB promoter. Luciferase activity, measured as luminescence, was determined after three hours. Hexameric GITRL IgG1 FP comprising monomeric subunits having the amino acid sequence set forth in SEQ ID NO: 6 or hexameric GITRL IgG4P FP comprising monomeric subunits having an amino acid sequence set forth in SEQ ID NO: 40 resulted in a concentration dependent increase in luminescence. The $EC_{50}$ of the hexameric GITRL IgG1 FP with respect to this effect was 182 pM. The $EC_{50}$ of the hexameric GITRL IgG4P FP with respect to this effect was 289 pM. An isotype control antibody had no effect. Experiments were conducted in triplicate wells. Error bars represent standard error of the mean.

The addition of hexameric GITRL FP to the assay system resulted in an increase in luminescence. The observed effect was concentration dependent with an $EC_{50}$ of approximately 180 pM. In contrast the addition of an isotype control antibody had no effect. Results are shown in FIG. 11. These data demonstrate that hexameric GITRL FP is a potent agonist of the GITR receptor.

Primary T Cell Activation

This experiment was conducted to assess the impact of GITR agonism, mediated by hexameric GITRL FP, on the proliferation and function of human T cells.

Method

Total human T cells were isolated from healthy human blood and antigen experienced, by culture in the presence of plate bound anti-CD3 for 4 days, in order to up-regulate the expression of GITR. Antigen experienced cells were rested for 2 days by culture in media alone before being restimulated with a sub-optimal concentration of anti-CD3 and anti-CD28 in the presence of hexameric GITRL FP. Proliferation of cells was assessed by quantitating the incorporation of thymidine into cells over an 18 hour period. The release of interferon gamma (IFN-γ) was quantitated using meso scale discovery.

Results

The addition of anti-CD3 together with anti-CD28 resulted in a minimal level of proliferation and a minimal release of IFN-γ. The addition of plate bound hexameric GITRL FP together with plate bound anti-CD3 and anti-CD28 resulted in a concentration dependent increase in the level of proliferation as well as the release of IFN-γ. Representative data is shown in FIG. 12 and FIG. 13. An isotype control antibody had no effect on proliferation or the release of cytokines.

ADCC

A mouse hexameric GITRL IgG1 FP has been shown in vivo to deplete intratumoral CD4 positive T cells, including FOXP3 positive regulatory T cells, resulting in an increased ratio of $CD8^+$ to $CD4^+$ T cells within the tumor. This experiment was conducted to determine the ability of hexameric GITRL FP to mediate depletion of human T cells via ADCC and to assess the resulting change in CD8:CD4 ratio in the surviving cell population.

Method

Primary human T cells, isolated from healthy human blood, were antigen experienced with phytohemagglutinin (PHA) and IL-2 in order to up-regulate GITR expression. They were then labelled with a fluorescent dye and incubated for 24 hours with primary NK cells, at the indicated ratio together with hexameric GITRL FP, at the indicated concentrations. Flow cytometry was used to quantitate the percentage of live T cells present at the end of the assay, and this was used to calculate a percentage lysis for treated relative to untreated wells. The proportion of CD4 and CD8 cells was also quantitated by flow cytometry.

Results

Figure 14:
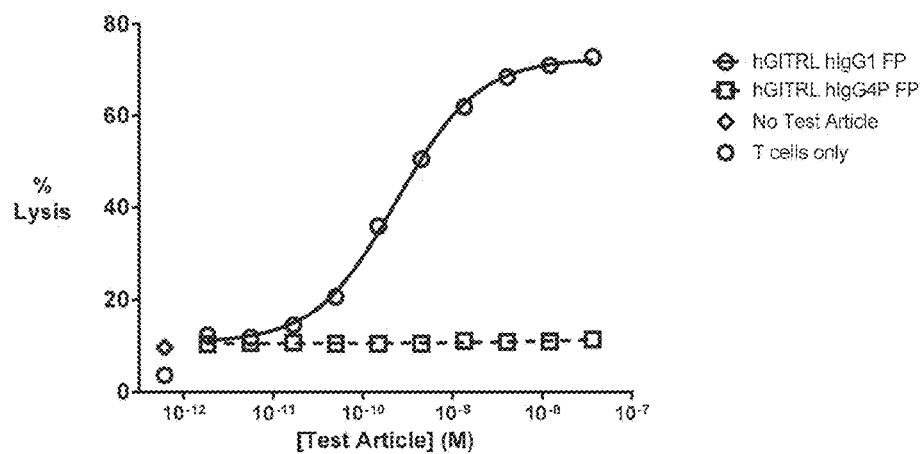
FIG. 14. Hexameric GITRL IgG1 FP mediates ADCC of primary human T cells by NK cells. Antigen experienced primary human T cells were fluorescently labelled and mixed with primary human NK cells at a ratio of 1 T cell to 32 NK cells. Test articles were added as indicated and the % lysis of T cells was calculated following 24 hours incubation. Hexameric GITRL FP IgG1 comprising monomeric subunits having the amino acid sequence set forth in SEQ ID NO: 6 results in an increase in the percentage of lysis. The effect was concentration dependent with an $EC_{50}$ of 239 pM. The negative control, hexameric GITRL IgG4P FP comprising monomeric subunits having the amino acid sequence set forth in SEQ ID NO: 40, did not result in any increase in the percentage lysis of T cells.

NK cells alone mediated a small amount of lysis of the primary T cells, which was significantly enhanced by the addition of hexameric GITRL FP comprising a GITRL fusion polypeptide subunit set forth in SEQ ID NO: 6 containing an IgG1 Fc domain in a concentration dependent manner. Hexameric GITRL FP comprising a GITRL fusion polypeptide subunit of SEQ ID NO: 40 containing an IgG4 Fc domain that cannot bind the Fc gamma receptors on NK cells, was used as a negative control and had no effect on the level of lysis measured (FIG. 14).

Figure 15:
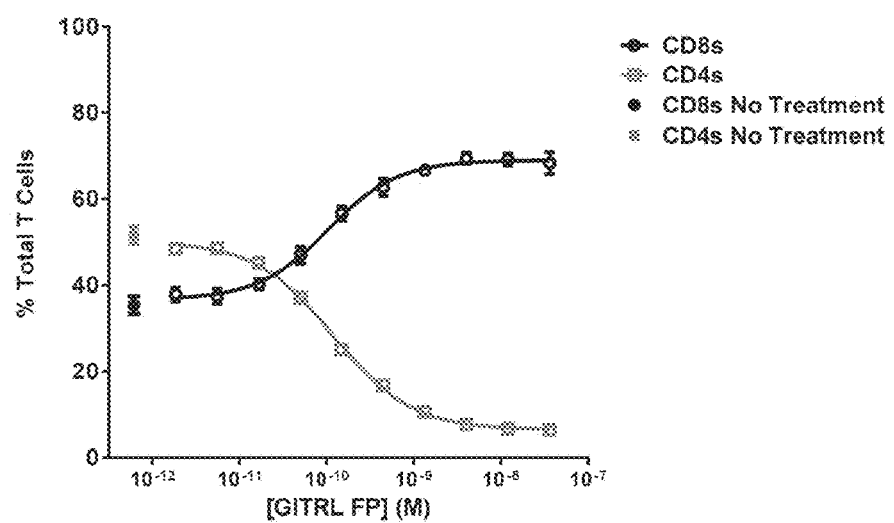
FIG. 15. ADCC mediated by hexameric GITRL IgG1 FP favors the generation of an increased CD8:CD4 T cell ratio. Antigen experienced primary human T cells were fluorescently labelled and mixed with primary human NK cells at a ratio of 1 T cell to 32 NK cells. Test articles were added as indicated and the percentage of $CD4^+$ and $CD8^+$ T cells present in the total T cell population was assessed by flow cytometry following 24 hours incubation. Hexameric GITRL IgG1 FP comprising monomeric subunits having the amino acid sequence set forth in SEQ ID NO: 6 results in a concentration dependent shift in the CD8:CD4 T cell ratio, which favors CD8 T cells.

Flow cytometric analysis of the percentage of $CD4^+$ and $CD8^+$ T cells present at the end of the assay indicated that ADCC mediated by hexameric GITRL FP favors the generation of an increased CD8:CD4 T cell ratio (FIG. 15).

Regulatory T-cell Assays

GITR is expressed at increased levels on regulatory T cells (T-regs) and signaling through GITR has been suggested to impact the ability of T-regs to suppress other T cells. This experiment was conducted in order to assess the impact of hexameric GITRL FP on T-reg function.

Method $CD4^+$ $CD25^-$ effector T cells and $CD4^+$ $CD25^+$ T-regs were isolated from the peripheral blood of healthy human donors. Effector T cells were labelled with CFSE prior to culture in the presence of anti-CD3 antibody, anti-CD28 antibody, T-regs at the ratio indicated and test articles. The percentage of proliferating effector T cells was analyzed by flow cytometry.

Results

Figure 16:
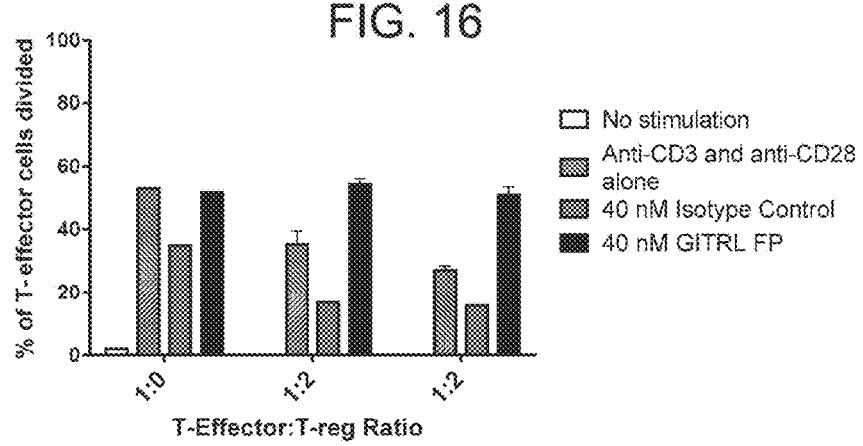
FIG. 16. Hexameric GITRL IgG1 FP overcomes regulatory T cell mediated suppression of effector T cell proliferation. The percentage of divided $CD4^+$ $CD25^-$ effector T cells was analyzed by flow cytometry following stimulation for five days with anti-CD3 and anti-CD28 antibodies. The percentage of dividing cells was reduced in the presence of increasing numbers of T-regs. Addition of plate bound isotype control further decreased the percentage of dividing cells. Addition of plate bound hexameric GITRL IgG1 FP comprising monomeric subunits having the amino acid sequence set forth in SEQ ID NO: 6 at the concentration indicated restored the percentage of dividing cells to that observed in the absence of T-regs. Experiments using effectors alone were in single wells. All other experiments were conducted in duplicate wells. Error bars represent standard error of the mean.

Effector T cell proliferation was observed in response to the addition of anti-CD3 and anti-CD28. The addition of increasing numbers of T-regs resulted in a reduction in the percentage of effector T cells that had divided during the assay. The addition of plate bound isotype control further decreased the percentage of divided cells, while addition of plate bound hexameric GITRL FP restored the percentage of divided to that observed in the absence of T-regs. Results are shown in FIG. 16.

This study demonstrates the ability of hexameric GITRL FP to overcome the effects of regulatory T-cell mediated suppression on other T cells.

Tests for Biological/Functional Activity In Vivo

Isotype Dependent Antitumor Activity

Because human GITRL does not cross-react to mouse GITR the human GITRL FP cannot be tested in immunocompetent mouse models of cancer. To enable this testing surrogate mouse mGITRL IgG1 FP and mGITRL IgG2a FP were generated. This study was conducted in order to evaluate the antitumor activity of mGITRL FP in the CT26 model of cancer, and to determine the impact of Fc isotype on the magnitude of this activity.

Method

Balb/c mice were implanted with the CT26 mouse colorectal cancer cell line. On day 6 following implantation animals were administered mGITRL FP by intraperitoneal (i.p.) injection either once or daily for 17 days. Two different versions of the mGITRL FP were tested; one containing a mIgG2a Fc domain and the other containing a mIgG1 Fc domain Two different dose levels of each mGITRL FP were tested; 5 mg/kg and 10 mg/kg. Saline treatment was employed as a negative control.

Results

Figure 17:
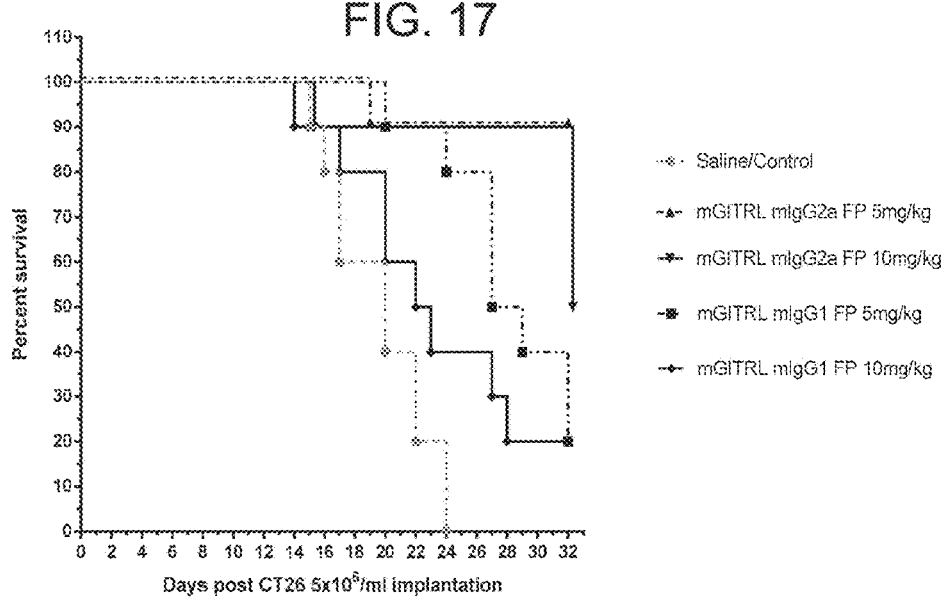
FIG. 17. Survival of mice treated with mGITRL FP is isotype dependent. Mice were treated by intraperitoneal administration of mGITRL FP mIgG2a or mGITRL IgG1 FP, both at 5 or 10 mg/kg, daily from day 6 to day 23 following subcutaneous implantation of CT26 cells. Saline was administered as a negative control.

The median survival in the saline treated group was 22 days and none of the mice in this group survived until the end of the study. Treatment with the mGITRL FP at 10 mg/kg extended median survival to 32 days and resulted in a 50% survival rate at the end of the study. In the group treated with the mGITRL FP at 5 mg/kg 9 out of 10 mice were alive at the end of the study and no median survival time could be defined. Treatment with the mGITRL FP mIgG1 at 5 or 10 mg/kg extended median survival to 28 and 22.5 days respectively and resulted in 2 out of 10 mice surviving until the end of the study. Results are presented in FIG. 17.

This study demonstrates the potential of the mGITRL FP to mediate antitumor activity and indicates that the isotype of the FP can impact the level of antitumor activity observed.

Pharmacodynamic Effects

This study was conducted to determine the impact of mGITRL FP on the activation state and proportion of T-cells in the spleen and the tumor of tumor bearing mice.

Method

CT26 tumor bearing Balb/c female mice aged 7-9 weeks were treated by intraperitoneal injection with mGITRL FP at either 0.2 or 1 mg/kg as indicated. Saline treatment was employed as a negative control. Mice were sacrificed 7 days following initiation of treatment and flow cytometry was used to assess the frequency and phenotype of cells in the spleen and the tumor.

Results

Figure 18:
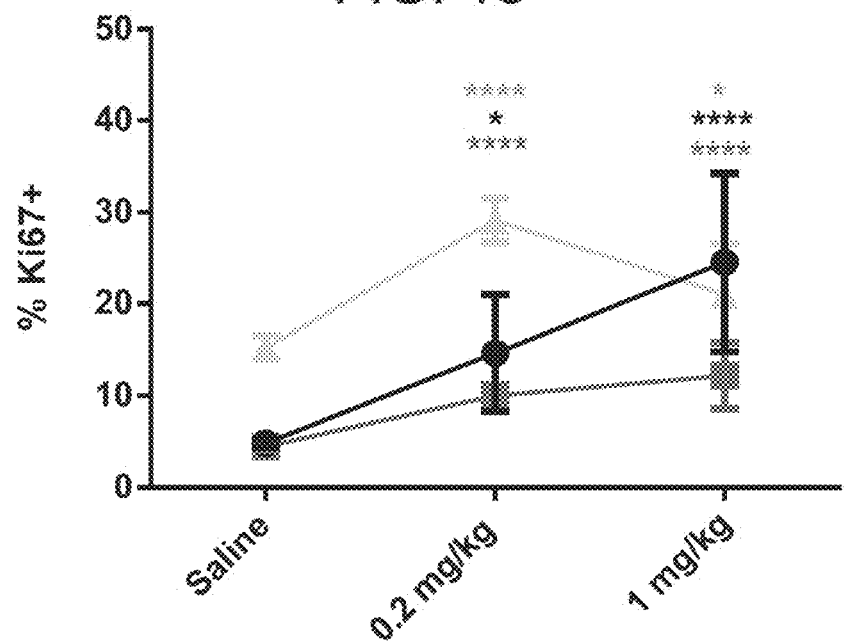
FIG. 18. mGITRL FP results in increased proliferation of T cells. The expression of Ki67 was measured by flow cytometry in splenic T cells seven days following treatment with a single dose of either 0.2 mg/kg or 1 mg/kg mGITRL FP. Black lines with circles=CD8 T cells; Dark Grey lines with squares=CD4$^+$ Foxp3$^-$; Light Grey lines with triangles=CD4$^+$ Foxp3$^+$ cells. Significance was calculated using the Student's T test where $*p<0.05$; $p<0.01$, $*p<0.001$, $****p<0.0001$.

Treatment with mGITRL FP resulted in an increase in the expression of the proliferation marker Ki67 in all T-cell sub-sets in the spleen suggesting an increase in the proliferation of these cells. See FIG. 18.

Figure 19:
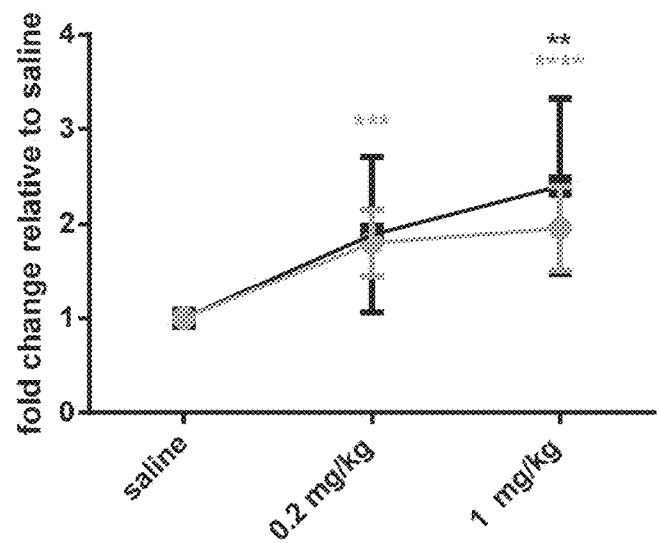
FIG. 19. mGITRL FP results in increased expression of the activation marker ICOS on T cells. The expression of ICOS was measured by flow cytometry in splenic T cells seven days following treatment with a single dose of either 0.2 mg/kg or 1 mg/kg mGITRL FP. Dark grey lines with circles=CD8 T cells; black lines with squares=CD4$^+$ Foxp3. Significance was calculated using the Student's T test where $*p<0.05$; $p<0.01$, $*p<0.001$, $****p<0.0001$. Treatment with mGITRL FP resulted in a decrease in the frequency of CD4$^+$ FOXP3$^+$ regulatory T cells and CD4$^+$ FOXP3$^-$ helper cells within the tumor, but did not alter the frequency of CD8$^+$ cytotoxic T cells. The overall result was an increased CD8:CD4 ratio within the tumor microenvironment.

Treatment with mGITRL FP resulted in an increase in the expression of the activation marker ICOS in all T-cell sub-sets in the spleen suggesting an increase in the activation of these cells. See FIG. 19.

Figure 20:
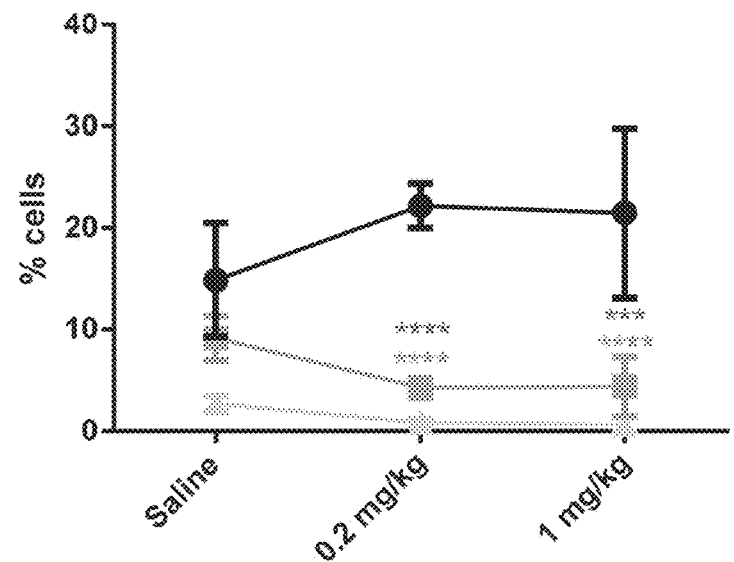
FIG. 20. mGITRL FP results in an increased CD8:CD4 ratio within the tumor. The frequency of CD8 T cells (black line with circles); CD4$^+$ Foxp3$^-$ cells (dark grey line with squares); CD4$^+$ Foxp3$^+$ cells (light grey lines with triangles) was measured by flow cytometry within the tumor 7 days following treatment with a single dose of either 0.2 mg/kg or 1 mg/kg mGITRL FP. Significance was calculated using the Student's T test where $*p<0.05$; $p<0.01$, $*p<0.001$, $****p<0.0001$.

Treatment with mGITRL FP resulted in a decrease in the frequency of CD4+ FOXP3+ regulatory T-cells and CD4+ FOXP3− helper cells within the tumor, but did not alter the frequency of CD8+ cytotoxic T-cells. The overall result was an increased CD8:CD4 ratio within the tumor microenvironment. See FIG. 20.

Method

Cell Lines and Reagents

The TC-1 tumor line was obtained from ATCC (Cat # CRL 6475, Manassas, Va.) and maintained in DMEM+10% FBS+1% penicillin/streptomycin. The CT26 tumor line was obtained from ATCC (Manassas, Va.) and was maintained in RPMI 1640 medium supplemented with 10% fetal bovine serum. DTA-1 and isotype antibodies were purchased from Bio X Cell (West Lebanon, N.H.).

Tumor Models

TC-1 experiments used female C57BL/6 mice (Cat# 000664) mice obtained from Jackson Labs (Bar Harbor, Me.). CT26 experiments used female Balb/C mice obtained from Envigo (Frederick, Md.). Mice were between 6 and 8 weeks of age at the time of tumor implantation. All animal experiments were conducted in accordance with guidelines established by the Institutional Animal Care and Use Committee. For TC-1 tumor implantation, $2 \times 10^4$ viable TC-1 cells was implanted subcutaneously into the left hind footpad. For CT26 tumor implantation, $5 \times 10^5$ cells were implanted in the right flank. Tumor growth was evaluated by direct measurement with calipers 1. Bi-directional measurements were collected every 2-4 days, and tumor volume calculated using volume=(length·width2)/2. Tumors were allowed to develop for 6-14 days and then tumor bearing mice were randomized to treatment groups by tumor volume. Mice were euthanized when the primary tumor exceeded 1000 mm$^3$ for TC-1/footpad and 2000 mm$^3$ for CT26/flank in accordance with IACUC protocol. For PD studies, mice were euthanized and tumors and spleens were harvested, crushed through a 70 uM filter (Corning, Corning, N.Y.), and processed to a single cell suspension.

Functional T-cell Responses and Flow Cytometry

For antigen specific stimulations, $1-2 \times 10^6$ live cells were plated per well with 1 ug AH1 peptide sequence SPSYVYHQF (SEQ ID NO: 56) (Anaspec, Fremont, Calif.) For all stains the order of stain was live/dead blue (Life Tech), extracellular proteins, FOXP3 Fix/Perm Kit (Ebioscience), and followed by intracellular cytokines. Antibodies included GITR (Clone DTA-1). All samples were run on either an LSR-II or Fortessa (BD San Jose, Calif.). All data was analyzed using FlowJo (Treestar, Ashland, Oreg.).

Figure 40P:
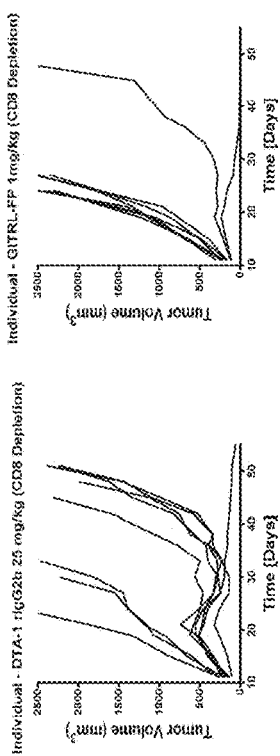
FIG. 40 (A)-(U). (A) CT26 cells were implanted subcutaneously into Balb/C mice, 5×105 cells/mouse. The mice were randomized by tumor volume on day 6 and dosing was initiated (Group n=10 mice). The mice were dosed IP with mGITRL FP IgG2a either with (B-F) a single dose or (G)-(K) every other day for 9 doses, Q2D×9. They were dosed at 5, 1, 0.5, 0.2, 0.1 and 0.04 mg/kg. Data shown is a representative of two repeat experiments. (L)-(O) On day 11 they were randomized based on tumor size and were treated with nothing, DTA-1 (anti-GITR mAb), or mGITRL-FP (Group n=9). (P)-(S) Mice were depleted of CD8 T-cells on day 8, 10, 12, 14, and 16. On day 11 they were randomized based on tumor size and treated with nothing, DTA-1, or mGITRL-FP IgG2a. (T) Median survival. (U) On day 18, untreated mice with CT26 tumors were sacrificed to examine GITR expression on CD8 T-cells and Tregs in the spleen and tumor.
Figure 40Q:
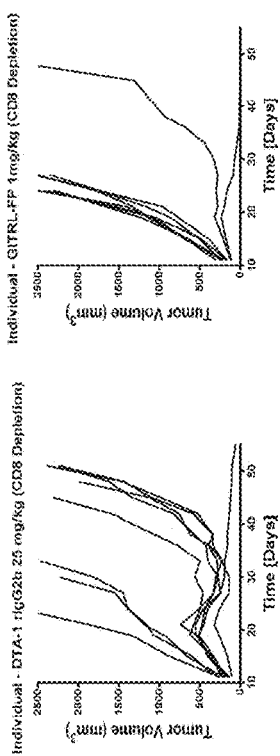
Figure 40R:
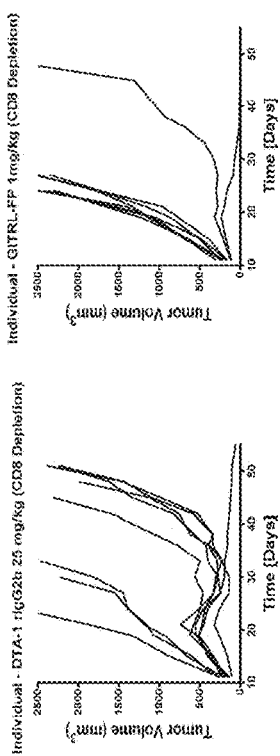
Figure 40S:
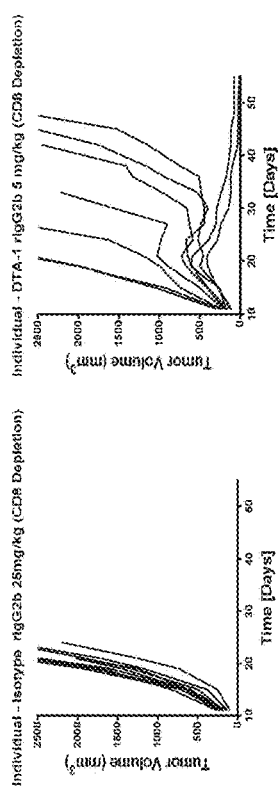
Figures 40T, 40U:
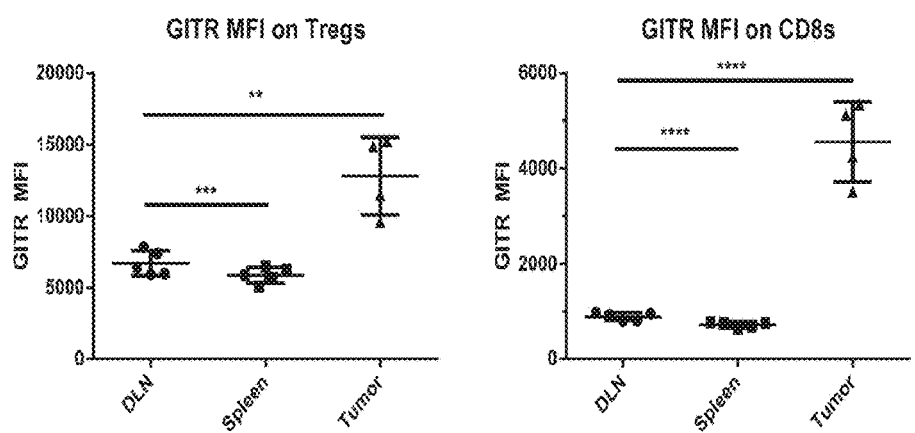

Results mGITRL-FP is a Highly Effective GITR Agonist and this Leads to the Rejection of CT26 Tumors It has previously been shown that GITR agonism is effective at causing the regression and elimination of the CT26 tumor in Bablc mice. Balb/c mice were implanted with CT26 tumor cells and after 6 days were randomized by tumor volume (group n=10) and treated with a single administration or repeat administration of mGITRL-FP IgG2a (Q2D×9). The dose range was from 5 mg/kg body weight down to 0.04 mg/kg body weight. For the single administration, doses down to 1 mg/kg of mGITRL-FP eliminated all but one CT26 mouse tumor to day 30 (FIG. 40B). The lowest doses yielded 3 eliminations in 0.2 mg/kg and 2 in the 0.1 mg/kg groups. Adding additional administrations of mGITRL-FP increased efficacy and all but the lowest dose group of 0.04 mg/kg saw a 100% elimination rate (FIG. 40C). The lowest repeat administration group saw 4 eliminations.

For evaluation of mGITRL-FP function, it was compared to DTA-1, a known monoclonal GITR agonist. Use of a dose ranging from 100 ug to 500 ug per mouse has previously been described. Each mouse was estimated to be roughly 20 grams, so doses ranged from 5 mg/kg to 25 mg/kg. Balb/c mice were implanted with CT26 tumor cells and after 10 days were randomized by tumor volume (group n=10) and then treated with a single administration of either mGITRL-FP IgG2a at 1 mg/kg or DTA-1 at 5 mg/kg or 25 mg/kg (FIG. 40D).

Increasing the dose of DTA-1 increased efficacy, however 1 mg/kg of mGITRL-FP showed similar efficacy and tumor growth kinetics as those of DTA-1 at 5 mg/kg. To determine if CD8 T-cells were necessary for our drug effect, the same groups were evaluated but selectively depleted CD8 T-cells using a monoclonal depletion antibody (FIG. 40E). Without CD8 T-cells, the ability for either DTA-1 or mGITRL-FP to completely eliminate CT26 tumor was significantly diminished. Only 1-2 mice from each group survived tumor free.

Additionally, without CD8 T-cells, mGITRL-FP was less effective than DTA-1 at increasing median overall survival (FIG. 40F). To understand how mGITRL-FP interacts with CD8s, GITR expression on individual lymphoid populations was evaluated. CD4+ Tregs express higher levels of GITR than CD8 T-cells; however, both Tregs and CD8 T-cells in the tumor express higher levels of GITR than their respective populations in the spleen (FIG. 40G).

mGITRL-FP Depletes Tregs and Increases Tumor Antigen Specific T-cells

Figure 41A:
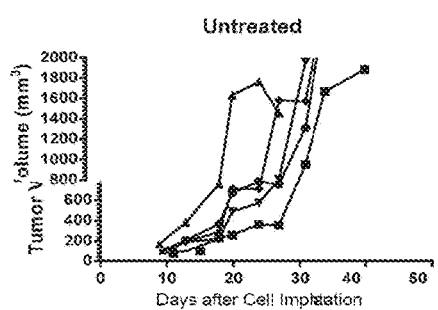
FIG. 41 (A)-(R). (A-B) CT26 cells were implanted subcutaneously into Balb/C mice, 5×105 cells/mouse. The mice were randomized by tumor volume on day 10 and dosing was initiated. The mice were dosed IP with mGITRL-FP IgG2a biweekly for 4 total doses. On day 18 mice were sacrificed to examine (C)-(E) Tregs, (F)-(H) CD8 T-cells. (I)-(J) Mouse spleens a tumors were re-stimulated with 101 µg/mL AH1 peptide/Protein Transport inhibitor for 5 hours and stained for IFNgamma and TNFalpha. (K)-(L) GITR Expression on CD8 cells (M)-(N) GITR Expression on Tregs in the spleen, lymph node, and tumor. (O)-(P) KI-67 on CD4 T-cells (Q)-(R) KI-67 on the CD8 T-cells.
Figure 41B:
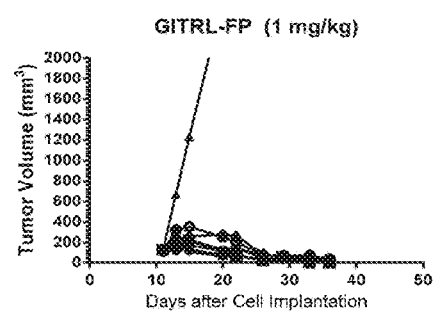
Figure 41C:
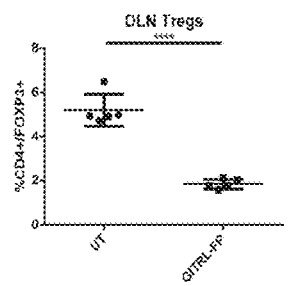
Figure 41D:
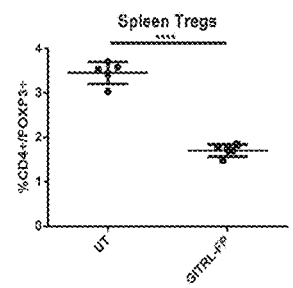
Figure 41E:
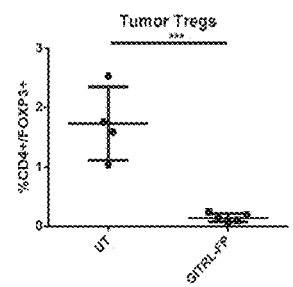
Figure 41F:
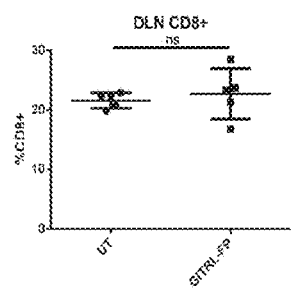
Figure 41G:
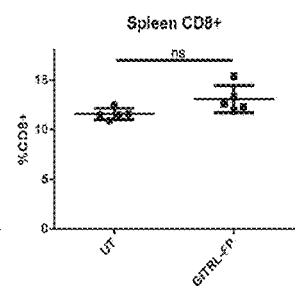
Figure 41H:
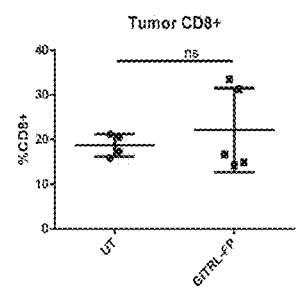
Figure 41I:
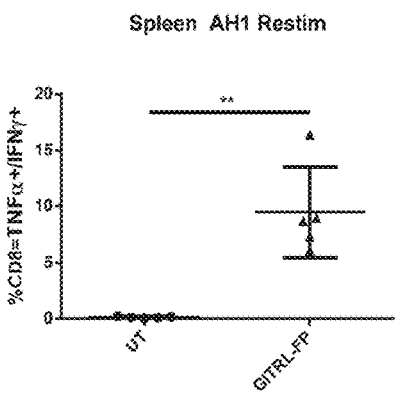
Figure 41J:
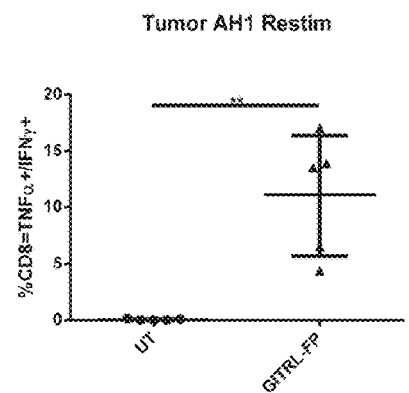
Figure 41K:
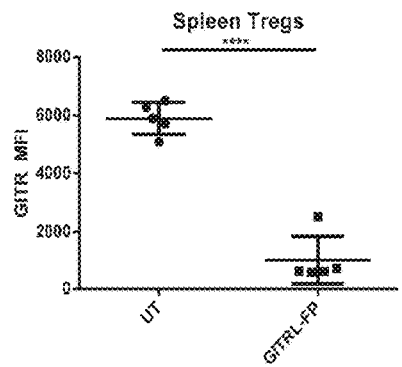
Figure 41L:
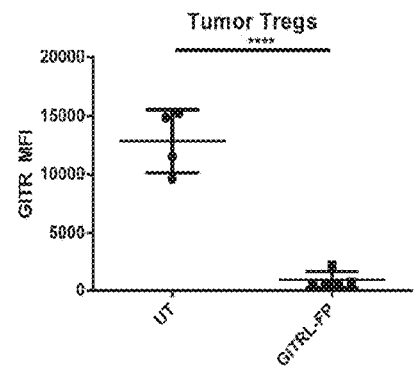
Figure 41M:
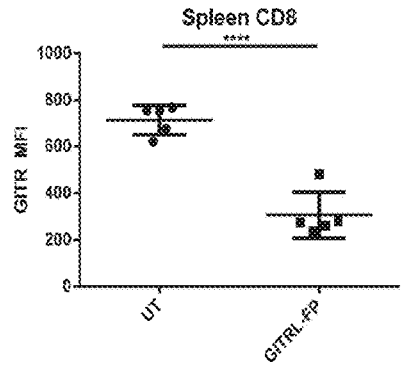
Figure 41N:
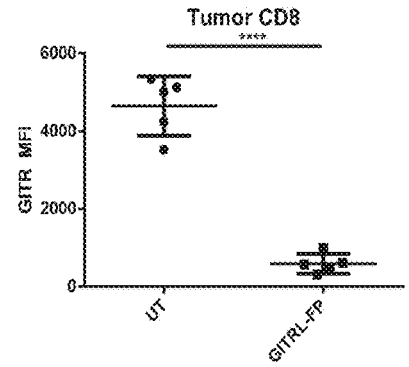
Figure 41O:
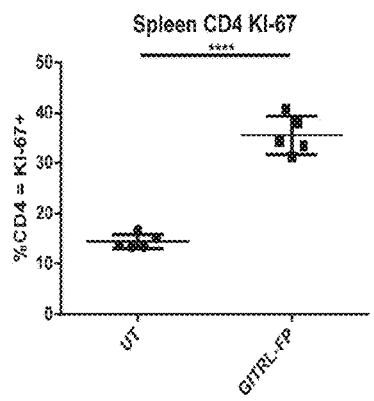
Figure 41P:
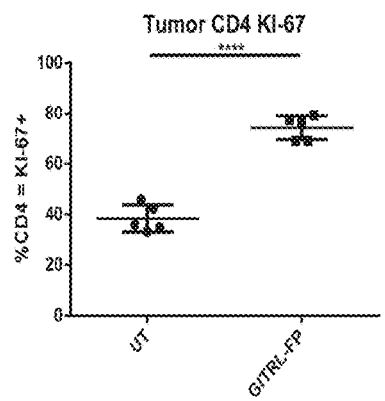
Figure 41Q:
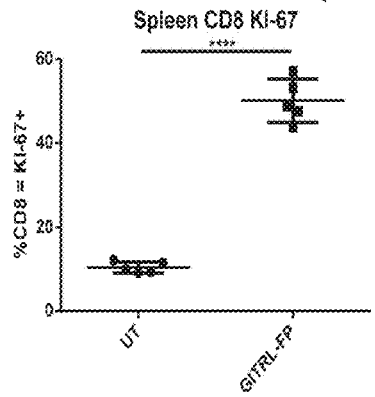
Figure 41R:
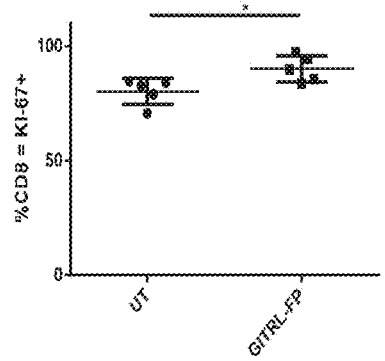

It has previously been shown that GITR agonists decrease Tregs as well as increase high avidity T-cell responses. To understand what pharmacodynamic effects GITRL-FP was capable of mediating, the CT26 model was evaluated during tumor regression. Balb/c mice with CT26 were treated with mGITRL-FP IgG2a and 8 days after dosing began, spleens and tumor were harvested. Two arms of the study were included, a TGI (tumor growth inhibition) group (n=5) and a PD (pharmacodynamic) group (n=5). All but a single mouse treated with mGITRL-FP was cured of CT26 (FIG. 41A). On day 18, the PD group was sacrificed and evaluated both the phenotypes of the immune cells present in the spleen and tumor. CD8 T-cell function was then evaluated by restimulation with AH1, the CT26 immunodominant epitope. mGITRL-FP significantly increased decreased the number of Tregs in the spleen and tumor (FIG. 41B). While mGITRL-FP did not change the percentage of CD8s, it significantly increased the number of CD8s that are antigen specific for AH1 (FIG. 41C-D). In the spleen 5-10% of the total CD8s were antigen specific and capable of producing IFNgamma and TNF alpha. In the tumor, the number was 5-15%. This is significant expansion of both tumor infiltrating lymphocytes as well as the peripheral reservoir. To evaluate whether mGITRL-FP had bound to both CD4 Tregs and CD8 T-cells, GITR was stained for using the DTA-1 antibody (FIG. 41 E-F). Tregs showed more than a 75% reduction in GITR MFI (mean fluorescence intensity). This same effect was observed on the CD8 T-cells, showing that mGITRL-FP was altering DTA-1 binding on the CD8 T-cells. Based on this data, it was hypothesized T-cells would show increased KI-67 proliferation. After evaluation on day 8 after treatments, both CD4 and CD8 T-cells show significantly more KI-67 positive cells in both the tumor and spleen (FIG. 41G-H).

mGITRL-FP Expands Antigen Specific CD8 T-cells in a Dose Dependent Manner

Figure 42E:
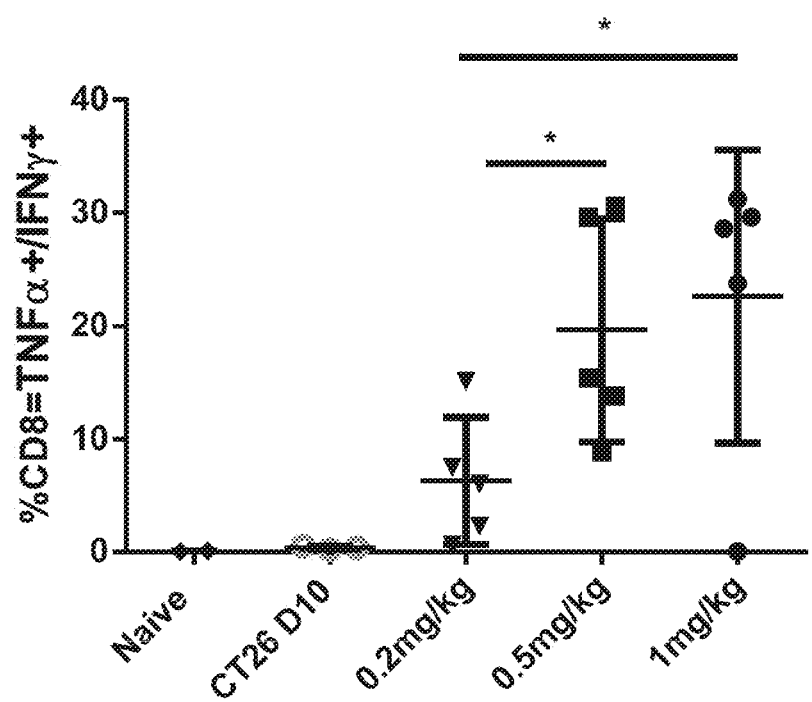
FIG. 42 (A)-(E). mGITRL FP expands antigen specific T-cells in a dose dependent manner. (A)-(C) CT26 tumor bearing mice treated with a single dose of mGITRL FP IgG2a clear tumors and are protected from to rechallenge with 5E5 CT26 cells/mouse on day 85[R Arrow]. (D) After re-challenge with CT26, on day 120, mouse spleen was harvested [PD Arrow], processed to single cell and restimulated with 101 μg/mL AH1 peptide/Protein Transport inhibitor for 5 hours. Mice had a dose dependent increase in AH1 specific T cells. (E) Representative plot of 5 mice from each group. For comparison, naïve mice and untreated mice with CT26 tumors at day 10 are included.

It was next investigated if mice cured of CT26 were protected from rechallenge with the same tumor. To evaluate this, cured mice were rechallenged from groups treated with a single dose of 1.0, 0.5, or 0.2 mg/kg of mGITRL-FP IgG2a (FIG. 42A). All mice from the initial dose down are show, but only mice cured at D85 were rechallenged. All mice originally cured of CT26 were protected from rechallenge of the tumor, although in the lowest dosed groups, a small mass was measured but was quickly eliminated. To further interrogate this result, at day 120 the mice were sacrificed, splenocytes pulled, and restimulated against AH1 peptide. There was a dose dependent increase in the numbers of AH1 specific T-cells (FIG. 42 B-C). In the 1 mg/kg mGITRL-FP group, 25% of the splenic CD8 T-cells are specific for a single epitope of CT26. These mice showed no increased in tumor size during re-challenge. The lowest dose, 0.2 mg/kg, had 6% antigen specific CD8s and showed a small growing mass upon rechallenge that was cleared by day 120.

Binding Affinity of a Hexameric GITRL IgG1 FP to Human GITR

The solution KD (dissociation constant) of a hexameric GITRL IgG1 FP comprising GITRL IgG1 FP monomeric subunits of SEQ ID NO: 6 for recombinant human GITR was determined using a kinetic exclusion assay (KinExA) using a KinExA 3200 instrument (Sapidyne Instruments, Boise Id.).

2 nM solutions of the hexameric GITRL IgG1 FP in D-PBS, 0.02% sodium and 1 mg mL$^1$ bovine serum albumin buffer were titrated with recombinant human GITR and equilibrated overnight at 25° C. Samples were transferred to the KinExA 3200 instrument which was temperature controlled at 25° C. Sampling of the equilibrated mixtures was achieved using azlactone bead-bound streptavidin that had been titrated with minimally amine-biotinylated human GITR. The secondary detection reagent used was the Fc specific reagent DyLight 650 labelled Protein G' (a fragment of Protein G available from Sigma). Data was processed and interpreted using KinExAPro software (version 3.6.8.). A $K_D$ of 82 nM was obtained for the binding of the hexameric GITRL IgG1 FP to human GITR.

Binding of a Hexameric GITRL IgG1 FP to Recombinant Cynomolgus Monkey GITR by KinExA The solution $K_D$ of a hexameric GITRL IgG1 FP comprising GITRL IgG1 FP monomeric subunits of SEQ ID NO: 6 for recombinant cynomolgous GITR was determined using a KinExA in the same manner as described in Section 6.1 for human GITR. A $K_D$ for the binding of the hexameric GITRL IgG1 FP to cynomolgus GITR of 107 nM was obtained.

Figure 21:
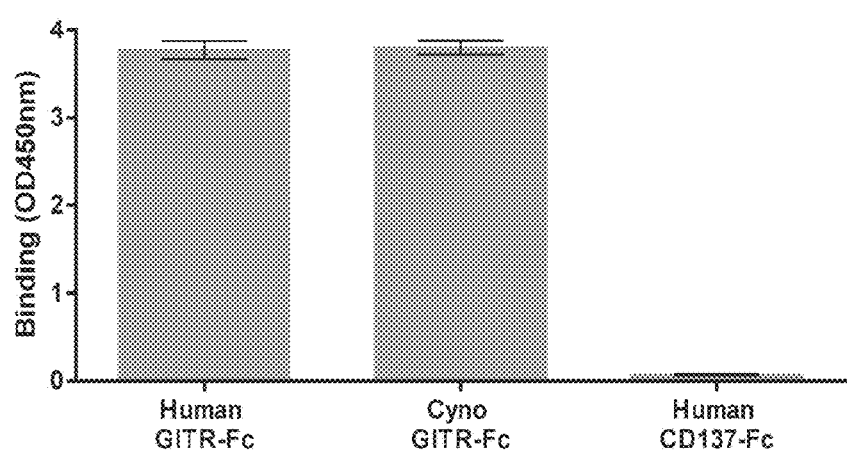
FIG. 21. ELISA data demonstrating that hexameric hGITRL IgG1 FP binds to human and cynomolgus GITR-Fc. Binding of biotinylated hexameric hGITRL IgG1 FP comprising monomeric subunits having the amino acid sequence set forth in SEQ ID NO: 6 to recombinant human and cynomolgus monkey (cyno) GITR. CD137-Fc was used as a negative control to determine the background signal in the assay. Experiments were conducted in triplicate wells. Error bars represent standard deviation. CD137=cluster of differentiation 137 (TNFRSF9); CD137-Fc=cluster of differentiation 137 extracellular domain linked to the Fc domain of hIgG1; Cyno=cynomolgus monkey; ELISA=enzyme-linked immunosorbent assay; GITR-Fc=glucocorticoid induced tumor necrosis factor receptor extracellular domain linked to the Fc domain of hIgG1; OD450 nm=optical density readings at 450 nm wavelength.

Binding of a Hexameric GITRL IgG1 FP to Recombinant Cynomolgus Monkey GITR by ELISA The cross-reactivity of a hexameric GITRL IgG1 FP comprising GITRL IgG1 FP monomeric subunits of SEQ ID NO: 6 to cynomolgus GITR was determined using an ELISA. The hexameric GITRL IgG1 FP was biotinylated and binding to immobilized cynomolgus GITR-Fc was detected using streptavidin-HRP and TMB substrate. FIG. 21 shows that the binding of the hexameric GITRL IgG1 FP to cynomolgus GITR is very similar to human GITR, and that no binding is observed to the negative control CD137-Fc protein.

Example 3

In Vivo Pharmacodynamic Effect of Intravenous GITRL IgG1 FP Treatment in the Cynomolgus Monkey To determine the pharmacodynamic parameters of a hexameric GITRL IgG1 fusion protein (FP) in the cynomolgus monkey, hexameric GITRL IgG1 FP comprising GITRL IgG1 FP monomeric subunits of SEQ ID NO: 6 was administered by intravenous (IV) bolus injection to groups (5/group) of male Cynomologus monkeys.

Method

Separate groups of animals were injected on day 1, day 3 and day 5 with 1 or 10 mg/kg hexameric GITRL IgG1 FP. Control animals received vehicle (20 mM Sodium Phosphate, 230 mM Sucrose, 0.02% P80, pH 7.5). Blood samples were taken during the predose phase and on Days 1, 3, 5, 9, 11, 15, 18, 22, and 29 for the measurement of pharmacodynamic endpoints.

Using standard flow cytometry methods, Ki67 positive T-cell populations were measured from the whole blood.

Results

Figure 22:
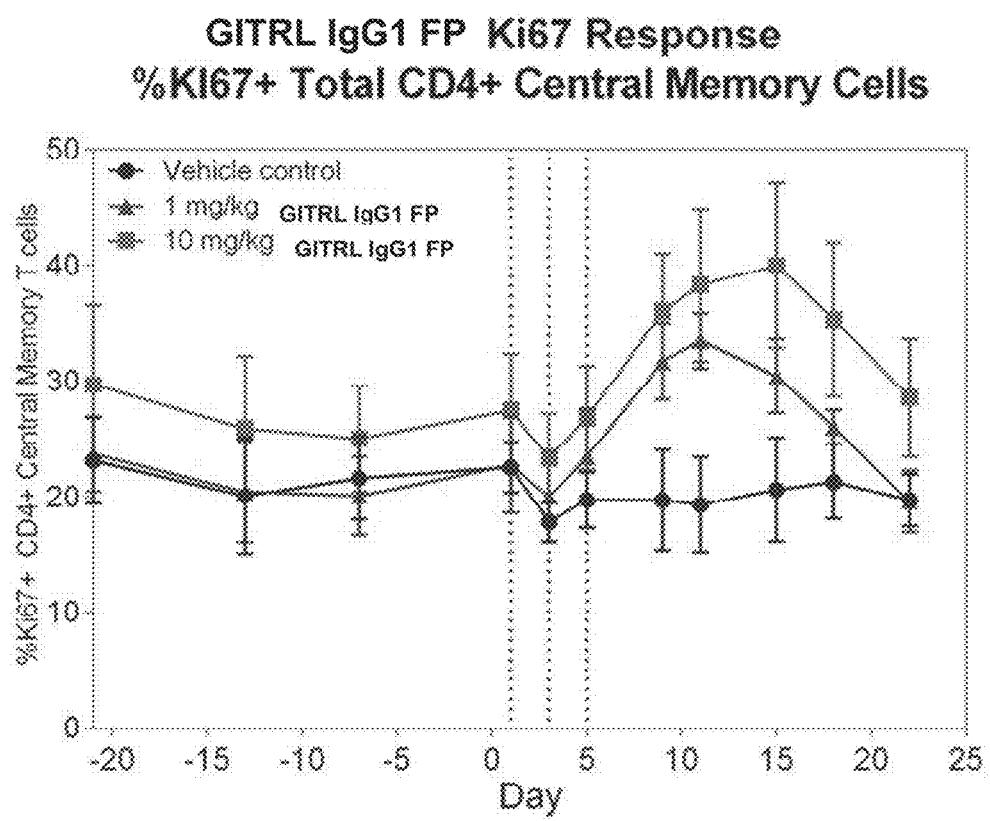
FIG. 22. Measurement of % K167 positive T cell subpopulations in hexameric hGITRL IgG1 FP treated Cynomolgus Monkeys. Cynomolgus monkeys were monitored for baseline levels of % KI67 positive T cell subpopulations for 20 days, treated with either a vehicle control (circles), 1 mg/kg hGITRL IgG1 FP (triangles), or 10 mg/kg hGITRL IgG1 FP (squares) at day 0, and then monitored for % KI67 positive T cell subpopulations days 1, 3, 5, 9, 11, 15, 18, 22, and 29.

An increase in the % Ki67 positive T-cell subpopulations was observed e.g. (CD3+CD4+CD95high CD28+/dim/– total memory CD4+ and CD3+CD8+CD95high CD28+/dim/– total memory CD8+ T-cells) indicative of cell proliferation (FIG. 22). This observation reached a maximum at Day 11 or 15 of the dosing phase and then declined towards the end of the study.

Example 4

Mutation of Amino Acids within GITRL FP and their Impact on Receptor Binding, Agonist Activity and Thermal Stability Generation of hGITRL FP variants with mutations in the GITRL Receptor Binding Domain hGITRL FP Variants were Generated and Tested for their Ability to Bind to and Agonise GITR. In some cases their thermal stability was also assessed.

Method

Using gene synthesis and standard DNA cloning techniques, DNA vectors encoding GITRL FP variants were generated. Suspension CHO cells were transiently transfected, using PEI, with DNA vectors encoding the different hexameric hGITRL fusion proteins and grown for eight days at 37° C., shaking at 140 rpm with 80% humidity. Forty milliliters of the conditioned media containing the secreted proteins was separated from cells and cell debris by centrifugation at 1,600×g and filtration. The proteins were purified using Mab SelectSure™ resin and their size and integrity was analysed by reducing SDS-PAGE.

Competition of GITRL FP Variants with Recombinant Trimeric Ligand for Binding to GITR The effect of the GITRL FP molecules on human GITRL binding to human GITR was determined using a Homogeneous Time Resolved Fluorescence (HTRF) assay.

Method

The GITRL FP molecules were titrated into an HTRF assay in which binding of GITRL-HA (hemagglutinin tag) to GITR-Fc was measured. The human GITR Fc was conjugated with europium cryptate and an anti-HA antibody conjugated with XL665 was used to detect the GITRL-HA protein. $IC_{50}$ values were determined by curve fitting the analyzed data to a four parameter logistic equation with Prism 5.01 software (GraphPad).

Results

Figure 23A:
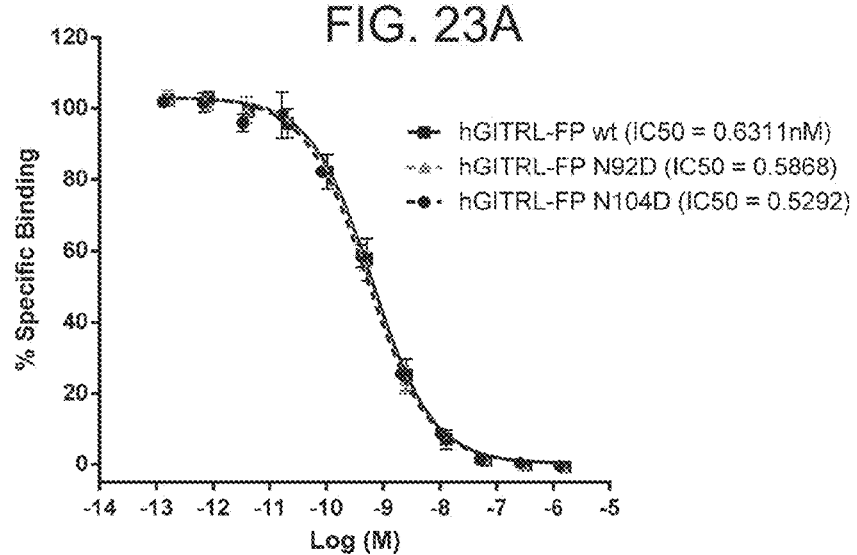
FIG. 23 A-B. Inhibition profiles for hGITRL FP proteins competing for binding of trimeric hGITRL to hGITR-Fc and IC$_{50}$ values. hGITRL FP wt, N92D and N104D (A) and hGITRL FP, N161D (B)
Figure 23B:
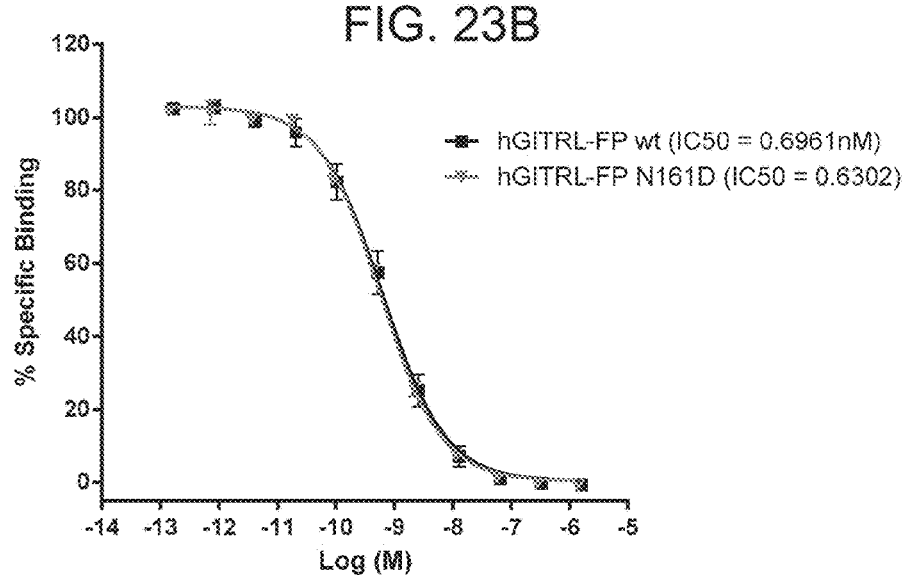

The mutated hexameric GITRL FP molecules (hGITRL-FP wt, N92D, N104D and N161D) are all potent inhibitors of trimeric GITRL-HA binding to GITR-Fc and produced similar inhibition profiles and $IC_{50}$ values (FIG. 23 A, B).

Binding of GITRL FP Variants to Recombinant GITR-Fc

The functional activity of the different hGITRL FP molecules was determined in an assay using NFκB-luciferase reporter cells stably expressing hGITR. Luminesence, driven by agonism of hGITR and subsequent activation of the NFκB pathway, was measured.

Method

The hGITRL FP molecules were titrated into an HTRF assay in which binding of the hGITRL FP to hGITR-Fc was measured. The human hGITR Fc was conjugated with europium cryptate and an anti-FLAG antibody conjugated with XL665 was used to detect the hGITRL FP protein. KD values were determined by curve fitting the analyzed data to a one site saturation binding equation with Prism 5.01 software (GraphPad).

Results

Figure 24:
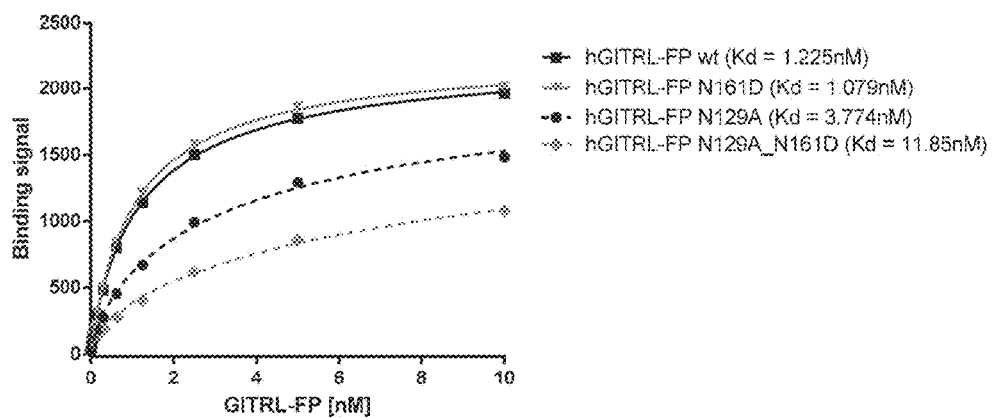
FIG. 24. Binding profiles for hGITRL FP proteins binding to hGITR-Fc and Kd values.

The binding profiles for hGITRL FP wt and hGITRL FP N161D were very similar (KDs of 1.225 nM and 1.079 nM, respectively), whereas the N129A mutated hGITRL FP showed reduced binding to hGITRFc (KD=3.774 nM). When the N129A mutation was combined with the N161D mutation, the binding capacity of the hGITRL FP molecules was further negatively impacted (KD=11.85 nM) (see FIG. 24).

Activity of GITRL FP Variants in a Reporter Assay

The functional activity of the different hGITRL-FP molecules was determined in an assay using NFκB-luciferase reporter cells stably expressing hGITR. Luminescence, driven by agonism of hGITR and subsequent activation of the NFκB pathway, was measured.

Method hGITRL FP proteins were serially diluted 4-fold for a 6-point data curve and added in triplicate to 96 well plates. Then Jurkat NF-κB luciferase reporter cells transfected with human GITR were added to all wells of the assay plates and incubated at 37° C. for three hours. Luciferase expression was detected by adding Steady-Glo reagent to all wells of the assay plates. The plates were incubated for five minutes at room temperature and then luminescence was measured and $EC_{50}$ values were generated using log(agonist) vs. response variable slope nonlinear curve fit in GraphPad™ Prism 5.01 (GraphPad Software, Inc. La Jolla, Calif. USA).

Results

Figure 25A:
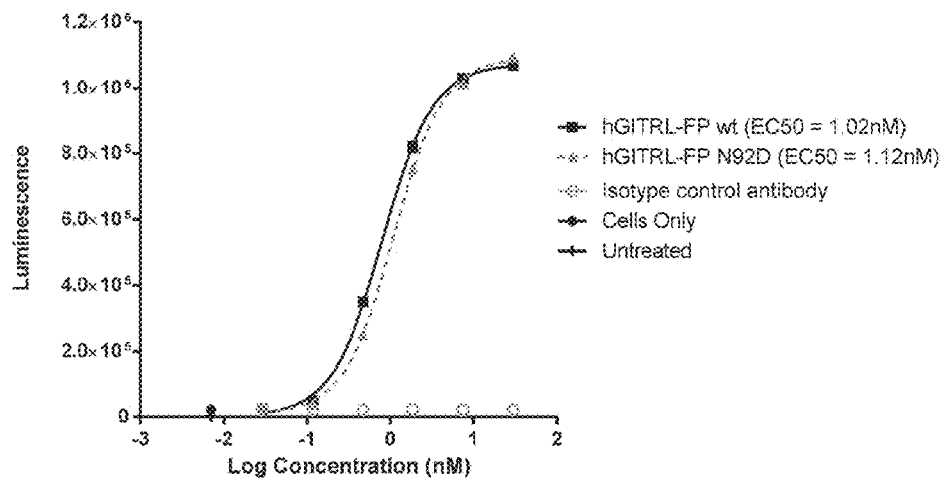
FIG. 25 A-C. Graphs showing the relative potency of the GITRL FP molecules using a human GITR transfected NF-κB luciferase gene reporter cell line and EC$_{50}$ values. hGITRL FP wt and N92D (A); hGITRL FP wt, N161D, N129A and N129A/N161D (B); N161D and N129A/N161D (C)
Figure 25B:
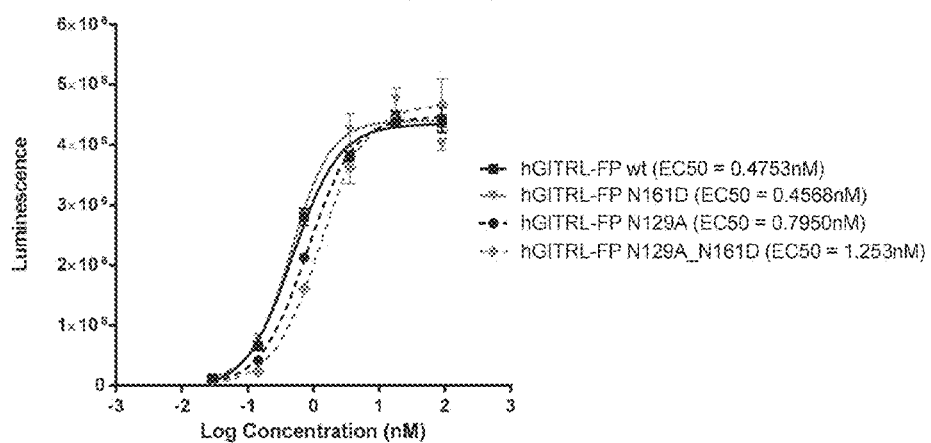
Figure 25C:
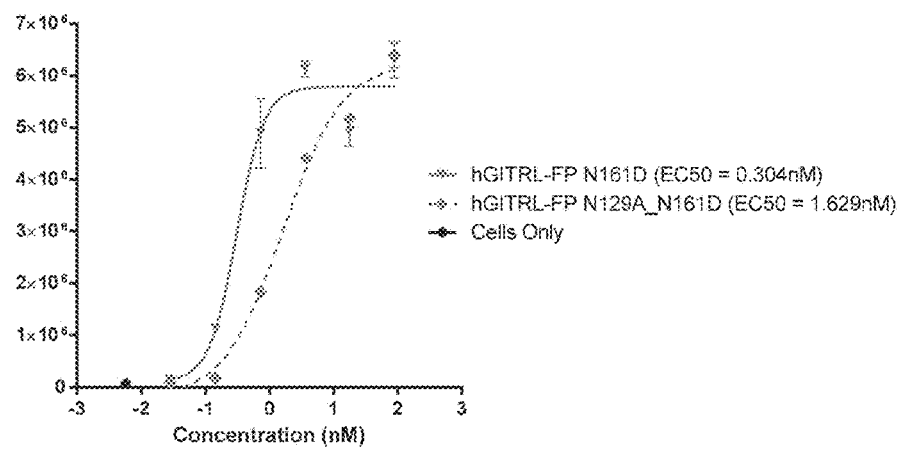

All GITRL FP proteins trigger NF-κB signalling. The N92D and N161D mutant hGITRL FP proteins generated similar potency profiles and $EC_{50}$ values to GITRL FP (wt). The N129A and N129A/N161D mutations negatively impacted the ability of the hGITRL FP to agonise GITR in this assay (FIG. 25 A-C).

Activity of GITRL FP Variants in a T Cell Re-Stimulation Assay

The functional activity of the different hGITRL FP molecules was determined in a co-stimulation assay using primary human T cells and a thymidine incorporation readout.

Methods

Human peripheral blood mononuclear cells (PBMCs)-derived $CD3^+$ T cells were stimulated via incubation in TC treated plates coated with mouse anti-human CD3 antibody for four days at 37° C. They were then pelleted by centrifugation, resuspended in assay media, added to a TC treated plate and incubated at 37° C. for two days (rest phase). hGITRL FP molecules were serially diluted in assay media 2-fold over 10 points and added in triplicate to TC treated plates pre-coated with mouse anti-human CD3. After two hours the assay plates were washed and the $CD3^+$ T cells prepared previously were added to each well and incubated at 37° C. for four days. After four days, tritiated thymidine in assay media was added into each well and plates were incubated at 37° C. for a further 18 hours. After the incubation, the incorporation of thymidine was measured using a Topcount™

Results

Figure 26A:
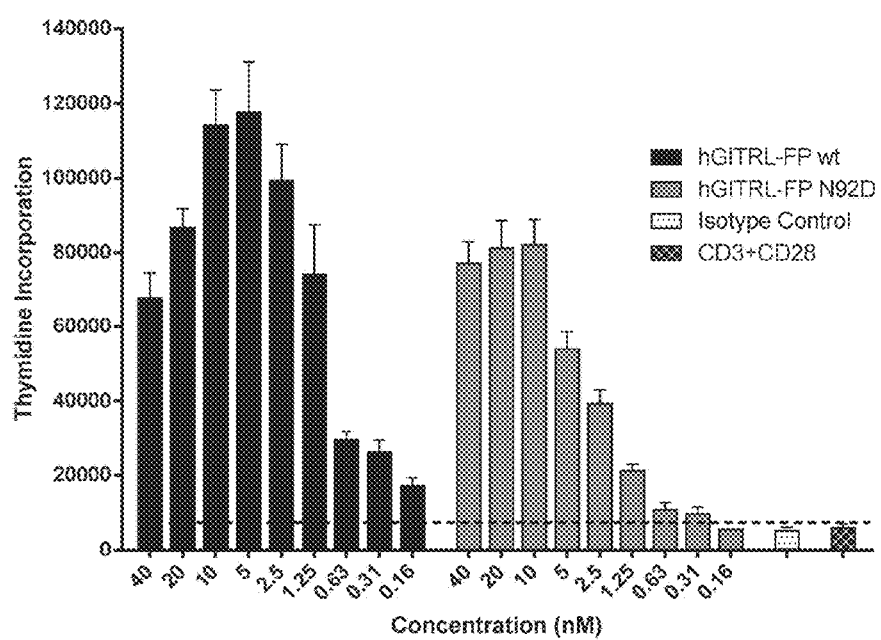
FIG. 26 A-C. Graphs showing the relative potency of the GITRL FP molecules using a human primary CD3$^+$ T cell re-stimulation assay with a thymidine incorporation readout. hGITRL FP wt and N92D (A); hGITRL FP wt, N92D and N104D (B); wt and N161D (C).
Figure 26B:
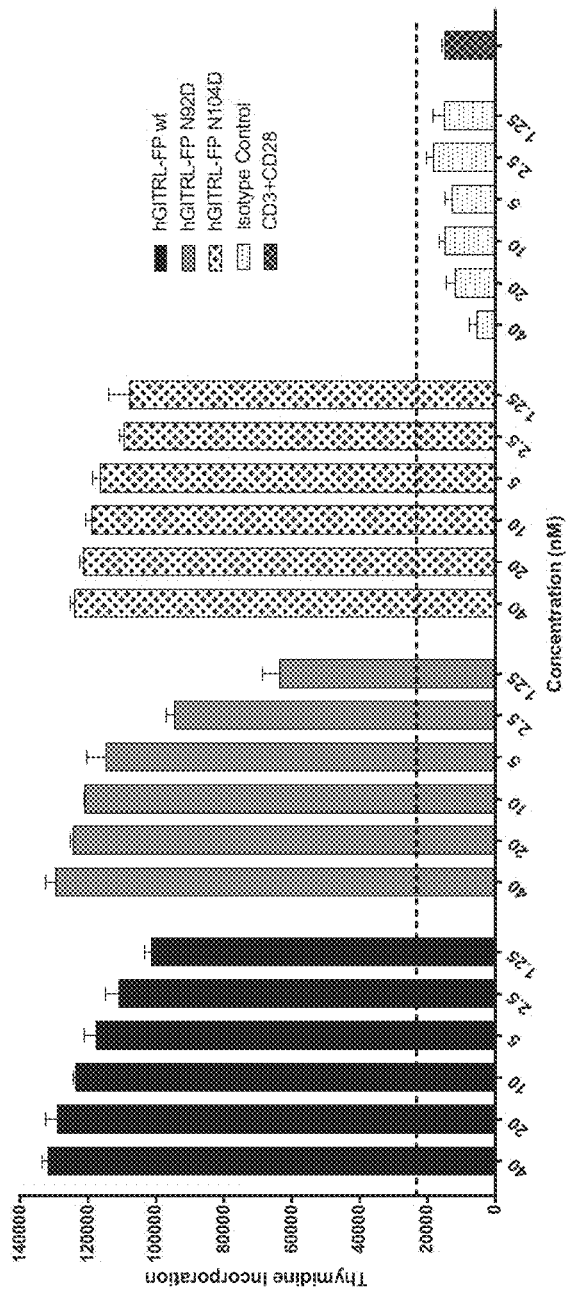
Figure 26C:
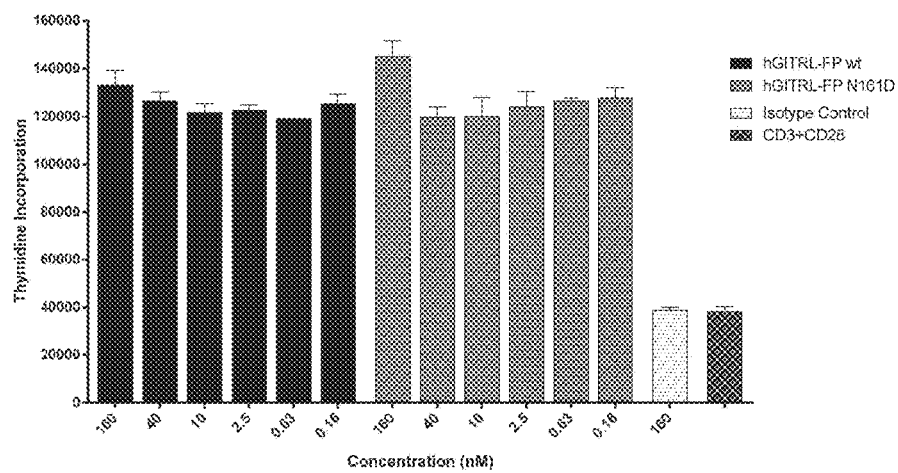

All hGITRL FP mutants tested demonstrated equivalent activity to hGITRL FP wt, with the exception of N92D which had reduced activity in two independent experiments (FIG. 26 A-C).

Melting Temperature of GITRL FP Variants

The melting temperature of the GITRL FP wt and N92D proteins was determined using a fluorescent dye (Sypro™ Orange), the emission properties of which change in the presence of an unfolded protein.

Method

Thermostability of wt and N92D GITRL FP variants was assessed using a Sypro Orange-based assay to calculate melting temperatures (Tm). The proteins were first diluted to 0.5 mg/mL in 2×PBS before dispensing into a 96 well PCR plate. Sypro™ Orange was added to each well on the plate, which was then sealed. Plates were read on a Real-Time PCR machine using a Chromo4™ continuous fluorescence detector. The temperature was set to increase from 20° C. to 90° C. with a read every 1° C. and a hold time of is. Unfolding transitions were determined by plotting the fluorescence intensity and fluorescence derivative as a function of temperature. Each GITRL FP protein was analysed in duplicate.

Results

Figure 27A:
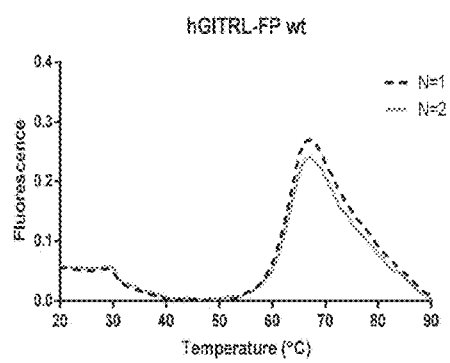
FIG. 27 (A)-(B). Unfolding transitions of GITRL FP wt (A) and N92D variant (B).
Figure 27B:
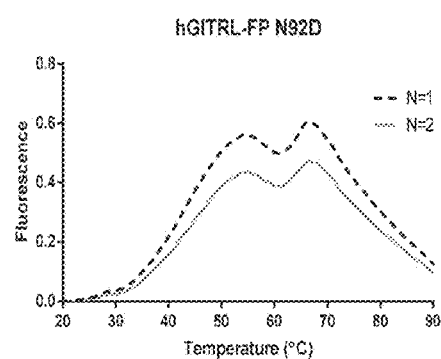

Melting temperatures for the two GITRL FP proteins are summarised in Table 4-1 below. Both variants have a transition peak at 67° C., however, hGITRL FP N92D displays an additional broad transition peak at a low temperature (54° C.) suggesting structural instability (FIG. 27).

TABLE 4-1

Transition temperatures for the 2 GITRL FP proteins

| # | Test sample | Tm1 (° C.) | Tm2 (° C.) |
|---|---|---|---|
| 1 | GITRL FP wt | / | 67 |
| 2 | GITRL FP N92D | 54 | 67 |

Data Summary and Conclusions

The N104D GITRL FP protein demonstrated equivalent activity to the wild-type hGITRL FP counterpart in the GITR/GITRL competition binding assay and the primary T cell re-stimulation assay suggesting that N104 does not play a key role in the activity of hGITRL FP. The mutation of Asn161 to Asp represents the removal of an N-linked glycosylation site (see data in example 4) and this mutant (hGITRL FP N161D) retained activity in all assays (GITR/GITRL competition binding, direct binding, reporter and primary T cell re-stimulation assays), suggesting that Asn161, and the glycans at this site are not involved in important functions such as binding and agonism of GITR.

The N129A mutant demonstrated reduced binding to hGITR and reduced activity in the reporter assay suggesting it plays a role in binding to hGITR and subsequent agonism of hGITR. Interestingly, when this mutation was combined with the N161D mutation (which alone did not impact activity) the binding and agonism of GITR was reduced even further.

The N92D mutation did not appear to impact activity of hGITRL FP when it was tested in the reporter assay, however, reduced activity of hGITRL FP N92D was observed in the primary T cell re-stimulation assay. When the thermal stability of the N92D mutant was investigated, an additional very broad lower melting temperature transition peak was observed compared to hGITRL FP, suggesting some structural instability at lower temperatures (including 37° C.). Due to the longer timecourse of the primary T cell assay (4 days), it could be envisaged that the hGITRL FP N92D molecule becomes unstable and unfolds, leading to reduced activity in this assay compared to the reporter assay (3 hours). Thus, the mutation of Asn92 to Asp appears to be unfavourable in terms of structural stability.

Example 5

Identification of Amino Acid Residues within hGITRL FP that are Glycosylated

There are two potential N-glycosylation consensus sites within the GITR binding domain (N161 and N129). The presence and structure of the glycans at these sites, as well as at the canonical N-glycosylation site within the Fc domain (N297 in the context of an IgG; N78 in the mature hGITRL FP sequence), were determined by mass spectrometry.

Methods

Recombinant Protein Expression and Purification

Recombinant hGITRL FP wt and N161D proteins were purified from the conditioned media of CHO cells transiently transfected with vectors encoding the relevant proteins using affinity chromatography and subsequent size exclusion chromatography.

Tryptic Peptide Mapping

Samples of hGITRL FP wt and hGITRL FP N161D were denatured, reduced and the reduced cysteines were alkylated. The samples were then digested with trypsin. After 4 hours at 37 C, the digestion was quenched by addition of acid. The peptides were separated by reverse phase on a UPLC and measured using a UV detector and a mass spectrometer. The resultant tryptic peptide sequences are provided in Table 5-1.

Results:

TABLE 5-1

| ID | Sequence | Sample |
|---|---|---|
| T7 | EEQYNSTYR (SEQ ID NO: 43) | hGITRL FP wt & hGITRL FP N161D |
| T40 | DMIQTLTNK (SEQ ID NO: 44) | hGITRL FP wt & hGITRL FP N161D |
| T42-43 | IQNVGGTYELHVGDT IDLIFNSEHQVLKNN TYWGIILLANPQFIS (SEQ ID NO: 45) | hGITRL FP wt |
| T43' | DNTYWGIILLANPQF IS (SEQ ID NO: 46) | hGITRL FP N161D |

Figure 28:
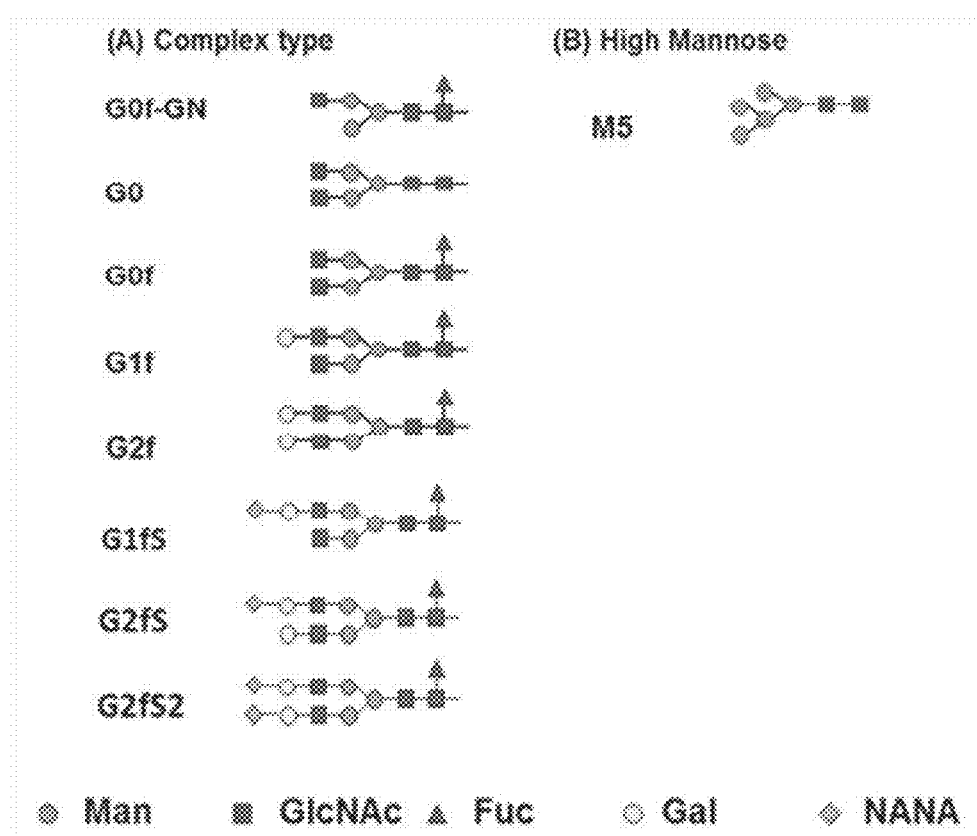
FIG. 28. (A)-(B). Predominant oligosaccharide structures found in hGITRL FP produced in Chinese Hamster Ovary cells; Complex type (A); High mannose (B). Man=Mannose; GlcNAc=N-acetylglucosamine; Fuc=Fucose; Gal=Galactose; NANA=Nacetylneuraminic acid (Sialic acid).
Figure 29A:
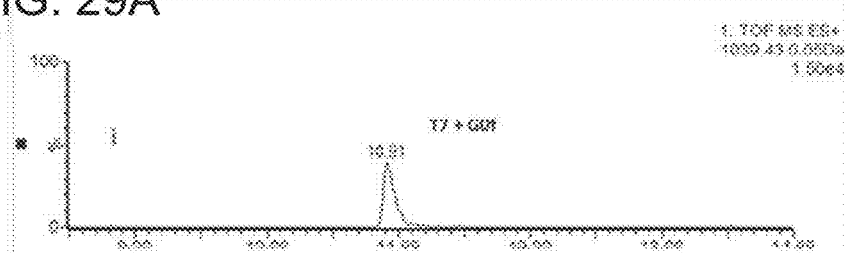
FIG. 29 (A)-(L). GITRL FP peptide mapping. Extracted ion chromatograms for tryptic peptide 7 (T7), which contains the Fc N-glycosylation site, for GITRL FP wt (A) and GITRL FP N161D (B). Combined, deconvoluted mass spectra for T7, showing the predominant glycoforms, for GITRL FP wt (C) and GITRL FP N161D (D). Extracted ion chromatograms for tryptic peptide 40 (T40), which contains the GITRL ECD N129 N-glycosylation consensus sequence, for GITRL FP wt (E) and GITRL FP N161D (F). Combined, deconvoluted mass spectra for T40, showing a mass consistent with the absence of N-glycosylation at N129, for GITRL FP wt (G) and GITRL FP N161D (H). Extracted ion chromatograms for tryptic peptide 42-43 (T42-43) and 43 (T43) for GITRL FP wt (I) and GITRL FP N161D (J), respectively. Combined, deconvoluted mass spectra for T42-43 for GITRL FP wt (K) showing the predominant glycoforms at the GITRL ECD N161 N-glycosylation site. Combined, deconvoluted mass spectra for T43 for GITRL FP N161D (L), showing a mass confirming the N161D substitution and the absence of N-glycosylation.
Figure 29B:
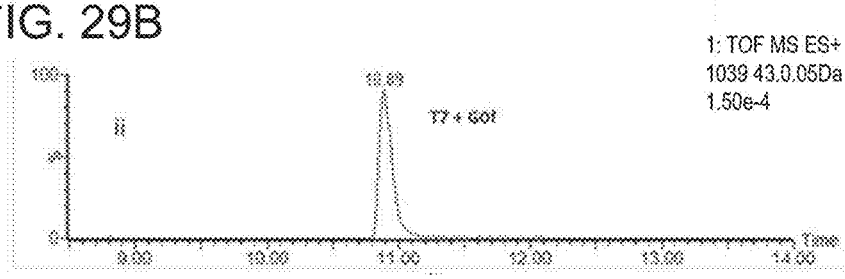
Figure 29C:
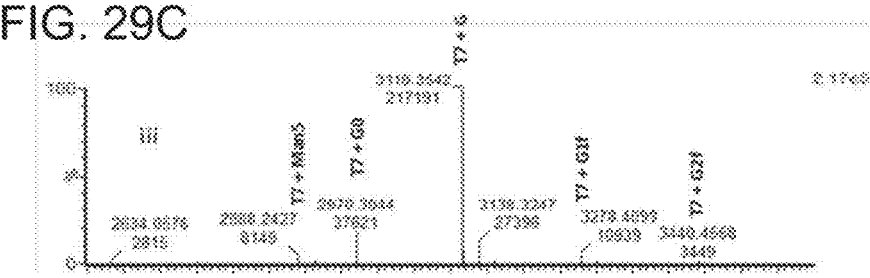
Figure 29D:
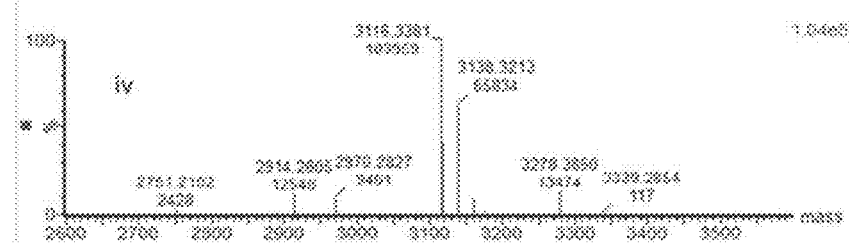
Figure 29E:
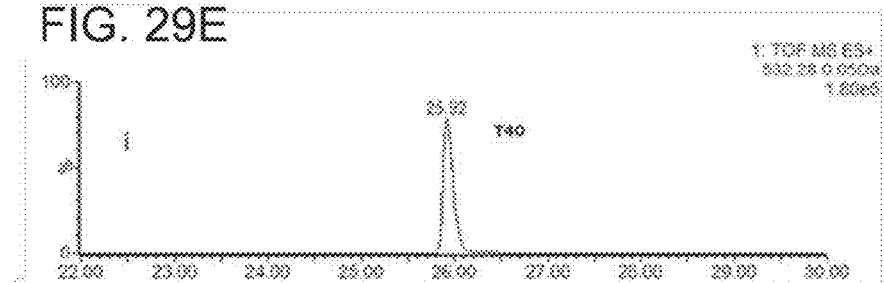
Figure 29F:
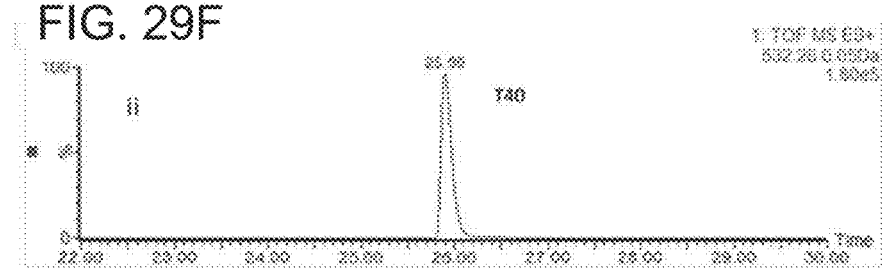
Figure 29G:
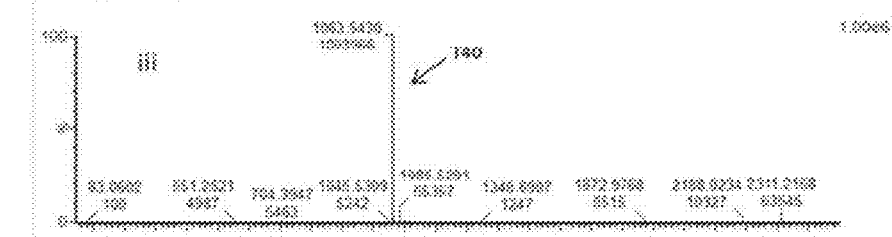
Figure 29H:
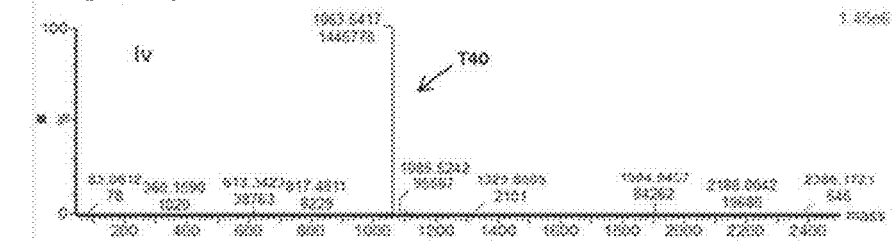
Figure 29I:
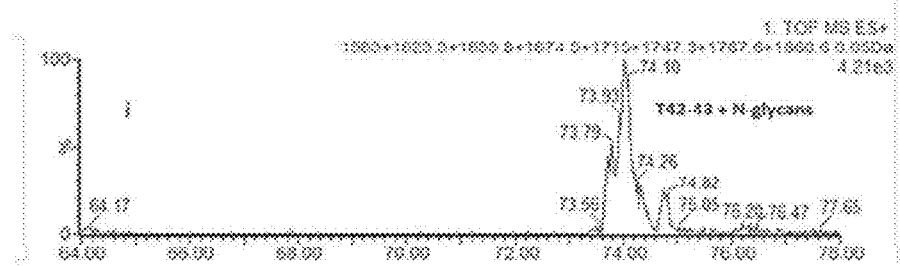
Figure 29J:
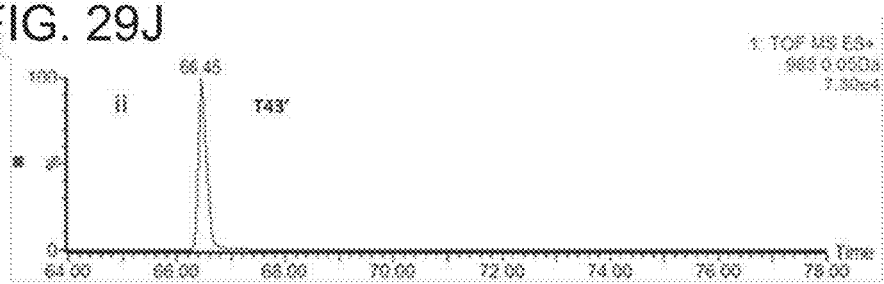
Figure 29K:
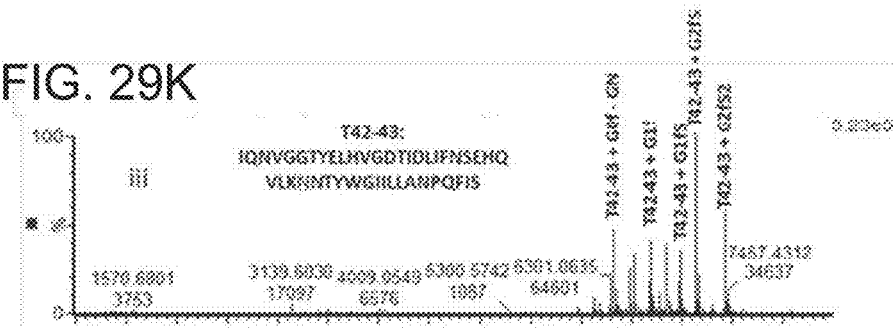
Figure 29L:
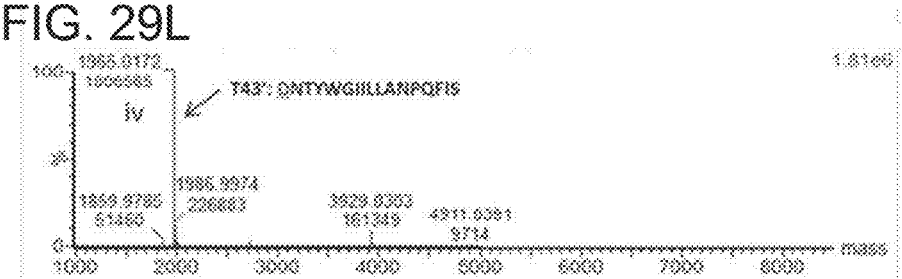

N = Asparagine part N-glycosylation consensus sequence.
D = N161D substitution in hGITRL FP N161D A schematic diagram of the types of oligosaccharide structures found in the various hGITRL FP is provided in FIG. 28. Mass spectrometry data is provided in FIGS. 29 A, B, and C.

Conclusion

Peptide mapping analysis was used to determine N-glycosylation site occupancy in the GITRL and Fc domains, as well as the structure of the predominant oligosaccharides at each site. In both hGITRL FP wt and hGITRL FP N161D proteins the canonical Fc N-glycosylation site (N78) was glycosylated and the predominant carbohydrate structures were neutral, biantennary complex type oligosaccharides; typical for IgG Fc regions expressed in CHO cells. The N-glycosylation consensus site at N129 within the GITRL RBD was not occupied with any oligosaccharide structures in either hGITRL FP wt or hGITRL FP N161D. The N-glycosylation consensus site at N161 within the GITRL RBD was occupied in hGITRL FP wt and the predominant carbohydrate structures were found to be neutral and charged, biantennary complex type oligosaccharides. In the hGITRL FP N161D protein, peptide mapping confirmed the N161D amino acid substitution, which removes the N161 N-glycosylation consensus site from the GITRL RBD. As expected no N-glycosylation was detected at D161.

Example 6

Murine Models and OX40 Combination Studies

In order to better understand targeting of GITR, the activity and pharmacodynamic effects of murine GITRL-FP were compared to those of an agonistic murine OX40L FP targeting OX40.

Materials and Methods

NF-κB Reporter Assay

Jurkat mGITR or human OX40 NFκB cells were cultured at 37° C., 5% CO$_2$ and 85% humidity in 96 well plates at 50,000 cells (Jukat mGITR) or 200,000 cells (Jurkat human OX40) /well together with anti-GITR antibody DTA-1 (Biolegend), NIP rIgG2b isotype control, mGITRL-FP mIgG2a or plate immobilized mOX40L-FP mIgG1 or isotype control (comprised a single amino acid mutation at a position (Y182A) that rendered the protein unable to signal via OX40) as indicated. Steady Glo® Reagent (Promega) containing luciferin substrate, was added to the plates after 5 hours or after 16 hours for assays containing mOX40L-FP mIgG1 and the plates were incubated for 30 min in the dark on a plate shaker. Assay signal was detected using an Envision plate reader (Perkin Elmer).

Sds Page

Five micrograms of protein were mixed with loading buffer and reducing agent, denatured at 80° C. for 10 mins and loaded onto a 4-20% Tris-Glycine SDS-PAGE gel (Thermo Fisher), alongside a protein molecular weight marker (Rainbow Marker, GE Healthcare). The proteins were electrophoresed for 45 mins at 200V and stained using Instant Blue protein stain (Sigma).

Mice and Tumor Models 8-10-week-old BALB/c or C57BL/6 female mice were obtained from Charles River UK Ltd. or Harlan Laboratories Inc. A 100 µL suspension of CT26 or B16F10-Luc2 cells in PBS at a cell density of $5 \times 10^6$ cells/mL or $5 \times 10^4$ cells/mL 100 µl was subcutaneously injected into the right flank of each animal. The B16F10-Luc2 cell line incorporated a luciferase reporter under the control of the CAG promoter and cells were implanted in 50% PBS and 50% growth factor reduced and phenol red free matrigel (Corning). Measurable tumors were randomized based on tumor volume. The length (mm) and width (mm) of each tumor was measured with an electronic caliper 3 times per week. Volumes of tumors (mm$^3$) were calculated based on the formula (length [mm]× width [mm]$^2$)/2. Tumor growth responses were categorized as a response if there was no measureable tumor or a sustained tumor growth inhibition such that volume was less than 200 mm$^3$ at the end of the study. Number of regressions indicated on each spider plot is the proportion relative to the total number of tumors implanted. Mice were dosed i.p. with either mGITRL-FP or mOX40L-FP at day 6 post implantation of syngeneic tumors, or when they reached a volume of 200 mm$^3$. Dosing of 25 mg/kg mGITRL-FP in B16F10-Luc2 bearing mice was only tolerated for four doses.

Flow Cytometry

Tumour, spleen or tumor draining lymph node were dissected and placed into RPMI-1640 media on ice. Tissues were disaggregated by passing each through a 40 or 100 µm nylon cell strainer (Falcon), and cells were pelleted by centrifugation and resuspended in red blood cell lysis buffer (Sigma). Following incubation for 2 minutes at room temperature, cells were washed and resuspended in flow cytometry buffer (Ebioscience). Tumor tissue samples were processed using the gentle MACS dissociator and tumor dissociation kit (Miltenyi Biotec) following manufacturer's instructions.

Samples were stained for viability using live dead fixable blue (Life Technologies) following manufacturer's instructions and then blocked with anti-CD16/32 (ebioscience) before staining with fluorochrome conjugated antibodies. CD4 (Rm4.5), Foxp3 (FJK-16S), Ki67 (Sol A15), ICOS (7E. 17G9), Eomes (Dan11mag), T-bet (Apr-46) and GITR (DTA-1) were purchased from ebioscience. CD45 (30-F11), CD44 (IM7), CD62L (MEL-14), PD-1 (29F.1A12), and OX40 (OX86) were purchased from Biolegend. CD8 (53-6.7) was purchased from BD Pharmingen. For staining of intracellular antigens, the Foxp3 staining kit (ebioscience) was used according to manufacturer's instructions. Samples were fixed in 3.7% formalin before acquisition of samples using a Fortessa (Becton Dickinson). Data were analyzed with FlowJo software (Ashland, Oreg.).

Pharmacokinetic Modelling

Balb/c mice were administered 5 or 15 mg/kg mGITRL-FP mIgG2a once. Three mice per group were sacrificed 5 minutes 0.5, 1, 2, 6, 24, 72, 144, and 240 hours following treatment. Serum samples were collected and the levels of circulating mGITRL-FP mIgG2a present were assessed in a sandwich ELISA using anti-murine GITRL mAb (R&D Systems) as both capture and detection.

Pharmacokinetic (PK) data obtained from the 2 dosing groups were pooled and simultaneously modeled using a population approach. Population analysis was conducted using a pharmacostatistical software package NONMEM (Version 7.2, ICON Development Solutions, Ellicott City, Md.). The FOCE method with Interaction option was employed. Murine GITRL-FP mIgG2a PK was adequately described by a two-compartment model.

Cell Lines

HEK293T-17 cells (ATCC, CRL-11268) were maintained in DMEM (Invitrogen) plus 10% v/v heat inactivated fetal bovine serum (HI FBS, HyClone) and 1× non-essential amino acids (NEAA, Invitrogen). Jurkat cells (ATCC, TIB-152) were maintained in RPMI 1640 (Invitrogen) plus 10% v/v HI FBS. Jurkat mGITR NFκB cells were maintained in RPMI 1640 supplemented with 10% HI FBS, 5 µg/mL blasticidin (Invitrogen) and 5 µg/mL puromycin (Invitrogen).

Cell Line Generation

Jurkat mGITR NFκB cell line was generated by lentiviral transduction using a third generation lentiviral system (Systems Biosciences). The murine GITR gene (NM_009400.2) was cloned into the expression plasmid under the control of a CAG promoter and containing a puromycin resistance gene. The NFκB reporter expression plasmid was designed to express five copies of the NFκB response element under a minimal promoter and upstream of a firefly luciferase reporter (luc2, Promega), together with a blasticidin resistance gene. Each expression plasmid alongside the packaging plasmids (Systems Biosciences) were co-transfected into HEK293T-17 using lipofectamine 2000 (Invitrogen). Supernatant containing viral particles was collected 48 h post transfection and used to transduce Jurkat cells. Virally transduced Jurkat cells were cultured in culture media plus selection antibiotics, 5 µg/mL blasticidin and 5 µg/mL puromycin from 48 h post transduction. Jurkat human OX40 NFκB cell line was generated using similar procedures, except a lentiviral vector designed to constitutively express human OX40 was transduced. Mouse OX40L binds to human OX40; therefore, a human OX40-expressing NFκB luciferase reporter Jurkat cell line can be used to assess the activity of murine OX40L fusion proteins.

ELISA

Recombinant mouse GITR-Fc and OX40-Fc (R&D Systems) glycoproteins were coated overnight at 1 µg/mL in PBS onto 96-well plates (Greiner). Plates were washed with PBST (PBS+0.01% Tween-20), blocked for 1 hour at room temperature with PBS containing 1% (w/v) BSA, and washed in PBST again. Twenty-five microlitres of 1 µg/mL mouse GITRL or OX40L FPs diluted in assay buffer [PBS+1% bovine serum albumin (BSA)] was added to wells, and plates were incubated for 2 hours at room temperature. After 3 washes, 25 µL of 1 µg/mL horseradish peroxidase-conjugated anti-mouse Fc antibody (Sigma) diluted in assay buffer was added to each well, and plates were incubated for 1 hour. After incubation, plates were washed 3 times in PBST, 25 μL of tetramethylbenzidine substrate solution (KPL) was added to each well, and plates incubated for 5 minutes. After incubation 15 μL of 0.5 M sulphuric acid stop solution was added to all wells. The optical density at 450 nm was measured using an EnVision plate reader (PerkinElmer).

Statistics

All statistical analysis was carried out using the Prism Statistical Software Version 6.

Results mGITRL-FP In Vitro Potency

Figure 30A:
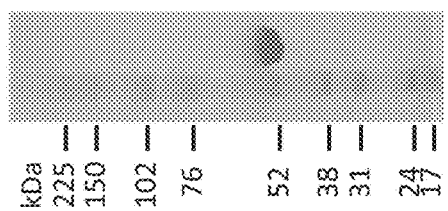
FIG. 30 (A)-(C). Structure and agonistic potential of a murine GITR ligand fusion protein. (A) Schematic of murine GITRL-FP consisting from N- to C-terminus, of a fragment crystallisable (Fc) region of an immunoglobulin G1 (IgG1) or 2a (IgG2a), a multimerisation domain (MD) and the extracellular (GITR-binding) domain (ECD) of murine GITR ligand (B) SDS-PAGE of the purified murine GITRL-FP. (C) NF-κB associated luminescence in a murine GITR receptor transduced Jurkat cell line following treatment with mGITRL-FP, DTA-1 rIgG2b isotype controls or mOX40L-FP. Data is representative of at least two independent experiments.
Figure 30B:
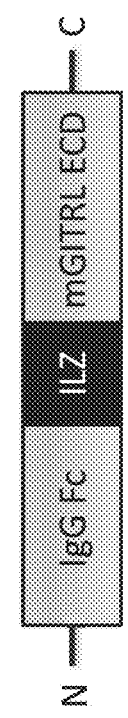
Figure 30C:
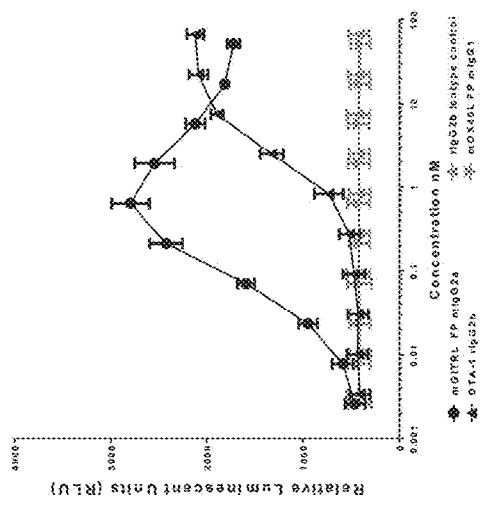

In order to investigate the effects of GITR receptor signalling on immune cell activation and antitumor activity in vivo, a tetrameric mGITRL-FP was generated. The mGITRL-FP was designed to elicit avid binding to the GITR receptor and FcγRs on effector cells. The molecule consisted, from N- to C-terminus, of a fragment crystallisable (Fc) region of an immunoglobulin G (IgG), an isoleucine zipper domain (ILZ) and the extracellular (GITR-binding) domain (ECD) of murine GITR ligand (FIG. 30A). When the purified denatured mGITRL-FP was visualised by SDS-PAGE (FIG. 30B), it demonstrated a high degree of homogeneity and a molecular weight that was slightly higher than the expected molecular weight of 48 kDa presumably due to glycosylation of the Fc and mGITRL domains. Both mGITRL-FP mIgG2a and an anti-GITR antibody (DTA-1) were able to induce NF-κB signalling in a GITR-dependent NFκB reporter gene cell assay, whereas a murine OX40L FP mIgG1 (mOX40L-FP mIgG1), and isotype control lacked any detectable signal (FIG. 30C). Importantly, the tetrameric mGITRL-FP demonstrated an $EC_{50}$ of 0.05 nM with respect to GITR agonism in this assay, which was nearly 50 times more potent than DTA-1, which demonstrated an $EC_{50}$ of 2.31 nM.

Antitumor Activity of mGITRL-FP Engineered with a mIgG2a Fc

Figure 31I:
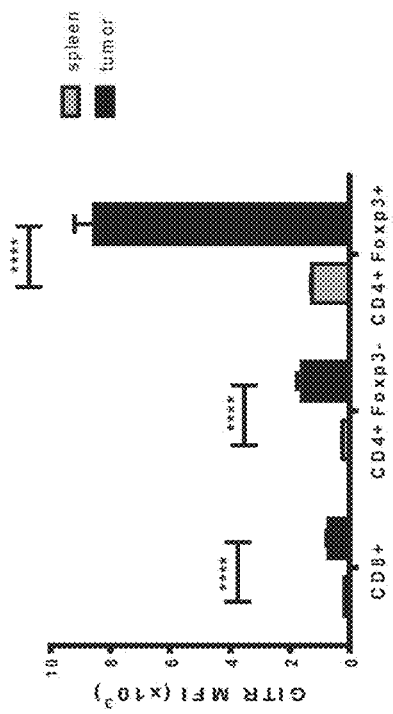
FIG. 31 (A)-(I). Comprehensive FcγR engagement increases antitumor activity but does not drive increased T-cell proliferation downstream of GITR. (A)-(E) Tumor growth in Balb/c mice. Mice were treated once by i.p. injection of saline control, mGITRL-FP mIgG1 or mGITRL-FP mIgG2a as indicated. Number of regressions are indicated on each individual graph. (F) Frequency of Ki67 expression in splenic T-cells 4 days following treatment of CT26 tumor-bearing mice. (G) Frequency of intratumoral T-cell sub-sets and (H) ratio of intratumoral CD8+ to CD4+ FoxP3+ cells 4 days following treatment of CT26 tumor-bearing mice with 10 mg/kg of mGITRL-FP or saline control as indicated. (I) Median fluorescence intensity of GITR expression on splenic and intratumoral T-cell sub-sets 4 days following treatment. Error bars indicate standard error of mean; n=7-10 mice per group. For (F) and (G) p<0.005*p<0.001 and ****p<0.0001, as calculated by two way ANOVA; Significance for G is black for changes in CD4+ Foxp3+ cells and gray for changes in CD4+ Foxp3– cells; for (H) *P<0.05, as calculated by one way ANOVA; for (I) ****p<0.0001, as calculated by Student's T-test.
Figure 31H:
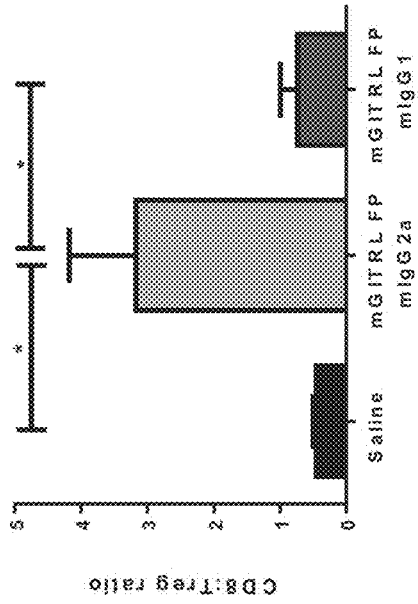

Previous studies have shown that activating FcγRs are required for the antitumor activity of the DTA-1 antibody, and that the antitumor activity of this antibody is increased when it carries a mIgG2a Fc, compared to a rIgG2b Fc or a N297A mutant Fc which lacks FcγR binding. To determine the impact of the Fc isotype on the antitumor activity of mGITRL-FP, CT26 tumor bearing mice were treated with mGITRL-FP with a mIgG2a or mIgG1 Fc isotype. Treatment of mice with 5 or 10 mg/kg of either isotype resulted in notable antitumor activity compared to saline treated controls, as evidenced by reduced tumor volume (FIG. 31A). The antitumor activity overall, however, was greater following treatment with mGITRL-FP mIgG2a (11/20 total regressions), as opposed to mGITRL-FP mIgG1 (7/20 total regressions, FIG. 31A).

To determine if this difference in activity of the Fc variants was due to a difference in their ability to mediate T-cell activation and subsequent events downstream of GITR agonism, the proliferation of splenic T-cell populations was assessed using flow cytometric analysis of Ki67 expression on $CD4^+$ $FoxP3^-$ (effector T-cells), $CD8^+$ (effector T-cells) and $CD4^+$ $FoxP3^+$ (T-regs) cells. Both isotypes of the mGITRL-FP caused a comparable significant increase in the proliferation of all three splenic T-cell subsets when compared to saline controls (FIG. 31B). The splenic T-reg cell population exhibited the highest expression of Ki67 after treatment (53.95%±0.75 after mGITRL-FP mIgG2a and 58.43%±1.26 after mGITRL-FP mIgG1 treatment), followed by $CD4^+$ FoxP3− (9.52%±0.58 with mGITRL-FP mIgG1 and 10.89%±0.56 with mGITRL-FP mIgG1) and $CD8^+$ T-cells (7.60%±0.27 with mGITRL-FP mIgG2a and 7.79±0.43 with mGITRL-FP mIgG1). This data suggested that splenic T-cell activation alone could not account for the differences observed in antitumor immunity between mIgG1 and mIgG2a Fc isotypes of the mGITRL-FP.

Figure 32A:
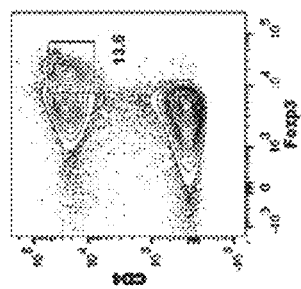
FIG. 32 (A)-(E). Intratumoral T-reg depletion and CD4+ Foxp3–: T-reg ratio after treatment with mGITRL-FP mIgG2a or mIgG1. CT26 tumor bearing mice were injected with either saline control, mGITRL-FP mIgG1 (10 mg/kg) or mGITRL-FP mIgG2a (10 mg/kg) once i.p. at 6 days post CT26 implantation. (A)-(D) Flow cytometric plots showing the proportion of CD4+ Foxp3+ T-regs in the tumor 4 days after treatment. CD4+ Foxp3+ flow cytometry analysis gate is positioned based on Foxp3 fluorescence minus one (FMO) control. (E) Intratumoral CD4+ Foxp3–: T-reg ratio measured at 4 days after treatment as indicated. Statistical analysis carried out using one way ANOVA where **** indicates a P-value <0.0001.
Figure 32B:
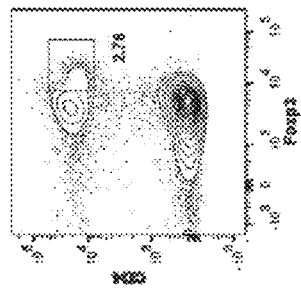
Figure 32C:
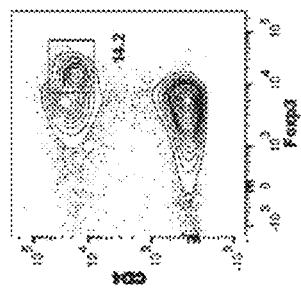
Figure 32D:
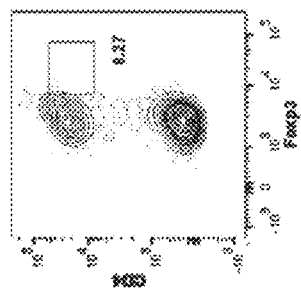
Figure 32E:
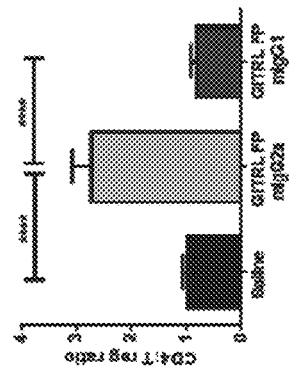

It was next investigated whether intratumoral changes in T-cell populations could explain the increased antitumor activity observed with the mIgG2a versus mIgG1 variants of mGITRL-FP. Treatment of mice with mGITRL-FP mIgG2a induced a significant decrease in the frequency of intratumoral T-regs from 13.31%±1.06 in saline treated animals to 3.60%±0.79 with a significance value of p<0.0001 (FIG. 31C and Figure. 32) and a subsequent increase in the CD8:T-reg (Figure. 31D) and CD4:T-reg (FIG. 32B) ratios compared to control treated animals. In contrast, the decrease in intratumoural T-regs was not evident for the mIgG1 Fc variant of mGITRL-FP (12.95%±1.34). There was also evidence for a significant decrease in the proportion of intratumoral $CD4^+$ $Foxp3^-$ T-cells after treatment with mGITRL-FP mIgG2a (8.64%±1.21) compared to control animals (13.01%±1.12), but this was not to the extent of that observed for T-regs. The preferential depletion of T-regs by mGITRL-FP mIgG2a is likely attributable to the high expression of GITR on intratumoral T-regs (FIG. 31E) and the high expression of activating FcγRs in the tumor microenvironment of CT26 tumors, and is suggestive of clearance by antibody dependent cellular cytotoxicity (ADCC) or antibody dependent cellular phagocytosis (ADCP). Collectively these data suggest that for optimal antitumor activity following mGITRL-FP treatment, proliferation of peripheral $CD4^+$ and $CD8^+$ T-cells coincident with a decrease in intratumoral T-regs is required.

mGITRL-FP mIgG2a Mediated Antitumor Activity

Figure 33H:
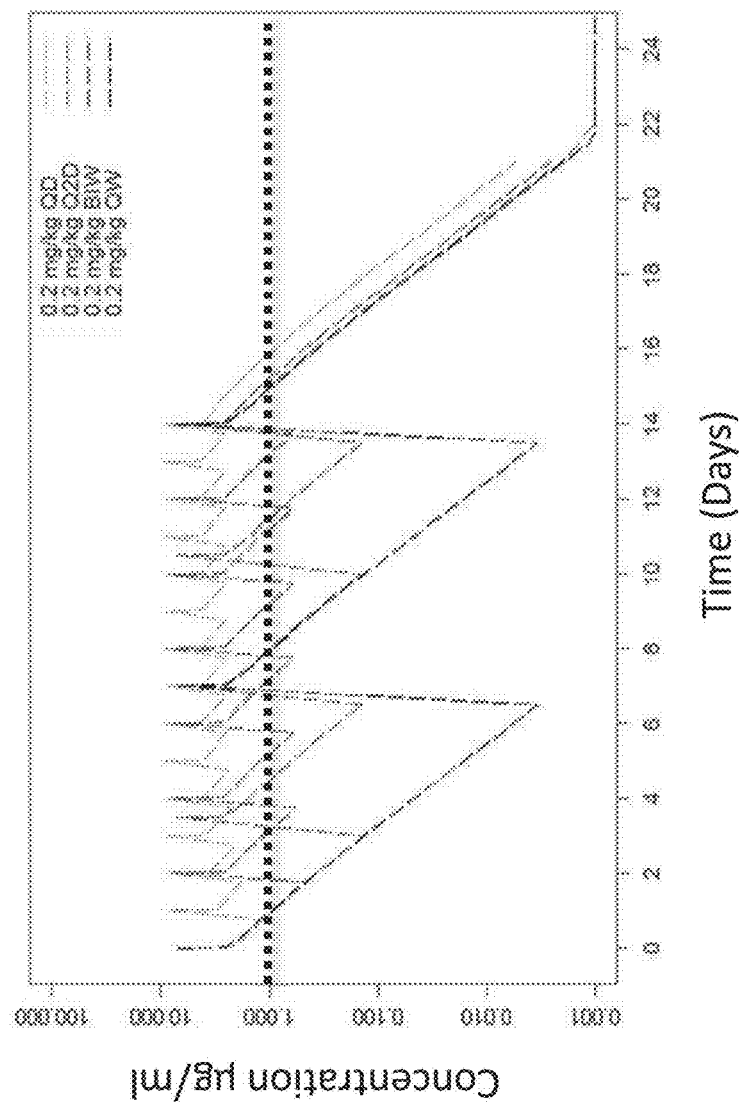
FIG. 33 (A)-(H). Murine GITRL-FP mIgG2a mediates antitumor activity in a dose and schedule dependent manner. Tumor growth in Balb/c mice. Mice were treated by i.p. injection of (A)-(D) a single dose of mGITRL-FP mIgG2a, at the dose level indicated or (E)-(G) multiple doses of 0.2 mg/kg mGITRL-FP mIgG2a given daily [Q1D] or weekly [Q1W]. (H) Predicted serum concentration of mGITRL-FP following administration using the dose and schedule indicated. Dotted line indicates the blood concentration threshold of mGITRL-FP mIgG2a required to achieve maximum antitumor activity.

Because mGITRL-FP mIgG2a elicited increased antitumor activity compared to the mGITRL-FP mIgG1, how exposure levels and time of exposure of the mGITRL-FP mIgG2a in the blood related to antitumor responses in CT26 tumor-bearing mice was next characterised. First, the effect of increasing dose level on tumor growth by treating mice with one single dose of saline control or 0.2, 1, or 5 mg/kg mGITRL-FP mIgG2a was measured. Treatment with 0.2 mg/kg mGITRL-FP mIgG2a resulted in only 1/10 complete regressions, however there was evidence for a dose dependent increase in antitumor immunity when the dose was raised from 0.2 to 1 mg/kg or 5 mg/kg, which resulted in 6/10 and 9/10 regressions respectively (FIG. 33A). Furthermore, the antitumor activity could also be improved by increasing the frequency of 0.2 mg/kg dosing to once every day (Q1D) or once every week (Q1W) (FIG. 33B). These results indicated that there was a required exposure level of mGITRL-FP mIgG2a needed to induce optimal antitumor activity, as defined by complete tumor regression and minimal residual tumor volume, which was reached only when using the Q1D schedule. To determine this threshold the concentration of mGITRL-FP mIgG2a was measured in the blood of mice treated with 2 alternative dose levels of mGITRL-FP and then these results were incorporated into a PK model. Based on this model, the blood concentration of mGITRL-FP mIgG2a sustained by the Q1D schedule, and considered as required to maintain optimal antitumor activity was calculated to be equal to or greater than 1 μg/mL (FIG. 33C).

PD biomarkers of anti-tumor activity was next investigated following mGITRL-FP mIgG2a treatment. The expression of Ki67 was used to assess proliferation, while ICOS, PD-1 and OX40, which are all known to be expressed on T-cells following activation, were also analysed. Increasing the exposure of mGITRL-FP mIgG2a, either by increasing the dose level or by increasing the frequency of administration, resulted in progressively greater increases in the frequency of Ki67, ICOS, PD-1 and OX40 expressing peripheral CD4+ T-cells (FIG. 34A-D).

Comparative Analysis of mGITRL-FP and mOX40L-FP Antitumor Activity

In order to understand the relative mechanism of GITR, as opposed to OX40 targeting, the antitumor activities of the mGITRL-FP were directly compared with mOX40L-FP, which comprises a similar protein structure, does not cross react with the GITR receptor and is able to induce NFκB expression in an OX40 reporter cell assay (FIGS. 35A and B).

Figure 5A:
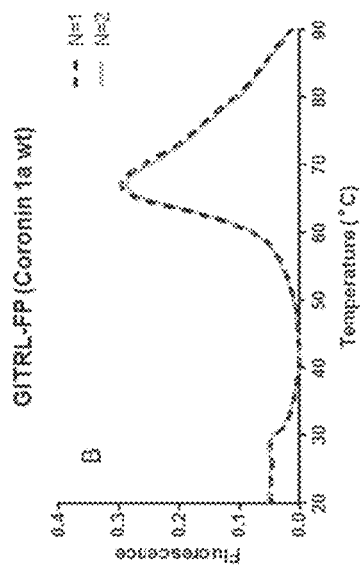
FIG. 5A-D. Unfolding transitions of hexameric GITRL FP (GCN4 pII), GITRL FP (Coronin 1a wt), GITRL FP (Langerin wt) and GITRL FP (Langerin variant).
Figure 5B:
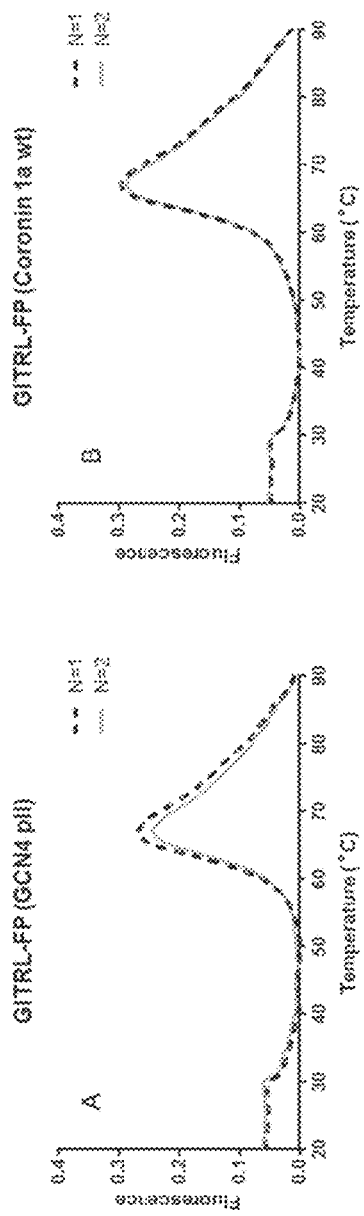
Figure 5C:
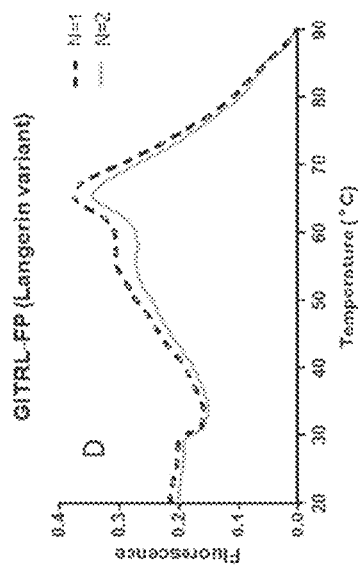
Figure 5D:
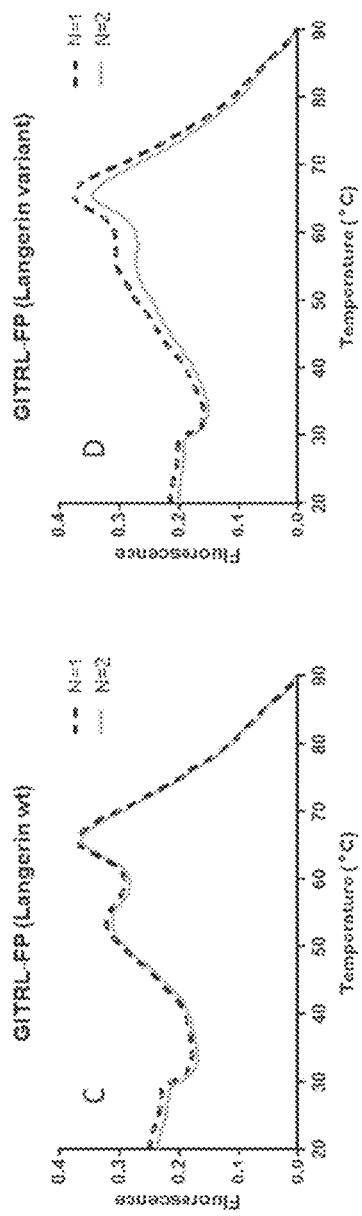
Figure 36G:
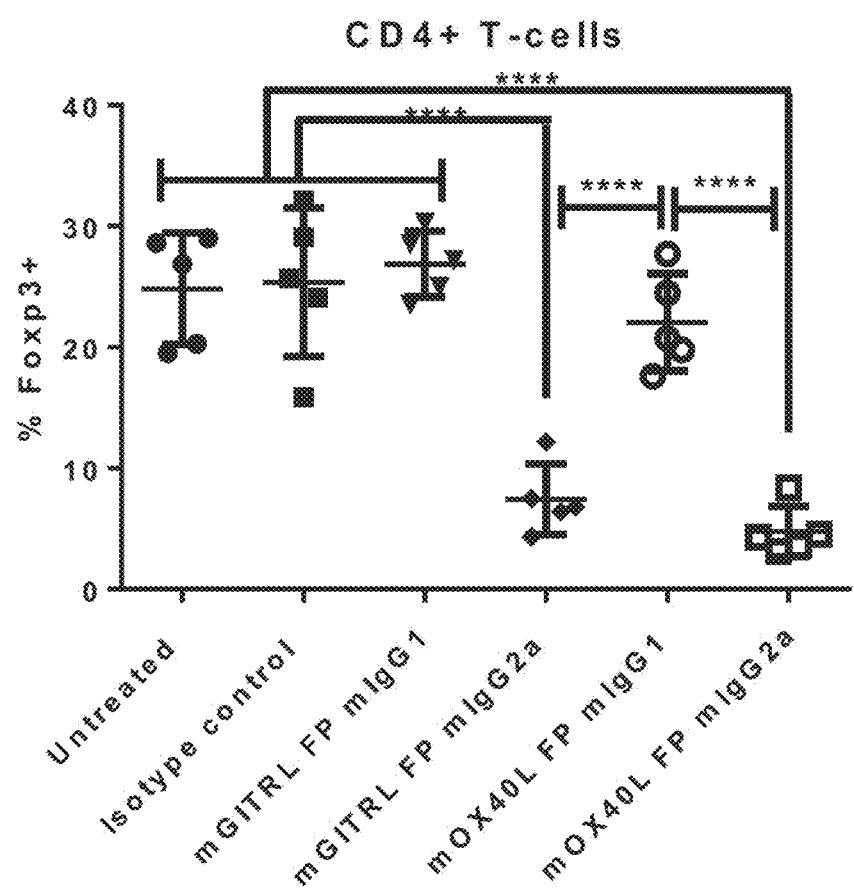
FIG. 36 (A)-(G). The antitumor activity of mGITRL-FP is superior to that of mOX40L-FP in the CT26 model. (A)-(F) Tumor growth in Balb/c mice. Mice were treated twice weekly with an i.p. injection of 5 mg/kg mIgG2a or mIgG1 mGITRL-FP or mOX40L-FP, 5 mg/kg mIgG1 fusion protein isotype control or saline, Number of total regressions are indicated on each individual graph. (G) Frequency of intratumoral CD4+, FoxP3+ T-regs in CT26 tumor-bearing Balb/c mice at 10 days following treatment as indicated.

CT26 tumor bearing mice were treated twice a week with 5 mg/kg mGITRL-FP or mOX40L-FP of either mIgG1 or mIgG2a Fc isotypes and tumor growth was measured. As seen with mGITRL-FP, the antitumor activity observed with mOX40L-FP was greater following treatment with the mIgG2a isotype (9/10 regressions) than with the mIgG1 (1/10 regressions; FIG. 36A). However, treatment with the mGITRL-FP mIgG1 (6/10 regressions) elicited increased antitumor activity relative to that seen following treatment with mOX40L-FP mIgG1 and was marginally better with a mIgG2a isotype (10/10) compared to mOX40L-FP mIgG2a (FIG. 36A). A similar depletion in intratumoral T-regs was observed following treatment with both mGITRL-FP and mOX40L-FPs with mIgG2a Fc isotypes, but this was not evident for mIgG1 Fc isotypes of either molecule (FIG. 5B). This data indicates that the mIgG2a isotype is superior to the mIgG1 for inducing antitumor activity of both GITR and OX40 agonists in CT26 tumor bearing mice.

mGITRL-FP mIgG2a and mOX40L-FP mIgG1 Combination Studies

Given the upregulation of OX40 receptor on CD4+ T-cells following treatment with mGITRL-FP mIgG2a (FIG. 34D), the potential to maximise T-cell activation was further investigated. mGITRL-FP mIgG2a and mOX40L-FP mIgG1 were used to assess the potential benefits of combining agents targeting the GITR and OX40 pathways.

Figure 37A:
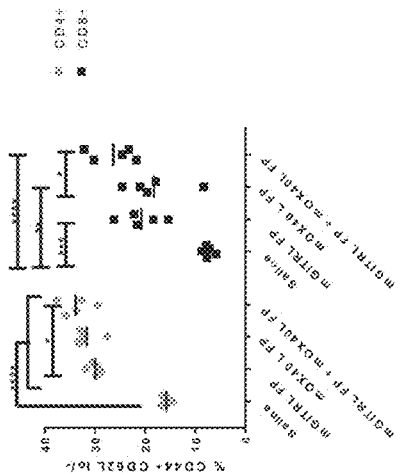
FIG. 37 (A)-(E). The pharmacodynamics (PD) changes mediated by mGITRL-FP mIgG2a and mOX40L-FP mIgG1 are differential and can be enhanced through combination. Frequency of (A) CD4+ FoxP3– or CD8+, Ki67+(B) CD4+ or CD8+, CD44+CD62L Lo/– effector memory, (C) CD4+ CD44+CD62L+ central memory, (D) CD4+ or CD8+, T-bet+ and (E) CD4+ EOMES+ T– cells in the spleens of CT26 tumor bearing mice 14 days following twice weekly treatment with either 25 mg/kg mGITRL-FP mIgG2a, 15 mg/kg mOX40L-FP mIgG1 or a combination of both molecules. *p<0.05, p<0.01*p<0.001, ****0<0.0001, as calculated by one way ANOVA.
Figure 37B:
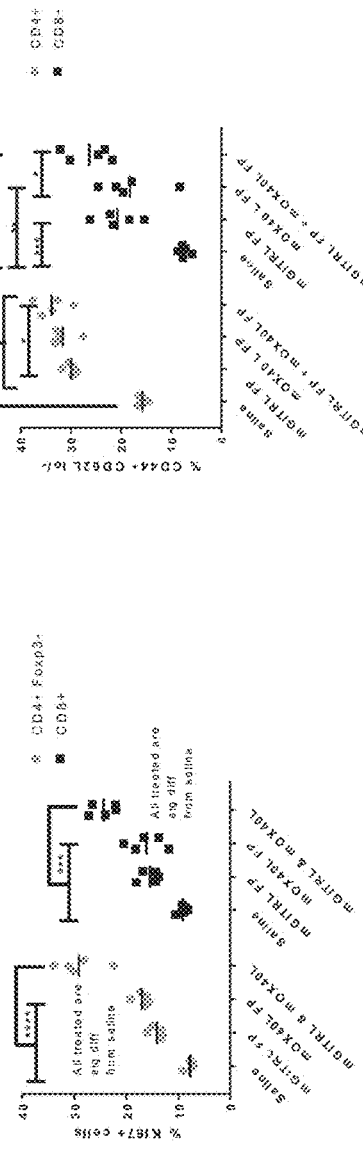
Figure 37C:
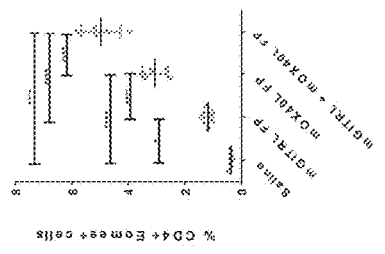
Figure 37D:
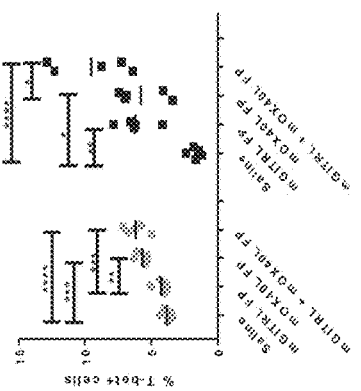
Figure 37E:
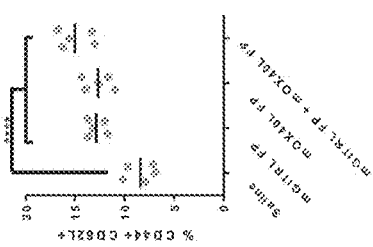

Biweekly treatment with mGITRL-FP mIgG2a and mOX40L-FP mIgG1 combination resulted in significantly increased expression of Ki67 in splenic CD4+ (29.16%±1.51) and CD8+ (24.4%±0.87) T-cells compared to saline controls (7.82%±0.30 and 9.22%±0.31) or treatment with either monotherapy (14.2%±0.45 and 15.52%±0.66 for mGITRL-FP treated CD4 and CD8 T-cells and 17.02%±0.49 and 16.22%±1.22 for mOX40L-FP treated CD4 and CD8 T-cells; FIG. 37A), showing an additive effect of combining both molecules. Additional analysis of the splenic CD4+ and CD8+ T-cell populations showed that combination treatment increased the frequency of both the CD4+ and CD8+ effector memory compartment, defined as CD44+ and CD6210 (FIG. 37B) and the CD4+ central memory population, as defined as CD44+ and CD62+ (FIG. 37C) above that of monotherapy treatment. The expression of the transcription factors T-bet (FIG. 37D) and Eomes (FIG. 37E) which have shown redundancy in IFNy production and cytotoxicity in CD8+ T-cell and also have roles in Th1 differentiation, were also increased to a greater degree on CD4+ and CD8+ T-cells during combination than with either monotherapy. A mechanistic difference between the GITR and OX40 pathways was the significantly higher expression of T-bet and Eomes on CD4+ T-cells in mOX40L-FP mIgG1 treated animals as compared to animals treated with mGITRL-FP mIgG2a.

Based on these findings, the effect of combining mGITRL-FP mIgG2a with mOX40L-FP mIgG1 on tumor growth was determined. It was next investigated whether treatment of mice with mOX40L-FP mIgG1 could be further improved by combination with a single sub-optimal dose of mGITRL-FP mIgG2a. Treatment with mOX40L-FP mIgG1 monotherapy induced 5/10 regressions, mGITRL-FP mIgG2a monotherapy treatment induced 3/10 regressions, but the combination of both mGITRL-FP mIgG2a and mOX40L-FP mIgG1 resulted in enhanced antitumor activity showing 8/10 regressions (FIG. 38A).

Given that monotherapy treatment with mGITRL-FP mIgG2a at high doses induced complete tumor regression in the majority of mice in the CT26 model, the combination of high doses of mOX40L-FP mIgG1 and mGITRL-FP mIgG2a was investigated for increased benefit in a B16F10-Luc 2 model. Dosing with either monotherapy did not induce any tumor regression in this model, however the combination of both molecules resulted in improved antitumor activity; a delay in tumour growth and the survival increased compared to monotherapy treatment (FIG. 38B and FIG. 39).

Example 7

T Cell Priming Agent in Combination with mGITRL-FP

Materials and Methods
Cell Lines and Reagents

The TC-1 tumor line was obtained from ATCC (Cat # CRL 6475, Manassas, Va.) and maintained in DMEM+10% FBS+1% penicillin/streptomycin. The CT26 tumor line was obtained from ATCC (Manassas, Va.) and was maintained in RPMI 1640 medium supplemented with 10% fetal bovine serum. DTA-1 and isotype antibodies were purchased from Bio X Cell (West Lebanon, N.H.).

E7 SLP and Vaccination

E7 Synthetic Long Peptide (SLP) consisting of the 45-mer HPV16-E7 sequence SSEEEDEIDGPAGQAEP-DRAHYNIVTFCCKCDSTLRLCVQSTHVD (SEQ ID NO: 57) was synthesized from New England Peptide (Gardner, Mass.). E7 SLP was dosed at 10 or 3.3 µg and was formulated with 20 µg CpG ODN 2395 (TriLink, San Diego, Calif.) in Addavax (Life Technologies, Carlsbad, Calif.) and PBS in a total volume of 50 µL. Vaccinations were administered subcutaneously into the dorsal surface of the base of tail.

Tumor Models

TC-1 experiments used female C57BL/6 mice (Cat# 000664) mice obtained from Jackson Labs (Bar Harbor, Me.). CT26 experiments used femail Balb/C mice obtained from Envigo (Frederick, Md.). Mice were between 6 and 8 weeks of age at the time of tumor implantation. All animal experiments were conducted in accordance with guidelines established by the Institutional Animal Care and Use Committee. For TC-1 tumor implantation, $2\times10^4$ viable TC-1 cells was implanted subcutaneously into the left hind footpad. For CT26 tumor implantation, $5\times10^5$ cells were implanted in the right flank. Tumor growth was evaluated by direct measurement with calipers 1. Bi-directional measurements were collected every 2-4 days, and tumor volume calculated using volume=(length·width2)/2. Tumors were allowed to develop for 6-14 days and then tumor bearing mice were randomized to treatment groups by tumor volume. Mice were euthanized when the primary tumor exceeded 1000 mm³ for TC-1/footpad and 2000 mm³ for CT26/flank in accordance with IACUC protocol. For PD studies, mice were euthanized and tumors and spleens were harvested, crushed through a 70 uM filter (Corning™, Corning, N.Y.), and processed to a single cell suspension.

Functional T-cell Responses and Flow Cytometry

For antigen specific stimulations, 1-2×10⁶ live cells were plated per well with 1 ug AH1 peptide sequence SPSYVYHQF (SEQ ID NO: 56) (Anaspec, Fremont, Calif.) or 10 ug E7 peptide sequence RAHYNIVTF (SEQ ID NO: 58) (Anaspec) and Protein Transport Inhibitor (Ebioscience, Santa Clara, Calif.). After 5 hours, cells were stained. For all stains the order of stain was live/dead blue (Life Tech), extracellular proteins, FOXP3 Fix/Perm Kit (Ebioscience), and followed by intracellular cytokines. Antibodies included CD45 (Clone 30-F11), CD4 (Clone RM4-5) CD8 (Clone 53-6.7), GITR (Clone DTA-1), IFNgamma (Clone XMG 1.2), TNFalpha (Clone MP6-XT22), FOXP3 (Clone FJK-16s), KI-67 (Clone SolA15). H2-Db E7 Dextramer loaded with RAHYNIVTF was purchased from Immudex (Fairfax, Va.) and we followed their protocol for staining. All samples were run on either an LSR-II or Fortessa (BD San Jose, Calif.). All data was analyzed using FlowJo (Treestar, Ashland, Oreg.).

mGITRL-FP Requires Antigen Specific Cells

CT26 is a very immunogenic tumor model with high Intratumoral CD45 and basal CTL levels. CT26 has been shown to self prime low levels of AH1 specific T-cells. To assess whether mGITRL-FP could lead to the de novo generation of antigen specific responses the E6/E7 transformed TC-1 tumor model was used. This model has known CD8 T-cell epitopes and that E7 specific immune response can lead to protection from tumors that carry E7. TC-1 tumor cells were implanted in the footpad of C57/b6 mice. Mice were measured at day 14, randomized based on tumor size and treated with mGITRL-FP IgG2a at 1 mg/kg, 5 mg/kg, and 20 mg/kg (FIG. 43A). There was delay or inhibition of tumor growth at any dose tested (FIG. 43B). On day 24, subsets of untreated and the 1 mg/kg treated mice were sacrificed and spleens and tumors harvested. T-cell populations and E7 antigen specific responses were assessed. GITR levels were present on the CD4 and CD8 T-cells, and were significantly higher in the tumor (FIG. 43C). Without E7 priming, mGITRL-FP could not delay TC-1 tumor growth or generate an anti-tumor immune response.

mGITRL-FP Expands Primed Antigen Specific CD8 T-cells

Figure 44M:
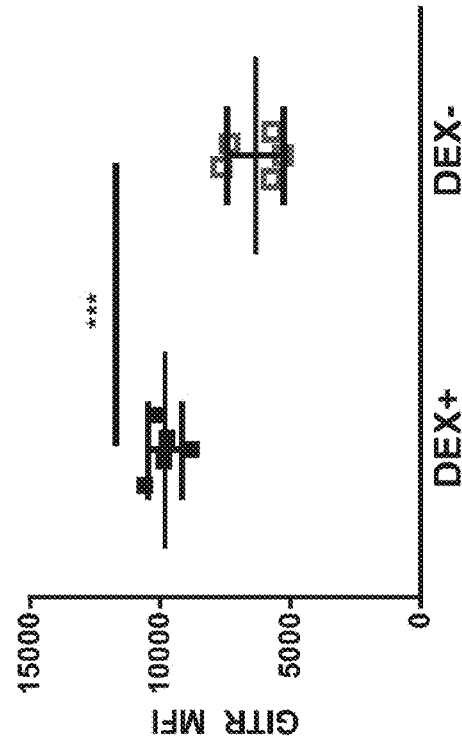
FIG. 44 (A)-(M). (A) To generate E7 specific T-cells, naïve C57BL/6 mice were injected with 10 ug of E7 SLP in CpG (Addavax) at the base of tail. Mice were then treated with mGITRL-FP IgG2a at 1 mg/kg for 3 doses. Mice were evaluated for splenic (B) CD4 T-cells (C) CD8 T-cells (D-F) E7 Dextramer+ T-cells (G) Tregs, (H) GITR levels on the antigen specific cells. (I) TC-1 cells were implanted into the footpad of C57BL/6 mice, 2×104 cells/mouse. The mice were randomized by tumor volume on day 14 and dosing was initiated. C57BL/6 mice were injected with 10 ug of E7 SLP in CpG (Addavax) at the base of tail. At day 28, mice were sacrificed. Spleen and tumor were evaluated for (J)-(K) E7 and specific CD8 T-cells (L)-(M).
Figure 44L:
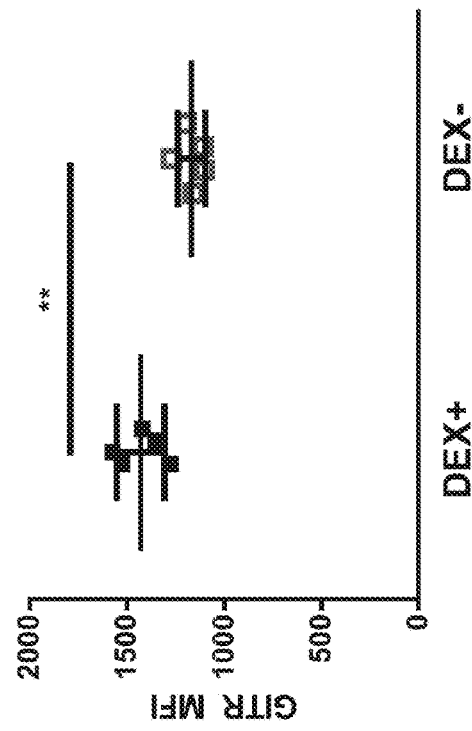

Vaccination with DNA vaccines has been shown to be effective in generation of E7 specific responses that lead to the prevention and inhibition of tumor growth of the TC-1 tumor model. This study hypothesized that mGITRL-FP may need primed antigen specific T-cells to drive an anti-tumor response. To generate this response, naïve C57/b6 mice were vaccinated with 10 ug of an E7 synthetic long peptide (SLP) with CpG (addavax) at the base of tail. During this time the mice were treated with 3 doses of mGITRL-FP IgG2a. After 7 days, splenocytes were pulled and evaluated T-cells for antigen specificity with an E7 dextramer (FIG. 44A). No differences in CD4 and CD8 percentages were seen, but a large increase in antigen specific cells was observed when treated with mGITRL-FP (FIG. 44 B-D).

Figure 45A:
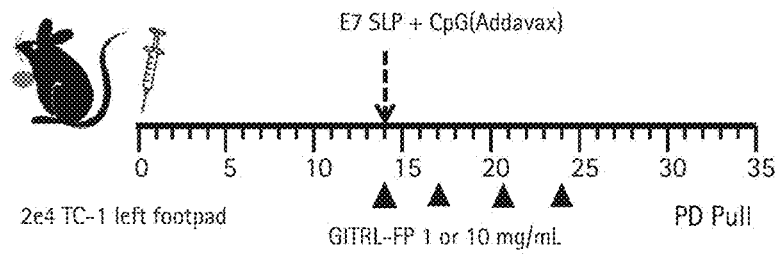
FIG. 45. (A)-(L). (A) TC-1 cells were implanted into the footpad of C57BL/6 mice, 2×104 cells/mouse. The mice were randomized by tumor volume on day 14 and dosing was initiated. (B-D) Vaccinated C57BL/6 mice were injected with 3.3 ug of E7 SLP in CpG (Addavax) at the base of tail. Treated mice were dosed IP with GITRL-FP IgG2a biweekly for 4 total doses. (E) Kaplan-Meier survival of mice after TC-1 implant with a P<0.05. (F) Median survival of the groups. (G) To examine pharmacodynamic effects, groups of mice treated the same in (A) were sacrificed and the spleens and tumor harvested. Tumors were pooled and spleens were left as individuals. (H) CD45+ cells were evaluated in the tumor. (I)-(L) Mouse spleens and tumors were restimulated with 1 μg/mL E7 peptide/Protein Transport inhibitor for 5 hours and stained for IFNgamma and TNFalpha, and spleen and tumor Tregs were measured.
Figures 45B, 45C, 45D:
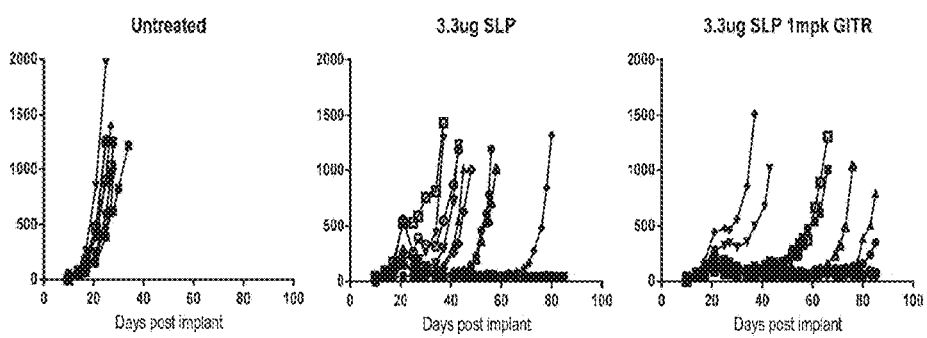
Figure 45E:
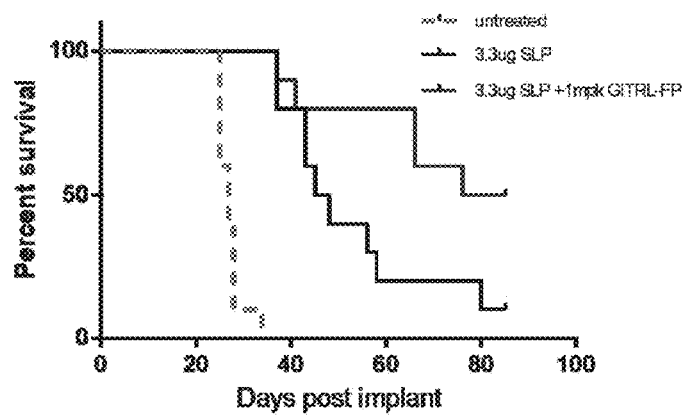

Additionally, GITR levels on vaccinated mice alone were evaluated, the antigen specific Dex+ cells had a higher GITR MFI than Dex− CD8 T-cells (FIG. 44E-F). It was hypothesized that this difference would be even higher in mice with tumor, as GITR levels seemed to be highest in the tumor microenvironment. C57/b6 mice were implanted with TC-1 tumors and vaccinated with E7 SLP/CpG (Addavax) (FIG. 44G). Priming of antigen specific E7 cells was observed as measured by dextamer in both spleen and in the tumor (FIG. 44H-I). The cells that stained positive with the dextramer were also higher for GITR in both the spleen and the tumor (FIG. 44J-K). E7 SLP was able to successfully prime an E7 specific response with or without the presence of tumor and the antigen specific cells that were primed expressed higher levels of GITR than other CD8 T-cells.

mGITRL-FP can Expand Antigen Specific Cells Primed by E7 SLP and Generate Protective Immune Response to TC-1 Tumors To evaluate whether mGITRL-FP could expand an E7 sepcific response to TC-1 tumor cells, TC-1 tumor cells were implanted into the footpad and randomized mice by tumor volume on day 14. A single dose of E7 SLP given with CpG (Addavax) at the base of tail with mGITRL-FP IgG2a for four doses starting the day of vaccination (FIG. 45A). Two arms of the study were included, a TGI (tumor growth inhibition) group (n=10) and a PD (pharmacodynamic) group (n=5). Control mice tumors quickly grew and all mice died with a median survival of 27 days. E7 SLP alone provided survival advantage to mice with TC-1 tumors with 1 of 10 mice alive and tumor free at day 85 and a median survival of 46.5 days (FIG. 45B). E7 SLP+ mGITRL-FP significantly delayed tumor growth with 3/10 mice tumor free and 5/10 alive at day 85 and a media survival of 80.5 days (FIG. 45C-D). Vaccination alone provided a delay in tumor progression and adding mGITRL-FP on top further delay progression. It was hypothesized that this occurred because of selection expansion of tumor specific CD8s. At day 21, the group of PD mice was sacrificed and harvested spleen and tumor for pharmacodynamics analysis. Tumors from the footpad were pooled due to amount of tissue harvested (FIG. 45E). Vaccination alone or in combination with mGITRL-FP resulted in a significant increase in CD45+ cells into the tumor (FIG. 45F). To evaluate antigen specific function, single cell suspensions of tumor or spleen were restimulated with 1 ug/mL of E7 peptide. Vaccination provided a basal increase in antigen specific cells and addition of mGITRL-FP further boosted this to higher levels in both the spleen and tumor (FIG. 45G). mGITRL-FP appeared to not deplete Tregs in the spleen and was only able to deplete Tregs in the tumor when E7 SLP vaccine was present (FIG. 45G).

Example 8

Nucleotide and Protein Sequences

Annotated versions of nucleotide and protein sequences disclosed here are provide in Table 6-1.

TABLE 6-1

| SEQ ID NO. | Description | Sequence |
|---|---|---|
| 1 | Amino Acid Sequence of full-length WT GITRL | MCLSHLENMPLSHSRTQGAQRSSWKLWLFCSIVMLL FLCSFSWLIFIFLQLETAKEPCMAKFGPLPSKWQMA SSEPPCVNKVSDWKLEILQNGLYLIYGQVAPNANYN DVAPFEVRLYKNKDMIQTLTNKSKIQNVGGTYELHV |

TABLE 6-1-continued

| SEQ ID NO. | Description | Sequence |
|---|---|---|
|  |  | GDTIDLIFNSEHQVLKNNTYWGIILLANPQFIS |
| 2 | Amino Acid Sequence of full-length GITRL Variant | MCLSHLENMPLSHSRTQGAQRSSWKLWLFCSI$X_1$$X_2$L LFLCSFSWLIFIFLQL$X_3$TAKEPCMAK$X_4$GPL$X_5$$X_6$K WQ$X_7$ASSEP$X_8$C$X_9$NKV$X_{10}$DWKLEILQNGLYLIY$X_{11}$ QVAPNANYNDVA$X_{12}$FEV$X_{13}$LYKNKD$X_{14}$IQTLTNKS KIQNVGGTYELHVGDTIDLIF$X_{15}$SEHQ$X_{16}$LK$X_{17}$NT YWG$X_{18}$$X_{19}$LLANPQFIS<br>$X_1$ = Gly or Val,<br>$X_2$ = Thr, Met, or Val;<br>$X_3$ = Glu or Ala,<br>$X_4$ = Ser or Phe,<br>$X_5$ = Thr or Pro,<br>$X_6$ = Leu or Ser,<br>$X_7$ = Thr or Met,<br>$X_8$ = Leu or Pro,<br>$X_9$ = Met or Val,<br>$X_{10}$ = Thr, Phe, or Ser,<br>$X_{11}$ = Ser or Gly,<br>$X_{12}$ = Arg or Pro,<br>$X_{13}$ = Trp or Arg,<br>$X_{14}$ = Leu or Met,<br>$X_{15}$ = Ser or Asn,<br>$X_{16}$ = Phe or Val,<br>$X_{17}$ = Any amino acid other than Asn,<br>$X_{18}$ = Val or Ile, and<br>$X_{19}$ = Leu or Ile |
| 3 | Amino Acid Sequence of full-length GITRL N161X Variant | MCLSHLENMPLSHSRTQGAQRSSWKLWLFCSIVMLL FLCSFSWLIFIFLQLETAKEPCMAKFGPLPSKWQMA SSEPPCVNKVSDWKLEILQNGLYLIYGQVAPNANYN DVAPFEVRLYKNKDMIQTLTNKSKIQNVGGTYELHV GDTIDLIFNSEHQVLKXNTYWGIILLANPQFIS<br>X is any amino acid except Asn. |
| 4 | Amino Acid Sequence of full-length GITRL N161D Variant | MCLSHLENMPLSHSRTQGAQRSSWKLWLFCSIVMLL FLCSFSWLIFIFLQLETAKEPCMAKFGPLPSKWQMA SSEPPCVNKVSDWKLEILQNGLYLIYGQVAPNANYN DVAPFEVRLYKNKDMIQTLTNKSKIQNVGGTYELHV GDTIDLIFNSEHQVLKDNTYWGIILLANPQFIS |
| 5 | Nucleic Acid sequence encoding a mature GITRL IgG1 FP subunit (w/o signal peptide encoding region) | CTGGACAAGACCCATACCTGTCCTCCATGCCCTGCC CCCGAACTGCTGGGAGGCCCTTCTGTGTTCCTGTTC CCCCCAAAGCCCAAGGACACCCTGATGATCTCCCGG ACCCCCGAAGTGACCTGCGTGGTGGTGGATGTGTCC CACGAGGACCCTGAAGTGAAGTTCAATTGGTACGTG GACGGCGTGGAAGTGCACAACGCCAAGACCAAGCCC AGAGAGGAACAGTACAACTCCACCTACCGGGTGGTG TCCGTGCTGACCGTGCTGCACCAGGATTGGCTGAAC GGCAAAGAGTACAAGTGCAAGGTGTCCAACAAGGCC CTGCCTGCCCCCATCGAAAAGACCATCTCCAAGGCC AAGGGCCAGCCCCGGGAACCCCAGGTGTACACACTG CCCCCTAGCCGGGAAGAGATGACCAAGAACCAGGTG TCCCTGACCTGTCTCGTGAAGGGCTTCTACCCCTCC GATATCGCCGTGGAATGGGAGTCCAACGGCCAGCCT GAGAACAACTACAAGACCACCCCCCCTGTGCTGGAC TCCGACGGCTCATTCTTCCTGTACTCCAAGCTGACA GTGGACAAGTCCCGGTGGCAGCAGGGCAACGTGTTC TCCTGCTCCGTGATGCACGAGGCCCTGCACAACCAC TACACCCAGAAGTCCCTGTCCCTGAGCCCTGGAAAA GGCGGCGGAGGATCTGGCGGAGGCGGTTCTGGTGGT GGCGGATCTGGGGGCGGAGGTAGCGGAGGTGGTGGC TCTGTGTCTCGGCTGGAAGAGGAAATGCGGAAGCTG CAGGCCACCGTGCAGGAACTGCAGAAGCGGCTGGAC AGACTGGAAGAGACAGTGCAGGCTAAGGGCGGTGGC GGACAGCTCGAGACAGCCAAAGAACCCTGCATGGCC AAGTTCGGCCCCCTGCCTTCCAAGTGGCAGATGGCC TCTTCCGAGCCCCCCTGCGTGAACAAAGTGTCCGAC TGGAAGCTGGAAATCCTGCAGAACGGCCTGTACCTG ATCTACGGCCAGGTGGCCCCCAACGCCAACTACAAC GATGTGGCCCCCTTCGAAGTGCGGCTGTACAAGAAC AAGGACATGATCCAGACCCTGACCAACAAGAGCAAG ATCCAGAACGTGGGCGGCACCTACGAGCTGCACGTG GGCGATACCATCGACCTGATCTTCAACTCCGAGCAC CAGGTGCTGAAGGACAACACCTACTGGGGCATCATC CTGCTGGCCAACCCCCAGTTCATCTCC |

TABLE 6-1-continued

| SEQ ID NO. | Description | Sequence |
|---|---|---|
| 6 | Amino Acid Sequence of a mature GITRL IgG1 FP subunit (Linker 1 and Linker 2 are underlined) | LDKTHTCPPCPAPELLGGPSVFLFPPKPKDTLMISR TPEVTCVVVDVSHEDPEVKFNWYVDGVEVHNAKTKP REEQYNSTYRVVSVLTVLHQDWLNGKEYKCKVSNKA LPAPIEKTISKAKGQPREPQVYTLPPSREEMTKNQV SLTCLVKGFYPSDIAVEWESNGQPENNYKTTPPVLD SDGSFFLYSKLTVDKSRWQQGNVFSCSVMHEALHNH YTQKSLSLSPGK<u>GGGGSGGGGSGGGGSGGGGSGGGG S</u>VSRLEEEMRKLQATVQELQKRLDRLEETVQAK<u>GGG GQ</u>LETAKEPCMAKFGPLPSKWQMASSEPPCVNKVSD WKLEILQNGLYLIYGQVAPNANYNDVAPFEVRLYKN KDMIQTLTNKSKIQNVGGTYELHVGDTIDLIFNSEH QVLKDNTYWGIILLANPQFIS |
| 7 | Nucleic Acid encoding precursor GITRL IgG1 FP subunit (including signal peptide encoding region) | ATGGCCATCATCTACCTGATCCTGCTGTTCACCGCC GTGCGGGGCCTGGACAAGACCCATACCTGTCCTCCA TGCCCTGCCCCCGAACTGCTGGGAGGCCCTTCTGTG TTCCTGTTCCCCCCAAAGCCCAAGGACACCCTGATG ATCTCCCGGACCCCCGAAGTGACCTGCGTGGTGGTG GATGTGTCCCACGAGGACCCTGAAGTGAAGTTCAAT TGGTACGTGGACGGCGTGGAAGTGCACAACGCCAAG ACCAAGCCCAGAGAGGAACAGTACAACTCCACCTAC CGGGTGGTGTCCGTGCTGACCGTGCTGCACCAGGAT TGGCTGAACGGCAAAGAGTACAAGTGCAAGGTGTCC AACAAGGCCCTGCCTGCCCCCATCGAAAAGACCATC TCCAAGGCCAAGGGCCAGCCCCGGGAACCCCAGGTG TACACACTGCCCCCTAGCCGGGAAGAGATGACCAAG AACCAGGTGTCCCTGACCTGTCTCGTGAAGGGCTTC TACCCCTCCGATATCGCCGTGGAATGGGAGTCCAAC GGCCAGCCTGAGAACAACTACAAGACCACCCCCCCT GTGCTGGACTCCGACGGCTCATTCTTCCTGTACTCC AAGCTGACAGTGGACAAGTCCCGGTGGCAGCAGGGC AACGTGTTCTCCTGCTCCGTGATGCACGAGGCCCTG CACAACCACTACACCCAGAAGTCCCTGTCCCTGAGC CCTGGAAAAGGCGGCGGAGGATCTGGCGGAGGCGGT TCTGGTGGTGGCGGATCTGGGGGCGGAGGTAGCGGA GGTGGTGGCTCTGTGTCTCGGCTGGAAGAGGAAATG CGGAAGCTGCAGGCCACCGTGCAGGAACTGCAGAAG CGGCTGGACAGACTGGAAGAGACAGTGCAGGCTAAG GGCGGTGGCGGACAGCTCGAGACAGCCAAAGAACCC TGCATGGCCAAGTTCGGCCCCCTGCCTTCCAAGTGG CAGATGGCCTCTTCCGAGCCCCCTGCGTGAACAAA GTGTCCGACTGGAAGCTGGAAATCCTGCAGAACGGC CTGTACCTGATCTACGGCCAGGTGGCCCCCAACGCC AACTACAACGATGTGGCCCCCTTCGAAGTGCGGCTG TACAAGAACAAGGACATGATCCAGACCCTGACCAAC AAGAGCAAGATCCAGAACGTGGGCGGCACCTACGAG CTGCACGTGGGCGATACCATCGACCTGATCTTCAAC TCCGAGCACCAGGTGCTGAAGGACAACACCTACTGG GGCATCATCCTGCTGGCCAACCCCCAGTTCATCTCC |
| 8 | Amino Acid Sequence of a precursor GITRL IgG1 FP subunit (including signal peptide encoding region; Linker 1 and Linker 2 are underlined) | MAIIYLILLFTAVRGLDKTHTCPPCPAPELLGGPSV FLFPPKPKDTLMISRTPEVTCVVVDVSHEDPEVKFN WYVDGVEVHNAKTKPREEQYNSTYRVVSVLTVLHQD WLNGKEYKCKVSNKALPAPIEKTISKAKGQPREPQV YTLPPSREEMTKNQVSLTCLVKGFYPSDIAVEWESN GQPENNYKTTPPVLDSDGSFFLYSKLTVDKSRWQQG NVFSCSVMHEALHNHYTQKSLSLSPGK<u>GGGGSGGGG SGGGGSGGGGSGGGG</u>SVSRLEEEMRKLQATVQELQK RLDRLEETVQAK<u>GGGGQ</u>LETAKEPCMAKFGPLPSKW QMASSEPPCVNKVSDWKLEILQNGLYLIYGQVAPNA NYNDVAPFEVRLYKNKDMIQTLTNKSKIQNVGGTYE LHVGDTIDLIFNSEHQVLKDNTYWGIILLANPQFIS |
| 9 | Amino Acid Sequence of Human Coronin 1a (hCor1a) | MSRQVVRSSKFRHVFGQPAKADQCYEDVRVSQTTWD SGFCAVNPKFVALICEASGGGAFLVLPLGKTGRVDK NAPTVCGHTAPVLDIAWCPHNDNVIASGSEDCTVMV WEIPDGGLMLPLREPVVTLEGHTKRVGIVAWHTTAQ NVLLSAGCDNVIMVWDVGTGAAMLTLGPEVHPDTIY SVDWSRDGGLICTSCRDKRVRIIEPRKGTVVAEKDR PHEGTRPVRAVFVSEGKILTTGFSRMSERQVALWDT KHLEEPLSLQELDTSSGVLLPFFDPDTNIVYLCGKG DSSIRYFEITSEAPFLHYLSWSSKESQRGMGYMPKR GLEVNKCEIARFYKLHERRCEPIAMTVPRKSDLFQE DLYPPTAGPDPALTAEEWLGGRDAGPLLISLKDGYV PPKSRELRVNRGLDTGRRRAAPEASGTPSSDAVSRL EEEMRKLQATVQELQKRLDRLEETVQAK |

TABLE 6-1-continued

| SEQ ID NO. | Description | Sequence |
|---|---|---|
| 10 | Amino Acid Sequence of hCor1a Trimerization Domain Consensus | XSRXEEEXRKXQATXQELQKRXDRLEETVQAK X = Ala, Leu, Ile, or Val |
| 11 | Amino Acid Sequence of hCor1a wt Trimerization Domain | VSRLEEEMRKLQATVQELQKRLDRLEETVQAK |
| 12 | Amino Acid Sequence of hCor1a variant 1 Trimerization Domain | VSRLEEEIRKLQATVQELQKRLDRLEETVQAK |
| 13 | Amino Acid Sequence of hCor1a variant 2 Trimerization Domain | VSRIEEEIRKLQATVQELQKRLDRLEETVQAK |
| 14 | Amino Acid Sequence of hCor1a variant 3 Trimerization Domain | ISRIEEEIRKLQATVQELQKRLDRLEETVQAK |
| 15 | Amino Acid Sequence of hCor1a variant 4 Trimerization Domain | ISRIEEEIRKIQATVQELQKRLDRLEETVQAK |
| 16 | Amino Acid Sequence of hCor1a variant 5 Trimerization Domain | ISRIEEEIRKIQATVQELQKRIDRLEETVQAK |
| 17 | Amino Acid Sequence of hCor1a variant 6 Trimerization Domain | ISRIEEEIRKINATVQELQKRIDRLEETVQAK |
| 18 | Amino Acid Sequence of hCor1a variant 7 Trimerization Domain | ISRIEEEIRKINATIQELQKRIDRLEETVQAK |
| 19 | Amino Acid Sequence of Gly(4)Ser Motif where n = 1 | GGGGS |
| 20 | Amino Acid Sequence of Linker 1 | GGGGSGGGGSGGGGSGGGGSGGGGS |
| 21 | Amino Acid Sequence of IgG1 Fc region used in the GITRL IgG1 FP of SEQ ID NO: 6 | LDKTHTCPPCPAPELLGGPSVFLFPPKPKDTLMISR TPEVTCVVVDVSHEDPEVKFNWYVDGVEVHNAKTKP REEQYNSTYRVVSVLTVLHQDWLNGKEYKCKVSNKA LPAPIEKTISKAKGQPREPQVYTLPPSREEMTKNQV SLTCLVKGFYPSDIAVEWESNGQPENNYKTTPPVLD SDGSFFLYSKLTVDKSRWQQGNVFSCSVMHEALHNH YTQKSLSLSPGK |
| 22 | Amino Acid Sequence of Ser(Gly4Ser)n motif where n = 1 | SGGGGS |

TABLE 6-1-continued

| SEQ ID NO. | Description | Sequence |
|---|---|---|
| 23 | Amino Acid Sequence of Linker region | GGGGSGGGGSGGGGSAL |
| 24 | Amino Acid Sequence of Linker region | GGGGSGGGGSGGGGSA |
| 25 | Amino Acid Sequence of Gly(4)Ser Motif where n = 3 | GGGGSGGGGSGGGGS |
| 26 | Amino Acid Sequence of Linker region | GGGGSGGGGSGGGG |
| 27 | Amino Acid Sequence of yeast GCN4 pII | IKQIEDKIEEILSKIYHIENEIARIKKL |
| 28 | Amino Acid Sequence of Matrilin 1 wt trimerisation domain | CACESLVKFQAKVEGLLQALTRKLEAVSKRLAILEN TVV |
| 29 | Amino Acid Sequence of Matrilin 1 variant trimerisation domain | CACESLVKFQAKVEGLIQALTRKLEAVSKRIAILEN TVV |
| 30 | Amino Acid Sequence of DMPK wt trimerisation domain | EAEAEVTLRELQEALEEEVLTRQSLSREMEAIRTDN QNFASQLREAEARNRDLEAHVRQLQERMELLQAE |
| 31 | Amino Acid Sequence of DMPK variant trimerisation domain | IAEIEVTIRELQEAIEEEVLTRQSLSREIEAIRTDI QNIASQLREIEARIRDLEAHVRQLQERMELLQAE |
| 32 | Amino Acid Sequence of Langerin wt trimerisation domain | ASALNTKIRALQGSLENMSKLLKRQNDILQVVS |
| 33 | Amino Acid Sequence of Langerin variant trimerisation domain | ISALNTKIRAIQGSIENMSKLIKRQNDIIQVVS |
| 34 | Amino Acid Sequence of Mature WT GITRL extracellular domain | QLETAKEPCMAKFGPLPSKWQMASSEPPCVNKVSDW KLEILQNGLYLIYGQVAPNANYNDVAPFEVRLYKNK DMIQTLTNKSKIQNVGGTYELHVGDTIDLIFNSEHQ SVLKNNTYWGIILLANPQFI |
| 35 | Amino Acid Sequence of Mature GITRL Variant extracellular domain | QL$\mathbf{X}_1$TAKEPCMAK$\mathbf{X}_2$GPL$\mathbf{X}_3\mathbf{X}_4$KWQ$\mathbf{X}_5$ASSEP$\mathbf{X}_6$C$\mathbf{X}_7$N KV$\mathbf{X}_8$DWKLEILQNGLYLIY$\mathbf{X}_9$QVAPNANYNDVA$\mathbf{X}_{10}$F EV$\mathbf{X}_{11}$LYKNKD$\mathbf{X}_{12}$IQTLTNKSKIQNVGGTYELHVGD TIDLIF$\mathbf{X}_{13}$SEHQ$\mathbf{X}_{14}$LK$\mathbf{X}_{15}$NTYWG$\mathbf{X}_{16}\mathbf{X}_{17}$LLANPQF IS<br>$X_1$ = Glu or Ala,<br>$X_2$ = Ser or Phe,<br>$X_3$ = Thr or Pro,<br>$X_4$ = Leu or Ser,<br>$X_5$ = Thr or Met, |

TABLE 6-1-continued

| SEQ ID NO. | Description | Sequence |
|---|---|---|
| | | $X_6$ = Leu or Pro,<br>$X_7$ = Met or Val,<br>$X_8$ = Thr, Phe, or Ser,<br>$X_9$ = Ser or Gly,<br>$X_{10}$ = Arg or Pro,<br>$X_{11}$ = Trp or Arg,<br>$X_{12}$ = Leu or Met,<br>$X_{13}$ = Ser or Asn,<br>$X_{14}$ = Phe or Val,<br>$X_{15}$ = Any amino acid other than Asn,<br>$X_{16}$ = Val or Ile, and<br>$X_{17}$ = Leu or Ile |
| 36 | Amino Acid Sequence of Mature GITRL N161X Variant extracellular domain | QLETAKEPCMAKFGPLPSKWQMASSEPPCVNKVSDW<br>KLEILQNGLYLIYGQVAPNANYNDVAPFEVRLYKNK<br>DMIQTLTNKSKIQNVGGTYELHVGDTIDLIFNSEHQ<br>VLKXNTYWGIILLANPQFIS<br>X IS ANY AMINO ACID EXCEPT Asn. |
| 37 | Amino Acid Sequence of Mature GITRL N161D Variant extracellular domain | QLETAKEPCMAKFGPLPSKWQMASSEPPCVNKVSDW<br>KLEILQNGLYLIYGQVAPNANYNDVAPFEVRLYKNK<br>DMIQTLTNKSKIQNVGGTYELHVGDTIDLIFNSEHQ<br>VLKDNTYWGIILLANPQFIS |
| 38 | Amino Acid Sequence of IgG1 Fc region used in the GITRL IgG4P FP (S228P mutation underlined) | ESKYGPPCPPCPAPEFLGGPSVFLFPPKPKDTLMIS<br>RTPEVTCVVVDVSQEDPEVQFNWYVDGVEVHNAKTK<br>PREEQFNSTYRVVSVLTVLHQDWLNGKEYKCKVSNK<br>GLPSSIEKTISKAKGQPREPQVYTLPPSQEEMTKNQ<br>VSLTCLVKGFYPSDIAVEWESNGQPENNYKTTPPVL<br>DSDGSFFLYSRLTVDKSRWQEGNVFSCSVMHEALHN<br>HYTQKSLSLSLGK |
| 39 | Nucleic Acid encoding a mature GITRL IgG4P FP subunit (w/o signal peptide encoding region) | GAGTCTAAGTACGGCCCTCCTTGTCCTCCTTGCCCT<br>GCCCCTGAGTTTCTGGGCGGACCTTCCGTGTTCCTG<br>TTCCCCCCAAAGCCCAAGGACACCCTGATGATCTCC<br>CGGACCCCCGAAGTGACCTGCGTGGTGGTGGATGTG<br>TCCCAGGAAGATCCCGAGGTGCAGTTCAATTGGTAC<br>GTGGACGGCGTGGAAGTGCACAACGCCAAGACCAAG<br>CCCAGAGAGGAACAGTTCAACTCCACCTACCGGGTG<br>GTGTCCGTGCTGACCGTGCTGCACCAGGATTGGCTG<br>AACGGCAAAGAGTACAAGTGCAAGGTGTCCAACAAG<br>GGCCTGCCCTCCAGCATCGAAAAGACCATCTCCAAG<br>GCCAAGGGCCAGCCCCGGGAACCCCAGGTGTACACA<br>CTGCCTCCAAGCCAGGAAGAGATGACCAAGAACCAG<br>GTGTCCCTGACCTGTCTCGTGAAGGGCTTCTACCCC<br>TCCGATATCGCCGTGGAATGGGAGTCCAACGGCCAG<br>CCTGAGAACAACTACAAGACCACCCCCCCTGTGCTG<br>GACTCCGACGGCTCCTTCTTCCTGTACTCCCGCCTG<br>ACCGTGGACAAGTCCAGATGGCAGGAAGGCAACGTG<br>TTCTCCTGCTCCGTGATGCACGAGGCCCTGCACAAC<br>CACTACACCCAGAAGTCCCTGTCCCTGTCTCTGGGC<br>AAGGGCGGCGGAGGATCTGGCGGAGGCGGTTCTGGT<br>GGTGGTGGATCTGGTGGCGGAGGAAGTGGGGGAGGG<br>GGATCTGTGTCTCGGCTGGAAGAGGAAATGCGGAAG<br>CTGCAGGCCACCGTGCAGGAACTGCAGAAGCGGCTG<br>GACAGACTGGAAGAGACAGTGCAGGCTAAGGGCGGT<br>GGCGGACAGCTCGAGACAGCCAAAGAACCCTGCATG<br>GCCAAGTTCGGCCCCCTGCCTTCCAAGTGGCAGATG<br>GCCTCTTCCGAGCCCCCTGCGTGAACAAAGTGTCC<br>GACTGGAAGCTGGAAATCCTGCAGAACGGCCTGTAC<br>CTGATCTACGGCCAGGTGGCCCCCAACGCCAACTAC<br>AACGATGTGGCCCCCTTCGAAGTGCGGCTGTACAAG<br>AACAAGGACATGATCCAGACCCTGACCAACAAGAGC<br>AAGATCCAGAACGTGGGCGGCACCTACGAGCTGCAC<br>GTGGGCGATACCATCGACCTGATCTTCAACTCCGAG<br>CACCAGGTGCTGAAGGACAACACCTACTGGGGCATC<br>ATCCTGCTGGCCAACCCCCAGTTCATCTCC |
| 40 | Amino Acid Sequence of a mature GITRL IgG4P FP subunit | ESKYGPPCPPCPAPEFLGGPSVFLFPPKPKDTLMIS<br>RTPEVTCVVVDVSQEDPEVQFNWYVDGVEVHNAKTK<br>PREEQFNSTYRVVSVLTVLHQDWLNGKEYKCKVSNK<br>GLPSSIEKTISKAKGQPREPQVYTLPPSQEEMTKNQ<br>VSLTCLVKGFYPSDIAVEWESNGQPENNYKTTPPVL |

TABLE 6-1-continued

| SEQ ID NO. | Description | Sequence |
|---|---|---|
| | | DSDGSFFLYSRLTVDKSRWQEGNVFSCSVMHEALHN HYTQKSLSLSLGKGGGGSGGGGSGGGGSGGGGSGGG GSVSRLEEEMRKLQATVQELQKRLDRLEETVQAKGG GGGQLETAKEPCMAKFGPLPSKWQMASSEPPCVNKVS DWKLEILQNGLYLIYGQVAPNANYNDVAPFEVRLYK NKDMIQTLTNKSKIQNVGGTYELHVGDTIDLIFNSE HQVLKDNTYWGIILLANPQFIS |
| 41 | Nucleic Acid encoding a precursor GITRL IgG4P FP subunit (including signal peptide encoding region) | ATGGCCATCATCTACCTGATCCTGCTGTTCACCGCC GTGCGGGGCGAGTCTAAGTACGGCCCTCCTTGTCCT CCTTGCCCTGCCCCTGAGTTTCTGGGCGGACCTTCC GTGTTCCTGTTCCCCCCAAAGCCCAAGGACACCCTG ATGATCTCCCGGACCCCCGAAGTGACCTGCGTGGTG GTGGATGTGTCCCAGGAAGATCCCGAGGTGCAGTTC AATTGGTACGTGGACGGCGTGGAAGTGCACAACGCC AAGACCAAGCCCAGAGAGGAACAGTTCAACTCCACC TACCGGGTGGTGTCCGTGCTGACCGTGCTGCACCAG GATTGGCTGAACGGCAAAGAGTACAAGTGCAAGGTG TCCAACAAGGGCCTGCCCTCCAGCATCGAAAAGACC ATCTCCAAGGCCAAGGGCCAGCCCCGGGAACCCCAG GTGTACACACTGCCTCCAAGCCAGGAAGAGATGACC AAGAACCAGGTGTCCCTGACCTGTCTCGTGAAGGGC TTCTACCCCTCCGATATCGCCGTGGAATGGGAGTCC AACGGCCAGCCTGAGAACAACTACAAGACCACCCCC CCTGTGCTGGACTCCGACGGCTCCTTCTTCCTGTAC TCCCGCCTGACCGTGGACAAGTCCAGATGGCAGGAA GGCAACGTGTTCTCCTGCTCCGTGATGCACGAGGCC CTGCACAACCACTACACCCAGAAGTCCCTGTCCCTG TCTCTGGGCAAGGGCGGCGGAGGATCTGGCGGAGGC GGTTCTGGTGGTGGTGGATCTGGTGGCGGAGGAAGT GGGGGAGGGGGATCTGTGTCTCGGCTGGAAGAGGAA ATGCGGAAGCTGCAGGCCACCGTGCAGGAACTGCAG AAGCGGCTGGACAGACTGGAAGAGACAGTGCAGGCT AAGGGCGGTGGCGGACAGCTCGAGACAGCCAAAGAA CCCTGCATGGCCAAGTTCGGCCCCCTGCCTTCCAAG TGGCAGATGGCCTCTTCCGAGCCCCCCTGCGTGAAC AAAGTGTCCGACTGGAAGCTGGAAATCCTGCAGAAC GGCCTGTACCTGATCTACGGCCAGGTGGCCCCCAAC GCCAACTACAACGATGTGGCCCCCTTCGAAGTGCGG CTGTACAAGAACAAGGACATGATCCAGACCCTGACC AACAAGAGCAAGATCCAGAACGTGGGCGGCACCTAC GAGCTGCACGTGGGCGATACCATCGACCTGATCTTC AACTCCGAGCACCAGGTGCTGAAGGACAACACCTAC TGGGGCATCATCCTGCTGGCCAACCCCCAGTTCATC TCC |
| 42 | Amino Acid Sequence of a precursor GITRL IgG4P FP subunit (with signal peptide encoding region) | MAIIYLILLFTAVRGESKYGPPCPPCPAPEFLGGPS VFLFPPKPKDTLMISRTPEVTCVVVDVSQEDPEVQF NWYVDGVEVHNAKTKPREEQFNSTYRVVSVLTVLHQ DWLNGKEYKCKVSNKGLPSSIEKTISKAKGQPREPQ VYTLPPSQEEMTKNQVSLTCLVKGFYPSDIAVEWES NGQPENNYKTTPPVLDSDGSFFLYSRLTVDKSRWQE GNVFSCSVMHEALHNHYTQKSLSLSLGKGGGGSGGG GSGGGGSGGGGSGGGGSVSRLEEEMRKLQATVQELQ KRLDRLEETVQAKGGGGQLETAKEPCMAKFGPLPSK WQMASSEPPCVNKVSDWKLEILQNGLYLIYGQVAPN ANYNDVAPFEVRLYKNKDMIQTLTNKSKIQNVGGTY ELHVGDTIDLIFNSEHQVLKDNTYWGIILLANPQFI S |
| 43 | hGITRL-FP wt & hGITRL-FP N161D polypeptide subunit tryptic fragment | EEQYNSTYR |
| 44 | hGITRL-FP wt & hGITRL-FP N161D polypeptide subunit tryptic fragment | DMIQTLTNK |
| 45 | hGITRL-FP wt polypeptide subunit tryptic | IQNVGGTYELHVGDTIDLIFNSEHQVLKNNTYWGII LLANPQFIS |

TABLE 6-1-continued

| SEQ ID NO. | Description | Sequence |
|---|---|---|
| | fragment | |
| 46 | hGITRL-FP N161D polypeptide subunit tryptic fragment | DNTYWGIILLANPQFIS |
| 47 | hGITR (human GITR) | MAQHGAMGAFRALCGLALLCALSLGQRPTGGPGCGP GRLLLGTGTDARCCRVHTTRCCRDYPGEECCSEWDC MCVQPEFHCGDPCCTTCRHHPCPPGQGVQSQGKFSF GFQCIDCASGTFSGGHEGHCKPWTDCTQFGFLTVFP GNKTHNAVCVPGSPPAEPLGWLTVVLLAVAACVLLL TSAQLGLHIWQLRSQCMWPRETQLLLEVPPSTEDAR SCQFPEEERGERSAEEKGRLGDLWV |
| 48 | mGITRL-FP | MAIIYLILLFTAVRGIKPCPPPCKCPAPNLLGGPSVF IFPPKIKDVLMISLSPIVTCVVVDVSEDDPDVQISW FVNNVEVHTAQTQTHREDYNSTLRVVSALPIQHQDW MSGKEFKCKVNNKDLPAPIERTISKPKGSVRAPQVY VLPPPEEEMTKKQVTLTCMVTDFMPEDIYVEWTNNG KTELNYKNTEPVLDSDGSYFMYSKLRVEKKNWVERN SYSCSVVHEGLHNEIHTTKSFSRTPGKGGGGSGGGG SGGGGSGGGGSGGGGSIKQIEDKIEEILSKIYHIEN EIARIKKLGGGGIESCMVKFELSSSKWHMTSPKPHC VNTTSDGKLKILQSGTYLIYGQVIPVDKKYIKDNAP FVVQIYKKNDVLQTLMNDFQILPIGGVYELHAGDNI YLKFNSKDHIQKTNTYWGIILMPDLPFIS |
| 49 | mOX40L-FP | VPRDCGCKPCICTVPEVSSVFIFPPKPKDVLTITLT PKVTCVVVDISKDDPEVQFSWFVDDVEVHTAQTQPR EEQFNSTFRSVSELPIMHQDWLNGKEFKCRVNSAAF PAPIEKTISKTKGRPKAPQVYTIPPPKEQMAKDKVS LTCMITDFFPEDITVEWQWNGQPAENYKNTQPIMDT DGSYFVYSKLNVQKSNWEAGNTFTCSVLHEGLHNHH TEKSLSHSPGKRLDQDKIEALSNKVQQLERSIGLKD LAMADLEQKVSELEVSTSSPAKDPPIQRLRGAVTRC EDGQLFISSYKNEYQTMEVQNNSVVIKCDGLYIIYL KGSFFQEVKIDLHFREDHNPISIPMLNDGRRIVFTV VASLAFKDKVYLTVNAPDTLCEHLQINDGELIVVQL TPGYCAPEGSYHSTVNQVPL |
| 50 | MEDI6383 | LATDKTHTCPPCPAPELLGGPSVFLFPPKPKDTLMI SRTPEVTCVVVDVSHEDPEVKFNWYVDGVEVHNAKT KPREEQYNSTYRVVSVLTVLHQDWLNGKEYKCKVSN KALPAPIEKTISKAKGQPREPQVYTLPPSREEMTKN QVSLTCLVKGFYPSDIAVEWESNGQPENNYKTTPPV LDSDGSFFLYSKLTVDKSRWQQGNVFSCSVMHEALH NHYTQKSLSLSPGKELLGGGSIKQIEDKIEEILSKI YHIENEIARIKKLIGERGHGGGSNSQVSHRYPRFQS IKVQFTEYKKEKGFILTSQKEDEIMKVQNNSVIINC DGFYLISLKGYFSQEVNISLHYQKDEEPLFQLKKVR SVNSLMVASLTYKDKVYLNVTTDNTSLDDFHVNGGE LILIHQNPGEFCVL |
| 51 | MEDI0562 VH | QVQLQESGPGLVKPSQTLSLTCAVGGSFSSGYWNW IRKHPGKGLEYIGYISYNGITYHNPSLKSRITINRD TSKNQYSLQLNSVTPEDTAVYYCARYKYDYDGGHAM DYWGQGTLVTVSSASTKGPSVFPLAPSSKSTSGGTA ALGCLVKDYFPEPVTVSWNSGALTSGVHTFPAVLQS SGLYSLSSVVTVPSSSLGTQTYICNVNHKPSNTKVD KRVEPKSCDKTHTCPPCPAPELLGGPSVFLFPPKPK DTLMISRTPEVTCVVVDVSHEDPEVKFNWYVDGVEV HNAKTKPREEQYNSTYRVVSVLTVLHQDWLNGKEYK CKVSNKALPAPIEKTISKAKGQPREPQVYTLPPSRE EMTKNQVSLTCLVKGFYPSDIAVEWESNGQPENNYK TTPPVLDSDGSFFLYSKLTVDKSRWQQGNVFSCSVM HEALHNHYTQKSLSLSPGK |
| 52 | MEDI0562 VL | DIQMTQSPSSLSASVGDRVTITCRASQDISNYLNWY QQKPGKAPKLLIYYTSKLHSGVPSRFSGSGSGTDYT LTISSLQPEDFATYYCQQGSALPWTFGQGTKVEIKR TVAAPSVFIFPPSDEQLKSGTASVVCLLNNFYPREA KVQWKVDNALQSGNSQESVTEQDSKDSTYSLSSTLT LSKADYEKHKVYACEVTHQGLSSPVTKSFNRGEC |
| 53 | Human OX40 | MCVGARRLGR GPCAALLLLG LGLSTVTGLH |

TABLE 6-1-continued

| SEQ ID NO. | Description | Sequence |
|---|---|---|
| | | CVGDTYPSND RCCHECRPGN GMVSRCSRSQ NTVCRPCGPG FYNDVVSSKP CKPCTWCNLR SGSERKQLCT ATQDTVCRCR AGTQPLDSYK PGVDCAPCPP GHFSPGDNQA CKPWTNCTLA GKHTLQPASN SSDAICEDRD PPATQPQETQ GPPARPITVQ PTEAWPRTSQ GPSTRPVEVP GGRAVAAILG LGLVLGLLGP LAILLALYLL RRDQRLPPDA HKPPGGGSFR TPIQEEQADA HSTLAKI |
| 54 | Human OX40 ligand | MERVQPLEENVGNAARPRFERNKLLLVASVIQGLGL LLCFTYICLHFSALQVSHRYPRIQSIKVQFTEYKKE KGFILTSQKEDEIMKVQNNSVIINCDGFYLISLKGY FSQEVNISLHYQKDEEPLFQLKKVRSVNSLMVASLT YKDKVYLNVTTDNTSLDDFHVNGGELILIHQNPGEF CVL |
| 55 | mOX40L-FP Y182A | VPRDCGCKPCICTVPEVSSVFIFPPKPKDVLTITLT PKVTCVVVDISKDDPEVQFSWFVDDVEVHTAQTQPR EEQFNSTFRSVSELPIMHQDWLNGKEFKCRVNSAAF PAPIEKTISKTKGRPKAPQVYTIPPPKEQMAKDKVS LTCMITDFFPEDITVEWQWNGQPAENYKNTQPIMDT DGSYFVYSKLNVQKSNWEAGNTFTCSVLHEGLHNHH TEKSLSHSPGKRLDQDKIEALSNKVQQLERSIGLKD LAMADLEQKVSELEVSTSSPAKDPPIQRLRGAVTRC EDGQLFISSYKNEYQTMEVQNNSVVIKCDGLYIIYL KGSFFQEVKIDLHFREDHNPISIPMLNDGRRIVFTV VASLAFKDKVYLTVNAPDTLCEHLQINDGELIVVQL TPGACAPEGSYHSTVNQVPL |
| 56 | AH1 peptide | SPSYVYHQF |
| 57 | E7 Synthetic Long Peptide (SLP) | SSEEEDEIDGPAGQAEPDRAHYNIVTFCCKCDSTLR LCVQSTHVD |
| 58 | E7 peptide | RAHYNIVTF |

\*\*\*

The breadth and scope of the present disclosure should not be limited by any of the above-described exemplary embodiments, but should be defined only in accordance with the following claims and their equivalents.

What is claimed is:

1. A hexameric protein comprising six single-chain polypeptide subunits each comprising: an IgG Fc domain; a functional trimerization domain derived from human Coronin 1a; and a receptor binding domain of a Glucocorticoid-Induced TNF Receptor Ligand (GITRL), wherein the GITRL receptor binding domain comprises the amino acid sequence of SEQ ID NO: 35 and wherein residue 112 of SEQ ID NO: 35 is an aspartyl residue.

2. The hexameric protein of claim 1, wherein each polypeptide subunit comprises from the amino terminus to the carboxy terminus, the IgG Fc domain, followed by the trimerization domain, followed by the GITRL receptor binding domain.

3. The hexameric protein of claim 2, wherein the carboxy terminus of the IgG Fc domain is fused to the amino terminus of the trimerization domain via a first linker region.

4. The hexameric protein of claim 3, wherein the carboxy terminus of the trimerization domain is fused to the amino terminus of the GITRL receptor binding domain via a second linker region.

5. The hexameric protein of claim 2, wherein the carboxy terminus of the IgG Fc domain is fused directly to the amino terminus of the trimerization domain.

6. The hexameric protein of claim 4 wherein the IgG Fc domain includes an IgG hinge region at its amino terminus.

7. The hexameric protein of claim 6, wherein the IgG hinge region comprises a mutation that confers complete inter heavy chain disulfide bond formation.

8. The hexameric protein of claim 6, wherein the IgG hinge region comprises an IgG1 hinge region, an IgG4 hinge region, or variants thereof.

9. The hexameric protein of claim 8, wherein the IgG4 hinge region has a serine to proline mutation at position 228 (S228P) according to EU numbering (IgG4P).

10. The hexameric protein of claim 4, wherein the first linker region, the second linker region, or the first and second linker regions, when present, are independently selected from a group consisting of a linker region containing a $(Gly_4)n$ motif, a $(Gly_4Ser)n$ motif (SEQ ID NO: 19), a $Ser(Gly_4Ser)n$ motif (SEQ ID NO: 22), GGGGSGGGGSGGGGSAL (SEQ ID NO:23), GGGGSGGGGSGGGGSA (SEQ ID NO: 24), and combinations thereof, wherein n is a positive integer selected from the group consisting of 1, 2, 3, 4, 5, 6, 7, 8, 9 and 10.

11. The hexameric protein of claim 10, wherein the first and second linker regions are independently selected from a group consisting of GGGGSGGGGSGGGGS (SEQ ID NO: 25), and GGGGSGGGGSGGGG (SEQ ID NO: 26).

12. The hexameric protein of claim 10 or 11, wherein the first linker region is GGGGSGGGGSGGGGSGGGGSGGGGS (SEQ ID NO: 20) and the second linker region is a $(Gly_4)$ motif.

13. The hexameric protein of claim 1, wherein the IgG Fc domain comprises an IgG1, IgG2, IgG3, IgG4, IG4P Fc domain, or variants thereof.

14. The hexameric protein of claim 1, wherein the IgG Fc domain contains one or more amino acid residue substitutions selected from the group consisting of 252Y, 254T, 256E, and combinations thereof, wherein the residues are numbered according to EU numbering.

15. The hexameric protein of claim 1, wherein the IgG Fc domain comprises the amino acid sequence of SEQ ID NO: 21.

16. The hexameric protein of claim 1, wherein the Coronin 1a trimerization domain comprises the amino acid sequence of SEQ ID NO: 10 SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, or any combination or variant thereof.

17. The hexameric protein of claim 1, wherein the GITRL receptor binding domain comprises the amino acid sequence of SEQ ID NO: 36 or SEQ ID NO: 37.

18. The hexameric protein of claim 1, wherein a hexameric protein assembled from six of the polypeptide subunits can specifically bind to human GITR.

19. The hexameric protein of claim 1 which can specifically bind to Glucocorticoid-Induced TNF Receptor (GITR) as expressed on $CD4^+$ or $CD8^+$ T cells, B cells, or NK cells, wherein the $CD4^+$ or $CD8^+$ T cells or B cells are optionally antigen experienced, or the NK cells are optionally activated, from human, or a non-human primate, optionally a cynomolgus monkey, a rhesus monkey, or any combination thereof.

20. A composition comprising the hexameric protein of claim 1, and a carrier.

* * * * *